US012410247B2

(12) United States Patent
Laine et al.

(10) Patent No.: US 12,410,247 B2
(45) Date of Patent: Sep. 9, 2025

(54) POLYNUCLEOTIDES ENCODING ANTIBODIES THAT SPECIFICALLY BIND TO HUMAN IL-15

(71) Applicant: Cephalon LLC, West Chester, PA (US)

(72) Inventors: David Jose Simon Laine, Macquarie Park (AU); Matthew Pollard, Pullenvale (AU); Anthony Gerard Doyle, Macquarie Park (AU); Lynn Dorothy Poulton, Macquarie Park (AU); Adam William Clarke, Macquarie Park (AU)

(73) Assignee: Cephalon LLC, West Chester, PA (US)

( * ) Notice: Subject to any disclaimer, the term of this patent is extended or adjusted under 35 U.S.C. 154(b) by 920 days.

(21) Appl. No.: 17/647,082

(22) Filed: Jan. 5, 2022

(65) Prior Publication Data

US 2022/0127352 A1   Apr. 28, 2022

Related U.S. Application Data

(62) Division of application No. 16/471,616, filed as application No. PCT/US2017/067917 on Dec. 21, 2017, now Pat. No. 11,267,883.

(60) Provisional application No. 62/437,143, filed on Dec. 21, 2016.

(51) Int. Cl.
| | | |
|---|---|---|
| C12N 15/09 | (2006.01) | |
| A61P 1/00 | (2006.01) | |
| A61P 3/00 | (2006.01) | |
| A61P 29/02 | (2006.01) | |
| A61P 37/00 | (2006.01) | |
| C07K 16/24 | (2006.01) | |
| A61K 39/00 | (2006.01) | |

(52) U.S. Cl.
CPC ............ *C07K 16/244* (2013.01); *A61P 1/00* (2018.01); *A61P 3/00* (2018.01); *A61P 29/02* (2018.01); *A61P 37/00* (2018.01); *A61K 2039/505* (2013.01); *C07K 2317/565* (2013.01); *C07K 2317/76* (2013.01)

(58) Field of Classification Search
CPC ... C12N 15/09; C12N 15/11; C07K 2317/565
See application file for complete search history.

(56) References Cited

U.S. PATENT DOCUMENTS

| | | |
|---|---|---|
| 6,165,466 A | 12/2000 | Grabstein et al. |
| 7,083,784 B2 | 8/2006 | Dall'Acqua et al. |
| 7,217,797 B2 | 5/2007 | Hinton et al. |
| 7,329,405 B2 | 2/2008 | van de Winkel et al. |
| 2003/0138421 A1 | 7/2003 | van de Winkel et al. |
| 2003/0235586 A1 | 12/2003 | van de Winkel et al. |
| 2004/0073011 A1 | 4/2004 | Hagay et al. |
| 2008/0187531 A1 | 8/2008 | Babcook et al. |
| 2009/0053243 A1 | 2/2009 | Kurosawa et al. |
| 2009/0068175 A1 | 3/2009 | Lazar et al. |
| 2009/0092599 A1 | 4/2009 | Lazar et al. |
| 2009/0142340 A1 | 6/2009 | Lazar et al. |
| 2013/0078251 A1 | 3/2013 | Freytag et al. |
| 2013/0115166 A1 | 5/2013 | Clark et al. |
| 2013/0330335 A1 | 12/2013 | Bremel et al. |
| 2014/0182003 A1 | 6/2014 | Bradley et al. |
| 2014/0248238 A1 | 9/2014 | Wilson et al. |
| 2014/0370019 A1 | 12/2014 | Bruenker et al. |
| 2016/0145354 A1 | 5/2016 | Bacac et al. |
| 2020/0270339 A1 | 8/2020 | Laine et al. |

FOREIGN PATENT DOCUMENTS

| | | |
|---|---|---|
| CL | 2019001001 A1 | 3/2020 |
| EP | 2963057 A1 | 1/2016 |
| KR | 20050103306 A | 10/2005 |
| WO | WO-0042072 A1 | 7/2000 |
| WO | WO-03017935 A2 | 3/2003 |
| WO | WO-2008151081 A1 | 12/2008 |
| WO | WO-2009047356 A1 | 4/2009 |
| WO | WO-16001275 A1 | 1/2016 |
| WO | WO-2016156440 A1 | 10/2016 |
| WO | WO-2017217985 A1 | 12/2017 |
| WO | WO-2018071919 A1 | 4/2018 |

OTHER PUBLICATIONS

McInnes et al., Interleukin-15: a new cytokine target for the treatment of inflammatory diseases. Curr Opin Pharmacol. Aug. 2004; 4(4):392-7.*

Abadie, V., et al., "IL-15: a central regulator of celiac disease immunopathology," Immunological Reviews 260(1): 221-234, Wiley-Blackwell Publishing Ltd., United Kingdom (Jul. 2014).

Baslund, B., et al., "Targeting interleukin-15 in patients with rheumatoid arthritis: a proof-of-concept study," Arthritis & Rheumatism 52(9): 2686-2692, W.B. Saunders Ltd., United Kingdom (Sep. 2005).

Bethune, M. T., et al., "A non-human primate model for gluten sensitivity," PLoS One 3(2):e1614, Public Library of Science, United States (Feb. 2008).

Biesiekierski, J., and Iven, J., "Non-coeliac gluten sensitivity: piecing the puzzle together," United European Gastroenterology Journal 3(2): 160-165, SAGE Publications Inc., United States (Apr. 2015).

Chen, J., et al., "Increased serum soluble IL-15Rα levels in T-cell large granular lymphocyte leukemia," Blood 119(1): 137-143, American Society of Hematology, United States (Jan. 2012).

(Continued)

*Primary Examiner* — Dong Jiang
(74) *Attorney, Agent, or Firm* — Sterne, Kessler, Goldstein & Fox P.L.L.C.

(57) ABSTRACT

Recombinant antibodies that specifically bind to IL-15 as well as a complex of IL-15 and the IL-15 Receptor-alpha are provided. The antibodies inhibit immune cell proliferation, and are capable of use in the treatment of any autoimmune or inflammatory disease or condition where IL-15 is dysregulated, including Celiac disease.

20 Claims, 57 Drawing Sheets

Specification includes a Sequence Listing.

(56) References Cited

OTHER PUBLICATIONS

Finch, D. K., et al., "Identification of a potent anti-IL-15 antibody with opposing mechanisms of action in vitro and in vivo," British Journal of Pharmacology 162(2): 480-490, Wiley-Blackwell, United States (Jan. 2011).

Labrijn, A. F., et al., "Therapeutic IgG4 antibodies engage in Fab-arm exchange with endogenous human IgG4 in vivo," Nature Biotechnology 27(8): 767-773, Nature Publishing Group, United Kingdom (Aug. 2009).

Lebrec, H., et al., "Homeostasis of human NK cells is not IL-15 dependent," The Journal of Immunology 191(11): 5551-5558, American Association of Immunologists, United States (Dec. 2013).

Padlan, E. A., et al., "Identification of specificity-determining residues in antibodies," The FASEB Journal 9(1): 133-139, Federation of American Societies for Experimental Biology, United States (Jan. 1995).

Rishi, A. R., et al., "Refractory celiac disease," Expert Review of Gastroenterology & Hepatology 10(4): 537-546, Taylor and Francis Ltd., United Kingdom (published online Dec. 2015; 2016).

Shrake, A., and Rupley, J. A., "Environment and exposure to solvent of protein atoms. Lysozyme and insulin," Journal of Molecular Biology 799(2): 351-371, Elsevier, Netherlands (Sep. 1973).

Sestak, K., et al., "Supplementation of Reduced Gluten Barley Diet with Oral Prolyl Endopeptidase Effectively Abrogates Enteropathy-Associated Changes in Gluten-Sensitive Macaques," Nutrients 8(7): 401, MDPI Multidisciplinary Digital Publishing Institute, Switzerland (Jun. 2016).

UniProtKB—P01857 (IGHG1_Human), "Immunoglobulin heavy constant gamma 1," Accession No. P01857, accessed at https://www.uniprot.org/uniprot/P01857, accessed on May 5, 2020, 2 pages.

Villadsen, L. S., et al., "Resolution of psoriasis upon blockade of IL-15 biological activity in a xenograft mouse model," The Journal of Clinical Investigation 112(10): 1571-1580, The American Society for Clinical Investigation, United States (Nov. 2003).

Waldmann, T. A., et al., "Targeting the interleukin-15/interleukin-15 receptor system in inflammatory autoimmune diseases," Arthritis Research & Therapy 6(4): 174-177, BioMed Central Ltd., United Kingdom (Jun. 2004).

Bernard, J., et al., "Identification of Interleukin-15 Receptor-binding Site on Human Interleukin-15," Journal of Biological Chemistry 279(23):417-433, American Society for Biochemistry, United States (Jun. 2004).

International Search Report and Written Opinion in international application No. PCT/US2017/067917, mailed May 8, 2018, ISA/US, Commissioner for Patents, Alexandria, Virginia, United States, 18 pages.

Thaysen-Andersen, M., et al., "Recombinant human heterodimeric IL-15 complex displays extensive and reproducible N- and O-linked glycosylation," Glycoconjugate Journal 33(3):417-433, Springer Science+Business Media, Germany (Nov. 2015).

Vicari, A. P., et al., "Discovery and characterization of a novel humanized anti-IL-15 antibody and its relevance for the treatment of refractory celiac disease and eosinophilic esophagitis," Monoclonal Antibodies 9(6):927-944, Taylor & Francis, United States (published online Jun. 2017, published in print Aug./Sep. 2017).

Edelman, G. M., et al., "The Covalent Structure of an Entire gammaG Immunoglobulin Molecule," Proc Natl Acad Sci USA 63(1):78-85, National Academy of Sciences, United States (May 1969).

Ku, J., and Schultz, P. G., "Alternate protein frameworks for molecular recognition," Proc Natl Acad Sci USA 92(14):6552-6556, National Academy of Sciences, United States (Jul. 1995).

Gorski, K., et al., "The Fully Human Anti-IL-15 Antibody AMG 714, in Development for Celiac and Refractory Celiac Disease, Does not Reduce Circulating Numbers of Human Natural Killer Cells or Preclude Their in Vitro Activation and Function," AGA Abstracts 150(4): S180, American Gastroenterological Association, United States (Apr. 2016).

Sestak, K., et al., "Beneficial Effects of Human Anti-Interleukin-15 Antibody in Gluten-Sensitive Rhesus Macaques with Celiac Disease," Frontiers in Immunology 9:1603, Frontiers Media S.A., Switzerland (Jul. 2018).

Waldmann, T. A., "The biology of IL-15: implications for cancer therapy and the treatment of autoimmune disorders," J Investig Dermatol Symp Proc 16(1):S28-30, Nature Publishing Group for the Society for Investigative Dermatology, United Kingdom (Dec. 2013).

\* cited by examiner

Figure 1

| Clone | Hybridoma supernatants incubated on | | | | | |
|---|---|---|---|---|---|---|
| | cells transfected with (CELISA)... | | plates coated with (ELISA)... | | | |
| | IL-15 complex | | IL-15 complex | | free receptor IL-15Rα | |
| | rfu | % positive | rfu | % positive | rfu | % positive |
| ANTIBODY 1A6 | 120 | 12% | 150 | 18% | 93 | 16% |
| ANTIBODY 1B3 | 1160 | 120% | 1629 | 191% | 1488 | 258% |
| ANTIBODY 2D | 972 | 98% | 1280 | 142% | 30 | 6% |
| ANTIBODY 4 | 1534 | 149% | 1242 | 140% | 97 | 19% |
| ANTIBODY 10A | 1435 | 119% | 1222 | 139% | 57 | 11% |
| ANTIBODY 10B | 1471 | 122% | 1160 | 132% | 72 | 14% |
| ANTIBODY 10F | 1235 | 102% | 831 | 95% | 96 | 19% |
| ANTIBODY 13E | 1435 | 118% | 1362 | 167% | 113 | 16% |
| ANTIBODY 5E | 994 | 100% | 810 | 94% | 41 | 10% |
| ANTIBODY 10H | 1137 | 119% | 1752 | 217% | 1440 | 316% |
| ANTIBODY 10F-7 | 43 | 4% | 152 | 19% | 88 | 19% |

Figure 4

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 1 | VL_Q024A | 338.1 | 1.35E+05 | 1.55E-04 | 1.15E-09 | 138.8 | 133.3 | 129.6 | 0.972 |
| 1 | VL_Q024L | 335.6 | 1.39E+05 | 1.60E-04 | 1.15E-09 | 139.5 | 134.5 | 130.6 | 0.971 |
| 1 | VL_Q024Y | 324.8 | 1.39E+05 | 1.45E-04 | 1.04E-09 | 134.3 | 129.4 | 126 | 0.974 |
| 1 | VL_Q024W | 358.3 | 1.36E+05 | 1.40E-04 | 1.03E-09 | 148.1 | 142.6 | 139 | 0.975 |
| 1 | VL_Q024K | 336.6 | 1.28E+05 | 1.65E-04 | 1.29E-09 | 134.8 | 128.4 | 124.6 | 0.970 |
| 1 | VL_G025Q | 309.3 | 8.36E+04 | 3.88E-04 | 4.64E-09 | 110.8 | 94.3 | 89.9 | 0.953 |
| 1 | VL_G025W | 387.8 | 7.42E+04 | 7.03E-03 | 9.47E-08 | 121 | 83.8 | 39.8 | 0.475 |
| 1 | VL_G025S | 370.9 | 8.85E+04 | 3.94E-04 | 4.45E-09 | 135 | 117.3 | 111.6 | 0.951 |
| 1 | VL_G025Y | 348.7 | 7.23E+04 | 3.65E-03 | 5.04E-08 | 115.4 | 85.9 | 57.3 | 0.667 |
| 1 | VL_G025H | 384.3 | 9.15E+04 | 2.90E-04 | 3.17E-09 | 140.6 | 123.5 | 118.8 | 0.962 |
| 1 | VL_D026A | 353 | 1.21E+05 | 1.65E-04 | 1.36E-09 | 139.2 | 131 | 127.4 | 0.973 |
| 1 | VL_D026Q | 417.8 | 1.12E+05 | 1.81E-04 | 1.61E-09 | 160.3 | 149.7 | 145.4 | 0.971 |
| 1 | VL_D026S | 356 | 1.20E+05 | 1.69E-04 | 1.41E-09 | 140.2 | 132.1 | 128.3 | 0.971 |
| 1 | VL_D026W | 396.7 | 1.15E+05 | 1.76E-04 | 1.53E-09 | 153.6 | 144.3 | 140.1 | 0.971 |
| 1 | VL_D026H | 366.2 | 1.19E+05 | 1.35E-04 | 1.13E-09 | 142.2 | 134.1 | 130.7 | 0.975 |
| 1 | VL_D026K | 328.7 | 1.15E+05 | 1.79E-04 | 1.55E-09 | 128.9 | 120.3 | 116.8 | 0.971 |

Figure 5

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 1 | VL_D026K | 429.2 | 1.30E+05 | 4.78E-04 | 3.69E-09 | 175.1 | 167 | 156.9 | 0.940 |
| 1 | VL_T027A | 322.1 | 9.77E+04 | 1.94E-04 | 1.99E-09 | 118.6 | 106.3 | 103.1 | 0.970 |
| 1 | VL_T027K | 385 | 6.16E+04 | 7.42E-03 | 1.21E-07 | 111.2 | 70.3 | 31.5 | 0.448 |
| 1 | VL_T027S | 412.1 | 1.25E+05 | 6.70E-04 | 5.37E-09 | 166.8 | 157.1 | 144.7 | 0.921 |
| 1 | VL_T027D | 331.7 | 1.28E+05 | 4.64E-03 | 3.62E-08 | 131 | 114.7 | 68.6 | 0.598 |
| 1 | VL_T027Y | 329.6 | 9.76E+04 | 4.14E-03 | 4.24E-08 | 120.6 | 98.7 | 62.1 | 0.629 |
| 1 | VL_T027H | 369.9 | 1.09E+05 | 4.82E-03 | 4.43E-08 | 137.8 | 115.4 | 67.8 | 0.588 |
| 1 | VL_L028A | 347.2 | 6.52E+04 | 1.15E-03 | 1.76E-08 | 118 | 89.7 | 78.8 | 0.878 |
| 1 | VL_L028K | 345.7 | 1.45E+05 | 1.22E-03 | 8.45E-09 | 7 | 6.7 | 5.8 | 0.866 |
| 1 | VL_L028Q | 336.9 | 5.98E+04 | 2.86E-03 | 4.78E-08 | 108.5 | 75.3 | 54.7 | 0.726 |
| 1 | VL_L028Y | 403.9 | 5.26E+04 | 3.02E-04 | 5.75E-09 | 126.1 | 89.3 | 86 | 0.963 |
| 1 | VL_L028D | 376.9 | 1.26E+05 | 4.93E-04 | 3.93E-09 | 7.1 | 7.4 | 7.1 | 0.959 |
| 1 | VL_R029A | 334.2 | 1.46E+05 | 1.63E-04 | 1.12E-09 | 146 | 141.3 | 137.3 | 0.972 |
| 1 | VL_R029K | 305.7 | 1.38E+05 | 1.66E-04 | 1.20E-09 | 129.8 | 124.5 | 120.9 | 0.971 |
| 1 | VL_R029Q | 372.9 | 1.45E+05 | 1.49E-04 | 1.02E-09 | 162.3 | 157.6 | 153.6 | 0.975 |
| 1 | VL_R029W | 339.7 | 1.35E+05 | 1.59E-04 | 1.18E-09 | 141.7 | 135.8 | 132.1 | 0.973 |
| 1 | VL_R029S | 348.9 | 1.45E+05 | 1.69E-04 | 1.17E-09 | 152.6 | 147.9 | 143.7 | 0.972 |

Figure 6

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 1 | VL_R029L | 398.9 | 1.42E+05 | 1.51E-04 | 1.06E-09 | 171.9 | 166.7 | 162.4 | 0.974 |
| 1 | VL_R029D | 384 | 1.40E+05 | 1.50E-04 | 1.07E-09 | 167.4 | 162.4 | 158.3 | 0.975 |
| 1 | VL_R029Y | 424.6 | 1.41E+05 | 1.39E-04 | 9.89E-10 | 180.3 | 175.3 | 170.8 | 0.974 |
| 1 | VL_R029H | 414 | 1.42E+05 | 1.35E-04 | 9.47E-10 | 177.9 | 173.3 | 169.1 | 0.976 |
| 1 | VL_N030H | 330.4 | 1.25E+05 | 3.05E-04 | 2.45E-09 | 134.9 | 127.3 | 121.9 | 0.958 |
| 1 | VL_N030D | 421.3 | 1.35E+05 | 6.28E-04 | 4.65E-09 | 180.2 | 172.5 | 159.5 | 0.925 |
| 1 | VL_N030Y | 357.1 | 1.39E+05 | 1.08E-03 | 7.80E-09 | 147.6 | 139.8 | 122.5 | 0.876 |
| 1 | VL_N030W | 434.1 | 1.14E+05 | 2.75E-03 | 2.40E-08 | 169 | 150.1 | 110.3 | 0.735 |
| 1 | VL_N030S | 342.8 | 1.42E+05 | 3.42E-04 | 2.41E-09 | 146.7 | 141.2 | 134.5 | 0.953 |
| 1 | VL_N030L | 305.5 | 1.42E+05 | 3.38E-03 | 2.38E-08 | 125.3 | 114.1 | 77.6 | 0.680 |
| 1 | VL_Y031A | 346.4 | 1.20E+05 | 3.21E-04 | 2.67E-09 | 7.9 | 7.2 | 7.1 | 0.986 |
| 1 | VL_Y031K | 288.3 | 1.06E+05 | 2.43E-04 | 2.29E-09 | 7.4 | 6.5 | 6.3 | 0.969 |
| 1 | VL_Y031Q | 392.9 | 1.36E+10 | 3.54E+02 | 2.61E-08 | 19.4 | 18.2 | 8.4 | 0.462 |
| 1 | VL_Y031S | 394 | 1.59E+05 | 1.87E-03 | 1.18E-08 | 10.7 | 10.8 | 9.2 | 0.852 |
| 1 | VL_Y031L | 3 | 8.54E+04 | 4.69E-04 | 5.49E-09 | 7.4 | 5.7 | 5.4 | 0.947 |
| 1 | VL_Y031D | 403.2 | 9.13E+04 | 5.59E-07 | 6.13E-12 | 7.8 | 7.5 | 7.6 | 1.013 |
| 1 | VL_Y031H | 363.6 | 1.49E+05 | 8.97E-04 | 6.00E-09 | 8.2 | 8 | 7.4 | 0.925 |

Figure 7

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 1 | VL_Y032A | 401.9 | 1.05E+05 | 7.29E-03 | 6.94E-08 | 144 | 144 | 112.8 | 0.470 |
| 1 | VL_Y032K | 281.5 | 8.23E+04 | 1.74E-03 | 2.11E-08 | 101 | 101 | 82.6 | 0.821 |
| 1 | VL_Y032Q | 353.6 | 9.69E+04 | 4.54E-04 | 4.69E-09 | 140.3 | 140.3 | 124.6 | 0.945 |
| 1 | VL_Y032W | 364.2 | 1.03E+05 | 2.06E-04 | 2.00E-09 | 138.8 | 138.8 | 126.1 | 0.971 |
| 1 | VL_Y032S | 344.3 | 2.66E+05 | 5.85E-03 | 2.20E-08 | 15.5 | 15.5 | 15.4 | 0.623 |
| 1 | VL_Y032L | 315 | 1.00E+05 | 6.45E-04 | 6.43E-09 | 125.5 | 125.5 | 112 | 0.925 |
| 1 | VL_Y032D | 353.2 | 2.21E+05 | 3.55E-02 | 1.61E-07 | 102.1 | 102.1 | 65.5 | 0.153 |
| 1 | VL_Y032H | 298.7 | 1.15E+05 | 1.80E-04 | 1.56E-09 | 122.9 | 122.9 | 114.5 | 0.972 |
| 1 | VL_A033L | 339.6 | 4.58E+04 | 3.34E-04 | 7.31E-09 | 112.5 | 112.5 | 73 | 0.960 |
| 1 | VL_A033D | 363.2 | 3.60E+04 | 6.17E-04 | 1.71E-08 | 110.3 | 110.3 | 61.2 | 0.930 |
| 1 | VL_A033Y | 389.5 | 3.93E+04 | 8.74E-03 | 2.22E-07 | 64.5 | 64.5 | 31.4 | 0.411 |
| 1 | VL_A033Q | 375.6 | 3.21E+04 | 9.43E-04 | 2.94E-08 | 107.5 | 107.5 | 55.2 | 0.900 |
| 1 | VL_A033W | 384 | 1.09E+05 | 3.34E-04 | 3.06E-09 | 7.4 | 7.8 | 7.8 | 0.923 |
| 1 | VL_A033H | 383.4 | 4.35E+04 | 6.08E-03 | 1.40E-07 | 101.8 | 55.7 | 55.7 | 0.522 |
| 1 | VL_A033K | 353.9 | 1.27E+05 | 8.64E-04 | 6.82E-09 | 7.2 | 7.2 | 7.2 | 0.889 |
| 1 | VL_S034A | 380.3 | 1.36E+05 | 1.55E-04 | 1.14E-09 | 159.2 | 153.1 | 153.1 | 0.973 |
| 1 | VL_S034L | 361.4 | 7.86E+04 | 1.07E-04 | 1.36E-09 | 7.1 | 5.6 | 5.6 | 0.982 |

Figure 8

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 1 | VL_S034D | 388.7 | 4.67E+04 | 8.33E-03 | 1.78E-07 | 44.9 | 24.2 | 10.3 | 0.426 |
| 1 | VL_S034Y | 351.5 | 8.05E+04 | 6.45E-07 | 8.01E-12 | 7.3 | 6 | 5.9 | 0.983 |
| 1 | VL_S034Q | 373.7 | 8.52E+07 | 6.82E-01 | 8.00E-09 | 9.8 | 10.3 | 6.7 | 0.650 |
| 1 | VL_S034W | 355.6 | 1.16E+05 | 2.17E-04 | 1.87E-09 | 7.3 | 6.9 | 6.5 | 0.942 |
| 1 | VL_S034H | 378.9 | 7.57E+05 | 1.33E-01 | 1.75E-07 | 68.3 | 42.3 | 7.3 | 0.173 |
| 1 | VL_G025K | 397.5 | 5.98E+04 | 5.25E-04 | 8.78E-09 | 125.3 | 93.7 | 88.1 | 0.940 |
| 1 | VL_G025L | 394.7 | 6.02E+04 | 4.22E-03 | 7.01E-08 | 126.9 | 86.3 | 54.6 | 0.633 |
| 1 | VL_G025D | 395.2 | 1.33E+05 | 2.31E-04 | 1.73E-09 | 165.4 | 158.3 | 152.9 | 0.966 |
| 1 | VL_D026Y | 470.1 | 1.18E+05 | 1.54E-04 | 1.30E-09 | 184.5 | 173.8 | 169.4 | 0.975 |
| 1 | VL_T027Q | 421.7 | 1.03E+05 | 2.51E-03 | 2.43E-08 | 161.2 | 140.1 | 105.7 | 0.754 |
| 1 | VL_T027W | 345.4 | 7.80E+04 | 4.75E-03 | 6.08E-08 | 121.6 | 90.7 | 53.4 | 0.589 |
| 1 | VL_T027L | 380 | 1.05E+05 | 2.35E-03 | 2.24E-08 | 150 | 130.6 | 100.3 | 0.768 |
| 1 | VL_L028S | 357.7 | 5.93E+04 | 4.48E-03 | 7.55E-08 | 114.9 | 76.6 | 46.7 | 0.610 |
| 1 | VL_L028W | 404.6 | 5.44E+04 | 5.20E-03 | 9.57E-08 | 116.3 | 71.4 | 41.9 | 0.587 |
| 1 | VL_L028H | 398.6 | 5.97E+04 | 7.56E-04 | 1.27E-08 | 134.7 | 99.8 | 91.6 | 0.918 |
| 1 | VL_N030K | 320.8 | 7.47E+04 | 1.00E-03 | 1.34E-08 | 112 | 90 | 80.2 | 0.891 |
| 1 | VL_N030Q | 379.1 | 1.20E+05 | 1.05E-03 | 8.71E-09 | 155.4 | 143.8 | 126.9 | 0.882 |

Figure 9

| Run # | Amino acid Substitution | Capture level | ka (1/Ms) | kd (1/s) | KD (M) | Rmax (RU) | binding early | binding late | binding late/binding early |
|---|---|---|---|---|---|---|---|---|---|
| 1 | VL_Y031W | 343.9 | 1.84E+05 | 8.74E-03 | 4.75E-08 | 145.1 | 126.2 | 48.6 | 0.385 |
| 1 | VL_G050L | 400.4 | 5.95E+04 | 8.12E-04 | 1.37E-08 | 126.1 | 93 | 84.8 | 0.912 |
| 1 | VL_G050D | 383 | 1.50E+05 | 4.97E-04 | 3.30E-09 | 169.8 | 164.3 | 154 | 0.937 |
| 1 | VL_G050Y | 368.2 | 8.91E+04 | 8.58E-04 | 9.62E-09 | 136.8 | 117.8 | 106.4 | 0.903 |
| 1 | VL_K051A | 358.7 | 1.48E+05 | 1.40E-04 | 9.42E-10 | 161.6 | 157 | 153.1 | 0.975 |
| 1 | VL_K051L | 391.7 | 1.40E+05 | 1.21E-04 | 8.65E-10 | 174.7 | 168.9 | 165.2 | 0.978 |
| 1 | VL_K051Q | 361.2 | 1.43E+05 | 1.47E-04 | 1.03E-09 | 162.8 | 157.3 | 153.3 | 0.975 |
| 1 | VL_K051Y | 312.9 | 1.34E+05 | 1.51E-04 | 1.12E-09 | 138.8 | 132.7 | 129.5 | 0.976 |
| 1 | VL_K051S | 415.3 | 7.08E+04 | 2.25E-04 | 3.18E-09 | 163.9 | 132.4 | 128.6 | 0.971 |
| 1 | VL_K051W | 447.3 | 1.26E+05 | 1.73E-04 | 1.38E-09 | 190.8 | 182.1 | 177.3 | 0.974 |
| 1 | VL_N052A | 320.3 | 1.34E+05 | 1.76E-04 | 1.31E-09 | 140.3 | 134.3 | 130.6 | 0.972 |
| 1 | VL_N052Q | 430.2 | 1.27E+05 | 1.67E-04 | 1.31E-09 | 184.9 | 176.8 | 172.2 | 0.974 |
| 2 | VH_G026A | 268.4 | 1.46E+05 | 1.85E-04 | 1.26E-09 | 107.8 | 104.7 | 101.4 | 0.968 |
| 2 | VH_G026K | 360 | 1.30E+05 | 1.78E-04 | 1.36E-09 | 145.1 | 139.5 | 135.3 | 0.970 |
| 2 | VH_G026W | 354.4 | 1.34E+05 | 1.60E-04 | 1.19E-09 | 144.8 | 140 | 136 | 0.971 |
| 2 | VH_G026S | 341.3 | 1.41E+05 | 1.66E-04 | 1.18E-09 | 143.6 | 139.4 | 135.3 | 0.971 |

Figure 10

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 2 | VH_G026L | 356.7 | 1.43E+05 | 1.66E-04 | 1.16E-09 | 150.7 | 147.2 | 142.8 | 0.970 |
| 2 | VH_G026D | 363.9 | 1.47E+05 | 1.88E-04 | 1.28E-09 | 155.9 | 152.8 | 148 | 0.969 |
| 2 | VH_G026Y | 341.7 | 1.38E+05 | 1.78E-04 | 1.30E-09 | 142.1 | 137.2 | 133.1 | 0.970 |
| 2 | VH_G026H | 386.6 | 1.36E+05 | 1.85E-04 | 1.36E-09 | 160.4 | 155.9 | 151.1 | 0.969 |
| 2 | VH_G027K | 366.2 | 1.30E+05 | 1.79E-04 | 1.38E-09 | 147.4 | 141.7 | 137.3 | 0.969 |
| 2 | VH_G027Q | 318.7 | 1.42E+05 | 1.96E-04 | 1.38E-09 | 135.6 | 131.2 | 126.9 | 0.967 |
| 2 | VH_G027W | 303.4 | 1.38E+05 | 1.90E-04 | 1.38E-09 | 126.8 | 121.8 | 117.8 | 0.967 |
| 2 | VH_G027S | 371.6 | 1.38E+05 | 1.77E-04 | 1.28E-09 | 154.9 | 150.8 | 146.1 | 0.969 |
| 2 | VH_G027L | 348.8 | 1.47E+05 | 1.67E-04 | 1.14E-09 | 149.5 | 145.7 | 141.3 | 0974 |
| 2 | VH_G027D | 314.6 | 1.44E+05 | 2.23E-04 | 1.55E-09 | 137.2 | 132.4 | 127.8 | 0.965 |
| 2 | VH_G027Y | 391.9 | 1.38E+05 | 1.82E-04 | 1.32E-09 | 164.8 | 160.3 | 155.5 | 0.970 |
| 2 | VH_G027H | 368.6 | 1.42E+05 | 1.88E-04 | 1.33E-09 | 156.3 | 152.4 | 147.6 | 0.969 |
| 2 | VH_S028A | 373.7 | 1.42E+05 | 1.63E-04 | 1.15E-09 | 158.8 | 155 | 150.5 | 0.971 |
| 2 | VH_S028L | 336.4 | 1.41E+05 | 1.85E-04 | 1.31E-09 | 142.9 | 137.9 | 133.6 | 0.969 |
| 2 | VH_S028Y | 342.1 | 1.39E+05 | 1.67E-04 | 1.20E-09 | 143.7 | 138.5 | 134.4 | 0.970 |
| 2 | VH_S028W | 341.9 | 1.34E+05 | 1.95E-04 | 1.46E-09 | 141.5 | 135.6 | 131.3 | 0.968 |
| 2 | VH_S028H | 310.9 | 1.39E+05 | 1.74E-04 | 1.25E-09 | 131.7 | 126.9 | 123.1 | 0.970 |

Figure 11

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 2 | VH_S028K | 385.6 | 1.25E+05 | 1.75E-04 | 1.40E-09 | 154.2 | 147.9 | 143.6 | 0.971 |
| 2 | VH_I029A | 368.5 | 1.38E+05 | 2.26E-04 | 1.64E-09 | 154.2 | 150.1 | 144.8 | 0.965 |
| 2 | VH_I029K | 319.9 | 1.27E+05 | 2.42E-04 | 1.91E-09 | 123.3 | 116.8 | 112.4 | 0.962 |
| 2 | VH_I029Q | 338.6 | 1.37E+05 | 2.24E-04 | 1.64E-09 | 140.5 | 135.9 | 131.2 | 0.965 |
| 2 | VH_I029W | 321.1 | 1.35E+05 | 2.26E-04 | 1.68E-09 | 131.8 | 125.7 | 121.4 | 0.966 |
| 2 | VH_I029L | 371.5 | 1.42E+05 | 1.56E-04 | 1.10E-09 | 158 | 153.5 | 149.1 | 0.971 |
| 2 | VH_I029H | 351.4 | 1.33E+05 | 2.41E-04 | 1.82E-09 | 143.5 | 137 | 132 | 0.964 |
| 2 | VH_S030A | 310.2 | 1.43E+05 | 1.56E-04 | 1.09E-09 | 133.3 | 128.5 | 124.9 | 0.972 |
| 2 | VH_S030L | 328.8 | 1.34E+05 | 1.88E-04 | 1.40E-09 | 139.3 | 133.4 | 129.3 | 0.969 |
| 2 | VH_S030D | 362.3 | 1.45E+05 | 1.88E-04 | 1.30E-09 | 159 | 154.4 | 149.6 | 0.969 |
| 2 | VH_S030Y | 358 | 1.29E+05 | 1.86E-04 | 1.44E-09 | 149.2 | 142.6 | 138.3 | 0.970 |
| 2 | VH_S030Q | 367 | 1.41E+05 | 1.39E-04 | 9.81E-10 | 157.2 | 152.4 | 148.4 | 0.974 |
| 2 | VH_S030W | 376.4 | 1.32E+05 | 1.76E-04 | 1.33E-09 | 155.5 | 149.6 | 145.1 | 0.970 |
| 2 | VH_S030H | 380.5 | 1.41E+05 | 1.51E-04 | 1.07E-09 | 160.7 | 155.9 | 151.6 | 0.972 |
| 2 | VH_S030K | 343.5 | 1.24E+05 | 1.61E-04 | 1.30E-09 | 136.7 | 129.7 | 126 | 0.971 |
| 2 | VH_S031A | 349.6 | 1.39E+05 | 1.78E-04 | 1.28E-09 | 148.6 | 143.4 | 139.1 | 0.970 |
| 2 | VH_S031L | 351.2 | 1.32E+05 | 1.96E-04 | 1.48E-09 | 148.3 | 142 | 137.6 | 0.969 |

Figure 12

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 2 | VH_S031D | 363.4 | 1.37E+05 | 2.79E-04 | 2.03E-09 | 158.3 | 152.6 | 146.5 | 0.960 |
| 2 | VH_S031Y | 371.5 | 1.35E+05 | 2.22E-04 | 1.64E-09 | 155.9 | 150.3 | 145.1 | 0.965 |
| 2 | VH_S031Q | 334.3 | 1.40E+05 | 1.78E-04 | 1.27E-09 | 142.5 | 137.3 | 133.2 | 0.970 |
| 2 | VH_S031W | 355.8 | 1.27E+05 | 1.75E-04 | 1.37E-09 | 142 | 135.3 | 131.2 | 0.970 |
| 2 | VH_S031H | 356.4 | 1.37E+05 | 1.95E-04 | 1.43E-09 | 150 | 144.5 | 139.8 | 0.967 |
| 2 | VH_S031K | 380.3 | 1.30E+05 | 2.73E-04 | 2.10E-09 | 156.7 | 150.7 | 144.8 | 0.961 |
| 2 | VH_S032A | 332.3 | 1.38E+05 | 1.36E-04 | 9.87E-10 | 140.6 | 135.6 | 132.2 | 0.975 |
| 2 | VH_S032L | 366.7 | 1.30E+05 | 1.54E-03 | 1.19E-08 | 149.7 | 139.7 | 116.8 | 0.836 |
| 2 | VH_S032D | 364.2 | 1.07E+05 | 2.77E-03 | 2.60E-08 | 149.3 | 129.9 | 95.4 | 0.734 |
| 2 | VH_S032Y | 313.6 | 1.39E+05 | 6.63E-04 | 4.77E-09 | 130.1 | 124.3 | 114.1 | 0.918 |
| 2 | VH_S032Q | 545.7 | 1.32E+05 | 2.52E-04 | 1.92E-09 | 224.6 | 216.9 | 208.9 | 0.963 |
| 2 | VH_S032W | 371.9 | 1.24E+05 | 3.25E-04 | 2.63E-09 | 144.5 | 137 | 130.7 | 0.954 |
| 2 | VH_S032H | 339.4 | 1.33E+05 | 5.65E-04 | 4.24E-09 | 141.1 | 133.6 | 124.1 | 0.929 |
| 2 | VH_S032K | 386.6 | 1.17E+05 | 8.48E-04 | 7.24E-09 | 148.9 | 138.3 | 124.8 | 0.902 |
| 2 | VH_N033A | 355.8 | 1.21E+05 | 2.63E-04 | 2.16E-09 | 146.2 | 138.5 | 133.3 | 0.962 |
| 2 | VH_N033K | 302.3 | 1.02E+05 | 2.65E-04 | 2.60E-09 | 116.1 | 105.8 | 101.6 | 0.960 |
| 2 | VH_N033Q | 365.1 | 1.38E+05 | 1.65E-04 | 1.19E-09 | 156.1 | 152.2 | 147.8 | 0.971 |

Figure 13

| Run # | Amino acid Substitution | Capture level | ka (1/Ms) | kd (1/s) | KD (M) | Rmax (RU) | binding early | binding late | binding late/binding early |
|---|---|---|---|---|---|---|---|---|---|
| 2 | VH_N033W | 381.1 | 1.31E+05 | 3.48E-04 | 2.65E-09 | 156.5 | 150.9 | 143.6 | 0.952 |
| 2 | VH_N033S | 321.5 | 1.28E+05 | 2.41E-04 | 1.88E-09 | 134.1 | 128 | 123.3 | 0.963 |
| 2 | VH_N033L | 344 | 1.29E+05 | 2.02E-04 | 1.56E-09 | 140.6 | 134.3 | 129.8 | 0.966 |
| 2 | VH_N033D | 372.7 | 1.03E+05 | 1.25E-03 | 1.21E-08 | 148.2 | 133 | 115.2 | 0.866 |
| 2 | VH_N033Y | 377.8 | 1.38E+05 | 2.11E-04 | 1.53E-09 | 160.5 | 155.8 | 150.5 | 0.966 |
| 2 | VH_N033H | 358.6 | 1.40E+05 | 1.41E-04 | 1.01E-09 | 153.5 | 148.6 | 144.6 | 0.973 |
| 2 | VH_N033A | 397.2 | 1.22E+05 | 2.68E-03 | 2.20E-08 | 164.1 | 148.8 | 110.1 | 0.740 |
| 2 | VH_N033Q | 378 | 1.25E+05 | 1.90E-03 | 1.51E-08 | 153.7 | 142.4 | 114.8 | 0.806 |
| 2 | Parent clone | 361.4 | 1.41E+05 | 1.38E-04 | 9.82E-10 | 156.5 | 151.9 | 147.9 | 0974 |
| 2 | VH_W034S | 446 | 9.21E+04 | 2.79E-03 | 3.03E-08 | 171.1 | 143.5 | 105.4 | 0.734 |
| 2 | VH_W034L | 335.3 | 1.33E+05 | 1.17E-03 | 8.85E-09 | 140.8 | 132.4 | 115.2 | 0.870 |
| 2 | VH_W034D | 344.6 | 1.31E+05 | 3.31E-03 | 2.53E-08 | 150 | 134.3 | 92.4 | 0.688 |
| 2 | VH_W034H | 366.3 | 1.04E+05 | 2.61E-03 | 2.51E-08 | 139.5 | 121.5 | 90.7 | 0.747 |
| 2 | VH_W035A | 23.7 | 1.04E+05 | 6.49E-04 | 6.21E-09 | 10.6 | 9.1 | 8.4 | 0.923 |
| 2 | VH_W035K | 20.7 | 9.20E+04 | 6.04E-04 | 6.56E-09 | 12.4 | 10.5 | 9.7 | 0.924 |
| 2 | VH_W035Q | 76.3 | 9.27E+04 | 3.20E-04 | 3.45E-09 | 31.1 | 27.7 | 26.5 | 0.957 |
| 2 | VH_W035Y | 327.9 | 1.38E+05 | 1.77E-04 | 1.29E-09 | 140.7 | 135.8 | 131.7 | 0.970 |

Figure 14

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 2 | VH_I029S | 334.2 | 1.39E+05 | 2.40E-04 | 2.65E-09 | 143.3 | 138.2 | 133.1 | 0.963 |
| 2 | VH_I029D | 343.6 | 1.43E+05 | 2.52E-04 | 1.88E-09 | 152.5 | 147.5 | 142.1 | 0.963 |
| 2 | VH_I029Y | 382.8 | 1.32E+05 | 2.09E-04 | 1.56E-09 | 159.8 | 153.7 | 148.6 | 0.967 |
| 2 | VH_W034K | 325.8 | 3.25E+05 | 4.06E-02 | 1.21E-08 | 68.4 | 48.4 | 10.8 | 0.223 |
| 2 | VL_R091D | 1.9 | 1.05E+05 | 6.94E-04 | 1.53E-09 | 9.3 | 8.2 | 7.5 | 0.915 |
| 2 | VH_E050S | 348.9 | 1.56E+05 | 1.86E-03 | 1.01E-09 | 155.4 | 147.7 | 118.9 | 0.805 |
| 2 | VH_E050L | 376.3 | 1.16E+05 | 7.91E-03 | 2.20E-08 | 132.2 | 105.4 | 44.2 | 0.419 |
| 2 | VH_E050D | 367.4 | 1.35E+05 | 3.40E-03 | 1.51E-08 | 156.5 | 141.5 | 96.5 | 0.682 |
| 2 | VH_E050Y | 379.9 | 1.07E+05 | 5.24E-03 | 9.82E-10 | 135.7 | 112.8 | 63.4 | 0.562 |
| 2 | VH_E050H | 352.9 | 1.46E+05 | 1.02E-03 | 3.03E-08 | 152.6 | 146.2 | 129 | 0.882 |
| 2 | VH_I051A | 361.3 | 1.45E+05 | 1.84E-04 | 8.85E-09 | 158.6 | 153.9 | 149.2 | 0.969 |
| 2 | VH_I051K | 359.9 | 1.16E+05 | 3.26E-04 | 2.53E-08 | 141.5 | 132.1 | 126.2 | 0.955 |
| 2 | VH_I051Y | 388.4 | 1.32E+05 | 1.73E-04 | 2.51E-08 | 163.7 | 156.6 | 152.1 | 0.971 |
| 2 | VL_P055Q | 370.6 | 1.35E+05 | 1.72E-04 | 6.21E-09 | 161.8 | 155.4 | 150.9 | 0.971 |
| 2 | VL_R054D | 377.5 | 8.42E+04 | 2.07E-04 | 6.56E-09 | 97.6 | 84.4 | 81.7 | 0.968 |
| 2 | VH_P100Y | 350.1 | 6.91E+04 | 5.89E-04 | 3.45E-09 | 120.7 | 95.5 | 89.1 | 0.933 |
| 2 | VH_S100aD | 393.8 | 9.83E+04 | 3.07E-06 | 3.12E-11 | 10.1 | 9.6 | 9.5 | 0.990 |

Figure 15

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 2 | VL_S090W | 386.1 | 1.27E+05 | 4.87E-04 | 3.84E-09 | 10.3 | 10.4 | 9.9 | 0.952 |
| 2 | VL_N089H | 400.3 | 1.40E+05 | 5.11E-04 | 3.64E-09 | 175.2 | 168.7 | 157.9 | 0.936 |
| 2 | VL_P055H | 378.3 | 1.38E+05 | 1.44E-04 | 1.04E-09 | 164.8 | 159.7 | 155.6 | 0.974 |
| 2 | VH_Y102A | 407.7 | 1.36E+05 | 1.20E-04 | 8.80E-10 | 173.1 | 167.7 | 163.7 | 0.976 |
| 2 | VL_N053Y | 387.3 | 1.14E+05 | 3.56E-04 | 3.13E-09 | 157.5 | 146.8 | 139.9 | 0.953 |
| 2 | VL_S056A | 335.5 | 1.44E+05 | 1.51E-04 | 1.05E-09 | 148.9 | 144.8 | 140.8 | 0.972 |
| 2 | VL_S056Q | 360.8 | 1.41E+05 | 1.53E-04 | 1.09E-09 | 158.9 | 153.9 | 149.8 | 0.973 |
| 3 | VH_I097K | 479.1 | 1.38E+05 | 2.35E-04 | 1.70E-09 | 190.3 | 184.2 | 173.2 | 0.940 |
| 3 | VH_I097S | 640.8 | 1.32E+05 | 9.43E-04 | 7.15E-09 | 259.8 | 247.3 | 198.1 | 0.801 |
| 3 | VH_I097L | 572.5 | 1.40E+05 | 3.00E-04 | 2.15E-09 | 237.1 | 229.6 | 212.9 | 0.927 |
| 3 | VH_I097D | 585 | 1.55E+05 | 4.70E-03 | 3.04E-08 | 211.8 | 192.9 | 76.3 | 0.396 |
| 3 | VH_I097Y | 541.7 | 9.89E+04 | 2.27E-04 | 2.29E-09 | 206.5 | 186.9 | 176.6 | 0.945 |
| 3 | VH_I097H | 559.9 | 1.22E+05 | 1.46E-04 | 1.19E-09 | 218.6 | 207.7 | 199.5 | 0.961 |
| 3 | VH_G098K | 514 | 7.22E+04 | 1.69E-07 | 2.35E-12 | 5.7 | 6.2 | 7.5 | 1.210 |
| 3 | VH_G098W | 582.4 | 1.09E+05 | 4.29E-07 | 3.94E-12 | 4.8 | 6.5 | 6.6 | 1.015 |
| 3 | VH_G098S | 552.6 | 2.15E+05 | 3.20E-02 | 1.48E-07 | 168.6 | 111.8 | 6.6 | 0.059 |

Figure 16

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 3 | VH_G098D | 766.5 | 1.12E+05 | 4.84E-02 | 4.30E-07 | 153.7 | 59.5 | 9.9 | 0.166 |
| 3 | VH_G098Y | 622.4 | 7.45E+04 | 6.00E-09 | 8.06E-14 | 5.7 | 5.9 | 7 | 1.186 |
| 3 | VH_W099A | 544.2 | 9.58E+04 | 2.74E-07 | 2.85E-12 | 5.1 | 5.9 | 6.6 | 1.119 |
| 3 | VH_W099K | 583.7 | 6.75E+04 | 9.48E-08 | 1.40E-12 | 6 | 5.4 | 7 | 1.296 |
| 3 | VH_W099Q | 564.8 | 1.65E+05 | 2.81E-04 | 1.71E-09 | 6.4 | 9.6 | 8.1 | 0.844 |
| 3 | VH_W099Y | 610.4 | 2.12E+05 | 1.91E-02 | 9.02E-08 | 208.5 | 161.4 | 13.9 | 0.086 |
| 3 | VH_W099S | 693.4 | 1.54E+05 | 2.69E-07 | 1.75E-12 | 5.9 | 7.4 | 7.9 | 1.068 |
| 3 | VH_W099D | 579.5 | 6.93E+04 | 3.51E-07 | 5.08E-12 | 4.9 | 5 | 5.7 | 1.140 |
| 3 | VH_W099H | 664.4 | 2.88E+05 | 3.94E-02 | 1.37E-07 | 207.8 | 139.4 | 8.4 | 0.060 |
| 3 | VH_P100A | 600.8 | 4.80E+05 | 9.72E-02 | 2.03E-07 | 129.4 | 76.1 | 7 | 0.092 |
| 3 | VH_P100K | 532.7 | 1.00E+05 | 7.84E-04 | 7.84E-09 | 6.1 | 10.4 | 7.1 | 0.683 |
| 3 | VH_P100Q | 638.1 | 1.47E+05 | 2.22E-06 | 1.50E-11 | 5.5 | 8.5 | 7.9 | 0.929 |
| 3 | VH_P100W | 744.8 | 9.12E+04 | 8.95E-07 | 9.81E-12 | 6 | 7.2 | 8.5 | 1.181 |
| 3 | VH_P100S | 520.8 | 7.99E+05 | 1.93E-01 | 2.42E-07 | 109.9 | 58.3 | 6.2 | 0.106 |
| 3 | VH_P100L | 912.7 | 1.26E+05 | 2.13E-06 | 1.69E-11 | 6.7 | 10.6 | 9.9 | 0.934 |
| 3 | VH_P100D | 679.9 | 7.17E+04 | 2.92E-07 | 4.07E-12 | 4.8 | 5.3 | 6.2 | 1.170 |
| 3 | VH_P100H | 736.3 | 1.48E+05 | 1.32E-04 | 8.91E-10 | 15.5 | 18.5 | 17.1 | 0.924 |

Figure 17

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 3 | VH_S100aA | 655.9 | 1.16E+05 | 2.22E-04 | 1.92E-09 | 266.8 | 250.7 | 236.9 | 0.945 |
| 3 | VH_S100aL | 617.3 | 1.27E+05 | 7.29E-04 | 5.75E-09 | 253.9 | 240.5 | 202.3 | 0.841 |
| 3 | VH_S100aQ | 667.6 | 1.41E+05 | 1.77E-04 | 1.25E-09 | 282.2 | 274.5 | 261.8 | 0.954 |
| 3 | VH_S100aW | 616.1 | 1.10E+05 | 5.59E-04 | 5.08E-09 | 243.2 | 224.7 | 196.7 | 0.875 |
| 3 | VH_S100aH | 647.1 | 1.46E+05 | 2.06E-04 | 1.41E-09 | 281.3 | 274.2 | 259.9 | 0.948 |
| 3 | VH_S100aK | 799.8 | 3.10E+05 | 4.10E-02 | 1.32E-07 | 234.4 | 159.1 | 10.3 | 0.065 |
| 3 | VH_F100bA | 330.8 | 8.97E+04 | 4.80E-04 | 5.34E-09 | 123.2 | 107.5 | 96.2 | 0.895 |
| 3 | VH_F100bK | -2.9 | 9.43E+04 | 4.28E-03 | 4.54E-08 | 5 | 5 | 2.2 | 0.440 |
| 3 | VH_F100bQ | 283.7 | 7.88E+04 | 5.62E-04 | 7.13E-09 | 102.3 | 85 | 74.7 | 0.879 |
| 3 | VH_F100bW | 14.1 | 4.24E+05 | 6.96E-03 | 1.64E-08 | 8.8 | 7.5 | 2.7 | 0.360 |
| 3 | VH_F100bS | 355.8 | 9.81E+04 | 3.85E-04 | 3.92E-09 | 145.3 | 129.4 | 118.4 | 0.915 |
| 3 | VH_F100bL | 744.1 | 1.81E+05 | 3.80E-04 | 2.10E-09 | 360.2 | 355.3 | 325.5 | 0.916 |
| 3 | VH_F100bD | -9.8 | 8.83E+04 | 1.34E-02 | 1.51E-07 | 6.5 | 4.6 | 0 | 0.000 |
| 3 | VH_F100bH | -0.8 | 6.00E+04 | 1.21E-02 | 2.02E-07 | 7.2 | 4.3 | 0 | 0.000 |
| 3 | VH_D101A | 140.8 | 1.46E+05 | 4.56E-04 | 3.13E-09 | 69.4 | 68 | 60.8 | 0.894 |
| 3 | VH_D101L | -0.6 | 7.58E+04 | 1.47E-02 | 1.94E-07 | 6 | 4 | -0.2 | -0.050 |
| 3 | VH_D101Q | 735.8 | 1.83E+05 | 2.54E-04 | 1.39E-09 | 343.1 | 337.8 | 319 | 0.944 |

Figure 18

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 3 | VH_D101S | -2 | 1.57E+05 | 5.89E-03 | 3.76E-08 | 4.6 | 5.2 | 1.8 | 0.346 |
| 3 | VH_D101W | 245.1 | 1.51E+05 | 4.03E-04 | 2.67E-09 | 109.9 | 107.2 | 97.6 | 0.910 |
| 3 | VH_D101H | 534.2 | 2.09E+05 | 4.27E-04 | 2.04E-09 | 259 | 255.1 | 232.6 | 0.912 |
| 3 | VH_D101K | 698.6 | 2.13E+05 | 4.12E-04 | 1.93E-09 | 321.1 | 315.4 | 289.4 | 0.918 |
| 3 | VH_Y102K | 899.4 | 2.73E+05 | 2.21E-04 | 8.08E-10 | 450.8 | 451.8 | 430.5 | 0.953 |
| 3 | VH_Y102Q | 763.5 | 3.30E+05 | 2.37E-04 | 7.17E-10 | 394.6 | 396.2 | 376.4 | 0.950 |
| 3 | VH_Y102W | 660.2 | 3.26E+05 | 2.43E-04 | 7.46E-10 | 346.9 | 348.4 | 330.1 | 0.947 |
| 3 | VH_Y102L | 778.2 | 1.33E+05 | 1.56E-04 | 1.17E-09 | 328.1 | 316.4 | 303.2 | 0.958 |
| 3 | VH_Y102D | 339.3 | 1.51E+05 | 2.60E-04 | 1.72E-09 | 146.5 | 143.6 | 134.2 | 0.935 |
| 3 | VH_Y102H | 720 | 1.37E+05 | 1.62E-04 | 1.19E-09 | 308.2 | 298.4 | 285.7 | 0.957 |
| 3 | VH_E095A | 819.8 | 9.76E+04 | 4.61E-04 | 4.72E-09 | 298.7 | 269.4 | 241 | 0.895 |
| 3 | VH_E095K | 621.7 | 5.79E+10 | 2.61E-02 | 4.51E-09 | 12.5 | 19.9 | 11.2 | 0.563 |
| 3 | VH_E095Q | 0.5 | 9.82E+04 | 4.84E-03 | 4.93E-08 | 5 | 4.1 | 1.1 | 0.268 |
| 3 | VH_E095W | 735.9 | 1.09E+05 | 5.16E-10 | 4.71E-15 | 7.6 | 8.4 | 10.4 | 1.238 |
| 3 | VH_E095S | 158 | 1.13E+05 | 8.78E-04 | 7.78E-09 | 67.4 | 62.1 | 50.2 | 0.808 |
| 3 | VH_E095L | 878.7 | 9.70E+04 | 6.37E-04 | 6.57E-09 | 314.3 | 281.6 | 241.9 | 0.859 |
| 3 | VH_E095D | 776.9 | 8.75E+04 | 9.77E-04 | 1.12E-08 | 259.2 | 224.6 | 178.5 | 0.795 |

Figure 19

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 3 | VH_E095Y | 23.9 | 1.10E+05 | 1.31E-03 | 1.19E-08 | 15 | 14.3 | 10.6 | 0.741 |
| 3 | VH_E095H | 694.5 | 9.06E+04 | 8.47E-04 | 9.34E-09 | 244.1 | 213.6 | 175.2 | 0.820 |
| 3 | VH_G096A | 599 | 1.06E+05 | 9.02E-04 | 8.51E-09 | 250.1 | 227.6 | 184.5 | 0.811 |
| 3 | VH_G096K | -1 | 5.54E+05 | 8.41E-03 | 1.52E-08 | 5 | 5 | 2.4 | 0.480 |
| 3 | VH_G096Q | 609.8 | 9.98E+04 | 1.53E-03 | 1.53E-08 | 244.5 | 216.7 | 152.9 | 0.706 |
| 3 | VH_G096W | -2.7 | 4.37E+05 | 5.74E-03 | 1.32E-08 | 5.4 | 5.9 | 3.6 | 0.610 |
| 3 | VH_G096S | 939.9 | 1.01E+05 | 1.07E-03 | 1.06E-08 | 382.2 | 341.9 | 267.2 | 0.782 |
| 3 | VH_G096L | 807.4 | 3.47E+05 | 4.78E-02 | 1.38E-07 | 204.8 | 140.5 | 13 | 0.093 |
| 4 | VL_S090A | 399.4 | 1.21E+05 | 2.03E-04 | 1.68E-09 | 158.7 | 149.1 | 141.2 | 0.947 |
| 4 | VL_S090L | 382.7 | 9.53E+04 | 3.82E-03 | 4.01E-08 | 88.6 | 64.7 | 34.7 | 0.536 |
| 4 | VL_S090D | 388.3 | 9.69E+04 | 5.99E-03 | 6.19E-08 | 126.7 | 95.9 | 31.1 | 0.324 |
| 4 | VL_S090Y | 379.9 | 7.60E+08 | 1.15E-02 | 1.51E-07 | 37.4 | 26.4 | 4.5 | 0.170 |
| 4 | VL_S090Q | 395.2 | 1.83E+09 | 1.40E-02 | 7.65E-08 | 20.4 | 18.3 | 3.7 | 0.202 |
| 4 | VL_S090H | 383.2 | 1.56E+10 | 2.44E-02 | 1.56E-08 | 7.6 | 9.8 | 4.3 | 0.439 |
| 4 | VL_R091A | 421.8 | 7.20E+04 | 1.96E-03 | 2.72E-08 | 75.7 | 59.6 | 37.8 | 0.634 |
| 4 | VL_R091K | 404.1 | 1.74E+05 | 1.59E-02 | 9.14E-08 | 142.7 | 108.8 | 8.3 | 0.076 |

Figure 20

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 4 | VL_R091Q | 400.5 | 8.98E+07 | 2.00E-01 | 2.23E-07 | 72.7 | 38.2 | 4.4 | 0.115 |
| 4 | VL_R091W | 397.9 | 7.93E+04 | 4.22E-04 | 5.33E-09 | 4.4 | 5.1 | 4.4 | 0.863 |
| 4 | VL_R091L | 398.6 | 8.23E+04 | 3.12E-04 | 3.79E-09 | 4.7 | 5.2 | 4.7 | 0.904 |
| 4 | VL_R091Y | 408.2 | 1.24E+05 | 8.09E-04 | 6.52E-09 | 4.9 | 5.1 | 4.1 | 0.804 |
| 4 | VL_R091H | 388.3 | 1.40E+05 | 5.41E-02 | 3.87E-07 | 85 | 33.2 | 5.1 | 0.154 |
| 4 | VL_D092A | 404.3 | 7.79E+04 | 3.30E-04 | 4.24E-09 | 137.4 | 114.5 | 105.6 | 0.922 |
| 4 | VL_D092L | 393.1 | 1.85E+05 | 2.60E-02 | 1.41E-07 | 101.3 | 68.3 | 5.6 | 0.082 |
| 4 | VL_D092Q | 382.2 | 8.07E+04 | 2.18E-03 | 2.70E-08 | 126.2 | 102.3 | 62.7 | 0.613 |
| 4 | VL_D092Y | 380.6 | 1.15E+05 | 1.09E-02 | 9.41E-08 | 99.1 | 71.6 | 14.6 | 0.204 |
| 4 | VL_D092S | 384.7 | 1.09E+05 | 2.35E-04 | 2.15E-09 | 148.3 | 137.9 | 129.7 | 0.941 |
| 4 | VL_D092W | 380.4 | 8.75E+04 | 2.35E-03 | 2.68E-08 | 117.8 | 95.5 | 58.7 | 0.615 |
| 4 | VL_D092H | 380.3 | 6.82E+04 | 9.91E-04 | 1.45E-08 | 125 | 98.8 | 78.6 | 0.796 |
| 4 | VL_D092K | 396.8 | 9.43E+04 | 6.91E-03 | 7.32E-08 | 99.2 | 69.6 | 22.2 | 0.319 |
| 4 | VL_S093A | 390.7 | 1.32E+05 | 2.29E-04 | 1.74E-09 | 162.9 | 156.4 | 147.3 | 0.942 |
| 4 | VL_S093L | 405.5 | 1.47E+05 | 1.58E-04 | 1.08E-09 | 173.5 | 169 | 161.7 | 0.957 |
| 4 | VL_S093D | 399 | 1.33E+05 | 2.62E-04 | 1.98E-09 | 167.8 | 160.9 | 150.4 | 0.935 |
| 4 | VL_S093Y | 411.3 | 1.39E+05 | 1.72E-04 | 1.24E-09 | 171.9 | 165.9 | 158.2 | 0.954 |

Figure 21

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 4 | VL_S093Q | 388.9 | 1.35E+05 | 2.17E-04 | 1.61E-09 | 163.7 | 158.3 | 149.5 | 0.944 |
| 4 | VL_S093W | 413 | 1.40E+05 | 1.65E-04 | 1.18E-09 | 171.6 | 166 | 158.4 | 0.954 |
| 4 | VL_S093H | 388.9 | 1.26E+05 | 2.26E-04 | 1.79E-09 | 159.1 | 152.3 | 143.6 | 0.943 |
| 4 | VL_S093K | 396 | 1.15E+05 | 2.03E-04 | 1.77E-09 | 156.2 | 146 | 138.3 | 0.947 |
| 4 | VL_S094A | 411.6 | 1.27E+05 | 2.42E-04 | 1.91E-09 | 169 | 160.4 | 150.6 | 0.939 |
| 4 | VL_S094L | 395.2 | 1.37E+05 | 2.33E-04 | 1.70E-09 | 167.4 | 162 | 152.5 | 0.941 |
| 4 | VL_S094D | 404.5 | 1.31E+05 | 2.73E-04 | 2.08E-09 | 171 | 164 | 153 | 0.933 |
| 4 | VL_S094K | 409 | 1.29E+05 | 2.66E-04 | 2.07E-09 | 167.8 | 160.1 | 149.6 | 0.934 |
| 4 | VL_S094Q | 390.5 | 1.27E+05 | 2.05E-04 | 1.62E-09 | 158.6 | 150.6 | 142.7 | 0.948 |
| 4 | VL_S094W | 418.1 | 1.35E+05 | 2.59E-04 | 1.93E-09 | 172.5 | 165.4 | 154.5 | 0.934 |
| 4 | VL_S094H | 416.6 | 1.15E+05 | 2.50E-04 | 2.17E-09 | 164.2 | 153.2 | 143.7 | 0.938 |
| 4 | VL_S094K | 387.2 | 1.02E+05 | 2.73E-04 | 2.68E-09 | 146.8 | 134.1 | 125.1 | 0.933 |
| 4 | VL_G095A | 396.5 | 1.17E+05 | 1.45E-03 | 1.24E-08 | 156.5 | 144.3 | 103.1 | 0.714 |
| 4 | VL_G095K | 399.5 | 1.53E+05 | 2.34E-03 | 1.53E-08 | 8.8 | 13.8 | 6.4 | 0.464 |
| 4 | VL_G095Q | 406.1 | 1.45E+05 | 1.18E-02 | 8.13E-08 | 25.2 | 29.7 | 6.9 | 0.232 |
| 4 | VL_G095W | 419.5 | 1.94E+05 | 5.16E-02 | 2.66E-07 | 83.4 | 39.2 | 7 | 0.179 |
| 4 | VL_G095S | 405.3 | 1.99E+05 | 1.84E-02 | 9.23E-08 | 128.1 | 95.5 | 10.3 | 0.105 |

Figure 22

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 4 | VL_K095aD | 408.9 | 1.68E+05 | 6.66E-03 | 3.96E-08 | 171.9 | 153.7 | 39.1 | 0.254 |
| 4 | VL_G095L | 390.8 | 1.23E+05 | 2.37E-02 | 1.92E-07 | 113.2 | 71.1 | 6.7 | 0.094 |
| 4 | VL_G095D | 400.3 | 1.45E+05 | 3.91E-02 | 2.70E-07 | 96.7 | 49.5 | 7.1 | 0.143 |
| 4 | VL_G095Y | 404.5 | 6.00E+05 | 9.08E-02 | 1.51E-07 | 115.8 | 71.9 | 7 | 0.097 |
| 4 | VL_G095H | 403.3 | 2.16E+05 | 2.87E-03 | 1.33E-08 | 11.3 | 18.9 | 8.6 | 0.455 |
| 4 | VL_K095aD | 404.9 | 1.42E+05 | 4.49E-04 | 3.17E-09 | 176.5 | 171 | 153.2 | 0.896 |
| 4 | VL_K095aL | 408.7 | 1.38E+05 | 3.36E-04 | 2.43E-09 | 177.3 | 171.4 | 157.5 | 0.919 |
| 4 | VL_K095aQ | 406.1 | 1.49E+05 | 3.21E-04 | 2.16E-09 | 179.2 | 174.8 | 161.2 | 0.922 |
| 4 | VL_K095aY | 438.6 | 1.35E+05 | 4.46E-04 | 3.30E-09 | 184.6 | 176.5 | 158.1 | 0.896 |
| 4 | VL_K095aS | 410.9 | 1.41E+05 | 3.98E-04 | 2.82E-09 | 178.2 | 173 | 156.7 | 0.906 |
| 4 | VL_K095aW | 431.4 | 1.31E+05 | 1.20E-03 | 9.11E-09 | 174.9 | 164.8 | 124.1 | 0.753 |
| 4 | VL_N095bA | 413.5 | 1.43E+05 | 2.05E-04 | 1.43E-09 | 176.8 | 172.1 | 162.8 | 0.946 |
| 4 | VL_N095bK | 408.6 | 1.27E+05 | 1.84E-04 | 1.45E-09 | 168.1 | 160.6 | 152.7 | 0.951 |
| 4 | VL_N095bQ | 403 | 1.36E+05 | 2.29E-04 | 1.67E-09 | 170.1 | 165 | 155.3 | 0.941 |
| 4 | VL_N095bW | 397 | 1.45E+05 | 1.91E-04 | 1.31E-09 | 170.9 | 167.3 | 158.8 | 0.949 |
| 4 | VL_N095bS | 423.4 | 1.42E+05 | 1.92E-04 | 1.35E-09 | 181.1 | 175.7 | 166.7 | 0.949 |
| 4 | VL_N095bL | 418.8 | 1.37E+05 | 1.97E-04 | 1.44E-09 | 177.5 | 171.6 | 162.6 | 0.948 |

Figure 23

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 4 | VL_N095bD | 424.5 | 1.48E+05 | 2.81E-04 | 1.90E-09 | 185.8 | 180.7 | 168 | 0.930 |
| 4 | VL_N095bY | 424.2 | 1.31E+05 | 2.87E-04 | 2.18E-09 | 170.2 | 163 | 151.3 | 0.928 |
| 4 | VL_N095bH | 395.5 | 1.40E+05 | 1.97E-04 | 1.40E-09 | 169.2 | 164.8 | 156.3 | 0.948 |
| 4 | VL_L096A | 407.8 | 1.13E+05 | 4.70E-04 | 4.14E-09 | 161.5 | 150.8 | 134.4 | 0.891 |
| 4 | VL_L096K | 403.1 | 1.22E+06 | 1.25E-01 | 1.02E-07 | 88.7 | 67.8 | 10.2 | 0.150 |
| 4 | VL_L096Q | 409.3 | 1.15E+05 | 2.16E-04 | 1.88E-09 | 161.7 | 152.4 | 144 | 0.945 |
| 4 | VL_L096Y | 416.2 | 1.18E+05 | 1.32E-03 | 1.11E-08 | 171.4 | 158.9 | 117 | 0.736 |
| 4 | VL_L096S | 419.5 | 1.09E+05 | 3.64E-04 | 3.34E-09 | 163.1 | 151.1 | 137.9 | 0.913 |
| 4 | VL_L096W | 410.5 | 1.27E+05 | 2.88E-03 | 2.27E-08 | 166.1 | 152.6 | 79.5 | 0.521 |
| 4 | VL_L096D | -2.8 | 8.50E+04 | 1.28E-03 | 1.51E-08 | 7.5 | 6.5 | 4.6 | 0.708 |
| 4 | VL_L096H | 410.3 | 1.26E+05 | 1.69E-04 | 1.34E-09 | 173.8 | 166.5 | 159 | 0.955 |
| 4 | VL_V097A | 408.9 | 1.36E+05 | 2.30E-04 | 1.69E-09 | 174.3 | 169.1 | 159.1 | 0.941 |
| 4 | VL_V097K | 426.9 | 1.01E+05 | 4.58E-04 | 4.54E-09 | 163.4 | 147.6 | 132 | 0.894 |
| 4 | VL_V097Q | 427.8 | 1.24E+05 | 3.45E-04 | 2.79E-09 | 175.9 | 166.6 | 152.8 | 0.917 |
| 4 | VL_V097W | 416.4 | 1.06E+05 | 9.69E-04 | 9.18E-09 | 163.2 | 148.6 | 118.5 | 0.797 |
| 4 | VL_V097L | 421.7 | 1.19E+05 | 4.81E-04 | 4.03E-09 | 172.4 | 162.5 | 144.5 | 0.889 |
| 4 | VL_V097D | 440 | 1.44E+05 | 2.45E-04 | 1.71E-09 | 190.4 | 185.1 | 173.5 | 0.937 |

Figure 24

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 4 | VL_V097Y | 427.1 | 8.66E+04 | 7.91E-04 | 9.13E-09 | 158.5 | 136 | 112.9 | 0.830 |
| 4 | VL_V097H | 440.1 | 1.07E+05 | 4.14E-04 | 3.87E-09 | 174.5 | 159.9 | 144.5 | 0.904 |
| 4 | VL_N089A | 420 | 9.54E+04 | 6.32E-04 | 6.62E-09 | 57.7 | 52.5 | 44.9 | 0.855 |
| 4 | VL_N089K | 450.3 | 8.69E+04 | 1.09E-03 | 1.26E-08 | 154.6 | 132.1 | 102.4 | 0.775 |
| 4 | VL_N089Q | 446.1 | 1.22E+05 | 5.22E-04 | 4.27E-09 | 184.9 | 174.1 | 153.4 | 0.881 |
| 4 | VL_N089W | 419.9 | 9.00E+04 | 6.41E-03 | 7.12E-08 | 115.9 | 82 | 28.6 | 0.349 |
| 4 | VL_N089S | 408.9 | 1.34E+05 | 2.05E-04 | 1.53E-09 | 174.7 | 169 | 160 | 0.947 |
| 4 | VL_N089L | 425.2 | 1.49E+05 | 2.02E-04 | 1.36E-09 | 186.4 | 182.5 | 172.7 | 0.946 |
| 4 | VL_N089D | 458.8 | 5.19E+04 | 5.50E-04 | 1.06E-08 | 144.6 | 101.1 | 88.7 | 0.877 |
| 4 | VL_N089Y | 435.4 | 1.21E+05 | 8.81E-04 | 7.28E-09 | 168.5 | 157.2 | 127.4 | 0.810 |
| 4 | VL_S090K | 411.5 | 8.16E+04 | 1.03E-07 | 1.27E-12 | 7.7 | 7.8 | 8 | 1.026 |
| 4 | VL_K095aH | 447.6 | 1.32E+05 | 4.73E-04 | 3.59E-09 | 190.2 | 181.6 | 161.8 | 0.891 |
| 4 | Parent clone | 447 | 1.42E+05 | 1.82E-04 | 1.28E-09 | 193.4 | 188 | 178.9 | 0.952 |
| 4 | VL_K051W | 489.9 | 1.28E+05 | 2.16E-04 | 1.69E-09 | 207.5 | 198.1 | 187.2 | 0.945 |
| 4 | VL_N052Q | 434.8 | 1.26E+05 | 2.01E-04 | 1.59E-09 | 184.6 | 176.5 | 167.3 | 0.948 |
| 5 | VH_W034Y | 477.5 | 1.55E+05 | 5.98E-04 | 3.87E-09 | 198.1 | 191.4 | 165.8 | 0.866 |

Figure 25

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 5 | VH_G026Q | 489.2 | 1.67E+05 | 1.77E-04 | 1.06E-09 | 213.7 | 210 | 200.6 | 0.955 |
| 5 | VH_S035aL | 504.6 | 8.75E+04 | 5.54E-04 | 6.33E-09 | 159.3 | 136.9 | 120.1 | 0.877 |
| 5 | VH_G027A | 439.9 | 1.68E+05 | 1.63E-04 | 9.70E-10 | 192.2 | 189.3 | 181.4 | 0.958 |
| 5 | VH_S028D | 520.7 | 1.68E+05 | 1.94E-04 | 1.15E-09 | 232.6 | 227.9 | 217 | 0.952 |
| 5 | VH_S028Q | 482.1 | 1.67E+05 | 1.82E-04 | 1.09E-09 | 212.9 | 209.5 | 199.9 | 0.954 |
| 5 | VH_I051Q | 508.6 | 1.48E+05 | 1.91E-04 | 1.29E-09 | 205.4 | 198.8 | 189.2 | 0.952 |
| 5 | VH_I051W | 494.9 | 1.50E+05 | 2.35E-04 | 1.57E-09 | 205.8 | 199.7 | 188.3 | 0.943 |
| 5 | VH_I051S | 477.1 | 1.63E+05 | 2.03E-04 | 1.24E-09 | 206.2 | 202.4 | 192.2 | 0.950 |
| 5 | VH_I051L | 489.8 | 1.70E+05 | 1.70E-04 | 1.00E-09 | 211.1 | 207.8 | 198.8 | 0.957 |
| 5 | VH_I051D | 51.2 | 1.52E+05 | 5.21E-07 | 3.43E-09 | 19.5 | 17.9 | 15.8 | 0.883 |
| 5 | VH_N060H | 497 | 1.72E+05 | 1.54E-07 | 8.94E-10 | 220 | 217.1 | 208.4 | 0.960 |
| 5 | VH_I051H | 366.2 | 1.59E+05 | 2.26E-04 | 1.42E-09 | 153.1 | 149.2 | 140.9 | 0.944 |
| 5 | VH_Y052A | 495.6 | 1.42E+05 | 8.84E-04 | 6.22E-09 | 212.5 | 202.4 | 164.5 | 0.813 |
| 5 | VH_Y052K | 475.6 | 1.27E+05 | 1.51E-03 | 1.19E-08 | 187.4 | 174.3 | 122.9 | 0.705 |
| 5 | VH_Y052Q | 460.9 | 1.38E+05 | 8.48E-04 | 6.13E-09 | 196.5 | 186.9 | 153.3 | 0.820 |
| 5 | VH_Y052W | 484.1 | 1.68E+05 | 1.36E-04 | 8.13E-10 | 210.2 | 207.1 | 199.7 | 0.964 |
| 5 | VH_Y052S | 484.1 | 1.43E+05 | 9.42E-04 | 6.60E-09 | 209.1 | 199.5 | 160 | 0.802 |

Figure 26

| Run # | Amino acid Substitution | Capture level | ka (1/Ms) | kd (1/s) | KD (M) | Rmax (RU) | binding early | binding late | binding late/binding early |
|---|---|---|---|---|---|---|---|---|---|
| 5 | VH_Y052L | 512.7 | 1.54E+05 | 1.46E-04 | 9.47E-10 | 221.9 | 216.3 | 208.1 | 0.962 |
| 5 | VH_Y052D | 526.4 | 1.47E+05 | 6.08E-04 | 4.13E-09 | 234.6 | 225.3 | 195 | 0.866 |
| 5 | VH_Y052H | 508.9 | 1.57E+05 | 2.59E-04 | 1.64E-09 | 219.7 | 214.5 | 201.1 | 0.938 |
| 5 | VH_H053A | 528.2 | 1.52E+05 | 2.39E-04 | 1.57E-09 | 224.6 | 218.1 | 205.4 | 0.942 |
| 5 | VH_H053L | 511.9 | 1.51E+05 | 2.80E-04 | 1.85E-09 | 217.3 | 211.1 | 197 | 0.933 |
| 5 | VH_H053Q | 507.3 | 1.61E+05 | 2.00E-04 | 1.24E-09 | 220.6 | 216.3 | 205.5 | 0.950 |
| 5 | VH_H053Y | 518.6 | 1.60E+05 | 1.68E-04 | 1.05E-09 | 224.4 | 219.4 | 210 | 0.957 |
| 5 | VH_H053S | 519.4 | 1.62E+05 | 2.23E-04 | 1.43E-09 | 223.8 | 217.9 | 205.9 | 0.945 |
| 5 | VH_H053W | 529.4 | 1.56E+05 | 1.68E-04 | 1.04E-09 | 230.2 | 225.6 | 215.9 | 0.957 |
| 5 | VH_H053D | 549.6 | 1.42E+05 | 3.73E-04 | 2.63E-09 | 238.4 | 228.7 | 209 | 0.914 |
| 5 | VH_H053K | 505.8 | 1.55E+05 | 1.66E-04 | 1.07E-09 | 210.4 | 205.7 | 196.8 | 0.957 |
| 5 | VH_S054A | 539.2 | 1.68E+05 | 1.38E-04 | 8.22E-10 | 238.3 | 234.5 | 226 | 0.964 |
| 5 | VH_S054L | 515.3 | 1.68E+05 | 1.49E-04 | 8.89E-10 | 226.1 | 222.6 | 214 | 0.961 |
| 5 | VH_S054D | 489.1 | 1.43E+05 | 3.00E-04 | 2.10E-09 | 214.6 | 206.8 | 192.2 | 0.929 |
| 5 | VH_S054Y | 540.7 | 2.24E+05 | 1.38E-04 | 6.17E-10 | 249 | 248.9 | 239.7 | 0.963 |
| 5 | VH_S054Q | 531.1 | 1.73E+05 | 1.67E-04 | 9.70E-10 | 234.8 | 231.5 | 221.5 | 0.957 |
| 5 | VH_S054W | 532.2 | 2.69E+05 | 1.36E-04 | 5.06E-10 | 249.8 | 251 | 241.7 | 0.963 |

Figure 27

| Run # | Amino acid Substitution | Capture level | ka (1/Ms) | kd (1/s) | KD (M) | Rmax (RU) | binding early | binding late | binding late/binding early |
|---|---|---|---|---|---|---|---|---|---|
| 5 | VH_S054H | 549.4 | 1.91E+05 | 1.45E-04 | 7.57E-10 | 248.7 | 246.5 | 237.1 | 0.962 |
| 5 | VH_S054K | 518.7 | 1.58E+05 | 3.20E-04 | 2.03E-09 | 218.3 | 213.6 | 197.2 | 0.923 |
| 5 | VH_G055A | 548.7 | 1.66E+05 | 1.52E-04 | 9.15E-10 | 242.6 | 238.4 | 228.9 | 0.960 |
| 5 | VH_G055K | 536.2 | 1.45E+05 | 1.65E-04 | 1.14E-09 | 222.4 | 216 | 206.8 | 0.957 |
| 5 | VH_G055Q | 544.4 | 1.64E+05 | 1.61E-04 | 9.79E-10 | 238.8 | 234.4 | 224.7 | 0.959 |
| 5 | VH_G055W | 555.2 | 1.56E+05 | 1.81E-04 | 1.16E-09 | 234.6 | 229.1 | 218.5 | 0.954 |
| 5 | VH_G055S | 535 | 1.66E+05 | 1.58E-04 | 9.52E-10 | 235.4 | 231.3 | 222 | 0.960 |
| 5 | VH_G055L | 550 | 1.62E+05 | 1.53E-04 | 9.45E-10 | 240.3 | 235.6 | 226.2 | 0.960 |
| 5 | VH_G055D | 2.8 | 1.23E+02 | 1.74E-03 | 1.41E-01 | 0.1 | -1 | -0.6 | 0.600 |
| 5 | VH_G055Y | 531 | 1.60E+05 | 1.60E-04 | 1.00E-09 | 229.1 | 224.8 | 215.6 | 0.959 |
| 5 | VH_G055H | 556.9 | 1.60E+05 | 1.53E-04 | 9.59E-10 | 242.1 | 237.3 | 228 | 0.961 |
| 5 | VH_N056A | 587.1 | 1.59E+05 | 2.04E-04 | 1.28E-09 | 255.6 | 249.9 | 237.2 | 0.949 |
| 5 | VH_N056K | 569.3 | 1.39E+05 | 5.09E-04 | 3.67E-09 | 232.2 | 222.5 | 196.9 | 0.885 |
| 5 | VH_N056Q | 528.2 | 1.58E+05 | 1.97E-04 | 1.25E-09 | 231.2 | 226.5 | 215.3 | 0.951 |
| 5 | VH_N056W | 551.8 | 2.16E+05 | 1.42E-04 | 6.59E-10 | 253 | 253 | 243.5 | 0.962 |
| 5 | VH_N056S | 578.6 | 1.62E+05 | 2.31E-04 | 1.42E-09 | 254.7 | 249.4 | 235.4 | 0.944 |
| 5 | VH_N056L | 562.5 | 1.80E+05 | 1.53E-04 | 8.49E-10 | 252.4 | 249.7 | 239.8 | 0.960 |

Figure 28

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 5 | VH_N056D | 547.5 | 1.55E+05 | 1.41E-04 | 9.11E-10 | 245.3 | 239.6 | 230.9 | 0.964 |
| 5 | VH_N056Y | 566.6 | 1.85E+05 | 1.44E-04 | 7.78E-10 | 255.2 | 253.6 | 244 | 0.962 |
| 5 | VH_N056H | 598.7 | 1.83E+05 | 1.23E-04 | 6.74E-10 | 268 | 265.5 | 256.6 | 0.966 |
| 5 | VH_N058A | 594 | 1.67E+05 | 3.39E-04 | 2.03E-09 | 262.3 | 257.1 | 236.4 | 0.919 |
| 5 | VH_N058L | 581.7 | 1.52E+05 | 1.86E-04 | 1.23E-09 | 250.1 | 243.3 | 231.8 | 0.953 |
| 5 | VH_N058D | 528.4 | 1.49E+05 | 2.18E-04 | 1.46E-09 | 227.5 | 221.6 | 209.7 | 0.946 |
| 5 | VH_N058Y | 568.6 | 1.48E+05 | 7.03E-04 | 4.75E-09 | 242 | 233.3 | 197.5 | 0.847 |
| 5 | VH_N058H | 569.5 | 1.31E+05 | 1.20E-03 | 9.15E-09 | 233.9 | 219.6 | 166.1 | 0.756 |
| 5 | VH_Y059A | 192.3 | 1.88E+05 | 1.94E-04 | 1.03E-09 | 90 | 89.4 | 85 | 0.951 |
| 5 | VH_Y059K | 577.4 | 1.51E+05 | 2.14E-04 | 1.42E-09 | 247.6 | 241.2 | 228.5 | 0.947 |
| 5 | VH_Y059Q | 604.4 | 1.67E+05 | 2.01E-04 | 1.20E-09 | 268.4 | 263.5 | 250.2 | 0.950 |
| 5 | VH_Y059W | 587.3 | 1.61E+05 | 2.05E-04 | 1.27E-09 | 257.8 | 252.4 | 239.6 | 0.949 |
| 5 | VH_Y059S | 596.1 | 1.72E+05 | 1.87E-04 | 1.09E-09 | 267.1 | 263.3 | 250.8 | 0.953 |
| 5 | VH_Y059L | 598.9 | 1.67E+05 | 1.98E-04 | 1.18E-09 | 267 | 262.7 | 249.7 | 0.951 |
| 5 | VH_Y059D | 600.1 | 1.79E+05 | 1.71E-04 | 9.57E-10 | 275.3 | 272.3 | 260.5 | 0.957 |
| 5 | VH_Y059H | 609.9 | 1.67E+05 | 1.76E-04 | 1.05E-09 | 272 | 267.3 | 255.2 | 0.955 |
| 5 | VH_N060A | 618.5 | 1.76E+05 | 1.63E-04 | 9.24E-10 | 278.1 | 274.7 | 263.1 | 0.958 |

Figure 29

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 5 | VH_N060K | 613.1 | 1.67E+05 | 1.78E-04 | 1.06E-09 | 273.2 | 269 | 256.9 | 0.955 |
| 5 | VH_N060Q | 623.1 | 1.77E+05 | 1.53E-04 | 8.66E-10 | 281.5 | 278.2 | 267.1 | 0.960 |
| 5 | VH_N060W | 605.3 | 1.77E+05 | 1.53E-04 | 8.62E-10 | 273.6 | 270.6 | 259.9 | 0.960 |
| 5 | VH_N060L | 600.4 | 1.82E+05 | 1.38E-04 | 7.58E-10 | 272.5 | 270.1 | 260.2 | 0.963 |
| 5 | VH_N060D | 623.6 | 1.87E+05 | 1.62E-04 | 8.66E-10 | 287.8 | 285.5 | 273.5 | 0.958 |
| 5 | VH_N060Y | 622.3 | 1.81E+05 | 1.33E-04 | 7.33E-10 | 282.8 | 280.3 | 270.2 | 0.964 |
| 5 | Parent clone | 623.1 | 1.70E+05 | 1.66E-04 | 9.79E-10 | 278.3 | 274.1 | 262.4 | 0.957 |

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 5 | VL_S034K | 399.8 | 2.40E+04 | 3.73E-07 | 1.56E-11 | 5 | 0.9 | 3.3 | 3.667 |
| 5 | VL_G050A | 407.9 | 1.45E+05 | 1.86E-04 | 1.28E-09 | 172.8 | 167.2 | 159.4 | 0.953 |
| 5 | VL_G050K | 392.1 | 7.58E+04 | 6.76E-04 | 8.92E-09 | 121 | 99.4 | 84.9 | 0.854 |
| 5 | VL_G050Q | 403.2 | 9.54E+04 | 2.72E-04 | 2.85E-09 | 141.9 | 126.2 | 118.1 | 0.936 |
| 5 | VL_G050W | 393.6 | 7.54E+04 | 1.79E-04 | 2.38E-09 | 138.1 | 114.9 | 110 | 0.957 |
| 5 | VL_G050S | 401.2 | 1.35E+05 | 2.13E-04 | 1.58E-09 | 163.5 | 156.9 | 148.6 | 0.947 |
| 5 | VL_Q024D | 419 | 1.51E+05 | 1.46E-04 | 9.66E-10 | 181.1 | 176.8 | 170 | 0.962 |
| 5 | VL_Q024S | 390.5 | 1.46E+05 | 1.39E-04 | 9.52E-10 | 166.6 | 162.3 | 156.4 | 0.964 |
| 5 | VL_Q024H | 392.2 | 1.44E+05 | 1.44E-04 | 9.97E-10 | 166.3 | 161.5 | 155.5 | 0.963 |

Figure 30

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 6 | VL_G025A | 383.7 | 1.17E+05 | 1.64E-04 | 1.40E-09 | 154.6 | 145.5 | 139.7 | 0.960 |
| 6 | VL_N030A | 402.5 | 1.74E+05 | 2.95E-04 | 1.70E-09 | 177.4 | 175 | 162.5 | 0.929 |
| 6 | VL_G050H | 385.3 | 9.19E+04 | 2.67E-04 | 2.90E-09 | 141.6 | 126 | 118 | 0.937 |
| 6 | VL_K051D | 400.9 | 6.14E+04 | 5.79E-04 | 9.42E-09 | 151.1 | 114.4 | 100.2 | 0.876 |
| 6 | VL_K051H | 394.9 | 1.34E+05 | 9.78E-05 | 7.30E-10 | 171.4 | 165.4 | 161.1 | 0.974 |
| 6 | VL_N052K | 407.2 | 1.01E+05 | 1.92E-04 | 1.90E-09 | 156.9 | 142.2 | 135.7 | 0.954 |
| 6 | VL_N052W | 403 | 1.21E+05 | 2.75E-04 | 2.27E-09 | 162.7 | 153.2 | 143.2 | 0.935 |
| 6 | VL_N052S | 382.7 | 1.42E+05 | 1.81E-04 | 1.27E-09 | 163.3 | 158.5 | 151.3 | 0.955 |
| 6 | VL_N052L | 398 | 1.06E+05 | 1.75E-04 | 1.65E-09 | 161.9 | 148.3 | 142 | 0.958 |
| 6 | VL_N052D | 398.7 | 1.50E+05 | 1.43E-04 | 9.50E-10 | 176 | 172.1 | 165.7 | 0.963 |
| 6 | VL_N052Y | 410.3 | 1.30E+05 | 2.01E-04 | 1.55E-09 | 168.2 | 160.7 | 152.7 | 0.950 |
| 6 | VL_N052H | 413.5 | 1.27E+05 | 1.90E-04 | 1.49E-09 | 169.3 | 160.9 | 153.4 | 0.953 |
| 6 | VL_N053A | 411.7 | 1.36E+05 | 2.23E-04 | 1.64E-09 | 172.2 | 165.6 | 156.6 | 0.946 |
| 6 | VL_N053K | 398.1 | 1.14E+05 | 2.13E-04 | 1.88E-09 | 152.2 | 142.3 | 135 | 0.949 |
| 6 | VL_N053Q | 375.2 | 1.41E+05 | 1.93E-04 | 1.37E-09 | 159.3 | 154.6 | 147.1 | 0.951 |
| 6 | VL_N053W | 399.4 | 1.01E+05 | 3.18E-04 | 3.14E-09 | 148.4 | 134.9 | 125 | 0.927 |
| 6 | VL_N053S | 390.8 | 1.51E+05 | 1.71E-04 | 1.14E-09 | 167.7 | 164.3 | 157 | 0.956 |

Figure 31

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 6 | VL_N053L | 411.2 | 1.32E+05 | 2.32E-04 | 1.76E-09 | 171.9 | 164.4 | 155.1 | 0.943 |
| 6 | VL_N053D | 418.1 | 1.64E+05 | 1.59E-04 | 9.69E-10 | 188.6 | 185.6 | 178.1 | 0.960 |
| 6 | VL_N053H | 391.1 | 1.26E+05 | 2.07E-04 | 1.65E-09 | 158.4 | 151.1 | 143.5 | 0.950 |
| 6 | VL_R054A | 401.5 | 1.45E+05 | 1.39E-04 | 9.54E-10 | 174 | 169.2 | 163 | 0.963 |
| 6 | VL_R054K | 428.1 | 1.46E+05 | 1.46E-04 | 9.99E-10 | 183.4 | 178 | 171.2 | 0.962 |
| 6 | VL_R054Q | 421.5 | 1.49E+05 | 1.33E-04 | 8.92E-10 | 182.9 | 178.2 | 172 | 0.965 |
| 6 | VL_R054W | 405.7 | 1.24E+05 | 1.18E-04 | 9.49E-10 | 165.7 | 157.6 | 152.6 | 0.968 |
| 6 | VL_R054L | 422.4 | 1.49E+05 | 1.26E-04 | 8.45E-10 | 184.6 | 179.6 | 173.6 | 0.967 |
| 6 | VL_R054Y | 405.2 | 1.42E+05 | 1.11E-04 | 7.84E-10 | 174.1 | 169.2 | 164.2 | 0.970 |
| 6 | VL_R054H | 413.7 | 1.45E+05 | 1.58E-04 | 1.09E-09 | 177 | 171.7 | 164.7 | 0.959 |
| 6 | VL_P055A | 395.2 | 1.37E+05 | 1.41E-04 | 1.03E-09 | 168.6 | 163.2 | 157.2 | 0.963 |
| 6 | VL_P055K | 418.4 | 1.22E+05 | 1.55E-04 | 1.27E-09 | 169.2 | 159.8 | 153.5 | 0.961 |
| 6 | VL_P055L | 392.7 | 1.40E+05 | 1.44E-04 | 1.03E-09 | 166.5 | 161.5 | 155.5 | 0.963 |
| 6 | VL_P055D | 412.4 | 1.41E+05 | 1.54E-04 | 1.09E-09 | 178 | 172.2 | 165.5 | 0.961 |
| 6 | VL_P055Y | 423.8 | 1.31E+05 | 1.59E-04 | 1.22E-09 | 175.1 | 167.1 | 160.3 | 0.959 |
| 6 | VL_S056L | 395.4 | 1.48E+05 | 1.38E-04 | 9.36E-10 | 169.6 | 165.6 | 159.6 | 0.964 |
| 6 | VL_S056D | 382.4 | 1.56E+05 | 1.40E-04 | 9.00E-10 | 168.5 | 165.5 | 159.4 | 0.963 |

Figure 32

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 6 | VL_S056Y | 417.4 | 1.41E+05 | 1.38E-04 | 9.79E-10 | 174.7 | 169.2 | 163 | 0.963 |
| 6 | VL_S056W | 372.2 | 1.36E+05 | 1.38E-04 | 1.02E-09 | 154.2 | 149.2 | 143.8 | 0.964 |
| 6 | VL_S056H | 428.9 | 1.45E+05 | 1.36E-04 | 9.39E-10 | 181.9 | 176.8 | 170.3 | 0.963 |
| 6 | VL_S056K | 413.5 | 1.38E+05 | 1.40E-04 | 1.02E-09 | 171.5 | 165.9 | 159.8 | 0.963 |
| 6 | VL_Y031L | 400.6 | 1.21E+05 | 2.56E-02 | 2.11E-07 | 106.1 | 63.5 | 6.4 | 0.101 |
| 6 | VH_W035L | 430.2 | 1.17E+05 | 1.15E-04 | 9.82E-10 | 151.6 | 142.6 | 138.1 | 0.968 |
| 6 | VH_W035D | 84.2 | 8.74E+04 | 5.11E-04 | 5.85E-09 | 27.7 | 24.3 | 21.6 | 0.889 |
| 6 | VH_W035H | 415.3 | 1.18E+05 | 1.93E-04 | 1.63E-09 | 162.4 | 153.1 | 145.7 | 0.952 |
| 6 | VH_S035aA | 427.8 | 1.48E+05 | 1.26E-04 | 8.48E-10 | 180.4 | 175.8 | 169.8 | 0.966 |
| 6 | VH_S035aD | 432.7 | 1.07E+05 | 9.84E-04 | 9.23E-09 | 167.4 | 151.1 | 120.2 | 0.795 |
| 6 | VH_S035aY | 405.1 | 4.28E+04 | 6.71E-07 | 1.57E-11 | 5.9 | 3.7 | 6.2 | 1.676 |
| 6 | VH_S035aQ | 393.7 | 1.58E+05 | 2.15E-02 | 1.36E-07 | 132 | 90.4 | 7 | 0.077 |
| 6 | VH_S035aW | 415.5 | 5.61E+04 | 2.71E-06 | 4.83E-11 | 4.7 | 3.5 | 5.7 | 1.629 |
| 6 | VH_S035aH | 415.5 | 9.64E+04 | 3.19E-02 | 3.31E-07 | 86.2 | 42 | 6.4 | 0.152 |
| 6 | VH_S035aK | 419.7 | 7.61E+04 | 7.25E-08 | 9.53E-13 | 7.3 | 7.4 | 7.5 | 1.014 |
| 6 | VH_E050A | 428.8 | 1.51E+05 | 3.53E-03 | 2.33E-08 | 177.7 | 165.1 | 74.2 | 0.449 |
| 6 | VH_E050K | 391.5 | 2.15E+05 | 2.74E-07 | 1.27E-12 | 3.7 | 3.8 | 5.8 | 1.526 |

Figure 33

| Run # | Amino acid Substitution | Capture level | ka (1/Ms) | kd (1/s) | KD (M) | Rmax (RU) | binding early | binding late | binding late/ binding early |
|---|---|---|---|---|---|---|---|---|---|
| 6 | VH_E050Q | 440.4 | 1.56E+05 | 5.21E-03 | 3.33E-08 | 181.1 | 163.4 | 51.7 | 0.316 |
| 6 | VH_E050W | 434.5 | 1.59E+05 | 1.83E-04 | 1.15E-08 | 6.1 | 12.8 | 5.9 | 0.461 |
| 6 | VH_T057A | 424.4 | 1.50E+05 | 1.94E-04 | 1.29E-09 | 181.6 | 177.1 | 168.5 | 0.951 |
| 6 | VH_T057K | 418.5 | 1.31E+05 | 1.91E-04 | 1.46E-09 | 169.2 | 161.8 | 154.1 | 0.952 |
| 6 | VH_T057Q | 418.3 | 1.53E+05 | 1.30E-04 | 8.52E-10 | 180.9 | 177.3 | 171.1 | 0.965 |
| 6 | VH_T057W | 406.2 | 1.52E+05 | 1.33E-04 | 8.73E-10 | 175.6 | 172.2 | 166.1 | 0.965 |
| 6 | VH_T057S | 441.8 | 1.53E+05 | 1.55E-04 | 1.01E-09 | 190.6 | 186.3 | 178.7 | 0.959 |
| 6 | VH_T057L | 420.7 | 1.52E+05 | 1.64E-04 | 1.08E-09 | 181.9 | 177.9 | 170.2 | 0.957 |
| 6 | VH_T057D | 433.8 | 1.65E+05 | 1.06E-04 | 6.40E-10 | 195.2 | 192.6 | 187 | 0.971 |
| 6 | VH_T057Y | 423 | 1.51E+05 | 1.50E-04 | 9.96E-10 | 182 | 178.1 | 171.2 | 0.961 |
| 6 | VH_T057H | 417.9 | 1.45E+05 | 2.02E-04 | 1.39E-09 | 177.2 | 172.5 | 163.8 | 0.950 |
| 6 | VH_N058K | 408.4 | 1.24E+05 | 7.45E-04 | 6.01E-09 | 161.5 | 151.7 | 127.3 | 0.839 |
| 6 | VH_N058Q | 423 | 1.45E+05 | 1.11E-04 | 7.65E-10 | 180.7 | 176.1 | 170.7 | 0.969 |
| 6 | VH_N058W | 412.4 | 1.34E+05 | 4.73E-04 | 3.52E-09 | 171.3 | 164.4 | 146.8 | 0.893 |
| 6 | VH_G098L | 408.7 | 4.32E+04 | 5.30E-07 | 1.23E-11 | 6.1 | 3.8 | 6.6 | 1.737 |
| 6 | Parent clone | 434.6 | 1.50E+05 | 1.60E-04 | 1.07E-09 | 186.1 | 181.8 | 174.3 | 0.959 |

Figure 34A

| ANTIBODY | Heavy Chain | Light Chain |
|---|---|---|
| ANTIBODY 4 | Wild type (WT) | Wild type (WT) |
| ANTIBODY 1 | S54F | WT |
| ANTIBODY 2 | S54Y | WT |
| ANTIBODY 3 | S54W | WT |
| ANTIBODY 6 | N56W | WT |
| ANTIBODY 7 | S54F + N56F | WT |
| ANTIBODY 8 | S54Y + N56F | WT |
| ANTIBODY 9 | S54W + N56F | WT |
| ANTIBODY 10 | S54F + N56Y | WT |
| ANTIBODY 11 | S54Y + N56Y | WT |
| ANTIBODY 12 | S54W + N56Y | WT |
| ANTIBODY 13 | S54F + N56W | WT |
| ANTIBODY 14 | S54Y + N56W | WT |
| ANTIBODY 15 | S54W + N56W | WT |
| ANTIBODY 16 | WT | D92S |
| ANTIBODY 20 | S35aA | WT |
| ANTIBODY 21 | W35L | WT |
| ANTIBODY 22 | Y52W | WT |
| ANTIBODY 23 | N56H | WT |
| ANTIBODY 24 | N56L | WT |
| ANTIBODY 25 | T57D | WT |
| ANTIBODY 26 | N58Q | WT |
| ANTIBODY 27 | N60Y | WT |
| ANTIBODY 29 | WT | G50S |
| ANTIBODY 30 | WT | K51A |
| ANTIBODY 31 | WT | K51H |

Figure 34B

| ANTIBODY | Heavy Chain | Light Chain |
|---|---|---|
| ANTIBODY 32 | WT | K51L |
| ANTIBODY 33 | WT | R54L |
| ANTIBODY 34 | WT | R54Q |
| ANTIBODY 35 | WT | R54Y |
| ANTIBODY 36 | Y102S | WT |
| ANTIBODY 37 | Y102L | WT |
| ANTIBODY 38 | Y102A | WT |
| ANTIBODY 39 | Y102H | WT |
| ANTIBODY 40 | S54F + N56W | K51H |
| ANTIBODY 41 | S54Y + N56W | K51H |
| ANTIBODY 42 | S54W + N56W | K51H |
| ANTIBODY 43 | S54F + N56W | R54Y |
| ANTIBODY 44 | S54Y + N56W | R54Y |
| ANTIBODY 45 | S54W + N56W | R54Y |
| ANTIBODY 46 | S54W+N60Y | WT |
| ANTIBODY 47 | N56W+N60Y | WT |
| ANTIBODY 48 | S54W+N56W+N60Y | WT |
| ANTIBODY 49 | WT | K51H + R54L |
| ANTIBODY 50 | WT | K51H + R54Y |
| ANTIBODY 51 | WT | N30S |
| ANTIBODY 52 | S54Y + N56W | N30S |
| ANTIBODY 53 | S54Y + N56Y | N30S |
| ANTIBODY 54 | WT | D92E |
| ANTIBODY 55 | S54Y + N56W | D92E |
| ANTIBODY 56 | S54Y + N56Y | D92E |
| ANTIBODY 57 | I82aS | WT |
| ANTIBODY 58 | S54Y + N56W + I82aS | WT |
| ANTIBODY 59 | I82aS | N30S |
| ANTIBODY 60 | S54Y + N56W + I82aS | N30S |

Figure 34C

| ANTIBODY | Heavy Chain | Light Chain |
|---|---|---|
| ANTIBODY 61 | I82aS | D92E |
| ANTIBODY 62 | S54Y + N56Y + I82aS | D92E |
| ANTIBODY 63 | S54Y + N56Y + I82aS | WT |
| ANTIBODY 64 | S54Y + N56Y + I82aS | N30S |
| ANTIBODY 65 | S54Y + N56Y + I82aS | D92E |
| ANTIBODY 66 | S54Y + N56Y + I82aS | S93L |
| ANTIBODY 67 | S54Y + N56Y + I82aS | S93E |
| ANTIBODY 68 | S54Y + N56Y + I82aS | S93F |
| ANTIBODY 69 | S54Y + N56Y + I82aS | N30S+92E |
| ANTIBODY 70 | S54Y + N56Y + I82aS | N30S+S93L |
| ANTIBODY 71 | S54Y + N56Y + I82aS | N30S+S93E |
| ANTIBODY 72 | S54Y + N56Y + I82aS | N30S+S93F |
| ANTIBODY 73 | S54Y + N56Y | N30S |
| ANTIBODY 74 | S54Y + N56Y | D92E |
| ANTIBODY 75 | S54Y + N56Y | S93L |
| ANTIBODY 76 | S54Y + N56Y | S93E |
| ANTIBODY 77 | S54Y + N56Y | S93F |
| ANTIBODY 78 | S54Y + N56Y | N30S+D92E |
| ANTIBODY 79 | S54Y + N56Y | N30S+S93L |
| ANTIBODY 80 | S54Y + N56Y | N30S+S93E |
| ANTIBODY 81 | S54Y + N56Y | N30S+S93F |

Figure 36

| Sample | Ligand | ka (1/Ms) | | kd (1/s) | | KD (nM) | |
|---|---|---|---|---|---|---|---|
| Human IL-15 complex | ANTIBODY 70a | 2.52e+05 | 2.61e+05 | 3.47e-05 | 3.75e-05 | 0.133 | 0.149 |
| | ANTIBODY 70b | 2.49e+05 | 2.54e+05 | 3.92e-05 | 3.89e-05 | 0.154 | 0.157 |
| | ANTIBODY 70e | 2.37e+05 | 2.47e+05 | 4.31e-05 | 4.58e-05 | 0.174 | 0.193 |
| | ANTIBODY 70f | 2.49e+05 | 2.60e+05 | 4.44e-05 | 4.32e-05 | 0.171 | 0.173 |
| | ANTIBODY 4 | 1.48e+05 | 1.50e+05 | 9.43e-05 | 9.31e-05 | 0.630 | 0.628 |
| | AMG714 | 2.09e+05 | 2.14e+05 | 3.98e-04 | 3.80e-04 | 1.86 | 1.82 |

Figure 43A

| H1 | H2 | H3 |
|---|---|---|
| 58 | 18 or 19 | 20 |
| 59 | 18 or 19 | 20 |
| 60 | 18 or 19 | 20 |
| 61 | 18 or 19 | 20 |
| 62 | 18 or 19 | 20 |
| 63 | 18 or 19 | 20 |
| 64 | 18 or 19 | 20 |
| 65 | 18 or 19 | 20 |
| 66 | 18 or 19 | 20 |
| 67 | 18 or 19 | 20 |
| 68 | 18 or 19 | 20 |
| 69 | 18 or 19 | 20 |
| 70 | 18 or 19 | 20 |
| 71 | 18 or 19 | 20 |
| 72 | 18 or 19 | 20 |
| 73 | 18 or 19 | 20 |
| 74 | 18 or 19 | 20 |
| 75 | 18 or 19 | 20 |
| 76 | 18 or 19 | 20 |
| 77 | 18 or 19 | 20 |
| 78 | 18 or 19 | 20 |
| 79 | 18 or 19 | 20 |
| 80 | 18 or 19 | 20 |
| 81 | 18 or 19 | 20 |
| 82 | 18 or 19 | 20 |
| 83 | 18 or 19 | 20 |
| 84 | 18 or 19 | 20 |
| 85 | 18 or 19 | 20 |
| 86 | 18 or 19 | 20 |
| 87 | 18 or 19 | 20 |
| 88 | 18 or 19 | 20 |
| 89 | 18 or 19 | 20 |
| 90 | 18 or 19 | 20 |
| 91 | 18 or 19 | 20 |
| 92 | 18 or 19 | 20 |
| 93 | 18 or 19 | 20 |
| 94 | 18 or 19 | 20 |
| 95 | 18 or 19 | 20 |
| 96 | 18 or 19 | 20 |
| 97 | 18 or 19 | 20 |
| 98 | 18 or 19 | 20 |

| H1 | H2 | H3 |
|---|---|---|
| 99 | 18 or 19 | 20 |
| 100 | 18 or 19 | 20 |
| 101 | 18 or 19 | 20 |
| 102 | 18 or 19 | 20 |
| 103 | 18 or 19 | 20 |
| 104 | 18 or 19 | 20 |
| 105 | 18 or 19 | 20 |
| 106 | 18 or 19 | 20 |
| 107 | 18 or 19 | 20 |
| 108 | 18 or 19 | 20 |
| 109 | 18 or 19 | 20 |
| 110 | 18 or 19 | 20 |
| 111 | 18 or 19 | 20 |
| 112 | 18 or 19 | 20 |
| 113 | 18 or 19 | 20 |
| 114 | 18 or 19 | 20 |
| 115 | 18 or 19 | 20 |
| 116 | 18 or 19 | 20 |
| 117 | 18 or 19 | 20 |
| 118 | 18 or 19 | 20 |
| 119 | 18 or 19 | 20 |
| 120 | 18 or 19 | 20 |
| 121 | 18 or 19 | 20 |
| 122 | 18 or 19 | 20 |
| 123 | 18 or 19 | 20 |
| 124 | 18 or 19 | 20 |
| 125 | 18 or 19 | 20 |
| 126 | 18 or 19 | 20 |
| 127 | 18 or 19 | 20 |
| 128 | 18 or 19 | 20 |
| 129 | 18 or 19 | 20 |
| 130 | 18 or 19 | 20 |
| 131 | 18 or 19 | 20 |
| 132 | 18 or 19 | 20 |
| 133 | 18 or 19 | 20 |
| 134 | 18 or 19 | 20 |
| 135 | 18 or 19 | 20 |

Figure 43B

| H1 | H2 | H3 |
|---|---|---|
| 453 | 136 | 20 |
| 453 | 137 | 20 |
| 453 | 138 | 20 |
| 453 | 139 | 20 |
| 453 | 140 | 20 |
| 453 | 141 | 20 |
| 453 | 142 | 20 |
| 453 | 143 | 20 |
| 453 | 144 | 20 |
| 453 | 145 | 20 |
| 453 | 146 | 20 |
| 453 | 147 | 20 |
| 453 | 148 | 20 |
| 453 | 149 | 20 |
| 453 | 150 | 20 |
| 453 | 151 | 20 |
| 453 | 152 | 20 |
| 453 | 153 | 20 |
| 453 | 154 | 20 |
| 453 | 155 | 20 |
| 453 | 156 | 20 |
| 453 | 157 | 20 |
| 453 | 158 | 20 |
| 453 | 159 | 20 |
| 453 | 160 | 20 |
| 453 | 161 | 20 |
| 453 | 162 | 20 |
| 453 | 163 | 20 |
| 453 | 164 | 20 |
| 453 | 165 | 20 |
| 453 | 166 | 20 |

| H1 | H2 | H3 |
|---|---|---|
| 453 | 167 | 20 |
| 453 | 168 | 20 |
| 453 | 169 | 20 |
| 453 | 170 | 20 |
| 453 | 171 | 20 |
| 453 | 172 | 20 |
| 453 | 173 | 20 |
| 453 | 174 | 20 |
| 453 | 175 | 20 |
| 453 | 176 | 20 |
| 453 | 177 | 20 |
| 453 | 178 | 20 |
| 453 | 179 | 20 |
| 453 | 180 | 20 |
| 453 | 181 | 20 |
| 453 | 182 | 20 |
| 453 | 183 | 20 |
| 453 | 184 | 20 |
| 453 | 185 | 20 |
| 453 | 186 | 20 |
| 453 | 187 | 20 |
| 453 | 188 | 20 |
| 453 | 189 | 20 |
| 453 | 190 | 20 |
| 453 | 191 | 20 |
| 453 | 192 | 20 |
| 453 | 193 | 20 |
| 453 | 194 | 20 |
| 453 | 195 | 20 |
| 453 | 196 | 20 |
| 453 | 197 | 20 |

| H1 | H2 | H3 |
|---|---|---|
| 453 | 198 | 20 |
| 453 | 199 | 20 |
| 453 | 200 | 20 |
| 453 | 201 | 20 |
| 453 | 202 | 20 |
| 453 | 203 | 20 |
| 453 | 204 | 20 |
| 453 | 205 | 20 |
| 453 | 206 | 20 |
| 453 | 207 | 20 |
| 453 | 208 | 20 |
| 453 | 209 | 20 |
| 453 | 210 | 20 |
| 453 | 211 | 20 |
| 453 | 212 | 20 |
| 453 | 213 | 20 |
| 453 | 214 | 20 |
| 453 | 215 | 20 |
| 453 | 216 | 20 |
| 453 | 217 | 20 |
| 453 | 218 | 20 |
| 453 | 219 | 20 |
| 453 | 220 | 20 |
| 453 | 221 | 20 |
| 453 | 222 | 20 |
| 453 | 223 | 20 |
| 453 | 224 | 20 |
| 453 | 225 | 20 |
| 453 | 226 | 20 |

Figure 43C

| H1  | H2       | H3  |
|-----|----------|-----|
| 453 | 18 or 19 | 227 |
| 453 | 18 or 19 | 228 |
| 453 | 18 or 19 | 229 |
| 453 | 18 or 19 | 230 |
| 453 | 18 or 19 | 231 |
| 453 | 18 or 19 | 232 |
| 453 | 18 or 19 | 233 |
| 453 | 18 or 19 | 234 |
| 453 | 18 or 19 | 235 |
| 453 | 18 or 19 | 236 |
| 453 | 18 or 19 | 237 |
| 453 | 18 or 19 | 238 |
| 453 | 18 or 19 | 239 |
| 453 | 18 or 19 | 240 |
| 453 | 18 or 19 | 241 |
| 453 | 18 or 19 | 242 |
| 453 | 18 or 19 | 243 |
| 453 | 18 or 19 | 244 |
| 453 | 18 or 19 | 245 |
| 453 | 18 or 19 | 246 |
| 453 | 18 or 19 | 247 |
| 453 | 18 or 19 | 248 |
| 453 | 18 or 19 | 249 |
| 453 | 18 or 19 | 250 |
| 453 | 18 or 19 | 251 |
| 453 | 18 or 19 | 252 |
| 453 | 18 or 19 | 253 |
| 453 | 18 or 19 | 254 |
| 453 | 18 or 19 | 255 |
| 453 | 18 or 19 | 256 |
| 453 | 18 or 19 | 257 |
| 453 | 18 or 19 | 258 |
| 453 | 18 or 19 | 259 |
| 453 | 18 or 19 | 260 |
| 453 | 18 or 19 | 261 |
| 453 | 18 or 19 | 262 |
| 453 | 18 or 19 | 263 |
| 453 | 18 or 19 | 264 |
| 453 | 18 or 19 | 265 |
| 453 | 18 or 19 | 266 |
| 453 | 18 or 19 | 267 |
| 453 | 18 or 19 | 268 |

| H1  | H2       | H3  |
|-----|----------|-----|
| 453 | 18 or 19 | 269 |
| 453 | 18 or 19 | 270 |
| 453 | 18 or 19 | 271 |
| 453 | 18 or 19 | 272 |

Figure 44A

| L1 | L2 | L3 |
|---|---|---|
| 273 | 28 | 30, 31, or 519 |
| 274 | 28 | 30, 31, or 519 |
| 275 | 28 | 30, 31, or 519 |
| 276 | 28 | 30, 31, or 519 |
| 277 | 28 | 30, 31, or 519 |
| 278 | 28 | 30, 31, or 519 |
| 279 | 28 | 30, 31, or 519 |
| 280 | 28 | 30, 31, or 519 |
| 281 | 28 | 30, 31, or 519 |
| 282 | 28 | 30, 31, or 519 |
| 283 | 28 | 30, 31, or 519 |
| 284 | 28 | 30, 31, or 519 |
| 285 | 28 | 30, 31, or 519 |
| 286 | 28 | 30, 31, or 519 |
| 287 | 28 | 30, 31, or 519 |
| 288 | 28 | 30, 31, or 519 |
| 289 | 28 | 30, 31, or 519 |
| 290 | 28 | 30, 31, or 519 |
| 291 | 28 | 30, 31, or 519 |
| 292 | 28 | 30, 31, or 519 |
| 293 | 28 | 30, 31, or 519 |
| 294 | 28 | 30, 31, or 519 |
| 295 | 28 | 30, 31, or 519 |
| 296 | 28 | 30, 31, or 519 |
| 297 | 28 | 30, 31, or 519 |
| 298 | 28 | 30, 31, or 519 |
| 299 | 28 | 30, 31, or 519 |
| 300 | 28 | 30, 31, or 519 |
| 301 | 28 | 30, 31, or 519 |
| 302 | 28 | 30, 31, or 519 |
| 303 | 28 | 30, 31, or 519 |
| 304 | 28 | 30, 31, or 519 |
| 305 | 28 | 30, 31, or 519 |
| 306 | 28 | 30, 31, or 519 |
| 307 | 28 | 30, 31, or 519 |
| 308 | 28 | 30, 31, or 519 |
| 309 | 28 | 30, 31, or 519 |
| 310 | 28 | 30, 31, or 519 |
| 311 | 28 | 30, 31, or 519 |
| 312 | 28 | 30, 31, or 519 |

| L1 | L2 | L3 |
|---|---|---|
| 313 | 28 | 30, 31, or 519 |
| 314 | 28 | 30, 31, or 519 |
| 315 | 28 | 30, 31, or 519 |
| 316 | 28 | 30, 31, or 519 |
| 317 | 28 | 30, 31, or 519 |
| 318 | 28 | 30, 31, or 519 |
| 319 | 28 | 30, 31, or 519 |
| 320 | 28 | 30, 31, or 519 |
| 321 | 28 | 30, 31, or 519 |
| 322 | 28 | 30, 31, or 519 |
| 323 | 28 | 30, 31, or 519 |
| 324 | 28 | 30, 31, or 519 |
| 325 | 28 | 30, 31, or 519 |
| 326 | 28 | 30, 31, or 519 |
| 327 | 28 | 30, 31, or 519 |
| 328 | 28 | 30, 31, or 519 |
| 329 | 28 | 30, 31, or 519 |

Figure 44B

| L1 | L2 | L3 |
|---|---|---|
| 26 or 27 | 330 | 30, 31, or 519 |
| 26 or 27 | 331 | 30, 31, or 519 |
| 26 or 27 | 332 | 30, 31, or 519 |
| 26 or 27 | 333 | 30, 31, or 519 |
| 26 or 27 | 334 | 30, 31, or 519 |
| 26 or 27 | 335 | 30, 31, or 519 |
| 26 or 27 | 336 | 30, 31, or 519 |
| 26 or 27 | 337 | 30, 31, or 519 |
| 26 or 27 | 338 | 30, 31, or 519 |
| 26 or 27 | 339 | 30, 31, or 519 |
| 26 or 27 | 340 | 30, 31, or 519 |
| 26 or 27 | 341 | 30, 31, or 519 |
| 26 or 27 | 342 | 30, 31, or 519 |
| 26 or 27 | 343 | 30, 31, or 519 |
| 26 or 27 | 344 | 30, 31, or 519 |
| 26 or 27 | 345 | 30, 31, or 519 |
| 26 or 27 | 346 | 30, 31, or 519 |
| 26 or 27 | 347 | 30, 31, or 519 |
| 26 or 27 | 348 | 30, 31, or 519 |
| 26 or 27 | 349 | 30, 31, or 519 |
| 26 or 27 | 350 | 30, 31, or 519 |
| 26 or 27 | 351 | 30, 31, or 519 |
| 26 or 27 | 352 | 30, 31, or 519 |
| 26 or 27 | 353 | 30, 31, or 519 |
| 26 or 27 | 354 | 30, 31, or 519 |
| 26 or 27 | 355 | 30, 31, or 519 |
| 26 or 27 | 356 | 30, 31, or 519 |
| 26 or 27 | 357 | 30, 31, or 519 |
| 26 or 27 | 358 | 30, 31, or 519 |
| 26 or 27 | 359 | 30, 31, or 519 |
| 26 or 27 | 360 | 30, 31, or 519 |
| 26 or 27 | 361 | 30, 31, or 519 |
| 26 or 27 | 362 | 30, 31, or 519 |
| 26 or 27 | 363 | 30, 31, or 519 |
| 26 or 27 | 364 | 30, 31, or 519 |
| 26 or 27 | 365 | 30, 31, or 519 |
| 26 or 27 | 366 | 30, 31, or 519 |
| 26 or 27 | 367 | 30, 31, or 519 |
| 26 or 27 | 368 | 30, 31, or 519 |
| 26 or 27 | 369 | 30, 31, or 519 |

| L1 | L2 | L3 |
|---|---|---|
| 26 or 27 | 370 | 30, 31, or 519 |
| 26 or 27 | 371 | 30, 31, or 519 |
| 26 or 27 | 372 | 30, 31, or 519 |
| 26 or 27 | 373 | 30, 31, or 519 |
| 26 or 27 | 374 | 30, 31, or 519 |
| 26 or 27 | 375 | 30, 31, or 519 |
| 26 or 27 | 376 | 30, 31, or 519 |
| 26 or 27 | 377 | 30, 31, or 519 |
| 26 or 27 | 378 | 30, 31, or 519 |
| 26 or 27 | 379 | 30, 31, or 519 |
| 26 or 27 | 380 | 30, 31, or 519 |
| 26 or 27 | 381 | 30, 31, or 519 |
| 26 or 27 | 382 | 30, 31, or 519 |
| 26 or 27 | 383 | 30, 31, or 519 |
| 26 or 27 | 384 | 30, 31, or 519 |
| 26 or 27 | 385 | 30, 31, or 519 |
| 26 or 27 | 386 | 30, 31, or 519 |
| 26 or 27 | 387 | 30, 31, or 519 |
| 26 or 27 | 388 | 30, 31, or 519 |
| 26 or 27 | 389 | 30, 31, or 519 |
| 26 or 27 | 390 | 30, 31, or 519 |

Figure 44C

| L1 | L2 | L3 |
|---|---|---|
| 26 or 27 | 28 | 391 |
| 26 or 27 | 28 | 392 |
| 26 or 27 | 28 | 393 |
| 26 or 27 | 28 | 394 |
| 26 or 27 | 28 | 395 |
| 26 or 27 | 28 | 396 |
| 26 or 27 | 28 | 397 |
| 26 or 27 | 28 | 398 |
| 26 or 27 | 28 | 399 |
| 26 or 27 | 28 | 400 |
| 26 or 27 | 28 | 401 |
| 26 or 27 | 28 | 402 |
| 26 or 27 | 28 | 403 |
| 26 or 27 | 28 | 404 |
| 26 or 27 | 28 | 405 |
| 26 or 27 | 28 | 406 |
| 26 or 27 | 28 | 407 |
| 26 or 27 | 28 | 408 |
| 26 or 27 | 28 | 409 |
| 26 or 27 | 28 | 410 |
| 26 or 27 | 28 | 411 |
| 26 or 27 | 28 | 412 |
| 26 or 27 | 28 | 413 |
| 26 or 27 | 28 | 414 |
| 26 or 27 | 28 | 415 |
| 26 or 27 | 28 | 416 |
| 26 or 27 | 28 | 417 |
| 26 or 27 | 28 | 418 |
| 26 or 27 | 28 | 419 |
| 26 or 27 | 28 | 420 |
| 26 or 27 | 28 | 421 |
| 26 or 27 | 28 | 422 |
| 26 or 27 | 28 | 423 |
| 26 or 27 | 28 | 424 |
| 26 or 27 | 28 | 425 |
| 26 or 27 | 28 | 426 |
| 26 or 27 | 28 | 427 |
| 26 or 27 | 28 | 428 |
| 26 or 27 | 28 | 429 |
| 26 or 27 | 28 | 430 |

| L1 | L2 | L3 |
|---|---|---|
| 26 or 27 | 28 | 431 |
| 26 or 27 | 28 | 432 |
| 26 or 27 | 28 | 433 |
| 26 or 27 | 28 | 434 |
| 26 or 27 | 28 | 435 |
| 26 or 27 | 28 | 436 |
| 26 or 27 | 28 | 437 |
| 26 or 27 | 28 | 438 |
| 26 or 27 | 28 | 439 |
| 26 or 27 | 28 | 440 |
| 26 or 27 | 28 | 441 |
| 26 or 27 | 28 | 442 |
| 26 or 27 | 28 | 443 |
| 26 or 27 | 28 | 444 |
| 26 or 27 | 28 | 445 |
| 26 or 27 | 28 | 446 |
| 26 or 27 | 28 | 447 |
| 26 or 27 | 28 | 448 |
| 26 or 27 | 28 | 449 |
| 26 or 27 | 28 | 450 |
| 26 or 27 | 28 | 451 |
| 26 or 27 | 28 | 452 |
| 26 or 27 | 28 | 453 |
| 26 or 27 | 28 | 454 |
| 26 or 27 | 28 | 455 |
| 26 or 27 | 28 | 456 |
| 26 or 27 | 28 | 457 |
| 26 or 27 | 28 | 458 |
| 26 or 27 | 28 | 459 |
| 26 or 27 | 28 | 460 |
| 26 or 27 | 28 | 461 |
| 26 or 27 | 28 | 462 |
| 26 or 27 | 28 | 463 |
| 26 or 27 | 28 | 464 |
| 26 or 27 | 28 | 465 |
| 26 or 27 | 28 | 466 |
| 26 or 27 | 28 | 467 |
| 26 or 27 | 28 | 468 |
| 26 or 27 | 28 | 469 |
| 26 or 27 | 28 | 470 |

| L1 | L2 | L3 |
|---|---|---|
| 26 or 27 | 28 | 471 |
| 26 or 27 | 28 | 472 |
| 26 or 27 | 28 | 473 |
| 26 or 27 | 28 | 474 |

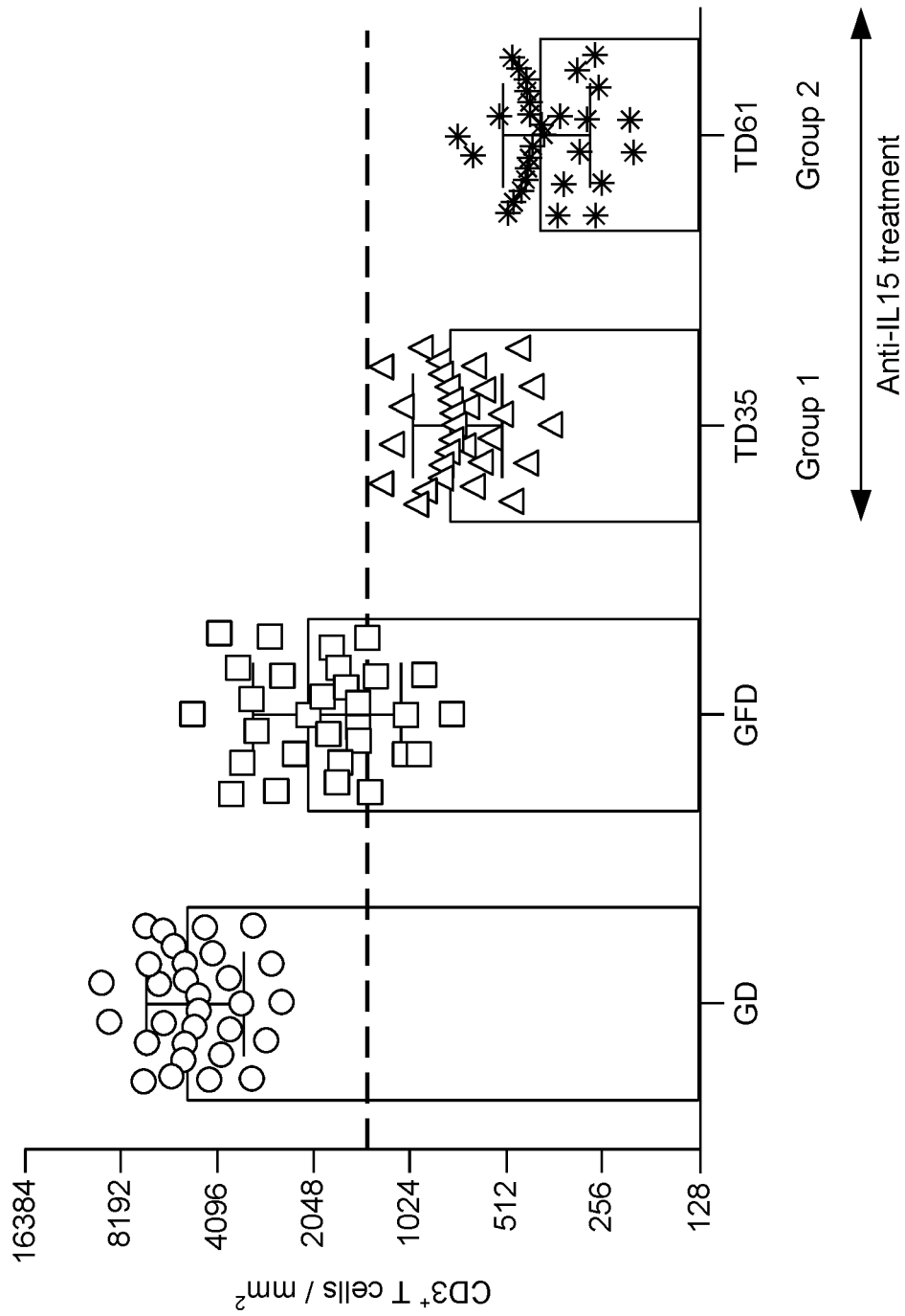

POLYNUCLEOTIDES ENCODING ANTIBODIES THAT SPECIFICALLY BIND TO HUMAN IL-15

CROSS REFERENCE TO RELATED APPLICATIONS

This application is a divisional of U.S. application Ser. No. 16/471,616, which is a National Stage Entry of International Application No. PCT/US2017/067917, filed Dec. 21, 2017, which claims priority to U.S. Provisional Application No. 62/437,143, filed Dec. 21, 2016, the contents of each of which is incorporated by reference herein in its entirety and for all purposes.

REFERENCE TO A SEQUENCE LISTING

This application includes a Sequence Listing entitled 2873_2730002_Seqlisting_ST25, generated on Dec. 10, 2021 with a size of 215,625 bytes. The Sequence Listing is incorporated by reference.

FIELD

The disclosure relates generally to the field of recombinant antibody production. More particularly, the disclosure relates to recombinant antibodies that specifically bind to human IL-15, whether uncomplexed or in a complex with the IL-15 Receptor-alpha.

BACKGROUND

Various references, including patents, published patent applications, technical articles, sequence accession numbers, and other references are cited throughout the specification. Each such reference is incorporated by reference herein, in its entirety and for all purposes.

The cytokine interleukin 15 (IL-15) is a member of IL-2 superfamily, which is secreted by a large number of cell types and tissues, including monocytes, macrophages, dendritic cells (DC), keratinocytes, fibroblasts and nerve cells. IL-15 binds to and signals through a complex composed of IL-2 receptor beta chain (CD122) and the common gamma chain (gamma-C, CD132). In vitro, IL-15 shares several biological activities with IL-2. In vivo, the specificity for IL-15 versus IL-2 is provided by unique private α-chain receptor (IL-15Rα) that completes the IL-15Rα/IL-2Rβγ heterotrimeric high-affinity receptor complex.

IL-15 has been isolated from synovial tissues from rheumatoid arthritis patients and reported to induce inflammatory cytokines and chemokines such as tumor-necrosis factor-α, IL-1β (Waldman T A (2004) Arthritis Res. Ther. 6:174-177). Blockade of IL-15 activity in a xenograft mouse model of human psoriasis resulted in a resolution of psoriasis (Villadsen L S et al. (2003) J. Clin. Invest. 112:1571-80). Increased levels of IL-15 complex in patients with T cell large granular lymphocytic leukemia, γΔ/Δ T cell lymphoma were reported (Chen J et al. (2012) Blood. 119:137-143).

Using mice deficient in IL-15, researchers have also shown that inhibiting the IL-15 signalling pathway can provide prophylactic or therapeutic benefit in several immune-mediated conditions, such as, experimental autoimmune encephalomyelitis (EAE; a model of multiple sclerosis), colitis, inflammatory bowel disease, psoriasis and arthritis.

In mouse models, overexpression of IL-15 in intestinal epithelia cells triggers a celiac-like enteropathy. In humans, the upregulation of IL-15 expression is a hallmark of celiac disease. IL-15 is overexpressed in both the lamina propria and intestinal epithelium of patients with active untreated celiac disease compared with healthy controls and gluten free diet treated celiac patients and IL-15 levels in the gut correlate with the degree of mucosal damage (Abadie V et al. (2014) Immunol. Rev. 260:221-234).

DISC0280 is a potent anti-IL-15 antibody with opposing mechanisms of action in vitro and in vivo. (Finch D K et al. (2011) Br. J. Pharmacol. 162:480-490). Disadvantageously, it was found that DISC0280 bound to the IL-15 receptor α binding site on IL-15 which allowed trans-presentation of IL-15 by the DISC0280 in vivo, similar to the trans-presentation by soluble IL-15 receptor α. Thus, DISC0280 acts as an agonist of IL-15 in vivo.

Two anti-IL-15 antibodies have been described as being able to neutralize the activity of IL-15 without competing with the binding of IL-15 to IL-15Rα. A fully human monoclonal anti-IL-15 antibody, AMG 714 (Amgen) showed improvements in disease activity in a phase I-II dose-escalation trial in patients with active rheumatoid arthritis (Baslund B et al. (2005) Arthritis Rheum. 52:2686-2692). A humanized antibody named huB-E29 has also been described to block the IL-15 activity in vitro and in vivo in a mouse model without competing with the binding of IL-15 to IL-15Rα (WO 16/001275).

Clinical trials examining new therapies for the treatment of celiac disease have as their endpoints: a) Attenuation of gluten-induced small intestinal mucosal injury as measured by the V/C ratio. The V/C is the morphometric measure of the length of the small intestinal villi with respect to the depth of the crypts taken from an intestinal biopsy sample. (b) Attenuation of gluten-induced small intestinal mucosal inflammation as measured by the enumeration of intraepithelial lymphocytes (IELs) in histological sections. (c) Attenuation of gluten-induced serum antibodies such as anti-gliadin antibodies and autoantibodies against transglutaminase. Currently no therapeutic has been shown to be efficacious in treating celiac disease as measured by the aforementioned endpoints. This disclosure features antibodies that attenuate gluten-induced small intestinal mucosal injury (improved V/C ratio), attenuate gluten-induced small intestinal mucosal inflammation (reduced IEL counts) and attenuate gluten-induced serum antibodies (reduced anti-gliadin antibodies) as measured in a rhesus macaque model of celiac disease. Antibodies of this disclosure present a new treatment for patients with celiac disease and other inflammatory diseases in which IL-15 is involved.

SUMMARY

In a first aspect, the disclosure features antibodies comprising a variable heavy chain and a variable light chain, which antibodies specifically binds to an epitope comprising the Gln 108 residue of human IL-15 (e.g., wherein the IL-15 is complexed with IL-15Rα). In some embodiments, human IL-15 comprises the amino acid sequence of SEQ ID NO: 511. In some embodiments, the epitope may further comprise the Ser 7 and Asn 112 residues of human IL-15 (e.g., wherein the IL-15 is complexed with IL-15Rα). In some embodiments, the antibody preferably has an affinity for the epitope comprising a KD of less than about $1.8 \times 10^{-9}$ M as determined by surface plasmon resonance. In some embodiments, the KD may be less than about $1.0 \times 10^{-9}$ M. In some embodiments, the antibody preferably has an affinity for the epitope comprising a KD of less than about $2 \times 10^{-10}$ M as determined by surface plasmon resonance. In some embodiments, the KD may be from about $1.6 \times 10^{-10}$ M to about $1.8 \times 10^{-10}$ M as determined by surface plasmon resonance. In some embodiments, the antibodies may inhibit proliferation of Natural Killer (NK) cells, e.g., NK-92 cells, at an $IC_{50}$ of less than about 900 pM in an NK cell proliferation assay, including from about 0.1 pM to about 900 pM. In some embodiments, the antibodies may inhibit proliferation of NK cells at an $IC_{50}$ of from about 1 pM to about 60 pM in an NK cell proliferation assay. In some embodiments, the antibodies may inhibit proliferation of NK cells at an $IC_{50}$ of from about 5 pM to about 35 pM in an NK cell proliferation assay. The antibodies may inhibit proliferation of NK cells at an $IC_{50}$ of from about 5 pM to about 25 pM in an NK cell proliferation assay. The antibodies can be capable of neutralizing IL-15. The antibodies can be capable of decreasing circulating NK cells.

In another aspect, the disclosure features antibodies that specifically bind to human IL-15, and that comprise an HCDR1 comprising the amino acid sequence of SEQ ID NO: 16, an HCDR2 comprising the amino acid sequence of SEQ ID NO: 17, an HCDR3 comprising the amino acid sequence of SEQ ID NO: 20, an LCDR1 comprising the amino acid sequence of SEQ ID NO: 25, an LCDR2 comprising the amino acid sequence of SEQ ID NO: 28, and an LCDR3 comprising the amino acid sequence of SEQ ID NO: 29. The human IL-15 may be complexed with the IL-15 Receptor-alpha. The antibodies are IL-15 antagonists. Polynucleotides encoding such antibodies are further provided.

In some embodiments, the antibodies (e.g., antibodies comprising HCDR1, HCDR2, HCDR3, LCDR1, LCDR2, and LCDR3 comprising the amino acid sequences of SEQ ID NOs: 16, 17, 20, 25, 28, and 29, respectively) may comprise an HCDR2 comprising the amino acid sequence of SEQ ID NO: 18. In some embodiments, the antibodies (e.g, antibodies comprising HCDR1, HCDR2, HCDR3, LCDR1, LCDR2, and LCDR3 comprising the amino acid sequences of SEQ ID NOs: 16, 17 or 18, 20, 25, 28, and 29, respectively) may comprise an LCDR1 comprising the amino acid sequence of SEQ ID NO: 27 and an LCDR3 comprising the amino acid sequence of SEQ ID NO: 31. In some embodiments, the antibodies may comprise a heavy chain variable region comprising the amino acid sequence of SEQ ID NO: 454 and a light chain variable region comprising the amino acid sequence of SEQ ID NO: 8, and/or may comprise a light chain comprising the amino acid sequence of SEQ ID NO: 9. In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 25, 28, and 29, respectively) may comprise a heavy chain FR3 comprising the amino acid sequence of SEQ ID NO: 12, or SEQ ID NO:13. Polynucleotides encoding such antibodies are further provided.

In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 25, 28, and 29, respectively) may comprise an LCDR1 comprising the amino acid sequence of SEQ ID NO: 26 and an LCDR3 comprising the amino acid sequence of SEQ ID NO: 31. In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 25 or 26, 28, and 29 or 31, respectively) may comprise a heavy chain variable region comprising the amino acid sequence of SEQ ID NO: 4 and a light chain variable region comprising the amino acid sequence of SEQ ID NO: 455, and/or may comprise a light chain comprising the amino acid sequence of SEQ ID NO: 456. Polynucleotides encoding such antibodies are further provided.

In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 25, 28, and 29, respectively) may comprise an LCDR1 comprising the amino acid sequence of SEQ ID NO: 27 and an LCDR3 comprising the amino acid sequence of SEQ ID NO: 30. In some embodiments, the antibodies (e.g, antibodies comprising HCDR1, HCDR2, HCDR3, LCDR1, LCDR2, and LCDR3 comprising the amino acid sequences of SEQ ID NOs: 16, 17 or 18, 20, 27, 28, and 30, respectively) may comprise a heavy chain variable region comprising the amino acid sequence of SEQ ID NO: 4 and a light chain variable region comprising the amino acid sequence of SEQ ID NO: 457, and/or may comprise a light chain comprising the amino acid sequence of SEQ ID NO: 458. Polynucleotides encoding such antibodies are further provided.

In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 25, 28, and 29, respectively) may comprise an LCDR1 comprising the amino acid sequence of SEQ ID NO: 27, and an LCDR3 comprising the amino acid sequence of SEQ ID NO: 29, wherein Xaa5 of SEQ ID NO: 29 is Phe (e.g., SEQ ID NO: 519). In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 27, 28, and 519, respectively) may comprise a heavy chain variable region comprising the amino acid sequence of SEQ ID NO: 4 and a light chain variable region comprising the amino acid sequence of SEQ ID NO: 459, and/or may comprise a light chain comprising the amino acid sequence of SEQ ID NO: 460. Polynucleotides encoding such antibodies are further provided.

In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 25, 28, and 29, respectively, and optionally an HFR3 comprising the amino acid sequence of SEQ ID NO:12 or 13) may comprise an LCDR1 comprising the amino acid sequence of SEQ ID NO: 26 and an LCDR3 comprising the amino acid sequence of SEQ ID NO: 30. In some embodiments, (e.g., antibodies comprising HCDR1, HCDR2, HCDR3, LCDR1, LCDR2, and LCDR3 comprising the amino acid sequences of SEQ ID NOs: 16, 17 or 18, 20, 26, 28, and 30, respectively) the antibodies may comprise an HCDR2 comprising the amino acid sequence of SEQ ID NO: 18, and a heavy chain FR3 comprising the amino acid sequence of SEQ ID NO: 13. In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 26, 28, and 30, respectively, and optionally an HFR3 comprising the amino acid sequence of SEQ ID NO:12 or 13) may comprise a heavy chain variable region comprising the amino acid sequence of SEQ ID NO: 4. In some embodiments, the antibodies (e.g., antibodies comprising HCDR1, HCDR2, HCDR3, LCDR1, LCDR2, and LCDR3 comprising the amino acid sequences of SEQ ID NOs: 16, 17 or 18, 20, 26, 28, and 30, respectively, and optionally an HFR3 comprising the amino acid sequence of SEQ ID NO:12 or 13 or antibodies comprising a heavy chain variable region comprising the amino acid sequence of SEQ ID NO:4) may comprise a light chain variable region comprising the amino acid sequence of SEQ ID NO: 5, and/or may comprise a light chain comprising the amino acid sequence of SEQ ID NO: 6. Polynucleotides encoding such antibodies are further provided.

In some embodiments, the antibodies (e.g., antibodies comprising HCDR1, HCDR2, HCDR3, LCDR1, LCDR2, and LCDR3 comprising the amino acid sequences of SEQ ID NOs: 16, 17 20, 25, 28, and 29, respectively, and optionally an HFR3 comprising the amino acid sequence of SEQ ID NO:12) may comprise an HCDR2 comprising the amino acid sequence of SEQ ID NO: 19, an LCDR1 comprising the amino acid sequence of SEQ ID NO: 27, an LCDR3 comprising the amino acid sequence of SEQ ID NO: 31, and a heavy chain FR3 comprising the amino acid sequence of SEQ ID NO: 14. In some embodiments, the antibodies (e.g., antibodies comprising HCR1, HCDR2, HCDR3, LCDR1, LCDR2, and LCDR3 comprising the amino acid sequences of SEQ ID NOs: 16, 19, 20, 27, 28, and 31, and an HFR3 comprising the amino acid sequence of SEQ ID NO:14) may comprise a heavy chain variable region comprising the amino acid sequence of SEQ ID NO: 7 and a light chain variable region comprising the amino acid sequence of SEQ ID NO: 8, and/or may comprise a light chain comprising the amino acid sequence of SEQ ID NO: 9. Polynucleotides encoding such antibodies are further provided.

In another aspect, the disclosure features antibodies that specifically bind to human IL-15 (e.g., IL-15 complexed with IL-15Rα), and that comprise a heavy chain variable region comprising the amino acid sequence of SEQ ID NO: 1 and a light chain variable region comprising the amino acid sequence of SEQ ID NO: 2. In some embodiments, the antibodies may comprise a heavy chain variable region comprising the amino acid sequence of SEQ ID NO: 4 and a light chain variable region comprising the amino acid sequence of SEQ ID NO: 5. In some embodiments, the antibodies may comprise a heavy chain variable region comprising the amino acid sequence of SEQ ID NO: 454 and a light chain variable region comprising the amino acid sequence of SEQ ID NO: 8. In some embodiments, the antibodies may comprise a heavy chain variable region comprising the amino acid sequence of SEQ ID NO: 4 and a light chain variable region comprising the amino acid sequence of SEQ ID NO: 455. In some embodiments, the antibodies may comprise a heavy chain variable region comprising the amino acid sequence of SEQ ID NO: 4 and a light chain variable region comprising the amino acid sequence of SEQ ID NO: 457. In some embodiments, the antibodies may comprise a heavy chain variable region comprising the amino acid sequence of SEQ ID NO: 4 and a light chain variable region comprising the amino acid sequence of SEQ ID NO: 459. Polynucleotides encoding such antibodies are further provided.

In another aspect, the disclosure features antibodies that specifically bind to human IL-15 (e.g., IL-15 complexed with IL-15Rα), and that comprises a heavy chain variable region comprising the amino acid sequence of SEQ ID NO:4 and a light chain variable region comprising the amino acid sequence of SEQ ID NO:8; a heavy chain variable region comprising the amino acid sequence of SEQ ID NO:4 and a light chain variable region comprising the amino acid sequence of SEQ ID NO:503; a heavy chain variable region comprising the amino acid sequence of SEQ ID NO:4 and a light chain variable region comprising the amino acid sequence of SEQ ID NO:505; a heavy chain variable region comprising the amino acid sequence of SEQ ID NO:4 and a light chain variable region comprising the amino acid sequence of SEQ ID NO:507; a heavy chain variable region comprising the amino acid sequence of SEQ ID NO:4 and a light chain variable region comprising the amino acid sequence of SEQ ID NO:509; a heavy chain variable region comprising the amino acid sequence of SEQ ID NO:4 and a light chain variable region comprising the amino acid sequence of SEQ ID NO:510; a heavy chain variable region comprising the amino acid sequence of SEQ ID NO:454 and a light chain variable region comprising the amino acid sequence of SEQ ID NO:455; a heavy chain variable region comprising the amino acid sequence of SEQ ID NO:454 and a light chain variable region comprising the amino acid sequence of SEQ ID NO:503; a heavy chain variable region comprising the amino acid sequence of SEQ ID NO:454 and a light chain variable region comprising the amino acid sequence of SEQ ID NO:457; a heavy chain variable region comprising the amino acid sequence of SEQ ID NO:454 and a light chain variable region comprising the amino acid sequence of SEQ ID NO:505; a heavy chain variable region comprising the amino acid sequence of SEQ ID NO:454 and a light chain variable region comprising the amino acid sequence of SEQ ID NO:506; a heavy chain variable region comprising the amino acid sequence of SEQ ID NO:454 and a light chain variable region comprising the amino acid sequence of SEQ ID NO:507; a heavy chain variable region comprising the amino acid sequence of SEQ ID NO:454 and a light chain variable region comprising the amino acid sequence of SEQ ID NO:5; a heavy chain variable region comprising the amino acid sequence of SEQ ID NO:454 and a light chain variable region comprising the amino acid sequence of SEQ ID NO:509; or a heavy chain variable region comprising the amino acid sequence of SEQ ID NO:454 and a light chain variable region comprising the amino acid sequence of SEQ ID NO:510. Polynucleotides encoding such antibodies are further provided.

The consensus sequence for the antibody VH is SEQ ID NO: 1, and encompasses the VH sequence of SEQ ID NO: 4 and SEQ ID NO: 454. The consensus sequence for the antibody VL is SEQ ID NO: 2, and encompasses the VL sequence of SEQ ID NO: 5, SEQ ID NO: 8, SEQ ID NO: 455, SEQ ID NO: 457, and SEQ ID NO: 459. The consensus sequence for the antibody L chain is SEQ ID NO: 3, and encompasses the L chain sequence of SEQ ID NO: 6, SEQ ID NO: 9, SEQ ID NO: 456, SEQ ID NO: 458, and SEQ ID NO: 460. The consensus sequence for the antibody VH FR3 is SEQ ID NO: 12, and encompasses the VH FR3 sequence of SEQ ID NO: 13 and SEQ ID NO: 14. The consensus sequence for the antibody VH CDR1 is SEQ ID NO: 17, and encompasses the VH sequence of SEQ ID NO: 18 and SEQ ID NO: 19. The consensus sequence for the antibody VL CDR1 is SEQ ID NO: 25, and encompasses the VH sequence of SEQ ID NO: 26 and SEQ ID NO: 27. The consensus sequence for the antibody VL CDR3 is SEQ ID NO: 29, and encompasses the VH sequence of SEQ ID NO: 30 and SEQ ID NO: 31 and SEQ ID NO:519.

Any of the antibodies that bind to IL-15 (e.g., human IL-15 complexed with IL-15Rα) as described or exemplified herein, including those of any of the preceding paragraphs, may comprise an IgG constant domain. In some embodiments, the IgG constant domain may comprise an IgG1 constant domain. In some embodiments, the IgG1 constant domain may comprise SEQ ID NO: 32, SEQ ID NO: 33, SEQ ID NO: 34, SEQ ID NO: 35, SEQ ID NO: 36, SEQ ID NO: 37, SEQ ID NO: 38 or SEQ ID NO: 39. In some embodiments, the IgG constant domain may comprise an IgG2 constant domain. In some embodiments, the IgG2 constant domain may comprise SEQ ID NO: 40, SEQ ID NO: 41, SEQ ID NO: 42 or SEQ ID NO: 43. In some embodiments, the IgG constant domain may comprise an IgG4 constant domain. In some embodiments, the IgG4 constant domain may comprise SEQ ID NO: 44, SEQ ID NO: 45, SEQ ID NO: 46, SEQ ID NO: 47, SEQ ID NO: 48, SEQ ID NO: 49, SEQ ID NO: 50 or SEQ ID NO: 51.

Any of the antibodies that bind to IL-15 (e.g., human IL-15 complexed with IL-15Rα) as described or exemplified herein, including those of any of the preceding paragraphs, may be formulated as a composition with a carrier or excipient. The carrier may comprise a pharmaceutically acceptable carrier.

In some embodiments, a method of treating Celiac disease comprises administering an antibody that binds to IL-15 (e.g., human IL-15 complexed with IL-15Rα) to a subject in need thereof. Administration of the IL-15 antibody can repair the mucosa of the small intestine in the subject. Administration of the IL-15 antibody can increase the mean villous height vs. crypt depths (V/C) ratio in the subject. Administration of the IL-15 antibody can increase the height of small intestinal villi in the subject. Administration of the IL-15 antibody can decrease anti-gliadin antibodies in the subject. Administration of the IL-15 antibody can repair gluten-induced small intestinal mucosal injury in a subject.

Any of the antibodies that bind to IL-15 (e.g., human IL-15 complexed with IL-15Rα) as described or exemplified herein, including those of any of the preceding paragraphs, may be administered as part of a treatment regimen to a subject in need thereof. Thus, in another aspect, the disclosure features methods for treating a subject in need thereof with an IL-15 antibody. The subject is preferably a human being. The antibodies may be administered as part of a treatment regimen to treat any autoimmune or inflammatory disease or condition where IL-15 is dysregulated, in particular, where IL-15 is upregulated.

In some detailed embodiments, the method may be for treating Celiac disease, and comprise administering to the subject any antibody as described or exemplified herein, including those of any of the preceding paragraphs, that binds to IL-15 (e.g. human IL-15 complexed with IL-15Rα), which antibody may be in a composition, which may include a pharmaceutically acceptable carrier or excipient. In some embodiments, a method for repairing the mucosa of a small intestine in a subject having gluten sensitivity, gluten allergy, or Celiac disease comprises administering to the subject any antibody as described or exemplified herein, including those of any of the preceding paragraphs, that binds to IL-15 (e.g. human IL-15 complexed with IL-15Rα), which antibody may be in a composition, which may include a pharmaceutically acceptable carrier or excipient. In some embodiments, a method for increasing the mean villous height vs. crypt depths (V/C) ratio in a subject having gluten sensitivity, gluten allergy, or Celiac disease comprises administering to the subject any antibody as described or exemplified herein, including those of any of the preceding paragraphs, that binds to IL-15 (e.g. human IL-15 complexed with IL-15Rα), which antibody may be in a composition, which may include a pharmaceutically acceptable carrier or excipient. In some embodiments, a method for increasing the height of small intestinal villi in a subject having gluten sensitivity, gluten allergy, or Celiac disease comprises administering to the subject any antibody as described or exemplified herein, including those of any of the preceding paragraphs, that binds to IL-15 (e.g. human IL-15 complexed with IL-15Rα), which antibody may be in a composition, which may include a pharmaceutically acceptable carrier or excipient. In some embodiments, a method for decreasing anti-gliadin antibodies in a subject in need thereof comprises administering to the subject any antibody as described or exemplified herein, including those of any of the preceding paragraphs, that binds to IL-15 (e.g. human IL-15 complexed with IL-15Rα), which antibody may be in a composition, which may include a pharmaceutically acceptable carrier or excipient. In some embodiments, a method for repairing gluten-induced small intestinal mucosal injury comprises administering to the subject any antibody as described or exemplified herein, including those of any of the preceding paragraphs, that binds to IL-15 (e.g. human IL-15 complexed with IL-15Rα), which antibody may be in a composition, which may include a pharmaceutically acceptable carrier or excipient. In some embodiments, the subject has gluten sensitivity, a gluten allergy, or Celiac disease. In some embodiments, the method may be for treating refractory Celiac disease, and comprise administering to the subject any antibody as described or exemplified herein, including those of any of the preceding paragraphs, that binds to IL-15 (e.g., human IL-15 complexed with IL-15Rα), which antibody may be in a composition, which may include a pharmaceutically acceptable carrier or excipient. In some embodiments, the method may be for treating rheumatoid arthritis, and comprise administering to the subject any antibody as described or exemplified herein, including those of any of the preceding paragraphs, that binds to IL-15 (e.g., human IL-15 complexed with IL-15Rα), which antibody may be in a composition, which may include a pharmaceutically acceptable carrier or excipient. In some embodiments, the method may be for treating psoriasis, and comprise administering to the subject any antibody as described or exemplified herein, including those of any of the preceding paragraphs, that binds to IL-15 (e.g., human IL-15 complexed with IL-15Rα), which antibody may be in a composition, which may include a pharmaceutically acceptable carrier or excipient. In some embodiments, the method may be for treating inflammatory bowel disease, and comprise administering to the subject any antibody as described or exemplified herein, including those of any of the preceding paragraphs, that binds to IL-15 (e.g., human IL-15 complexed with IL-15Rα), which antibody may be in a composition, which may include a pharmaceutically acceptable carrier or excipient. In some embodiments, the method may be for treating type 1 diabetes, and comprise administering to the subject any antibody as described or exemplified herein, including those of any of the preceding paragraphs, that binds to IL-15 (e.g., human IL-15 complexed with IL-15Rα), which antibody may be in a composition, which may include a pharmaceutically acceptable carrier or excipient. In some embodiments, the method may be for treating alopecia areata, and comprise administering to the subject any antibody as described or exemplified herein, including those of any of the preceding paragraphs, that binds to IL-15 (e.g., human IL-15 complexed with IL-15Rα), which antibody may be in a composition, which may include a pharmaceutically acceptable carrier or excipient. In some embodiments, the method may be for treating T cell large granular lymphocytic leukemia, and comprise administering to the subject any antibody as described or exemplified herein, including those of any of the preceding paragraphs, that binds to IL-15 (e.g., human IL-15 complexed with the IL-15 Receptor-alpha), which antibody may be in a composition, which may include a pharmaceutically acceptable carrier or excipient. In some embodiments, the method may be for treating or inhibiting symptoms of gluten exposure, for example, gluten exposure in a patient who has a gluten sensitivity or allergy, and comprise administering to the subject any antibody as described or exemplified herein, including those of any of the preceding paragraphs, that binds to IL-15 (e.g., human IL-15 complexed with IL-15Rα), which antibody may be in a composition, which may include a pharmaceutically acceptable carrier or excipient. The one or more symptoms of gluten exposure may include one or more of muscle pain, body pain, joint pain, fatigue, bloating, gas, nausea, cramps, constipation, diarrhea, skin rash, headache, migraine headache, depression, anxiety, brain fog, and/or irritability. See, Biesiekierski J R (2015) United European Gastroenterol. J. 3:160-165.

Any of the antibodies that bind to IL-15 (e.g., human IL-15 complexed with IL-15Rα) as described or exemplified herein, including those of any of the preceding paragraphs, may be used in the manufacture of a medicament. Any such antibodies may be used to treat any autoimmune or inflammatory disease or condition where IL-15 is dysregulated. In some embodiments, the antibodies may be used for treating Celiac disease or in the manufacture of a medicament for treating Celiac disease. The antibodies may be used for treating refractory Celiac disease or in the manufacture of a medicament for treating refractory Celiac disease. In some embodiments, the antibodies may be used for treating rheumatoid arthritis or in the manufacture of a medicament for treating rheumatoid arthritis. In some embodiments, the antibodies may be used for treating psoriasis or in the manufacture of a medicament for treating psoriasis. In some embodiments, the antibodies may be used for treating inflammatory bowel disease or in the manufacture of a medicament for treating inflammatory bowel disease. In some embodiments, the antibodies may be used for treating type 1 diabetes or in the manufacture of a medicament for treating type 1 diabetes. In some embodiments, the antibodies may be used for treating alopecia areata or in the manufacture of a medicament for treating alopecia areata. In some embodiments, the antibodies may be used for treating T cell large granular lymphocytic leukemia or in the manufacture of a medicament for treating T cell large granular lymphocytic leukemia.

Any of the antibodies that bind to IL-15 (e.g., human IL-15 complexed with IL-15Rα) as described or exemplified herein, including those of any of the preceding paragraphs, may be used in an in vitro method for detecting IL-15 (optionally complexed with IL-15Rα) in a tissue sample isolated from a subject, the method comprising contacting the antibody with a tissue sample isolated from a subject to form an antibody-IL-15 complex (optionally further complexed with the IL-15 Receptor-alpha), and detecting the complex in the tissue sample. Any of the antibodies that bind to IL-15 as described or exemplified herein, including those of any of the preceding paragraphs, may be used in an in vitro method for detecting the IL-15 complex with the IL-15 Receptor-alpha in a tissue sample isolated from a subject, comprising contacting the antibody with a tissue sample isolated from a subject to form an antibody-antigen complex of the antibody with IL-15 and IL-15 receptor α complex, and detecting the antibody-antigen complex in the tissue sample.

In another aspect, the disclosure further features transformed cells that express any of the antibodies that bind to IL-15 (e.g., human IL-15 complexed with IL-15Rα) as described or exemplified herein, including those of any of the preceding paragraphs. In some embodiments, the transformed cell may be a mammalian cell. In some embodiments, the mammalian cell may be a Chinese Hamster Ovary cell.

In another aspect, the disclosure further features polynucleotides that encode any of the antibodies that bind to IL-15 (e.g., human IL-15 complexed with IL-15Rα) as described or exemplified herein, including those of any of the preceding paragraphs. In some embodiments, a polynucleotide encoding an antibody heavy chain variable region comprises the nucleic acid sequence of SEQ ID NO: 517. In some embodiments, a polynucleotide encoding an antibody light chain variable region comprises the nucleic acid sequence of SEQ ID NO: 518. Vectors comprising these polynucleotides are also provided. Cells comprising these polynucleotides or vectors are also provided. Cells comprising a polynucleotide comprising a nucleic acid that encodes the variable heavy chain of an antibody that binds to IL-15 (e.g., human IL-15 complexed with IL-15Rα) as described or exemplified herein, including those of any of the preceding paragraphs and a nucleic acid that encodes the variable light chain of the antibody are also provided. The nucleic acid that encodes the variable heavy chain and the nucleic acid that encodes the variable light chain can be on the same vector or on different vectors.

BRIEF DESCRIPTION OF THE DRAWINGS

FIG. 1 shows binding of anti-IL-15 antibodies to the human IL-15 complex with the IL-15 Receptor-alpha, or uncomplexed IL-15Rα. The binding of representative hybridoma supernatants to uncomplexed recombinant human IL-15Rα or recombinant IL-15 complex with the IL-15 Receptor-alpha was determined by cell ELISA (cELISA) and ELISA. Results are expressed at relative fluorescence units.

FIG. 2A shows the inhibition of IL-15 mediated CTLL-2 proliferation by representative anti-IL-15 antibodies diluted at 2000, 200 and 20 pM, and FIG. 2B shows inhibition in a full dose response for 72 hours. Results are expressed as relative luminescence units.

FIGS. 4-33 show BIACORE® profiles of anti-IL-15 variants detailing antibody capture levels, single point affinity measurements and sequence changes relative to the parental antibody, Antibody 4.

FIGS. 34A, 34B, and 34C show anti-IL-15 antibody variants, detailing their heavy and light chain amino acid substitutions relative to the parent antibody, Antibody 4.

FIG. 36 shows the binding kinetics of Antibody 4 variants and AMG714 binding to IL-15 complexed with the IL-15 Receptor-alpha. Binding kinetics was determined using surface plasmon resonance on a Biacore T200 (GE Healthcare) system. Antibody 4 variants bound the IL-15 complex with higher affinity than AMG714.

Figure 38:
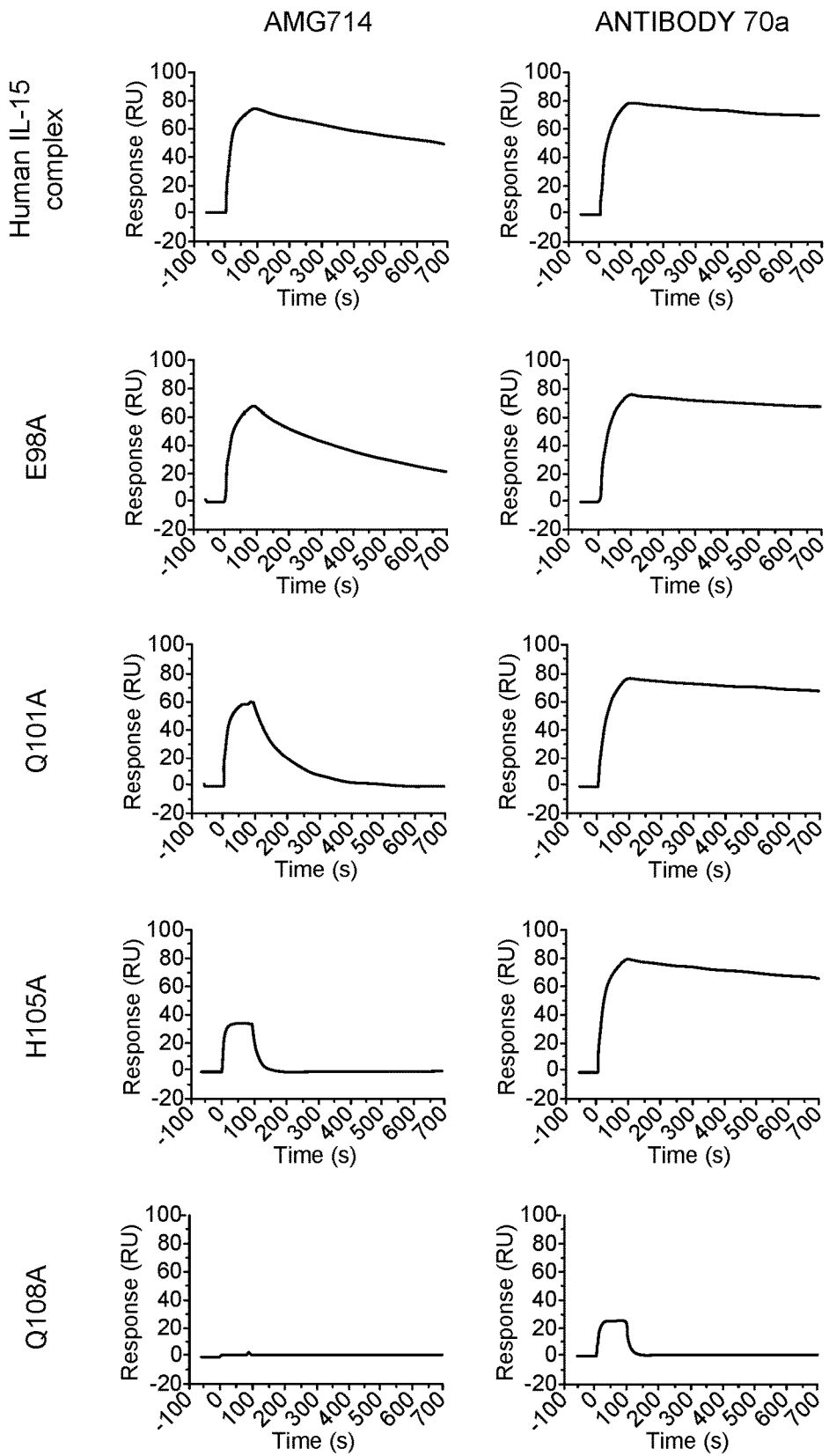

FIG. 38 shows surface-exposed residues on IL-15 were converted to alanine by site-directed mutagenesis and were co-expressed with human IL-15Rα in EXPI293® F. cells. Binding of anti-IL-15 antibodies to purified IL-15 variants was assessed using surface plasmon resonance on a BICAORE® T200 (GE Healthcare) system. AMG714 had significantly reduced or no binding to E98A, Q101A, H105A or Q108A as characterized by rapid dissociation or a faster dissociation rate. Antibody 70a had low binding to Q108A as characterized by a reduced association rate and a rapid dissociation.

Figure 39B:
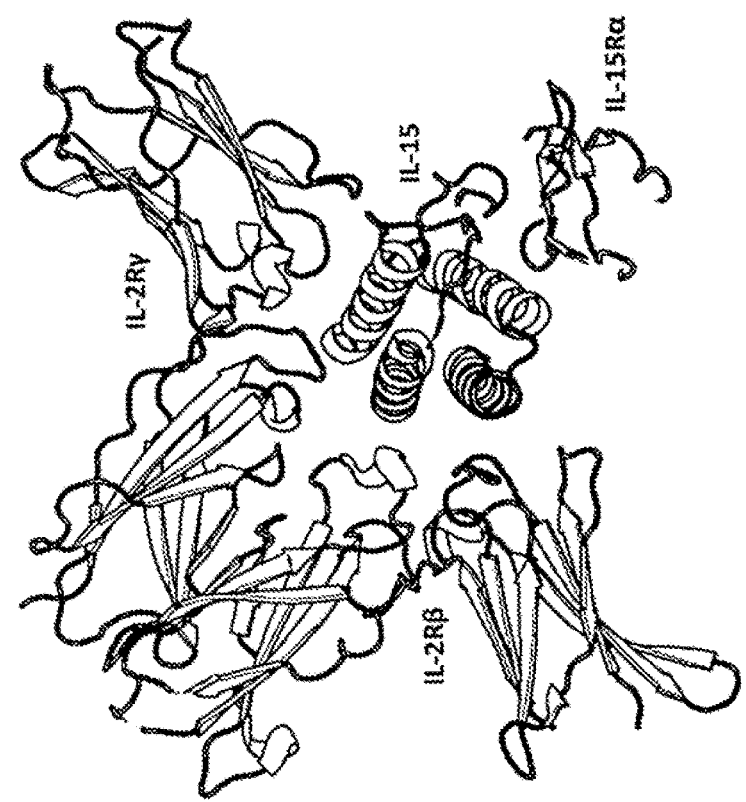
Figure 39A:
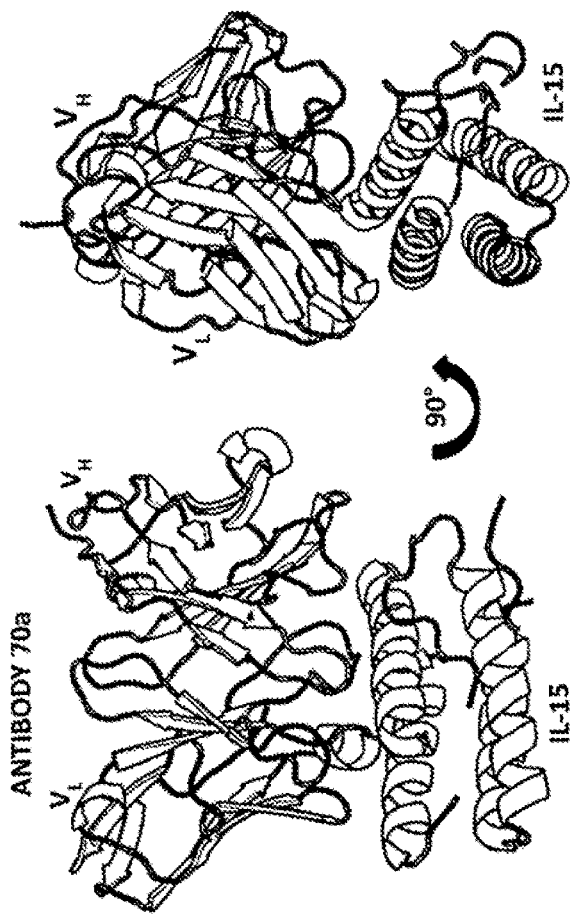

FIGS. 39A and 39B show the crystal structures of Antibody 70a.FAb/IL-15 complex and the quaternary IL-15 receptor complex. (FIG. 39A) Cartoon representation of the variable region of Antibody 70a.FAb binding human IL-15, front and side views. (FIG. 39B) The quaternary structure of the functional IL-15 complex. Cartoon representation of human IL-15 bound to IL-15Rα, IL-2Rβ and IL-2Rγ (pdb code, 4GS7). The Antibody 70a.FAb disrupts the binding of IL-15 to IL-2Rβ and IL-2Rγ. The Antibody 70a FAb binds to IL-15 distal to IL-15Rα and is able to bind the IL-15/IL-15Rα complex.

Figure 39E:
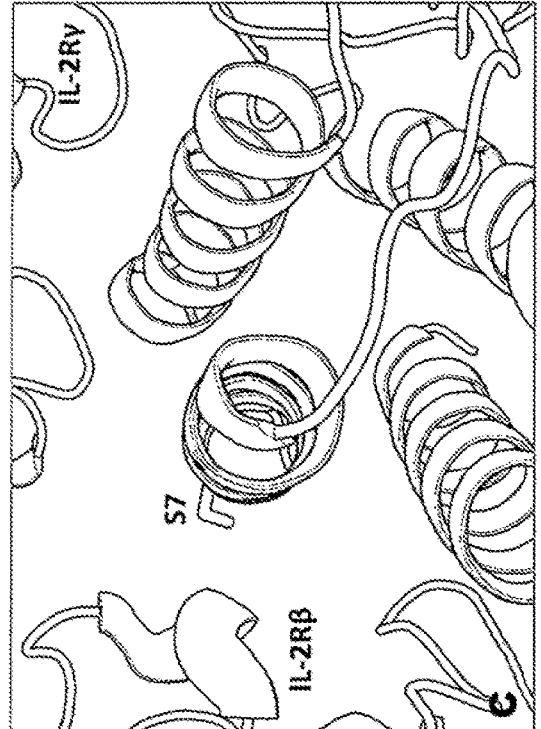
Figure 39C:
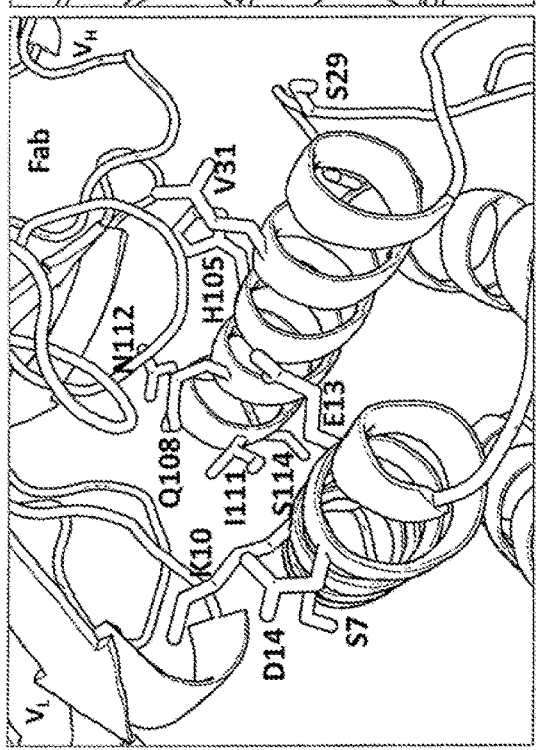
Figure 39D:
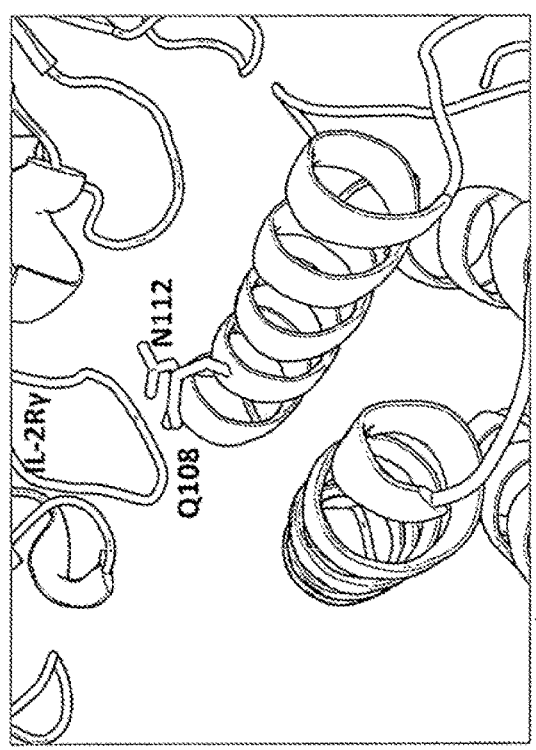

FIGS. 39C, 39D, and 39E show key binding residues of IL-15 interacting with Antibody 70a, IL-2Rγ and IL-2Rβ. Only the IL-15 residues that contact respective partner proteins via hydrogen bonding are depicted and numbered. (FIG. 39C) Residues used by IL-15 for interactions with Antibody 70a FAb (FIG. 39D) Selected IL-15 residues that mediate hydrogen bonding with IL-2Rγ including Q108, N112. (FIG. 39E) The IL-15 residue, S7, makes a hydrogen bond with IL-2Rβ.

Figure 39H:
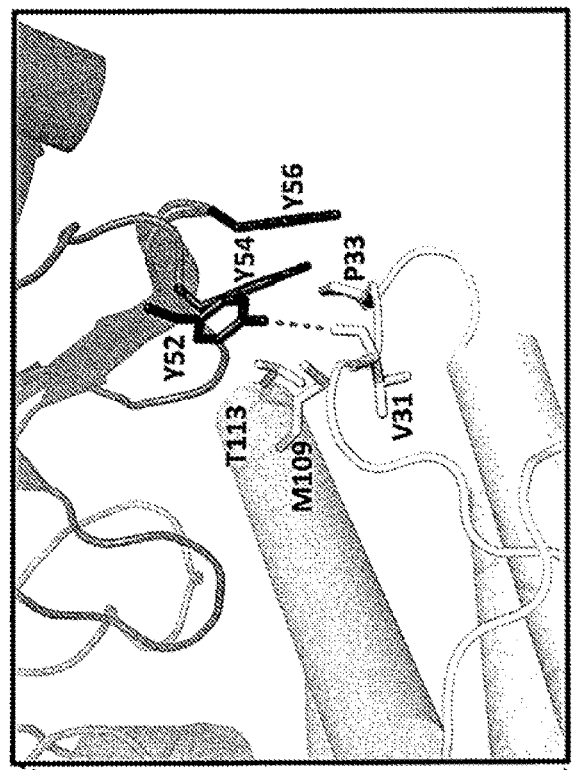
Figure 39G:
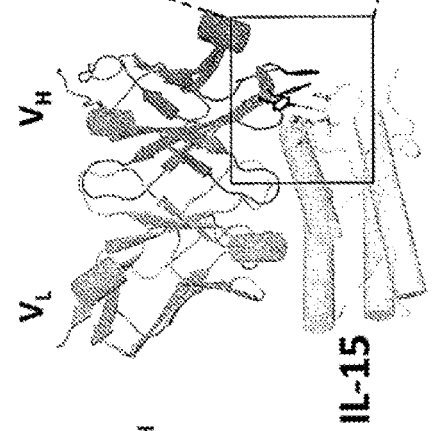
Figure 39F:
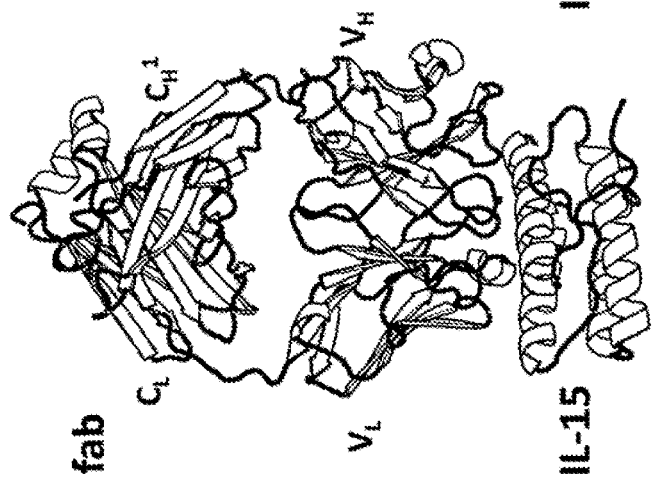

FIGS. 39F, 39G, and 39H show the crystal structure of human IL-15 with Antibody 70a. (FIG. 39F) Cartoon representation showing the antibody FAb binding to human IL-15. (FIG. 39G) A triple tyrosine motif comprising Y52/54/56 in CDRH2 is a key binding determinant of the antibody with human IL-15. (FIG. 39H) A close-up of the YYY motif from Antibody 70a mediating interactions with human IL-15. This motif veils and protects hydrophobic residues around helix 4 of IL-15 preventing solvation. Side chains from IL-15 and CDRH2 of residues involved in this interaction are indicated in white and black sticks, respectively.

Figure 40:
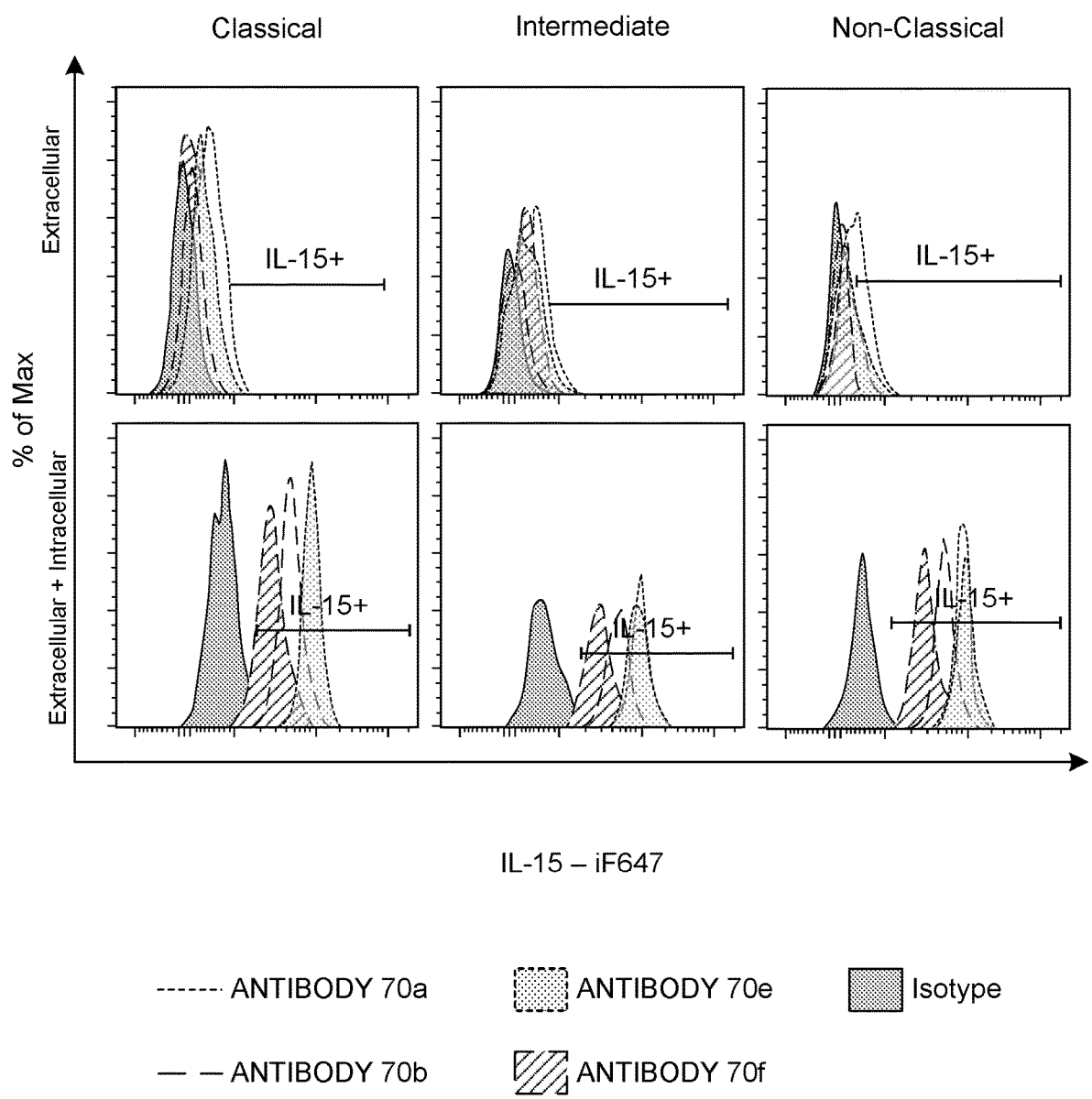

FIG. 40 shows binding of Antibody 70 variants to human IL-15. Extracellular and intracellular IL-15 binding by anti-IL-15 mAbs was assessed on human monocyte subsets: classical, intermediate and non-classical monocytes. Anti-KLH C3 IgG1 isotype control was included in the analysis (filled). Representative Donor A data shown.

Figure 41:
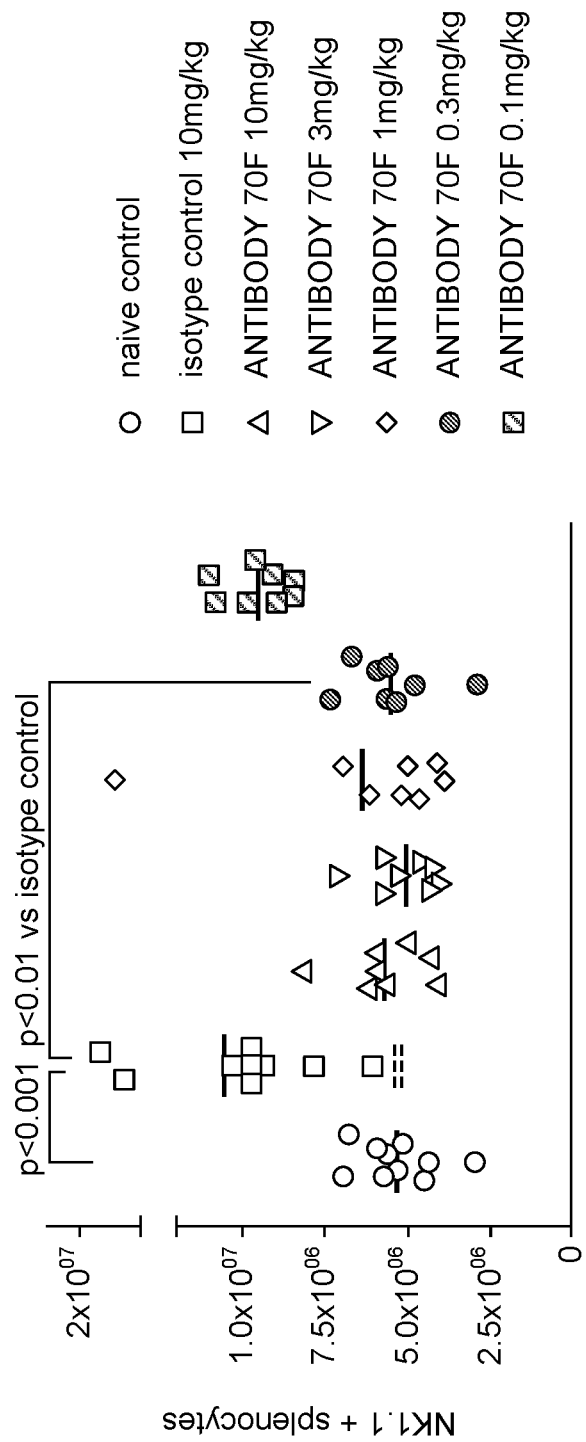

FIG. 41 shows inhibition of IL-15 activity in mice by an exemplary anti-IL-15 antibody. The results presented are an enumeration of circulating NK cells in the spleen of mice injected with vehicle control or IL-15/IL-15Rα-Fc complex followed by exemplary anti-IL-15 antibody or an Anti-KLH C3 IgG1 isotype control. Results are expressed as mean±standard deviation of 8 animals per group.

Figure 42:
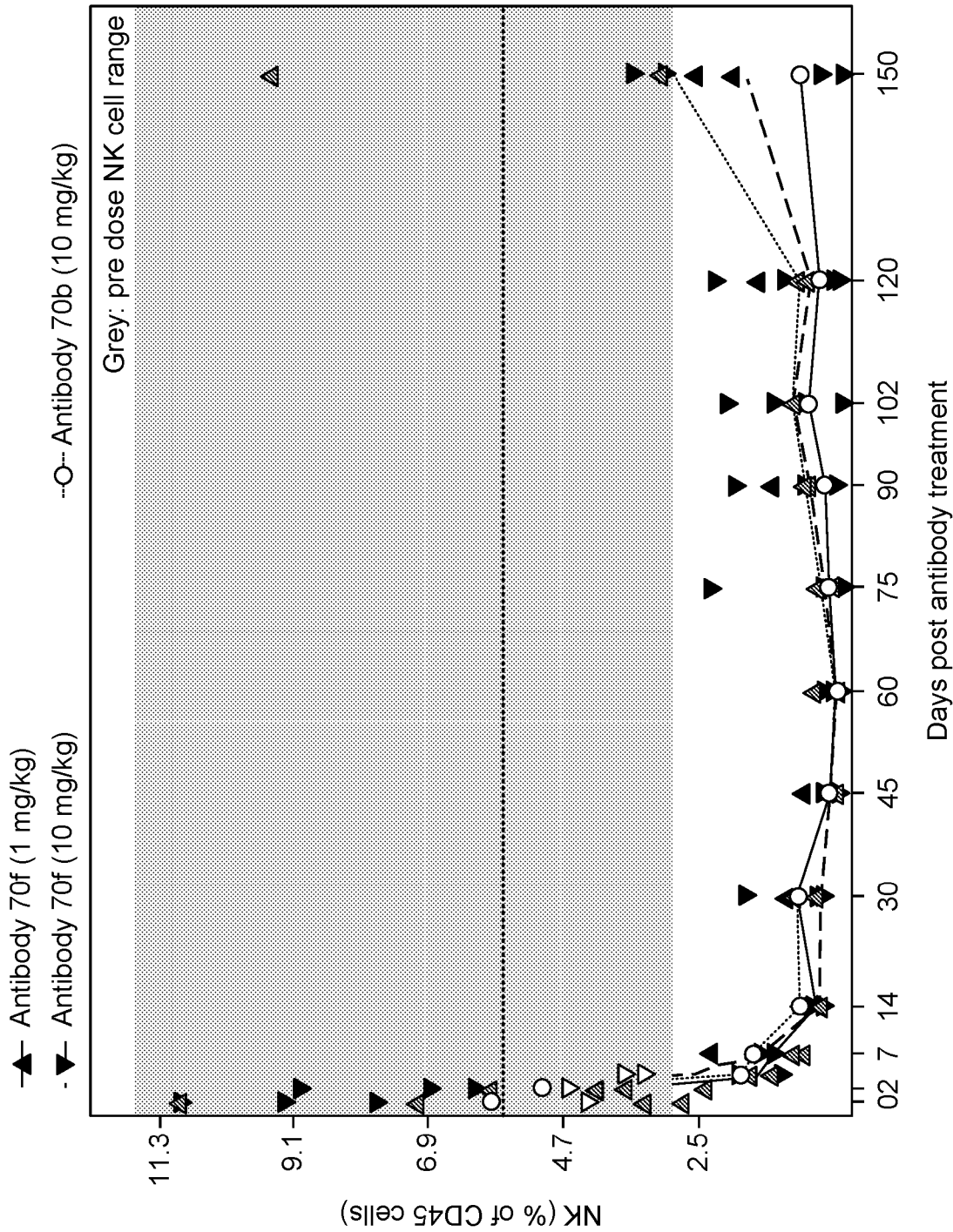

FIG. 42 shows inhibition of circulating median NK cell numbers in cynomolgus monkeys by exemplary anti-IL-15 antibodies. Enumeration of circulating median NK cells in cynomolgus monkeys injected with exemplary anti-IL-15 antibodies tested at 10 mg/kg or 1 mg/kg. Circulating median numbers of NK cells were quantified by expression of the NK cell marker CD159a (NKG2A) and CD16. Results are expressed as individual timepoints for each monkey with the solid line indicating the median NK cell numbers per group (n=4).

FIGS. 43A, 43B, and 43C show various HCDR1, HCDR2, and HCDR3 combinations.

FIGS. 44A, 44B, and 44C show various LCDR1, LCDR2, and LCDR2 combinations.

Figure 45A:
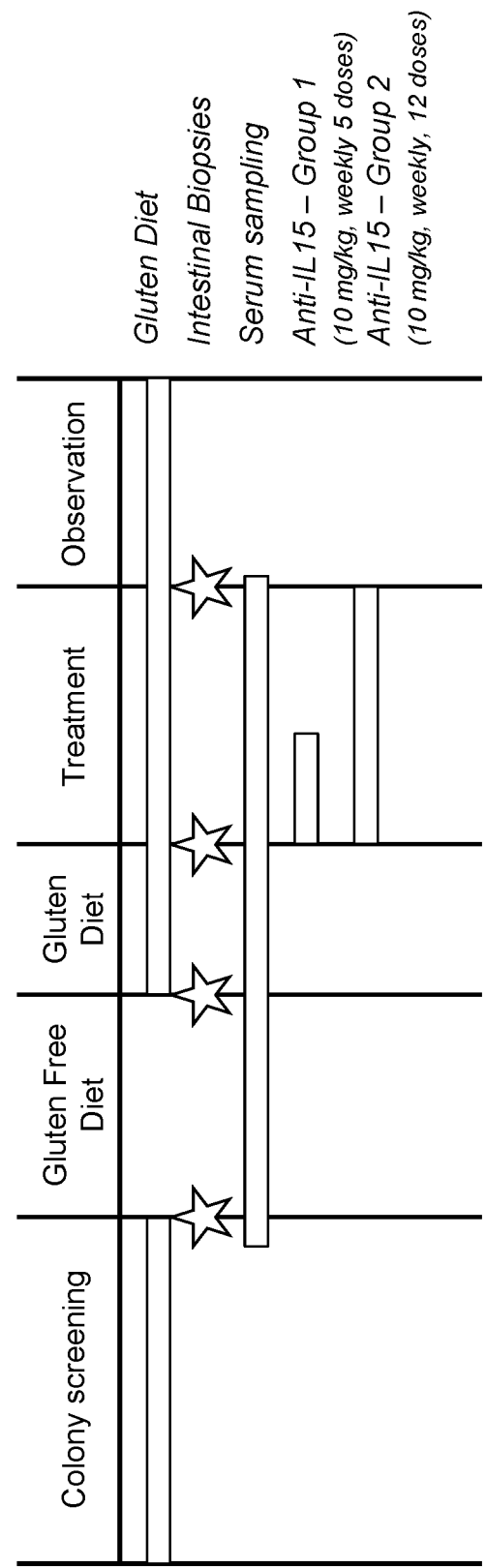

FIG. 45A shows the study design of the rhesus macaque celiac disease model indicating stages, endpoints and treatment with Anti-IL15 antibody in two groups.

Figure 45B:
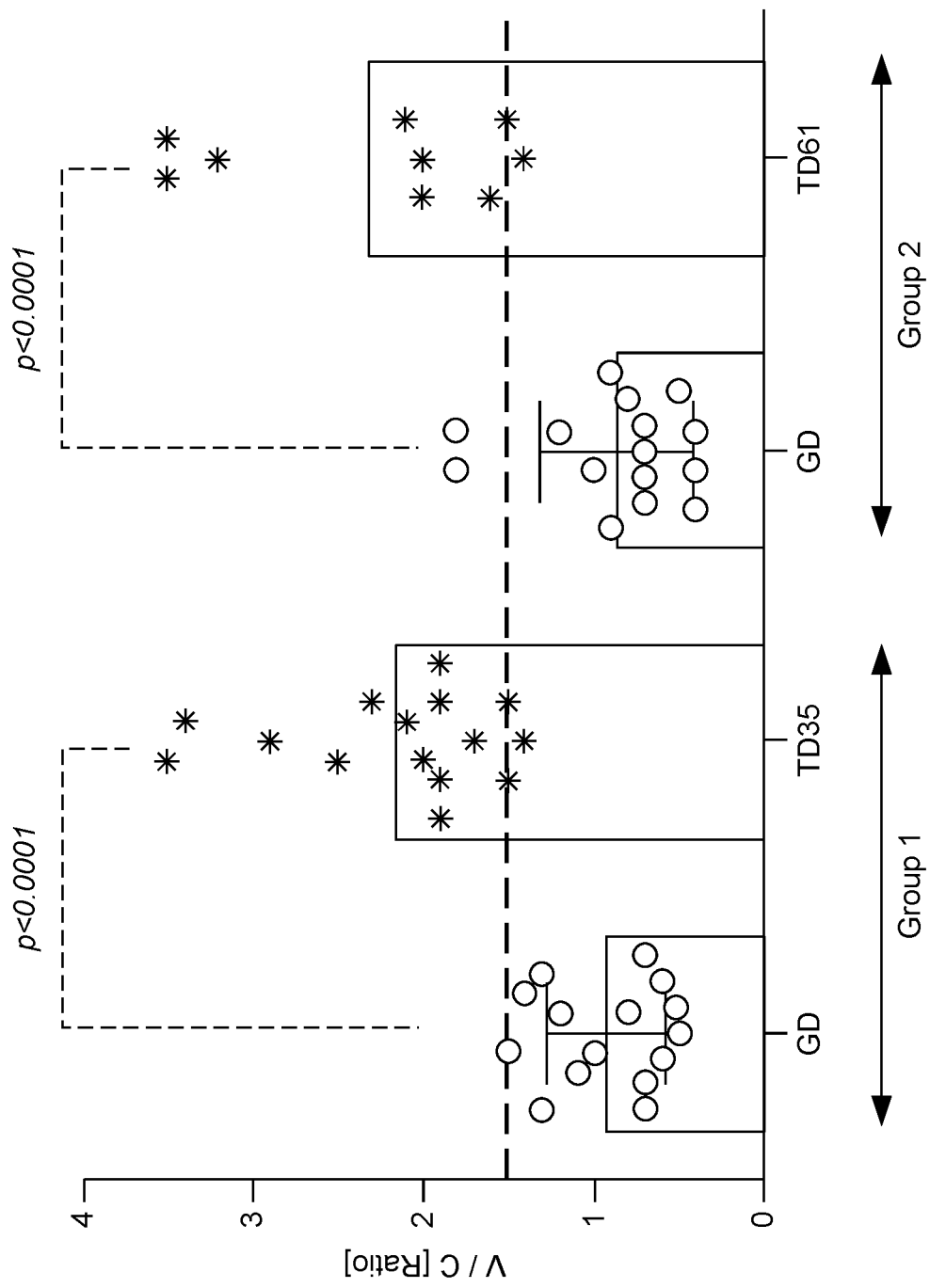

FIG. 45B shows the attenuation of gluten-induced small intestinal mucosal injury by Anti-IL15 treatment as measured by the ratio between small intestinal villous heights and crypt depths (V/C). Intestinal jejunum wedge biopsies collected from two groups of macaques at time points corresponding to 6 months of GD diet, 35 days of aIL-15 treatment in group 1 macaques (TD35), and 61 days of treatment in group 2 macaques (TD61) were used to determine the V/C ratios.

FIG. 45C shows the attenuation of gluten-induced small intestinal mucosal inflammation by Anti-IL15 treatment as measured by the enumeration of intraepithelial lymphocytes (IELs) in histological sections. Time points reflect 6 months of GD diet, 3 months of GFD diet, 35 days post Anti-IL15 treatment in group 1 macaques (TD35), and 61 days of treatment in group 2 macaques (TD61). Dashed blue lines indicate healthy control baselines.

Figure 45D:
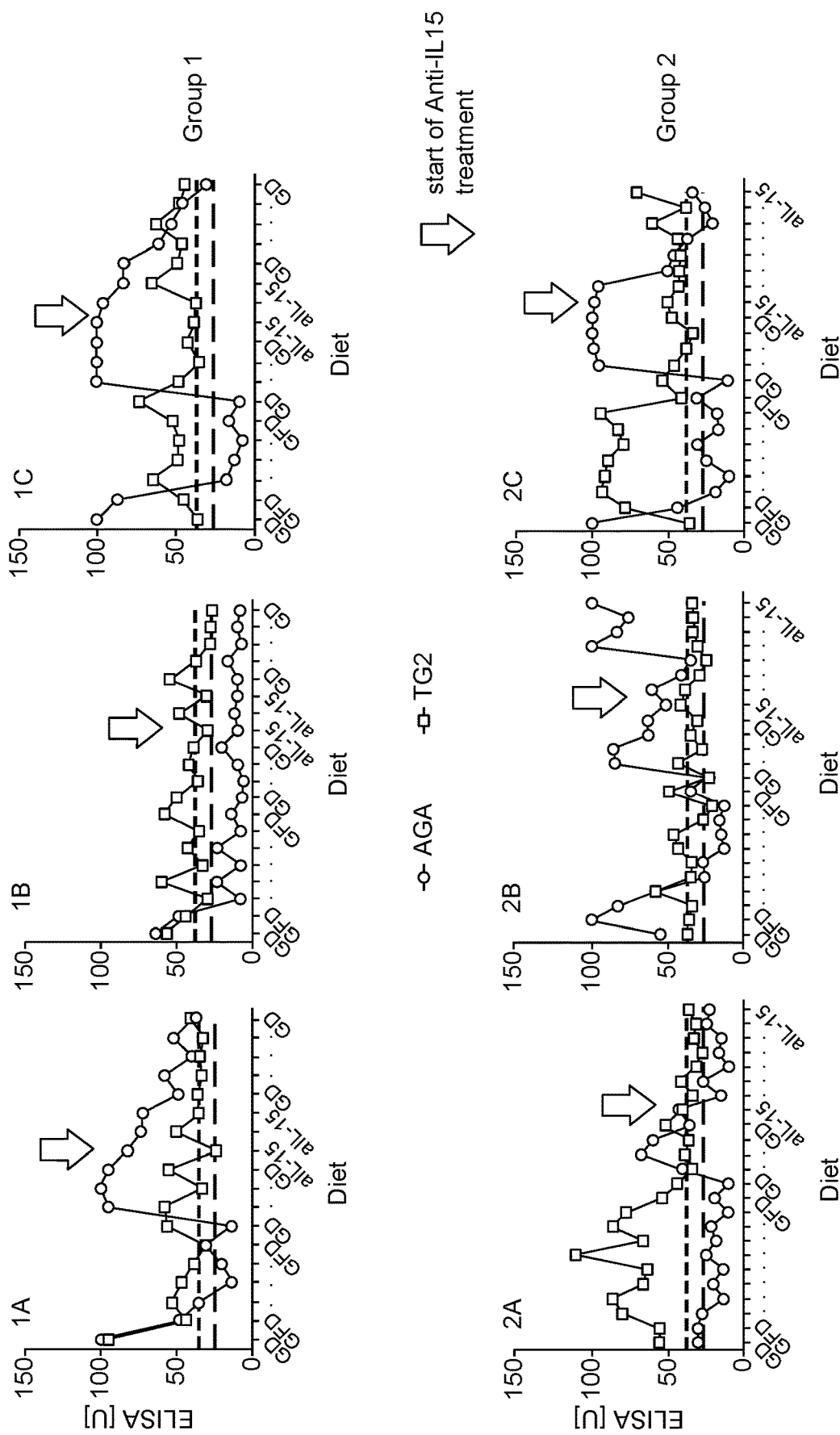

FIG. 45D shows the attenuation of gluten-induced serum antibodies (anti-gliadin antibodies) by Anti-IL15 treatment. AGA is anti-gliadin antibodies; TG2 is anti-transglutaminase 2 autoantibodies. Distances between time points correspond to two-weeks intervals. Negative base line levels are indicated by dashed lines. Start of Anti-IL15 treatment is indicated by an arrow.

DETAILED DESCRIPTION

Various terms relating to aspects of disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" and "patient" are used interchangeably and include any animal. Mammals are preferred, including companion mammals (e.g., cat, dog), farm mammals (e.g., pig, horse, cow), rodents (e.g., mice, rabbits, rats, guinea pigs), and non-human primates. Human beings are highly preferred.

As used herein, "IL-15 complex" refers to the interaction between IL-15 and the IL-15 Receptor alpha (IL-15Rα).

"Specificity" in the context of antibody-antigen interactions is not necessarily an absolute designation but may constitute a relative term signifying the degree of selectivity of an antibody for an antigen. Specificity of an antibody for an antigen mediated by the variable regions of the antibody, and usually by the complementarity determining regions (CDRs) of the antibody.

The disclosure provides recombinantly produced antibodies that specifically bind to free (uncomplexed) human interleukin 15 (IL-15), as well as IL-15 that has bound to the IL-15 receptor alpha (IL-15 Rα)—the IL-15 complex. The antibodies bind to their antigen with high affinity, and significantly reduce IL-15-mediated proliferation of immune cells. The antibodies antagonize IL-15.

In preferred aspects, the antibodies bind to an epitope on human IL-15 (e.g. human IL-15 complexed with IL-15Rα) that includes at least the glutamine at position 108. The epitope may further include one or more of the serine at position 7 and the asparagine at position 112 of human IL-15 (e.g. human IL-15 complexed with IL-15Rα).

The epitope for a given antibody/antigen interaction can be elucidated using a variety of experimental epitope mapping methods. The experimental methods include mutagenesis (including alanine scanning), X-ray crystallography and various other methods that are well known in the art.

An epitope for the interaction between the antigen and the antibody may include the spatial coordinates defining the atomic contacts present in the antigen-antibody interaction. The epitope may be characterized by the spatial coordinates defining the atomic contacts between the antigen and antibody. The epitope may be characterized by the amino acid residues defined by a specific criterion, e.g., by distance between atoms (e.g., non-hydrogen atoms).

In the context of an X-ray derived crystal structure defined by spatial coordinates of a complex between an antibody, e.g., a FAb fragment, and its antigen, the term epitope includes IL-15 residues characterized by having water-mediated hydrogen bonds between atom pairs; hydrogen bonds of heteroatoms between 2.5-3.5 Å; or a hydrogen bond corresponding to a donor/acceptor atom within an aromatic ring. Alternatively, a given IL-15 amino acid residue is considered to be part of an epitope if it participates in hydrophobic interaction or van der Waals interactions between atom pairs.

The epitope can also more generically include amino acid residues for which substitution by another amino acid will alter the characteristics of the interaction between the antibody and antigen (e.g., using alanine scanning). Alanine scanning mutagenesis experiments can be performed using a mutant IL-15 in which various residues of the IL-15 polypeptide have been replaced with alanine. By assessing binding of the antibody to the mutant IL-15, the importance of the particular IL-15 residues to antibody binding can be assessed. However, if burial of a nonpolar side chain occurs during the binding of antigen and antibody and results in the packing of the side chain against the antigen, then an alanine mutation at this position might not have a large impact on binding. It may be that although an alanine mutant results in reduced binding by the antibody, this does not mean that the residue is making contact, rather that the local three dimensional structure of the IL-15 could be perturbed by the introduction of an alanine. Further structural analysis of the complex, such as by X-ray crystallography, may be needed to assess contact residues between antibody and antigen.

The anti-IL-15 antibodies are preferably capable of inhibiting, reducing, or preventing the proliferation immune cells, such as natural killer (NK) cells and CD8+ T cells. In some aspects, the anti-IL-15 antibodies inhibit proliferation at an $IC_{50}$ of less than about 900 pM in an NK proliferation assay. In some aspects, the anti-IL-15 antibodies inhibit proliferation at an $IC_{50}$ of greater than 0 pM and less than about 900 pM in an NK proliferation assay. The anti-IL-15 antibodies may inhibit proliferation at an $IC_{50}$ of from about 1 pM to about 500 pM in an NK proliferation assay. The anti-IL-15 antibodies may inhibit proliferation at an $IC_{50}$ of from about 1 pM to about 250 pM in an NK proliferation assay. The anti-IL-15 antibodies may inhibit proliferation at an $IC_{50}$ of from about 1 pM to about 200 pM in an NK proliferation assay. The anti-IL-15 antibodies may inhibit proliferation at an $IC_{50}$ of from about 1 pM to about 150 pM in an NK proliferation assay. The anti-IL-15 antibodies may inhibit proliferation at an $IC_{50}$ of from about 1 pM to about 100 pM in an NK proliferation assay. The anti-IL-15 antibodies preferably inhibit proliferation at an $IC_{50}$ of from about 1 pM to about 60 pM in an NK proliferation assay. The anti-IL-15 antibodies preferably inhibit proliferation at an $IC_{50}$ of from about 5 pM to about 35 pM in an NK proliferation assay. The anti-IL-15 antibodies preferably inhibit proliferation at an $IC_{50}$ of from about 5 pM to about 30 pM in an NK proliferation assay.

As part of a suitable NK proliferation assay, cells such as CTLL-2 cells, may be cultured and induced to proliferate using a suitable concentration of a complex of IL-15 and the IL-15 Receptor alpha. Thus, a CTLL-2 proliferation assay may be used to determine the $IC_{50}$ of antibodies for proliferation inhibition. Any of the anti-IL-15 antibodies described or exemplified herein are added to the cell culture, and then the cells are incubated for a suitable period of time, including 48 hours, and assessed thereafter for proliferation or inhibition of proliferation owing to the presence of the antibodies, including by way of a cell viability assay.

As described or exemplified herein, amino acid positions assigned to CDRs and FRs may be according to Kabat Sequences of Proteins of Immunological Interest, National Institutes of Health, Bethesda, Md., 1987 and 1991 (also referred to herein as the Kabat numbering system). In addition, the amino acid positions assigned to CDRs and FRs may be according to the Enhanced Chothia Numbering Scheme (www.bioinfo.org.uk/mdex.html).

According to the numbering system of Kabat, VH FRs and CDRs may be positioned as follows: residues 1-30 (FR1), 31-35 (CDR1), 36-49 (FR2), 50-65 (CDR2), 66-94 (FR3), 95-102 (CDR3) and 103-113 (FR4), and VL FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). In some instances, variable regions may increase in length and according to the Kabat numbering system some amino acids may be designated by a number followed by a letter. This specification is not limited to FRs and CDRs as defined by the Kabat numbering system, but includes all numbering systems, including the canonical numbering system or of Chothia et al. (1987) J. Mol. Biol. 196:901-17; Chothia et al. (1989) Nature 342: 877-83; and/or Al-Lazikani et al. (1997) J. Mol. Biol. 273:927-48; the numbering system of Honnegher et al. (2001) J. Mol. Biol., 309:657-70; or the IMGT system discussed in Giudicelli et al. (1997) Nucleic Acids Res. 25:206-11. In preferred aspects, the CDRs are defined according to the Kabat numbering system.

In some particular aspects, for any of the heavy chain CDR2 subdomains described herein, according to the Kabat numbering system, the five C-terminal amino acids may not participate directly in antigen binding and, accordingly, it will be understood that any one or more of these five C-terminal amino acids may be substituted with another naturally-occurring amino acid without substantially adversely affecting antigen binding. In some aspects, for any of the light chain CDR1 subdomains described herein, according to the Kabat numbering system, the four N-terminal amino acids may not participate directly in antigen binding and, accordingly, it will be understood that any one or more of these four amino acids may be substituted with another naturally-occurring amino acid without substantially adversely affecting antigen binding. For example, as described by Padlan et al. (1995) FASEB J. 9:133-139, the five C terminal amino acids of heavy chain CDR2 and/or the four N-terminal amino acids of light chain CDR1 may not participate in antigen binding. In some aspects, both the heavy chain CDR2 and the light chain CDR1 do not directly participate in antigen binding.

In some aspects, the antibodies specifically bind to IL-15 (e.g. human IL-15 complexed with IL-15Rα), and comprise a heavy chain variable region CDR1 comprising the amino acid sequence of SEQ ID NO: 16, a heavy chain variable region CDR2 comprising the amino acid sequence of SEQ ID NO: 17 and a heavy chain variable region CDR3 comprising the amino acid sequence of SEQ ID NO: 20. In some preferred aspects, the antibodies comprise a heavy chain variable region CDR2 comprising the amino acid sequence of SEQ ID NO: 19, and in some preferred aspects, the antibodies comprise a heavy chain variable region CDR2 comprising the amino acid sequence of SEQ ID NO: 18. The antibodies may comprise a heavy chain variable region FR3 comprising the amino acid sequence of SEQ ID NO: 12, SEQ ID NO: 13, or SEQ ID NO: 14. The antibodies may further comprise a light chain variable region or a light chain. The light chain variable region may comprise the amino acid sequence of SEQ ID NO: 2, SEQ ID NO: 5, SEQ ID NO: 8, SEQ ID NO: 455, SEQ ID NO: 457, or SEQ ID NO: 459. The light chain variable region may comprise the amino acid sequence of SEQ ID NO: 503, SEQ ID NO:505, SEQ ID NO:506, SEQ ID NO:507, SEQ ID NO:509, or SEQ ID NO:510. The light chain may comprise the amino acid sequence of SEQ ID NO: 3, SEQ ID NO: 6, SEQ ID NO: 9, SEQ ID NO: 456, SEQ ID NO: 458, or SEQ ID NO: 460.

The heavy chain variable region CDR1 may comprise the amino acid sequence of any one of SEQ ID NO: 453 or SEQ ID NO: 52 through SEQ ID NO: 135. The heavy chain variable region CDR2 may comprise the amino acid sequence of any one of SEQ ID NO: 136 through SEQ ID NO: 226. The heavy chain variable region CDR3 may comprise the amino acid sequence of any one of SEQ ID NO: 227 through SEQ ID NO: 272. Suitable combinations of heavy chain variable region CDR1, CDR2, and CDR3 domains are shown in FIGS. 43A through 43C. Antibodies comprising such heavy chain variable region CDR1, CDR2, or CDR3 domains, or antibodies comprising the combinations of heavy chain variable region CDR1, CDR2, and CDR3 domains shown in FIGS. 43A through 43C may further comprise a light chain variable region or a light chain. The light chain variable region may comprise the amino acid sequence of SEQ ID NO: 2, SEQ ID NO: 5, SEQ ID NO: 8, SEQ ID NO: 455, SEQ ID NO: 457, or SEQ ID NO: 459. The light chain variable region may comprise the amino acid sequence of SEQ ID NO: 503, SEQ ID NO:505, SEQ ID NO:506, SEQ ID NO:507, SEQ ID NO:509, or SEQ ID NO:510. The light chain may comprise the amino acid sequence of SEQ ID NO: 3, SEQ ID NO: 6, SEQ ID NO: 9, SEQ ID NO: 456, SEQ ID NO: 458, or SEQ ID NO: 460.

In some aspects, the antibodies specifically bind to IL-15 (e.g. human IL-15 complexed with IL-15Rα), and comprise a light chain variable region CDR1 comprising the amino acid sequence of SEQ ID NO: 25, a light chain variable region CDR2 comprising the amino acid sequence of SEQ ID NO: 28, and a light chain variable region CDR3 comprising the amino acid sequence of SEQ ID NO: 29. In some preferred aspects, the antibodies comprise a light chain variable region CDR1 comprising the amino acid sequence of SEQ ID NO: 27, and in some preferred aspects, the antibodies comprise a light chain variable region CDR1 comprising the amino acid sequence of SEQ ID NO: 26. In some preferred aspects, the antibodies comprise a light chain variable region CDR3 comprising the amino acid sequence of SEQ ID NO: 31, and in some preferred aspects, the antibodies comprise a light chain variable region CDR3 comprising the amino acid sequence of SEQ ID NO: 30. The antibodies may further comprise a heavy chain variable region. The heavy chain variable region may comprise the amino acid sequence of SEQ ID NO: 1, SEQ ID NO: 4, SEQ ID NO: 7, or SEQ ID NO: 454.

The light chain variable region CDR1 may comprise the amino acid sequence of any one of SEQ ID NO: 273 through SEQ ID NO: 329. The light chain variable region CDR2 may comprise the amino acid sequence of any one of SEQ ID NO: 330 through SEQ ID NO: 390. The light chain variable region CDR3 may comprise the amino acid sequence of any one of SEQ ID NO: 391 through SEQ ID NO: 452. Suitable combinations of light chain variable region CDR1, CDR2, and CDR3 domains are shown in FIGS. 44A through 44C. Antibodies comprising such light chain variable region CDR1, CDR2, or CDR3 domains, or antibodies comprising the combinations of light chain variable region CDR1, CDR2, and CDR3 domains shown in FIGS. 44A through 44C may further comprise a heavy chain variable region. The heavy chain variable region may comprise the amino acid sequence of SEQ ID NO: 1, SEQ ID NO: 4, SEQ ID NO: 7, or SEQ ID NO: 454.

In some aspects, the antibodies specifically bind to IL-15 (e.g. human IL-15 complexed with IL-15Rα), and comprise a heavy chain variable region CDR1 comprising the amino acid sequence of SEQ ID NO: 16, a heavy chain variable region CDR2 comprising the amino acid sequence of SEQ ID NO: 17, a heavy chain variable region CDR3 comprising the amino acid sequence of SEQ ID NO: 20, a light chain variable region CDR1 comprising the amino acid sequence of SEQ ID NO: 25, a light chain variable region CDR2 comprising the amino acid sequence of SEQ ID NO: 28, and a light chain variable region CDR3 comprising the amino acid sequence of SEQ ID NO: 29. The antibodies may further comprise a heavy chain variable region FR3 comprising the amino acid sequence of SEQ ID NO: 12, SEQ ID NO: 13, or SEQ ID NO: 14.

In some preferred aspects, the antibodies comprise a heavy chain variable region CDR1 comprising the amino acid sequence of SEQ ID NO: 16, a heavy chain variable region CDR2 comprising the amino acid sequence of SEQ ID NO: 18, a heavy chain variable region CDR3 comprising the amino acid sequence of SEQ ID NO: 20, a light chain variable region CDR1 comprising the amino acid sequence of SEQ ID NO: 26, a light chain variable region CDR2 comprising the amino acid sequence of SEQ ID NO: 28, and a light chain variable region CDR3 comprising the amino acid sequence of SEQ ID NO: 30. The antibodies may further comprise a heavy chain variable region FR3 comprising the amino acid sequence of SEQ ID NO: 12, or SEQ ID NO: 13.

In some aspects, the antibodies specifically bind to IL-15 (e.g. human IL-15 complexed with IL-15Rα), and comprise a heavy chain variable region CDR1 comprising the amino acid sequence of SEQ ID NO: 16, a heavy chain variable region CDR2 comprising the amino acid sequence of SEQ ID NO: 19, a heavy chain variable region CDR3 comprising the amino acid sequence of SEQ ID NO: 20, a light chain variable region CDR1 comprising the amino acid sequence of SEQ ID NO: 27, a light chain variable region CDR2 comprising the amino acid sequence of SEQ ID NO: 28, and a light chain variable region CDR3 comprising the amino acid sequence of SEQ ID NO: 31. The antibodies may further comprise a heavy chain variable region FR3 comprising the amino acid sequence of SEQ ID NO: 12, SEQ ID NO: 13, or SEQ ID NO: 14.

In some aspects, the antibodies specifically bind to IL-15 (e.g. human IL-15 complexed with IL-15Rα), and comprise a heavy chain variable region CDR1 comprising the amino acid sequence of SEQ ID NO: 16, a heavy chain variable region CDR2 comprising the amino acid sequence of SEQ ID NO: 18, a heavy chain variable region CDR3 comprising the amino acid sequence of SEQ ID NO: 20, a light chain variable region CDR1 comprising the amino acid sequence of SEQ ID NO: 27, a light chain variable region CDR2 comprising the amino acid sequence of SEQ ID NO: 28, and a light chain variable region CDR3 comprising the amino acid sequence of SEQ ID NO: 31. The antibodies may further comprise a heavy chain variable region FR3 comprising the amino acid sequence of SEQ ID NO: 12 or SEQ ID NO: 14.

In some aspects, the antibodies specifically bind to IL-15 (e.g. human IL-15 complexed with IL-15Rα), and comprise a heavy chain variable region CDR1 comprising the amino acid sequence of SEQ ID NO: 16, a heavy chain variable region CDR2 comprising the amino acid sequence of SEQ ID NO: 18, a heavy chain variable region CDR3 comprising the amino acid sequence of SEQ ID NO: 20, a light chain variable region CDR1 comprising the amino acid sequence of SEQ ID NO: 26, a light chain variable region CDR2 comprising the amino acid sequence of SEQ ID NO: 28, and a light chain variable region CDR3 comprising the amino acid sequence of SEQ ID NO: 31. The antibodies may further comprise a heavy chain variable region FR3 comprising the amino acid sequence of SEQ ID NO: 12 or SEQ ID NO: 13.

In some aspects, the antibodies specifically bind to IL-15 (e.g. human IL-15 complexed with IL-15Rα), and comprise a heavy chain variable region CDR1 comprising the amino acid sequence of SEQ ID NO: 16, a heavy chain variable region CDR2 comprising the amino acid sequence of SEQ ID NO: 18, a heavy chain variable region CDR3 comprising the amino acid sequence of SEQ ID NO: 20, a light chain variable region CDR1 comprising the amino acid sequence of SEQ ID NO: 27, a light chain variable region CDR2 comprising the amino acid sequence of SEQ ID NO: 28, and a light chain variable region CDR3 comprising the amino acid sequence of SEQ ID NO: 30. The antibodies may further comprise a heavy chain variable region FR3 comprising the amino acid sequence of SEQ ID NO: 12 or SEQ ID NO: 13.

In some aspects, the antibodies specifically bind to IL-15 (e.g. human IL-15 complexed with IL-15Rα), and comprise a heavy chain variable region CDR1 comprising the amino acid sequence of SEQ ID NO: 16, a heavy chain variable region CDR2 comprising the amino acid sequence of SEQ ID NO: 18, a heavy chain variable region CDR3 comprising the amino acid sequence of SEQ ID NO: 20, a light chain variable region CDR1 comprising the amino acid sequence of SEQ ID NO: 27, a light chain variable region CDR2 comprising the amino acid sequence of SEQ ID NO: 28, and a light chain variable region CDR3 comprising the amino acid sequence of SEQ ID NO: 29 wherein Xaa5 of SEQ ID NO: 29 is F (SEQ ID NO: 519). The antibodies may further comprise a heavy chain variable region FR3 comprising the amino acid sequence of SEQ ID NO: 12 or SEQ ID NO: 13.

In some aspects, the antibodies specifically bind to IL-15 (e.g. human IL-15 complexed with IL-15Rα), and comprise a heavy chain variable region comprising a CDR2 comprising the amino acid sequence of SEQ ID NO: 18, and a light chain variable region or a light chain. The light chain variable region may comprise the amino acid sequence of SEQ ID NO: 2, SEQ ID NO: 5, SEQ ID NO: 8, SEQ ID NO: 455, SEQ ID NO: 457, or SEQ ID NO: 459. The light chain variable region may comprise the amino acid sequence of SEQ ID NO: 503, SEQ ID NO:505, SEQ ID NO:506, SEQ ID NO:507, SEQ ID NO:509, or SEQ ID NO:510. The light chain may comprise the amino acid sequence of SEQ ID NO: 6, SEQ ID NO: 9, SEQ ID NO: 456, SEQ ID NO: 458, or SEQ ID NO: 460.

The antibodies may specifically bind to IL-15 (e.g. human IL-15 complexed with IL-15Rα), and comprise, or further comprise a heavy chain variable region comprising the subdomains comprising the amino acid sequence shown in the following table:

| | FR1 | H1 | FR2 | H2 | FR3 | H3 | FR4 |
|---|---|---|---|---|---|---|---|
| SEQ ID NO: | 10 | 16 | 11 | 19 | 14 | 20 | 15 |
| SEQ ID NO: | 10 | 16 | 11 | 18 | 14 | 20 | 15 |
| SEQ ID NO: | 10 | 16 | 11 | 18 | 13 | 20 | 15 |
| SEQ ID NO: | 10 | 16 | 11 | 18 | 13 | 20 | 15 |
| SEQ ID NO: | 10 | 16 | 11 | 18 | 13 | 20 | 15 |
| SEQ ID NO: | 10 | 16 | 11 | 18 | 13 | 20 | 15 |

The antibodies may specifically bind to IL-15 (e.g. human IL-15 complexed with IL-15Rα), and comprise, or further comprise a light chain variable region comprising the subdomains comprising the amino acid sequence shown in the following table:

| | FR1 | L1 | FR2 | L2 | FR3 | L3 | FR4 |
|---|---|---|---|---|---|---|---|
| SEQ ID NO: | 21 | 27 | 22 | 28 | 23 | 31 | 24 |
| SEQ ID NO: | 21 | 27 | 22 | 28 | 23 | 31 | 24 |
| SEQ ID NO: | 21 | 26 | 22 | 28 | 23 | 31 | 24 |
| SEQ ID NO: | 21 | 27 | 22 | 28 | 23 | 30 | 24 |
| SEQ ID NO: | 21 | 27 | 22 | 28 | 23 | 519 | 24 |
| SEQ ID NO: | 21 | 26 | 22 | 28 | 23 | 30 | 24 |

In some aspects, the antibodies specifically bind to IL-15 (e.g. human IL-15 complexed with IL-15Rα), and comprise a heavy chain variable region comprising the amino acid sequence of SEQ ID NO: 1. In some preferred aspects, the antibodies comprise a heavy chain variable region comprising the amino acid sequence of SEQ ID NO: 4. In some preferred aspects, the antibodies comprise a heavy chain variable region comprising the amino acid sequence of SEQ ID NO: 7. In some preferred aspects, the antibodies comprise a heavy chain variable region comprising the amino acid sequence of SEQ ID NO: 454. The antibodies may further comprise a light chain variable region or a light chain. The light chain variable region may comprise the amino acid sequence of SEQ ID NO: 2, SEQ ID NO: 5, SEQ ID NO: 8, SEQ ID NO: 454, SEQ ID NO: 457, or SEQ ID NO: 459. The light chain variable region may comprise the amino acid sequence of SEQ ID NO: 503, SEQ ID NO:505, SEQ ID NO:506, SEQ ID NO:507, SEQ ID NO:509, or SEQ ID NO:510. The light chain may comprise the amino acid sequence of SEQ ID NO: 3, SEQ ID NO: 6, SEQ ID NO: 9, SEQ ID NO: 456, SEQ ID NO: 458, or SEQ ID NO: 460.

In some aspects, the antibodies specifically bind to IL-15 (e.g. human IL-15 complexed with IL-15Rα), and comprise a light chain variable region comprising the amino acid sequence of SEQ ID NO: 2. In some preferred aspects, the antibodies comprise a light chain variable region comprising the amino acid sequence of SEQ ID NO: 5. In some preferred aspects, the antibodies comprise a light chain variable region comprising the amino acid sequence of SEQ ID NO: 8. In some preferred aspects, the antibodies comprise a light chain variable region comprising the amino acid sequence of SEQ ID NO: 455. In some preferred aspects, the antibodies comprise a light chain variable region comprising the amino acid sequence of SEQ ID NO: 457. In some preferred aspects, the antibodies comprise a light chain variable region comprising the amino acid sequence of SEQ ID NO: 459. In some preferred aspects, the antibodies comprise a light chain variable region comprising the amino acid sequence of SEQ ID NO: 503. In some preferred aspects, the antibodies comprise a light chain variable region comprising the amino acid sequence of SEQ ID NO: 505. In some preferred aspects, the antibodies comprise a light chain variable region comprising the amino acid sequence of SEQ ID NO: 506. In some preferred aspects, the antibodies comprise a light chain variable region comprising the amino acid sequence of SEQ ID NO: 507. In some preferred aspects, the antibodies comprise a light chain variable region comprising the amino acid sequence of SEQ ID NO: 509. In some preferred aspects, the antibodies comprise a light chain variable region comprising the amino acid sequence of SEQ ID NO: 510. The antibodies may further comprise a heavy chain variable region. The heavy chain variable region may comprise the amino acid sequence of SEQ ID NO: 1, SEQ ID NO: 4, SEQ ID NO: 7, or SEQ ID NO: 454.

In some aspects, the antibodies specifically bind to IL-15 (e.g. human IL-15 complexed with IL-15Rα), and comprise a light chain comprising the amino acid sequence of SEQ ID NO: 3. In some preferred aspects, the antibodies comprise a light chain comprising the amino acid sequence of SEQ ID NO: 6. In some preferred aspects, the antibodies comprise a light chain comprising the amino acid sequence of SEQ ID NO: 9. In some preferred aspects, the antibodies comprise a light chain comprising the amino acid sequence of SEQ ID NO: 456. In some preferred aspects, the antibodies comprise a light chain comprising the amino acid sequence of SEQ ID NO: 458. In some preferred aspects, the antibodies comprise a light chain comprising the amino acid sequence of SEQ ID NO: 460. The antibodies may further comprise a heavy chain variable region. The heavy chain variable region may comprise the amino acid sequence of SEQ ID NO: 1, SEQ ID NO: 4, SEQ ID NO: 7, or SEQ ID NO: 454.

The antibodies may comprise a heavy chain variable region comprising the amino acid sequence of SEQ ID NO: 1, and a light chain variable region comprising the amino acid sequence of SEQ ID NO: 2. The antibodies may comprise a heavy chain variable region comprising the amino acid sequence of SEQ ID NO: 1, and a light chain variable region comprising the amino acid sequence of SEQ ID NO: 5. The antibodies may comprise a heavy chain variable region comprising the amino acid sequence of SEQ ID NO: 1, and a light chain variable region comprising the amino acid sequence of SEQ ID NO: 8. The antibodies may comprise a heavy chain variable region comprising the amino acid sequence of SEQ ID NO: 1, and a light chain variable region comprising the amino acid sequence of SEQ ID NO: 455. The antibodies may comprise a heavy chain variable region comprising the amino acid sequence of SEQ ID NO: 1, and a light chain variable region comprising the amino acid sequence of SEQ ID NO: 457. The antibodies may comprise a heavy chain variable region comprising the amino acid sequence of SEQ ID NO: 1, and a light chain variable region comprising the amino acid sequence of SEQ ID NO: 459. Antibodies comprising such heavy chain variable region and light chain variable region pairs preferably specifically bind to IL-15 (e.g. human IL-15 complexed with IL-15Rα).

The antibodies may comprise a heavy chain variable region comprising the amino acid sequence of SEQ ID NO: 4, and a light chain variable region comprising the amino acid sequence of SEQ ID NO: 2. The antibodies may comprise a heavy chain variable region comprising the amino acid sequence of SEQ ID NO: 4, and a light chain variable region comprising the amino acid sequence of SEQ ID NO: 5. The antibodies may comprise a heavy chain variable region comprising the amino acid sequence of SEQ ID NO: 4, and a light chain variable region comprising the amino acid sequence of SEQ ID NO: 8. The antibodies may comprise a heavy chain variable region comprising the amino acid sequence of SEQ ID NO: 4, and a light chain variable region comprising the amino acid sequence of SEQ ID NO: 455. The antibodies may comprise a heavy chain variable region comprising the amino acid sequence of SEQ ID NO: 4, and a light chain variable region comprising the amino acid sequence of SEQ ID NO: 457. The antibodies may comprise a heavy chain variable region comprising the amino acid sequence of SEQ ID NO: 4, and a light chain variable region comprising the amino acid sequence of SEQ ID NO: 459. The antibodies may comprise a heavy chain variable region comprising the amino acid sequence of SEQ ID NO: 4, and a light chain variable region comprising the amino acid sequence of SEQ ID NO: 503. The antibodies may comprise a heavy chain variable region comprising the amino acid sequence of SEQ ID NO: 4, and a light chain variable region comprising the amino acid sequence of SEQ ID NO: 505. The antibodies may comprise a heavy chain variable region comprising the amino acid sequence of SEQ ID NO: 4, and a light chain variable region comprising the amino acid sequence of SEQ ID NO: 507. The antibodies may comprise a heavy chain variable region comprising the amino acid sequence of SEQ ID NO: 4, and a light chain variable region comprising the amino acid sequence of SEQ ID NO: 509. The antibodies may comprise a heavy chain variable region comprising the amino acid sequence of SEQ ID NO: 4, and a light chain variable region comprising the amino acid sequence of SEQ ID NO: 510. The antibodies may comprise a heavy chain variable region comprising the amino acid sequence of SEQ ID NO: 454, and a light chain variable region comprising the amino acid sequence of SEQ ID NO: 8. The antibodies may comprise a heavy chain variable region comprising the amino acid sequence of SEQ ID NO: 454, and a light chain variable region comprising the amino acid sequence of SEQ ID NO: 455. The antibodies may comprise a heavy chain variable region comprising the amino acid sequence of SEQ ID NO: 454, and a light chain variable region comprising the amino acid sequence of SEQ ID NO: 503. The antibodies may comprise a heavy chain variable region comprising the amino acid sequence of SEQ ID NO: 454, and a light chain variable region comprising the amino acid sequence of SEQ ID NO: 457. The antibodies may comprise a heavy chain variable region comprising the amino acid sequence of SEQ ID NO: 454, and a light chain variable region comprising the amino acid sequence of SEQ ID NO: 505. The antibodies may comprise a heavy chain variable region comprising the amino acid sequence of SEQ ID NO: 454, and a light chain variable region comprising the amino acid sequence of SEQ ID NO: 506. The antibodies may comprise a heavy chain variable region comprising the amino acid sequence of SEQ ID NO: 454, and a light chain variable region comprising the amino acid sequence of SEQ ID NO: 507. The antibodies may comprise a heavy chain variable region comprising the amino acid sequence of SEQ ID NO: 454, and a light chain variable region comprising the amino acid sequence of SEQ ID NO: 5. The antibodies may comprise a heavy chain variable region comprising the amino acid sequence of SEQ ID NO: 454, and a light chain variable region comprising the amino acid sequence of SEQ ID NO: 509. The antibodies may comprise a heavy chain variable region comprising the amino acid sequence of SEQ ID NO: 454, and a light chain variable region comprising the amino acid sequence of SEQ ID NO: 510. The antibodies may comprise a heavy chain variable region comprising the amino acid sequence of SEQ ID NO: 7, and a light chain variable region comprising the amino acid sequence of SEQ ID NO: 8. Antibodies comprising such heavy chain variable region and light chain variable region pairs preferably specifically bind to IL-15 (e.g. human IL-15 complexed with IL-15Rα).

The antibodies may comprise a heavy chain variable region comprising the amino acid sequence of SEQ ID NO: 1, and a light chain comprising the amino acid sequence of SEQ ID NO: 3. The antibodies may comprise a heavy chain variable region comprising the amino acid sequence of SEQ ID NO: 1, and a light chain comprising the amino acid sequence of SEQ ID NO: 6. The antibodies may comprise a heavy chain variable region comprising the amino acid sequence of SEQ ID NO: 1, and a light chain comprising the amino acid sequence of SEQ ID NO: 9. The antibodies may comprise a heavy chain variable region comprising the amino acid sequence of SEQ ID NO: 1, and a light chain comprising the amino acid sequence of SEQ ID NO: 456. The antibodies may comprise a heavy chain variable region comprising the amino acid sequence of SEQ ID NO: 1, and a light chain comprising the amino acid sequence of SEQ ID NO: 458. The antibodies may comprise a heavy chain variable region comprising the amino acid sequence of SEQ ID NO: 1, and a light chain comprising the amino acid sequence of SEQ ID NO: 460. Antibodies comprising such heavy chain variable region and light chain pairs preferably specifically bind to IL-15 (e.g. human IL-15 complexed with IL-15Rα).

The antibodies may comprise a heavy chain variable region comprising the amino acid sequence of SEQ ID NO: 4, and a light chain comprising the amino acid sequence of SEQ ID NO: 3. The antibodies may comprise a heavy chain variable region comprising the amino acid sequence of SEQ ID NO: 4, and a light chain comprising the amino acid sequence of SEQ ID NO: 6. The antibodies may comprise a heavy chain variable region comprising the amino acid sequence of SEQ ID NO: 4, and a light chain comprising the amino acid sequence of SEQ ID NO: 9. The antibodies may comprise a heavy chain variable region comprising the amino acid sequence of SEQ ID NO: 4, and a light chain comprising the amino acid sequence of SEQ ID NO: 456. The antibodies may comprise a heavy chain variable region comprising the amino acid sequence of SEQ ID NO: 4, and a light chain comprising the amino acid sequence of SEQ ID NO: 458. The antibodies may comprise a heavy chain variable region comprising the amino acid sequence of SEQ ID NO: 4, and a light chain comprising the amino acid sequence of SEQ ID NO: 460. The antibodies may comprise a heavy chain variable region comprising the amino acid sequence of SEQ ID NO: 454, and a light chain comprising the amino acid sequence of SEQ ID NO: 9. Antibodies comprising such heavy chain variable region and light chain pairs preferably specifically bind to IL-15 (e.g. human IL-15 complexed with IL-15Rα).

In some aspects, the antibodies specifically bind to IL-15 (e.g. human IL-15 complexed with IL-15Rα), and comprise a heavy chain variable region comprising the amino acid sequence of any one of, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, or SEQ ID NO: 490, and a light chain variable region or a light chain. In some aspects, the antibodies specifically bind to IL-15 (e.g. human IL-15 complexed with IL-15Rα), and comprise a heavy chain variable region comprising the amino acid sequence of any one of SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, SEQ ID NO: 472, SEQ ID NO: 473, SEQ ID NO: 474, SEQ ID NO: 475, SEQ ID NO: 476, SEQ ID NO: 477, SEQ ID NO: 478, SEQ ID NO: 479, SEQ ID NO: 480, SEQ ID NO: 481, SEQ ID NO: 482, SEQ ID NO: 483, SEQ ID NO: 484, SEQ ID NO: 485, SEQ ID NO: 486, SEQ ID NO: 487, SEQ ID NO: 488, SEQ ID NO: 489, or SEQ ID NO: 490, and a light chain variable region or a light chain, and the light chain variable region may be any one of SEQ ID NO: 491, SEQ ID NO: 492, SEQ ID NO: 493, SEQ ID NO: 494, SEQ ID NO: 495, SEQ ID NO: 496, SEQ ID NO: 497, SEQ ID NO: 498, or SEQ ID NO: 499. In some aspects, the antibodies specifically bind to IL-15 (e.g. human IL-15 complexed with IL-15Rα), and comprise a light chain variable region comprising the amino acid sequence of any one of SEQ ID NO: 491, SEQ ID NO: 492, SEQ ID NO: 493, SEQ ID NO: 494, SEQ ID NO: 495, SEQ ID NO: 496, SEQ ID NO: 497, SEQ ID NO: 498, or SEQ ID NO: 499, and a heavy chain variable region. Antibodies comprising such heavy chain variable region and light chain pairs preferably specifically bind to IL-15 (e.g. human IL-15 complexed with IL-15Rα).

In some aspects, the antibodies specifically bind to IL-15 (e.g. human IL-15 complexed with IL-15Rα), and comprise a heavy chain variable region comprising the amino acid sequence of any one of SEQ ID NO:7, SEQ ID NO:454, and SEQ ID NO:4, and a light chain variable region or a light chain. In some aspects, the antibodies specifically bind to IL-15 (e.g. human IL-15 complexed with IL-15Rα), and comprise a heavy chain variable region comprising the amino acid sequence of any one of SEQ ID NO:7, SEQ ID NO:454, and SEQ ID NO:4, and a light chain variable region or a light chain, and the light chain variable region can be any one of SEQ ID NO:5, SEQ ID NO:8, SEQ ID NO:455, SEQ ID NO:457, SEQ ID NO:459, SEQ ID NO:503, SEQ ID NO:505, SEQ ID NO:506, SEQ ID NO:507, SEQ ID NO:509, or SEQ ID NO:510. In some aspects, the antibodies specifically bind to IL-15 (e.g. human IL-15 complexed with IL-15Rα), and comprise a light chain variable region comprising the amino acid sequence of any one of SEQ ID NO:5, SEQ ID NO:8, SEQ ID NO:455, SEQ ID NO:457, SEQ ID NO:459, SEQ ID NO:503, SEQ ID NO:505, SEQ ID NO:506, SEQ ID NO:507, SEQ ID NO:509, or SEQ ID NO:510 and a heavy chain variable region.

The antibodies may specifically bind to IL-15 (e.g. human IL-15 complexed with IL-15Rα), and comprise VH and VL or light chain pair comprising the amino acid sequence shown in the following table:

|           | VH  | VL  | L   |
|-----------|-----|-----|-----|
| SEQ ID NO: | 7   | 8   | 9   |
| SEQ ID NO: | 454 | 8   | 9   |
| SEQ ID NO: | 4   | 455 | 456 |
| SEQ ID NO: | 4   | 457 | 458 |
| SEQ ID NO: | 4   | 459 | 460 |
| SEQ ID NO: | 4   | 5   | 6   |

The antibodies may specifically bind to IL-15 (e.g. human IL-15 complexed with IL-15Rα), and comprise VH and VL or light chain pair comprising the amino acid sequence shown in the following table:

|           | VH  | VL  |
|-----------|-----|-----|
| SEQ ID NO: | 4   | 8   |
| SEQ ID NO: | 4   | 503 |
| SEQ ID NO: | 4   | 505 |
| SEQ ID NO: | 4   | 509 |
| SEQ ID NO: | 4   | 510 |
| SEQ ID NO: | 454 | 455 |
| SEQ ID NO: | 454 | 503 |
| SEQ ID NO: | 454 | 457 |
| SEQ ID NO: | 454 | 505 |
| SEQ ID NO: | 454 | 406 |
| SEQ ID NO: | 454 | 507 |
| SEQ ID NO: | 454 | 5   |
| SEQ ID NO: | 454 | 509 |
| SEQ ID NO: | 454 | 510 |

Any of the antibodies described or exemplified herein bind to IL-15, which is preferably human IL-15. The antibodies may bind to uncomplexed IL-15 or IL-15 when in a complex with the IL-15 receptor alpha (IL-15R-alpha or IL-15Rα)—the IL-15 complex. In some aspects, human IL-15 comprises the amino acid sequence of SEQ ID NO: 511. In some aspects, the IL-15R-alpha comprises the amino acid sequence of SEQ ID NO: 512, without the AVI and His tags. In some aspects, the IL-15R-alpha comprises the amino acid sequence of SEQ ID NO: 520.

The antibodies may have an affinity to IL-15 (e.g. human IL-15 complexed with IL-15Rα) with a dissociation constant (KD) of less than about $1\times10^{-2}$ M. In some embodiments, the KD is less than about $1\times10^{-3}$ M. In other embodiments, the KD is less than about $1\times10^{-4}$ M. In some embodiments, the KD is less than about $1\times10^{-5}$ M. In still other embodiments, the KD is less than about $1\times10^{-6}$ M. In other embodiments, the KD is less than about $1\times10^{-7}$ M. In other embodiments, the KD is less than about $1\times10^{-8}$ M. In other embodiments, the KD is less than about $1\times10^{-9}$ M. In other embodiments, the KD is less than about $1\times10^{-10}$ M. In still other embodiments, the KD is less than about $1\times10^{-11}$ M. In some embodiments, the KD is less than about $1\times10^{-12}$ M. In other embodiments, the KD is less than about $1\times10^{-13}$ M. In other embodiments, the KD is less than about $1\times10^{-14}$ M. In still other embodiments, the KD is less than about $1\times10^{-15}$ M. In some aspects, the KD is less than about $1.8\times10^{-9}$ M. In some aspects, the KD is from about $1.2\times10^{-10}$ M to about $2\times10^{-10}$ M. In some aspects, the KD is from about $1.3\times10^{-10}$ M to about $1.9\times10^{-10}$ M. In some aspects, the KD is from about $1.33\times10^{-10}$ M to about $1.93\times10^{-10}$ M. In some aspects, the KD is from about $1.6\times10^{-10}$ M to about $1.8\times10^{-10}$ M. In some aspects, the KD is about $1.7\times10^{-10}$ M. Affinity values refer to those obtained by standard methodologies, including surface plasmon resonance (SPR) such as BIACORE® analyses or analysis using an OCTET® Red 96 (Forte Bio) Dip-and-Read system. In a preferred embodiment, the dissociation constant is determined by SPR.

In a general BIACORE® SPR analysis, an antibody is immobilized on a sensor chip surface, and suitable concentrations of IL-15 or the IL-15 complexed with the IL-15 Receptor alpha are passed across the surface. Changes in the index of refraction are detected, and software is used to generate sensorgrams for analysis. Interaction between the immobilized antibody and the IL-15 or IL-15 complex may be carried out for any suitable length of time, including about 1 to about 2 minutes. The temperature of the interaction can be any suitable temperature, including about 25 degrees C.

Antibodies that bind to IL-15 (e.g. human IL-15 complexed with IL-15Rα) may be monoclonal antibodies. Preferably, the antibodies are full-length antibodies comprising a heavy chain and a light chain. In some aspects, the antibodies comprise derivatives or fragments or portions of antibodies that retain the antigen-binding specificity, and also preferably substantially retain the affinity, of the full-length parent antibody molecule (e.g., for IL-15). For example, derivatives may comprise a single variable region (either a heavy chain or light chain variable region). Other examples of suitable antibody derivatives and fragments include, without limitation, antibodies with polyepitopic specificity, diabodies, minibodies, FAb, F(Ab')2, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or dimers, light chain monomers or dimers, dimers consisting of one heavy and one light chain, and other multimers. Single chain Fv antibodies may be multi-valent. Antibody derivatives, fragments, and/or portions may be recombinantly produced and expressed by any cell type, prokaryotic or eukaryotic.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Typically, the antigen binding properties of an antibody are less likely to be disturbed by changes to FR sequences than by changes to the CDR sequences. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The anti-IL-15 antibodies preferably are fully human. Fully human antibodies are those where the whole molecule is human or otherwise of human origin, or includes an amino acid sequence identical to a human form of the antibody. Fully human antibodies include those obtained from a human V gene library, for example, where human genes encoding variable regions of antibodies are recombinantly expressed. Fully human antibodies may be expressed in other organisms (e.g., mice and xenomouse technology) or cells from other organisms transformed with genes encoding human antibodies. Fully human antibodies may be expressed in an OMNIRAT® rat system (OMT, Inc.), according to WO 08/151081. Fully human antibodies may nevertheless include amino acid residues not encoded by naturally occurring human sequences, e.g., mutations introduced by random or site directed mutations.

In some aspects, the anti-IL-15 antibodies may comprise non-immunoglobulin derived protein frameworks. For example, reference may be made to (Ku et al. (1995) Proc. Natl. Acad. Sci. USA 92: 6552-6556), which describes a four-helix bundle protein cytochrome b562 having two loops randomized to create CDRs, which have been selected for antigen binding.

The anti-IL-15 antibodies may comprise post-translational modifications or moieties, which may impact antibody activity, circulating half-life, or shelf/storage stability. For example, the antibodies may be methylated, acetylated, glycosylated, sulfated, phosphorylated, carboxylated, and/or amidated, or may comprise other suitable moieties that are well known in the art. Moieties include any chemical group or combinations of groups commonly found on immunoglobulin molecules in circulation or otherwise added to antibodies by recombinant expression systems, including prokaryotic and eukaryotic expression systems.

Examples of side chain modifications contemplated by the disclosure include modifications of amino groups such as by reductive alkylation by reaction with an aldehyde followed by reduction with NaBH4; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH4.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivation, for example, to a corresponding amide. Sulfydryl groups may be modified by methods such as carboxymethylation with iodoacetic acid or iodoacetamide; performic acid oxidation to cysteic acid; formation of mixed disulfides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuri-4-nitrophenol and other mercurials; carbamoylation with cyanate at alkaline pH. Tryptophan residues may be modified by, for example, oxidation with N-bromosuccinimide or alkylation of the indole ring with 2-hydroxy-5-nitrobenzyl bromide or sulfenyl halides. Tyrosine residues on the other hand, may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate.

The anti-IL-15 antibodies may include modifications that modulate serum half-life and biodistribution, including without limitation, modifications that modulate the antibody's interaction with the neonatal Fc receptor (FcRn), a receptor with a key role in protecting IgG from catabolism, and maintaining high serum antibody concentration. Serum half-life modulating modifications may occur in the Fc region of IgG1, IgG2, or IgG4, including the triple substitution of M252Y/S254T/T256E (numbering according to the EU numbering system (Edelman, G M et al. (1969) Proc. Natl. Acad. USA 63:78-85)), as described in U.S. Pat. No. 7,083,784. Other substitutions may occur at positions 250 and 428, see e.g., U.S. Pat. No. 7,217,797, as well as at positions 307, 380 and 434, see, e.g., PCT Publ. No. WO 00/042072. Examples of constant domain amino acid substitutions which modulate binding to Fc receptors and subsequent function mediated by these receptors, including FcRn binding and serum half-life, are described in U.S. Publ. Nos. 2009/0142340, 2009/0068175, and 2009/0092599. Antibodies of any class may have the heavy chain C-terminal lysine omitted or removed to reduce heterogeneity (ΔK). The substitution of S228P (EU numbering) in the human IgG4 can stabilize antibody Fab-arm exchange in vivo (Labrin et al. (2009) Nature Biotechnol. 27:8; 767-773), and this substitution may be present at the same time as M252Y/S254T/T256E and/or ΔK modifications.

The anti-IL-15 antibodies preferably comprise human constant domains. The heavy chain constant domains preferably are human IgG1, IgG2, or IgG4 constant domains. The light chain constant domains preferably are human lambda constant domains.

Human heavy chain IgG1 constant regions that may be used with the anti-IL-15 antibodies may be selected from among human IgG1 (SEQ ID NO: 32), human IgG1 (ΔK) (SEQ ID NO: 33), human IgG1 252Y/254T/256E (SEQ ID NO: 34), human IgG1 252Y/254T/256E (ΔK) (SEQ ID NO: 35), human IgG1 L235A/G237A (SEQ ID NO: 36), human IgG1 L235A/G237A (ΔK) (SEQ ID NO: 37) human IgG1 L234A/L235A/G237A (SEQ ID NO: 38), and human IgG1 L234A/L235A/G237A (ΔK) (SEQ ID NO: 39). Human heavy chain IgG2 constant regions that may be used with the anti-IL-15 antibodies may be selected from among human IgG2 (SEQ ID NO: 40), human IgG2 (ΔK) (SEQ ID NO: 41), human IgG2 A330S/P331S (SEQ ID NO: 42), and human IgG (ΔK) (SEQ ID NO: 43). Human heavy chain IgG4 constant regions that may be used with the anti-IL-15 antibodies may be selected from among human IgG4 (SEQ ID NO: 44), human IgG4 (ΔK) (SEQ ID NO: 45), human IgG4 S228P (SEQ ID NO: 46), human IgG4 S228P (ΔK) (SEQ ID NO: 47), human IgG4 228P/252Y/254T/256E (SEQ ID NO: 48), human IgG4 228P/252Y/254T/256E (ΔK) (SEQ ID NO: 49), human IgG4 252Y/254T/256E (SEQ ID NO: 50), and human IgG4 252Y/254T/256E (ΔK) (SEQ ID NO: 51).

The anti-IL-15 antibodies may be labelled, bound, or conjugated to any chemical or biomolecule moieties. Labelled antibodies may find use in therapeutic, diagnostic, or basic research applications. Such labels/conjugates can be detectable, such as fluorochromes, electrochemiluminescent probes, quantum dots, radiolabels, enzymes, fluorescent proteins, and luminescent proteins, or may comprise biotin or PEG.

The antibodies may be derivatized by known protecting/blocking groups to prevent proteolytic cleavage or enhance activity or stability.

Polynucleotide sequences that encode the anti-IL-15 antibodies, their domains (e.g., VH and VL domains), and their subdomains (e.g., FRs and CDRs) are featured in the disclosure. Polynucleotides include, but are not limited to, RNA, DNA, cDNA, hybrids of RNA and DNA, and single, double, or triple stranded strands of RNA, DNA, or hybrids thereof. The complementary nucleic acid sequences are also within the scope of the disclosure.

In some aspects, a polynucleotide comprises a first nucleic acid sequence encoding an antibody heavy chain variable region comprising the amino acid sequence of SEQ ID NO: 1, SEQ ID NO: 4, or SEQ ID NO: 7. The polynucleotide may further comprise a second nucleic acid sequence encoding an antibody light chain variable region comprising the amino acid sequence of SEQ ID NO: 2, SEQ ID NO: 5, or SEQ ID NO: 8. The polynucleotide may further comprise a second nucleic acid sequence encoding an antibody light chain comprising the amino acid sequence of SEQ ID NO: 3, SEQ ID NO: 6, or SEQ ID NO: 9. The polynucleotide may further comprise a third nucleic acid sequence encoding an antibody heavy chain constant region, such as any of the IgG1, IgG2, or IgG4 constant regions described herein.

In some aspects, a polynucleotide comprises a first nucleic acid sequence encoding an antibody heavy chain variable region comprising the amino acid sequence of SEQ ID NO: 4, SEQ ID NO: 7, or SEQ ID NO:454. The polynucleotide may further comprise a second nucleic acid sequence encoding an antibody light chain variable region comprising the amino acid sequence of SEQ ID NO: 5, SEQ ID NO: 8, SEQ ID NO:455, SEQ ID NO:457, SEQ ID NO:459, SEQ ID NO:503, SEQ ID NO:505, SEQ ID NO:506, SEQ ID NO:507, SEQ ID NO:509, or SEQ ID NO:510. The polynucleotide may further comprise a second nucleic acid sequence encoding an antibody light chain comprising the amino acid sequence of SEQ ID NO: 6, SEQ ID NO: 9, SEQ ID NO:456, SEQ ID NO:458, or SEQ ID NO:460. The polynucleotide may further comprise a third nucleic acid sequence encoding an antibody heavy chain constant region, such as any of the IgG1, IgG2, or IgG4 constant regions described herein.

In some aspects, a polynucleotide comprises a first nucleic acid sequence encoding an antibody light chain variable region comprising the amino acid sequence of SEQ ID NO: 2, SEQ ID NO: 5, or SEQ ID NO: 8. In some aspects, a polynucleotide comprises a first nucleic acid sequence encoding an antibody light chain comprising the amino acid sequence of SEQ ID NO: 3, SEQ ID NO: 6, or SEQ ID NO: 9. In some aspects, a polynucleotide comprises the nucleic acid sequence of SEQ ID NO: 517. In some aspects, a polynucleotide comprises the nucleic acid sequence of SEQ ID NO: 518.

In some aspects, a polynucleotide comprises a first nucleic acid sequence encoding an antibody light chain variable region comprising the amino acid sequence of SEQ ID NO: 5, SEQ ID NO: 8, SEQ ID NO:455, SEQ ID NO:457, SEQ ID NO:459, SEQ ID NO:503, SEQ ID NO:505, SEQ ID NO:506, SEQ ID NO:507, SEQ ID NO:509, or SEQ ID NO:510. In some aspects, a polynucleotide comprises a first nucleic acid sequence encoding an antibody light chain comprising the amino acid sequence of SEQ ID NO: 6, SEQ ID NO: 9, SEQ ID NO:456, SEQ ID NO:458, or SEQ ID NO:460.

Any such polynucleotides may be comprised within a vector. Thus, vectors comprising polynucleotides are provided as part of the disclosure. The vectors may be expression vectors. Recombinant expression vectors containing a sequence encoding a polypeptide of interest are thus provided. The expression vector may contain one or more additional sequences, such as but not limited to regulatory sequences, a selection marker, a purification tag, or a polyadenylation signal. Such regulatory elements may include a transcriptional promoter, enhancers, mRNA ribosomal binding sites, or sequences that control the termination of transcription and translation.

Expression vectors, especially mammalian expression vectors, may include one or more nontranscribed elements, such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a specific host may also be incorporated.

The vectors may be used to transform any of a wide array of host cells well known to those of skill in the art, and preferably host cells capable of expressing antibodies. Vectors include without limitation, plasmids, phagemids, cosmids, bacmids, bacterial artificial chromosomes (BACs), yeast artificial chromosomes (YACs), and baculovirus, as well as other bacterial, eukaryotic, yeast, and viral vectors. Suitable host cells include without limitation CHO cells, NS0 cells, HEK293 cells, or any eukaryotic stable cell line known or produced, and also include bacteria, yeast, and insect cells.

The antibodies may also be produced by hybridoma cells; methods to produce hybridomas being well known and established in the art.

The disclosure also provides compositions comprising the anti-IL-15 antibodies. The compositions may comprise any of the antibodies described and/or exemplified herein and an acceptable carrier such as a pharmaceutically acceptable carrier. Suitable carriers include any media that does not interfere with the biological activity of the antibody and preferably is not toxic to a host to which it is administered. The carrier may be an aqueous solution. The compositions may comprise any of the antibodies described and/or exemplified herein and a pharmaceutically acceptable excipient.

The anti-IL-15 antibodies may be used to treat an autoimmune disease, including an autoimmune disease in which IL-15 is dysregulated. The anti-IL-15 antibodies may be used to treat an inflammatory disease, including an inflammatory disease in which IL-15 is dysregulated.

The anti-IL-15 antibodies may be used to treat an inflammatory disorder, including an inflammatory disorder in which IL-15 is dysregulated. In some aspects, the anti-IL-15 antibodies may be used to treat Celiac disease, refractory Celiac disease, rheumatoid arthritis, psoriasis, inflammatory bowel disease, type 1 diabetes, alopecia areata as well as certain type of cancer such as T cell large granular lymphocytic leukemia in a subject. Thus, the disclosure features treatment methods.

In some aspects, the treatment methods comprise administering an anti-IL-15 antibody, or composition thereof, to a subject in need of treatment for an autoimmune disease in which IL-15 is dysregulated, such that the autoimmune disease is treated in the subject. The anti-IL-15 antibodies are preferably administered in an amount that is effective to treat the autoimmune disease in which IL-15 is dysregulated in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for an inflammatory disease in which IL-15 is dysregulated, such that the inflammatory disease is treated in the subject. The anti-IL-15 antibodies are preferably administered in an amount that is effective to treat the inflammatory disease in which IL-15 is dysregulated in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for an inflammatory disorder in which IL-15 is dysregulated, such that the inflammatory disorder is treated in the subject. The anti-IL-15 antibodies are preferably administered in an amount that is effective to treat the inflammatory disorder in which IL-15 is dysregulated in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for Celiac disease, such that Celiac disease is treated in the subject, and the Celiac disease may be refractory. Refractory celiac disease (RCD) affects patients who have failed to heal and demonstrate continual symptoms of celiac disease, after 6-12 months of a strict gluten-free diet and when other causes of symptoms (including malignancy) have been ruled out. It may also occur in patients who previously responded to a long-term gluten-free diet, but who now display symptoms of celiac disease, while maintaining a strict gluten free diet (Rishi et al. *Expert Review of Gastroenterology & Hepatology:* 10 537-546 (2016)). The anti-IL-15 antibodies are preferably administered in an amount that is effective to treat Celiac disease in the subject. The effective amount may vary, for example, according to the needs or condition of the subject. Administration may be at the direction or control of a medical practitioner.

The anti-IL-15 antibodies may be used to treat or inhibit one or more symptoms of gluten exposure, for example, as caused by ingestion of gluten. The one or more symptoms include muscle pain, body pain, joint pain, fatigue, bloating, gas, nausea, cramps, constipation, diarrhea, skin rash, headache, migraine headache, depression, anxiety, brain fog, and irritability. In general, the methods comprise administering an anti-IL-15 antibody, or composition thereof, to a subject having gluten sensitivity who has been exposed to gluten such that the one or more symptoms of gluten exposure are inhibited or treated in the subject. The anti-IL-15 antibodies are preferably administered in an amount that is effective to treat or inhibit the one or more symptom of gluten exposure in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for rheumatoid arthritis, such that rheumatoid arthritis is treated in the subject. The anti-IL-15 antibodies are preferably administered in an amount that is effective to treat rheumatoid arthritis in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for psoriasis, such that psoriasis is treated in the subject. The anti-IL-15 antibodies are preferably administered in an amount that is effective to treat psoriasis in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for inflammatory bowel disease, such that inflammatory bowel disease is treated in the subject. The anti-IL-15 antibodies are preferably administered in an amount that is effective to treat inflammatory bowel disease in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for type 1 diabetes, such that type 1 diabetes is treated in the subject. The anti-IL-15 antibodies are preferably administered in an amount that is effective to treat type 1 diabetes in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for alopecia areata, such that alopecia areata is treated in the subject. The anti-IL-15 antibodies are preferably administered in an amount that is effective to treat alopecia areata in the subject. The effective amount may vary, for example, according to the needs or condition of the subject. Administration may be at the direction or control of a medical practitioner.

In some aspects, the treatment methods comprise administering an anti-IL-15 antibody, or composition thereof, to a subject in need of treatment for T cell large granular lymphocytic leukemia, such that T cell large granular lymphocytic leukemia is treated in the subject. The anti-IL-15 antibodies are preferably administered in an amount that is effective to treat T cell large granular lymphocytic leukemia in the subject. The effective amount may vary, for example, according to the needs or condition of the subject. Administration may be at the direction or control of a medical practitioner.

The anti-IL-15 antibodies may be used in the manufacture of a medicament. For example, the anti-IL-15 antibodies may be used in the manufacture or preparation of a medicament for use in the treatment of Celiac disease. The anti-IL-15 antibodies may be used in the manufacture or preparation of a medicament for use in the treatment of refractory Celiac disease. The anti-IL-15 antibodies may be used in the manufacture or preparation of a medicament for use in the treatment of rheumatoid arthritis. The anti-IL-15 antibodies may be used in the manufacture or preparation of a medicament for use in the treatment of psoriasis. The anti-IL-15 antibodies may be used in the manufacture or preparation of a medicament for use in the treatment of inflammatory bowel disease. The anti-IL-15 antibodies may be used in the manufacture or preparation of a medicament for use in the treatment of type 1 diabetes. The anti-IL-15 antibodies may be used in the manufacture or preparation of a medicament for use in the treatment of alopecia areata. The anti-IL-15 antibodies may be used in the manufacture or preparation of a medicament for use in the treatment of T cell large granular lymphocytic leukemia. The anti-IL-15 antibodies may be used in the manufacture or preparation of a medicament for use in the treatment or inhibition of one or more symptoms of gluten exposure, for example, gluten exposure in a patient who has a gluten sensitivity or allergy. The one or more symptoms may include muscle pain, body pain, joint pain, fatigue, bloating, gas, nausea, cramps, constipation, diarrhea, skin rash, headache, migraine headache, depression, anxiety, brain fog, and/or irritability.

The anti-IL-15 antibodies may be for use in the treatment of Celiac disease. The anti-IL-15 antibodies may be for use in the treatment of refractory Celiac disease. The anti-IL-15 antibodies may be for use in the treatment of rheumatoid arthritis. The anti-IL-15 antibodies may be for use in the treatment of psoriasis. The anti-IL-15 antibodies may be for use in the treatment of inflammatory bowel disease. The anti-IL-15 antibodies may be for use in the treatment of type 1 diabetes. The anti-IL-15 antibodies may be for use in the treatment of alopecia areata. The anti-IL-15 antibodies may be for use in the treatment of T cell large granular lymphocytic leukemia. The anti-IL-15 antibodies may be for use in the treatment or inhibition of one or more symptoms of gluten exposure, for example, gluten exposure in a patient who has a gluten sensitivity or allergy. The one or more symptoms may include muscle pain, body pain, joint pain, fatigue, bloating, gas, nausea, cramps, constipation, diarrhea, skin rash, headache, migraine headache, depression, anxiety, brain fog, and/or irritability.

The disclosure also features kits comprising any of the anti-IL-15 antibodies, and these kits may be used to supply antibodies and other agents for use in diagnostic, basic research, or therapeutic methods, among others. In some aspects, the kits comprise any anti-IL-15 antibody described or exemplified herein and instructions for using the antibody in a method for treating Celiac disease. In some aspects, the kits comprise any anti-IL-15 antibody described or exemplified herein and instructions for using the antibody in a method for treating refractory Celiac disease. In some aspects, the kits comprise any anti-IL-15 antibody described or exemplified herein and instructions for using the antibody in a method for treating or inhibiting one or more symptoms of gluten exposure, for example, in a patient with a gluten sensitivity or allergy. In some aspects, the kits comprise any anti-IL-15 antibody described or exemplified herein and instructions for using the antibody in a method for treating rheumatoid arthritis. In some aspects, the kits comprise any anti-IL-15 antibody described or exemplified herein and instructions for using the antibody in a method for treating psoriasis. In some aspects, the kits comprise any anti-IL-15 antibody described or exemplified herein and instructions for using the antibody in a method for treating inflammatory bowel disease. In some aspects, the kits comprise any anti-IL-15 antibody described or exemplified herein and instructions for using the antibody in a method for treating type 1 diabetes. In some aspects, the kits comprise any anti-IL-15 antibody described or exemplified herein and instructions for using the antibody in a method for treating alopecia areata. In some aspects, the kits comprise any anti-IL-15 antibody described or exemplified herein and instructions for using the antibody in a method for treating T cell large granular lymphocytic leukemia.

Also provided are methods for detecting IL-15 in a tissue sample isolated from a subject. Generally, such methods comprising contacting any anti-IL-15 antibody described or exemplified herein with a tissue sample isolated from a subject to form an antibody-IL-15 complex with the IL-15 Receptor-alpha, and detecting the complex in the tissue sample. The method may further comprise isolating the tissue sample from the subject. The tissue sample may be from gastrointestinal tissue, including esophageal tissue, stomach tissue, small intestine tissue, large intestine tissue, and other tissue from the gastrointestinal tract. The antibody may be conjugated to a detectable label. The antibody may be detected with a secondary antibody that is labelled with a detectable label. Such methods may be carried out in vivo, in vitro, or in situ.

Also provided are methods for detecting a complex of IL-15 and IL-15 Receptor-alpha in a tissue sample isolated from a subject. Generally, such methods comprising contacting any anti-IL-15 antibody described or exemplified herein with a tissue sample isolated from a subject to form an antibody-antigen complex of the anti-IL-15 antibody bound to a complex of IL-15 and IL-15 Receptor-alpha, and detecting the antibody-antigen complex in the tissue sample. The method may further comprise isolating the tissue sample from the subject. The tissue sample may be from gastrointestinal tissue, including esophageal tissue, stomach tissue, small intestine tissue, large intestine tissue, and other tissue from the gastrointestinal tract. The antibody may be conjugated to a detectable label. The antibody may be detected with a secondary antibody that is labelled with a detectable label. Such methods may be carried out in vivo, in vitro, or in situ.

The following examples are provided to describe the disclosure in greater detail. They are intended to illustrate, not to limit, the disclosure. In the examples, reference to a position of a residue is a reference to the position in the relevant sequence as set forth herein, unless otherwise indicated.

Example 1

Generation of Transgenic Rats, Immunization and Production of Hybridomas 1.1 IL-15 Protein and IL-15Rα Protein Human Interleukin 15 (IL-15) was purchased (Sigma) or produced in a mammalian HEK293F expression system, using plasmids encoding human IL-15 and the soluble IL-15 receptor α (IL-15Rα) with an N-terminally located HIS and AVI tag (SEQ ID NO: 512) in a 1:1 ratio.

1.2 Generation of Transgenic Rats

Transgenic rats were generated as described in PCT Publication No. WO 08/151081. In brief, a meganuclease expression construct was integrated into the genome of a subject animal.

Expression of the meganuclease in germ cells resulted in double-strand breaks in endogenous rat immunoglobulin genes. Mating of such transgenic rats resulted in offspring with mutated/inactivated endogenous rat immunoglobulin genes.

The transgenic rats are further modified to carry artificial human immunoglobulin genes such that the rats are capable of producing antibodies with fully human variable regions.

1.3 Immunizations

To generate fully human monoclonal antibodies to the IL-15 complex with the IL-15 Receptor-alpha, transgenic rats (generated as described above) were immunized with DNA encoding human IL-15 with and DNA encoding human IL-15Rα.

Ten animals were immunized and the immune response was monitored over the course of immunization with plasma samples obtained by submandibular bleeds. The plasma was screened for antibody expression by ELISA, and animals with sufficient titers of anti-IL-15 antibodies were selected for fusion and hybridoma generation. Animals with a high titer were boosted subcutaneously with recombinant human IL-15 complex 5 days before sacrifice.

1.4 Generation of Hybridomas Producing Monoclonal Antibodies to IL-15 Complex

To generate hybridomas producing monoclonal antibodies to the IL-15 complex with the IL-15 Receptor-alpha, splenocytes and lymph node cells from immunized animals were isolated and fused to an immortalized cell line. Single cell suspensions of lymphocytes were fused to P3X63Ag8.653 non secreting mouse myeloma cells (ATCC, CRL-1580). Cells were plated at approximately $1 \times 10^5$ cells/mL in flat bottom microtiter plates, followed by 2 week incubation in selective medium containing, besides usual reagents, 10% fetal clone serum and 1×HAT (Sigma). Individual wells were then screened by ELISA and BIACORE® for human IL-15 IgG antibodies with high affinity.

Example 2

Screening of Hybridomas 2.1 Use of ELISA to Select Antibodies that Bind to the IL-15 Complex but do not Bind to Uncomplexed IL-15 Receptor α

Microtiter plates were coated with purified IL-15 or purified IL-15Rα or purified IL-15 complex. Briefly, microtiter plates were coated with purified protein in PBS and then blocked with irrelevant proteins such as bovine serum albumin (BSA) diluted in PBS. Dilutions of hybridoma supernatants were added to each well and incubated for 1-2 hours at 37° C. The plates were washed with PBS/TWEEN® 20, and then incubated with a goat-anti-human IgG Fc-specific polyclonal reagent conjugated to a suitable detection reagent (e.g., horseradish peroxidase) alkaline phosphatase for 1 hour at 37° C. After washing, the plates were developed with suitable substrate (e.g., 3,3',5,5'-tetramethylbenzidine TMD) and analyzed at OD of 405. Hybridomas that produced antibodies showing positive reactivity with the IL-15 complex but not with IL-15Rα were selected for further characterization.

2.2 Use of Cell Based ELISA (cELISA) to Select Antibodies that Bind to the IL-15 Complex but do not Bind to Uncomplexed IL-15 Receptor α

Each of the hybridomas tested as above were also tested in a cell-based enzyme-linked immunosorbent assay (cELISA) to select for antibodies that bind to the IL-15 complex but do not bind to uncomplexed IL-15Rα.

cELISA was carried out as follows. HEK cells were transfected with DNA encoding IL-15 and IL-15Rα such that they expressed the IL-15 complex. The transfected HEK cells were coated onto an ELISA plate and dilutions of hybridoma supernatants was applied to the plate so that it could bind to the IL-15 complex expressed on the surface of the cells. The assay was repeated using HEK cells transfected with IL-15Rα such that they expressed uncomplexed IL-15Rα. The advantage of using cELISA in addition to classical ELISA is that a native protein complex is used to screen the antibodies.

As a positive control, cell surface expression of the IL-15 complex or uncomplexed IL-15Rα was analysed using an anti-human IL-15-Phycoerythrin (PE) antibody (R&D Systems, Cat. No. IC2471P). Hybridomas producing antibodies that showed positive reactivity with the IL-15 complex but not with IL-15Rα were selected for further characterization.

A representative selection of results in shown in FIG. 1. Antibody 4 bound to uncomplexed IL-15 and the IL-15 complex, but not to uncomplexed IL15Rα. Antibody 1A6 did not bind to uncomplexed IL-15, the IL-15 complex or, IL-15Rα, and was not selected for further characterization. Antibody 1B3 bound uncomplexed IL-15, the IL-15 complex and IL-15Rα. Binding to uncomplexed IL-15Rα is disadvantageous because it indicates that the clones are not IL-15 specific.

Example 3

Identification of Candidate Antibodies for Further Development 3.1 CTLL-2 Cell Based Assay 1500 hybridoma samples that bound IL-15 complex but not to IL-15a were tested in a murine CTLL-2 cell-based assay to determine which neutralize the biological activity of IL-15. The CTLL-2 cell line is derived from cytotoxic T cell lymphoma (ATCC: TIB-214) and is responsive to both IL-2 and IL-15.

Hybridoma supernatants (unpurified antibodies) were tested for their ability to neutralize IL-15-induced proliferation of CTLL-2 cells.

CTLL-2 cells were incubated in complete media without IL-2 or IL-15 for 4 hours prior testing. CTLL-2 cells ($5 \times 10^4$/well) were incubated in 96-well plates with IL-15 complex with the IL-15 Receptor-alpha at 200 pM to induce cell proliferation. Hybridoma supernatants were added to the plates and incubated for 48 hours. Inhibition of cell proliferation was then assessed using the CELLTITER-GLO® Luminescent Cell Viability Assay (Promega) according to manufacturer's instructions and read on GLOMAX® 96 Microplate Luminometer (Promega). Data not shown.

3.2 BIACORE® Assays

In parallel to the cell based assays described above, the 1500 hybridomas were also tested for IL-15 complex binding activity and their affinity was measured. A surface plasmon resonance (SPR) assay was used. SPR screening was conducted using a BIACORE® 4000 Biosensor (GE Healthcare) in a single concentration analyte pass assay. CM5 Series S (GE Healthcare) was docked in the machine. Normalization with Bia Normalisation solution (GE Healthcare) was used. Hydrodynamic addressing was performed on the docked chip and passed the internal quality control check.

An anti-rat Fc fragment antibody (Bethyl A110-136A) was immobilised on the surface of a CM5 sensor chip using an amine coupling kit (GE Healthcare). The antibody was diluted in sodium acetate pH 4.5 to a concentration of 50 μg/mL for immobilisation and was immobilised on Spots 1, 2, 4, 5 on flow cells 1~4 using the HBS-EP+ buffer (GE Healthcare) and a coupling time of 10 minutes. All interactions were measured at 25° C. This resulted in an immobilisation level of between 10,000-12,000 response units for each spot on the four flow cells. Cells were regenerated using a 100 mM phosphoric acid buffer.

For hybridoma binding assessment, 70 μL of HBS-EP+ running buffer was added to 50 μL of rat hybridoma supernatant. The followed method was used:

Startup—Regeneration 3 cycles 10 secs each at 30 μL/min
Sample Run:
  Capture—Spot 1—Flow cells 1-4—130 secs injection—30 μL/min—normal injection—4 different samples are loaded in this step onto spot 1 from each of the four flow cells
  Capture—Spot 5—Flow cells 1-4—130 secs injection—30 μL/min—normal injection—4 different samples are loaded in this step onto spot 1 from each of the four flow cells Sample—All spots, All flow cells—60 secs injection, 60 secs off-rate—30 µL/min—normal injection—human IL-15 complex (20 µg/mL; batch 491p90A) is injected over all flow cells and all spots.
Regeneration 1—20 sec 100 mM phosphoric acid
Regeneration 2—15 sec 100 mM phosphoric acid
Regeneration 3—10 sec 100 mM phosphoric acid
Between every 96-well plate another regeneration cycle was performed—as per the start-up cycle.

Analysis

Using the BiaEvaluation software, capture with kinetics was used for analysis.

Sensorgrams for 5-4 and 1-2 were analyzed. This allowed for the IL-15 complex signal to be subtracted from a spot that contained no antibody. Spot 3 was not used in the analysis. Each sensorgram was then analyzed and those samples that displayed no binding of antibody to complex were rejected and those that showed binding to the IL-15 complex with the IL-15 Receptor-alpha were approved. Curve fitting was performed and a table of the affinity measurements was obtained.

3.3 Variable Region Sequencing

The molecular identity of the antibody variable regions in the selected non-clonal hybridoma pellets was established by reverse transcription polymerase chain reaction.

Briefly, 96 well plates containing hybridoma pellets were defrosted following cryopreservation at −80° C. in RNALATER® (Thermo). Plates were spun at 1000×g for 5 minutes to pellet the cells and the RNALATER® buffer removed. RNA was isolated from the plates of hybridomas using a GENELUTE™ 96 well total RNA purification kit (Sigma #RTN9602, RTN9604) according to the manufacturer's protocol. The concentration and quality of the resulting RNA samples were determined using a NANODROP® 8000 spectrophotometer (Thermo). RNA was reverse transcribed into cDNA using an oligo(dT) primer and AccuScript reverse transcriptase (Agilent #600184). The cDNA synthesis reaction was assembled according the manufacturer's protocol and cDNA synthesis carried out at 42° C. for 30 minutes.

Amplification of human antibody variable regions from the transgenic rodent derived hybridomas was performed by PCR using either PfuUltraII (Agilent) or Q5 high fidelity DNA polymerases (NEB) according to the manufacturer's directions. Heavy chains were amplified using primer pairs specific to the rodent heavy chain constant region DNA sequence and the DNA sequences of the human heavy chain leader sequences. Lambda light chain variable regions were similarly amplified using primer pairs specific to the human lambda constant region DNA sequence and the DNA sequences of the human lambda chain leader sequences.

Successful amplification of the variable regions was confirmed by running a small aliquot of the PCR reaction on a gel using an e-gel electrophoresis system (Thermo). Post-PCR clean-up of the reactions was performed using a GENELUTE™ 96 well PCR clean-up system (Sigma #PCR9604) according to the manufacturer's protocol. The concentration of the resulting purified DNA was assessed using a Nanodrop spectrophotometer. Sanger sequencing of the PCR fragments was performed using oligos designed to bind internally to the heavy- or light chain amplicons. The resulting DNA sequences were conceptually translated into amino acid sequences for further analysis prior to their use in full length antibody chain generation. Antibody variable regions with unique amino acid sequences (with at least one amino acid change in the full sequence) were selected for conversion to full-length human antibodies.

3.4 Generation of Plasmids for Antibody Production

Variable region sequences were back-translated into DNA sequences using GENEOPTIMIZER® technology prior to synthesis of the resulting DNA de novo by assembly of synthetic oligonucleotides (GeneArt, Germany). Synthesized heavy and light chain variable region sequences were subcloned into mammalian expression vectors containing either a human IgG1 heavy chain constant region (such as Swissprot accession number PO1857) or a human lambda constant region (Swissprot accession number P0CG05) to yield full length antibody chains.

3.5 Expression of Antibodies

Antibodies were produced by co-transfecting plasmids encoding antibody heavy and light chains into EXPI293® cells (Life Technologies). The day before transfection, the number of cells needed for the experiment was determined. For each 20 mL transfection, $3.6 \times 10^7$ cells were required in 20 mL of EXPI293® Expression Medium. On the day prior to transfection, cells were seeded into TPP 50 mL bioreactor tubes at a density of $0.9 \times 10^6$ viable cells/mL and incubated overnight at 37° C. in a humidified atmosphere of 8% $CO_2$ in air on an orbital shaker rotating at 200 rpm. On the day of transfection, the cell number and viability were determined using an automated cell counter. Only cultures with >98% viable cells were used. For each 20 mL transfection, lipid-DNA complexes were prepared by diluting 10 µg of heavy chain DNA and 10 µg of light chain DNA in OPTI-MEM® I Reduced Serum Medium (Cat. no. 31985-062) to a total volume of 1.0 mL. 54 µL of EXPIFECTAMINE® 293 Reagent was diluted in OPTI-MEM® I medium to a total volume of 1.0 mL. Both vials were mixed gently and incubated for 5 minutes at room temperature. Following incubation, the diluted DNA was mixed with the diluted EXPIFECTAMINE® 293 Reagent and the DNA-EXPIFECTAMINE® 293 Reagent mixture incubated a further 20 minutes at room temperature to allow the formation of DNA-EXPIFECTAMINE® 293 Reagent complexes. Following incubation, 2 mL of DNA-EXPIFECTAMINE® 293 Reagent complex was added to each TPP 50 mL bioreactor tube. To the negative control tube, 2 mL of OPTI-MEM® I medium was added instead of DNA-EXPIFECTAMINE® 293 Reagent complex. The cells were incubated in a 37° C. incubator with a humidified atmosphere of 8% CO2 in air on an orbital shaker rotating at 200 rpm. Approximately 16-18 hours post-transfection, 100 µL of EXPIFECTAMINE® 293 Transfection Enhancer 1 and 1.0 mL of EXPIFECTAMINE® 293 Transfection Enhancer 2 were added to each tube. Antibodies were harvested approximately 72 hours post-transfection.

3.6 Purification of Antibodies

Cultures of transfected EXPI293® cells were spun down in 50 mL falcon tubes at 3000×g for 20 minutes, and supernatants were filtered using a 0.22 µm filter (Corning). Antibody-containing supernatants were purified using a Gilson ASPEC GX274 robot by Protein A chromatography. Briefly, SPE cartridges (Agilent, 12131014) packed with 1.2 mL MABSELECT SURE® protein A resin (GE Healthcare) were pre-equilibrated with 3 column volumes of 1×PBS. 18 mL of supernatant was run over the columns followed by a 4 ml 1×PBS wash. Each column was pre-eluted with 0.9 mL of 0.1M citric acid, pH 2.9. Purified antibodies were eluted with 2 mL 0.1 M citric acid, pH 2.9. Antibodies were desalted into Sørensens PBS (59.5 mM $KH_2PO_4$, 7.3 mM $Na_2HPO_4 \cdot 2H_2O$, 145.4 mM NaCl (pH~5.8)) using PD-10 columns (GE Healthcare).

3.7 Three Point Dilution on CTLL-2 Cells

Each purified antibody was tested at three different dilutions for its ability to inhibit IL-15 mediated proliferation of CTLL2 cells.

CTLL-2 cells were incubated in complete media without IL-2 or IL-15 for 4 hours prior to testing. Cells ($5\times10^4$/well) were incubated in 96-well plates with 200 pM of IL-15 complex with the IL-15 Receptor-alpha, the concentration that induced 50% of the maximum cell proliferation ($EC_{50}$). Antibody dilutions were added to the plates and incubated for 48 hours. Three anti-IL-15 antibody dilutions were used: 2000 pM, 200 pM and 20 pM. Inhibition of cell proliferation was then assessed using the CELLTITER-GLO® Luminescent Cell Viability Assay (Promega) according to manufacturer's instructions and read on a GLOMAX® 96 Microplate Luminometer (Promega). Data were expressed as relative luminescence units (the number of viable cells in culture based on quantitation of the ATP present, an indicator of metabolically active cells).

Figure 2A:
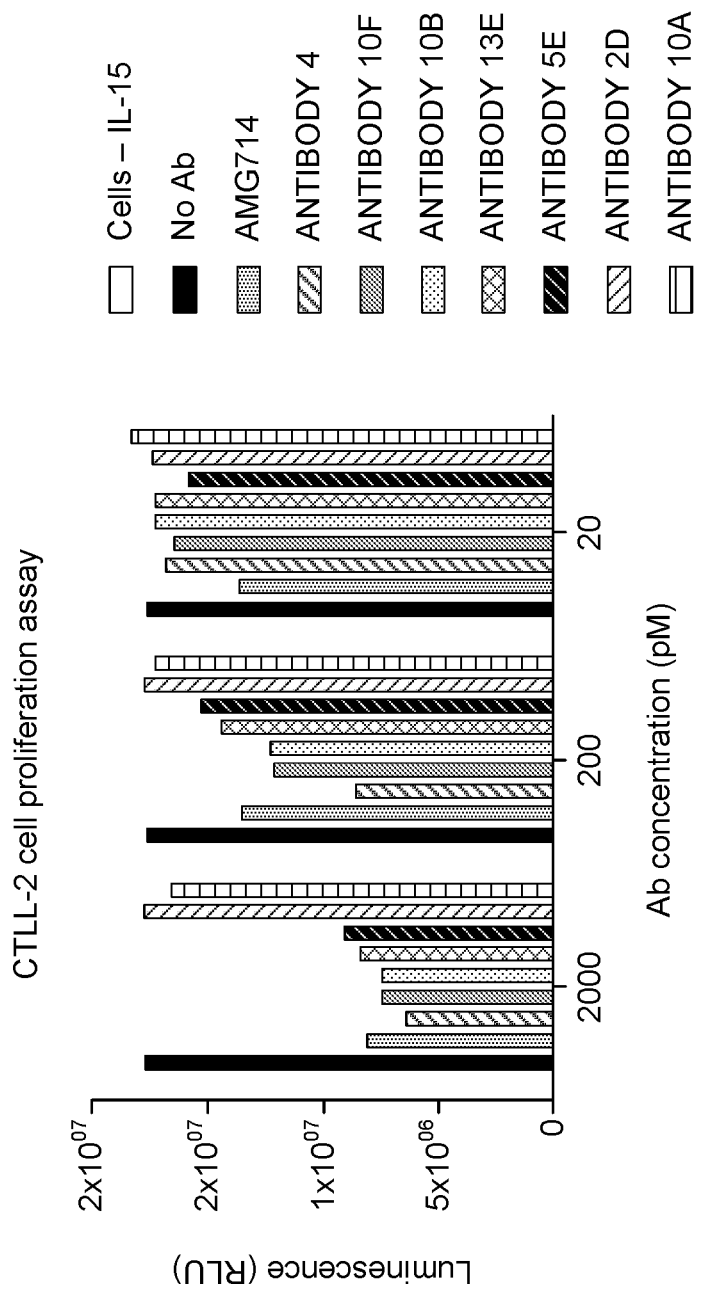
FIGS. 2A and 2B show dose response inhibition of IL-15 mediated CTLL-2 proliferation by anti-IL-15 antibodies.

This crude dose response of the antibodies' ability to functionally neutralize the biological activity of IL-15 was used to select antibodies for further analysis. A representative selection of results is shown in FIG. 2A. Antibody 4 was a highly potent antagonist of IL-15 activity.

3.8 Full Dose Response on CTLL-2 Cells

Selected antibodies were run in a 10-point version of the above CTLL-2 cell assay with the aim of generating full dose response curves.

Figure 2B:
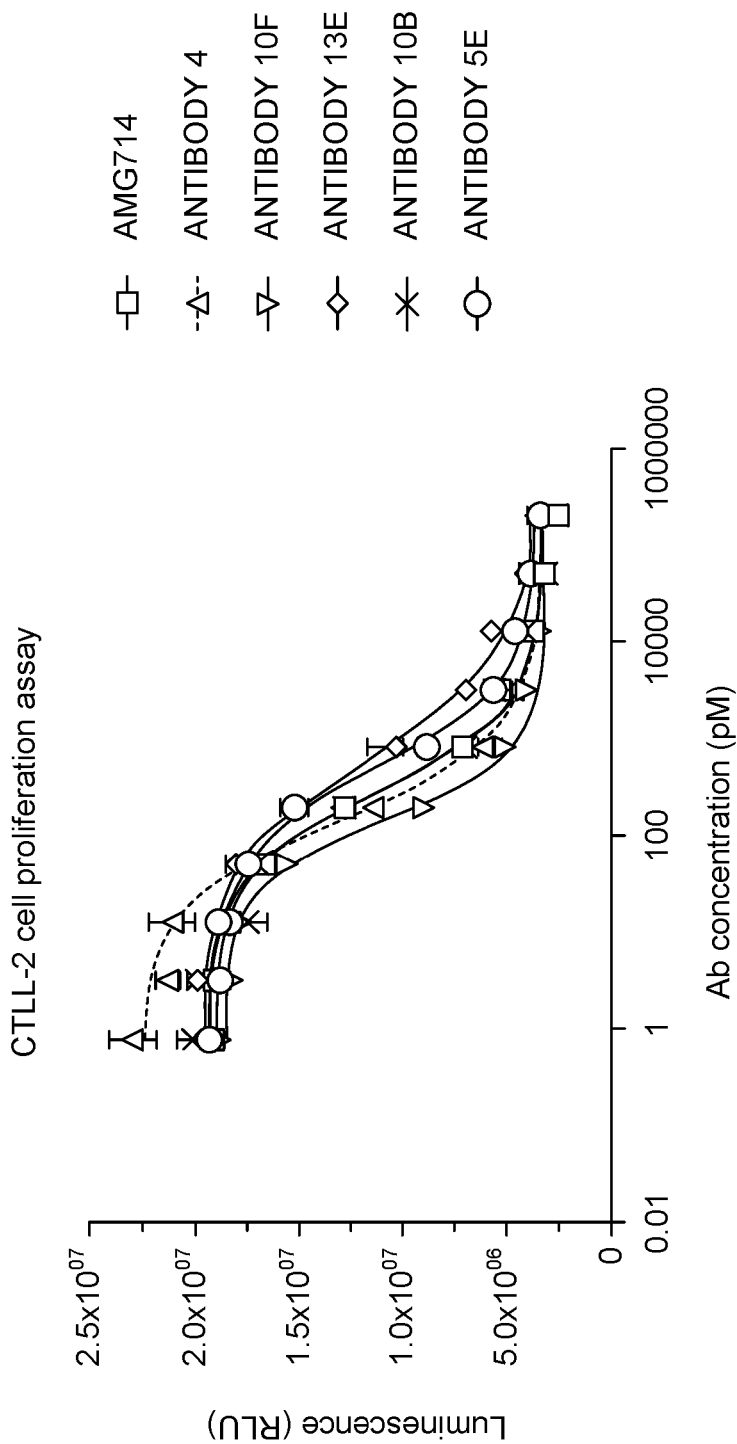

A representative selection of results is shown in FIG. 2B. The relative inhibition profile of each antibody was assessed using the $IC_{50}$ value (the concentration of anti-IL-15 antibodies at which the cell proliferation is reduced by half). Out of the antibodies tested, the most potent antibodies were Antibody 4 and Antibody 10F.

3.9 Full Dose Response on NK-92 Cells

The most potent antibodies in the CTLL-2 cell assay were subjected to a further cell assay using NK-92 cells. The cell line is derived from NK malignant non-Hodgkin's lymphoma (ATCC: CRL-2407).

NK-92 cells were incubated in complete media without IL-2 or IL-15 for 4 hours prior testing. Cells ($5\times10^4$/well) were incubated in 96-well plates with IL-15 complexed with the IL-15 Receptor-alpha at 25 pM ($EC_{50}$) to induce cell proliferation. Antibody doses were added to the plates and incubated for 48 hours. Inhibition of cell proliferation was then assessed using the CELLTITER-GLO® Luminescent Cell Viability Assay (Promega) according to manufacturer's instructions and read on GLOMAX® 96 Microplate Luminometer (Promega) as described above. Data were expressed as relative luminescence units.

Figure 3:
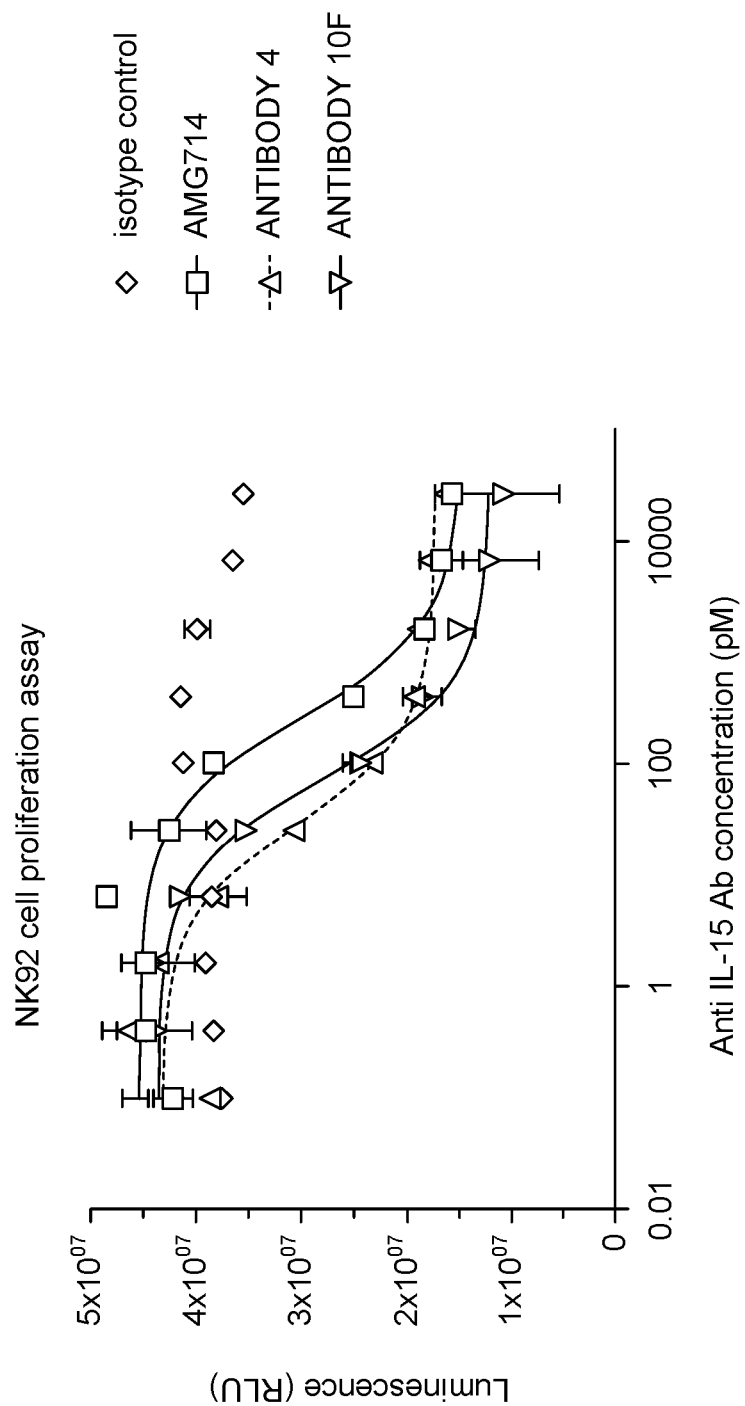
FIG. 3 shows inhibition of IL-15 mediated NK-92 proliferation by representative anti-IL-15 antibodies, AMG714 or isotype control (anti-KLH C3 IgG1). The readout was taken at 72 hours and is expressed as relative luminescence units. Results are expressed as mean±error 3 replicates.

A representative selection of results is shown in FIG. 3. The relative inhibition profile of each antibody was assessed using the IC50 value. Antibody 4 had the lowest inhibitory IC50 value (0.1 nM and was identified as the most potent inhibitor of IL-15 driven cell based proliferation.

Example 4

Modification of the Antibody

Antibody 4 was altered with the aim of yielding a positive effect on the antibody's biophysical properties, as well as improving the potency.

4.1 Location of Critical Amino Acids for Binding

Variants of the parent antibody were generated by modifying each residue in the CDR sequences and assessing the effect on antibody potency and binding properties (CDR scanning). Nine variants at each CDR position were generated by modifying the residues to alanine (A), aspartic acid (D), histidine (H), lysine (K), leucine (L), glutamine (Q), serine (S), tryptophan (W) or tyrosine (Y). These nine amino acids were chosen due to their range of properties so that all functional properties were tested, as shown in Table 1.

TABLE 1

| Amino acid functional properties. | |
|---|---|
| Amino acid | Functional property |
| Alanine (A) | Small size |
| Aspartic acid (D) | Acidic |
| Histidine (H) | Basic; ring structure |
| Lysine (K) | Basic |
| Leucine (L) | Hydrophobic |
| Glutamine (Q) | Amide |
| Serine (S) | Nucleophilic |
| Tryptophan (W) | Aromatic |
| Tyrosine (Y) | Aromatic |

This resulted in the selection of ~520 variants of the Antibody 4 each differing from Antibody 4 by 1 amino acid. Antibodies were generated as described previously and screening was performed using surface plasmon resonance on a Biacore T200 (GE Healthcare) system using a CM5 Protein A (GE Healthcare) chip. The running buffer used was HBS-EP+(GE Healthcare) and all interactions were measured at 25° C. and data collection rate was set to 10 Hz. Before running the method, a start-up cycle was performed in which both flow cells of the chip were cleaned with two consecutive 60 s pulses of 0.1 M citric acid (pH 3.0).

Supernatants of EXPI293® F cells co-expressing antibody variants were diluted 1 in 100 in HBS-EP+ (GE Healthcare) and human IL-15 complex was diluted to 10 μg/mL in the same buffer. Antibodies were captured onto the second flow cell of the chip and binding was measured by injection of 30 μL of human IL-15 complex at a flow rate of 30 μL/min across both flow cells and allowing 120 s of dissociation time. The chip surface was regenerated between cycles with two consecutive 60 s pulses of 0.1 M citric acid (pH 3.0) over both flow cells.

Data from FC2-1 was used for analysis. The resultant sensorgrams were analysed by creating two custom report points, each calculated for a 1 s window starting either 5 s after injection of the sample ('early binding') or 5 s before the end of dissociation ('late binding'). Antibodies were ranked based on the ratio of these two report points ('late binding'/'early binding') as an estimation of dissociation rate. Relative capture levels were used as a rough indicator of productivity. The results of the CDR modification experiments are shown in FIGS. 5-34. FIGS. 5-33 show single modifications that led to an improved antibody (shaded grey) and FIG. 34 summarizes the single and multiple modifications tested that led to an improved antibody.

These experiments identified the amino acids that were critical for binding and potency as well as the amino acids that could be substituted with no change in binding or potency. Surprisingly, it was found that substitution of amino acids in position 54 or 56 in CDR2 of the heavy chain by aromatic amino acids Y or W led to an increase in potency of the antibody.

Further variants were made to test the substitution of amino acids in position 54 or 56 in CDR2 of the heavy chain by aromatic amino acid phenylalanine (F). These two variants also showed an increase in potency in the NK-92 cell proliferation assay.

Double variants were generated where both of the amino acids in position 54 or 56 of CDR2 of the heavy chain were modified to either Y, W or F. The potency of the double variants was assessed in the NK-92 cell proliferation assay as described in section 3.9. Results are shown in Table 2.

TABLE 2

54-56 double variants.

| | | Position 54 | | |
|---|---|---|---|---|
| | | F | Y | W |
| Position 56 | F | 4.9 pM | 6.6 pM | 3.4 pM |
| | Y | 11.2 pM | 7.4 pM | 10.1 pM |
| | W | 8.3 pM | 7.6 pM | 5.1 pM |

It was found that the effect of including two aromatic amino acids at positions 54 and 56, rather than being counteractive, instead led to a cumulative improvement in potency.

Figure 35:
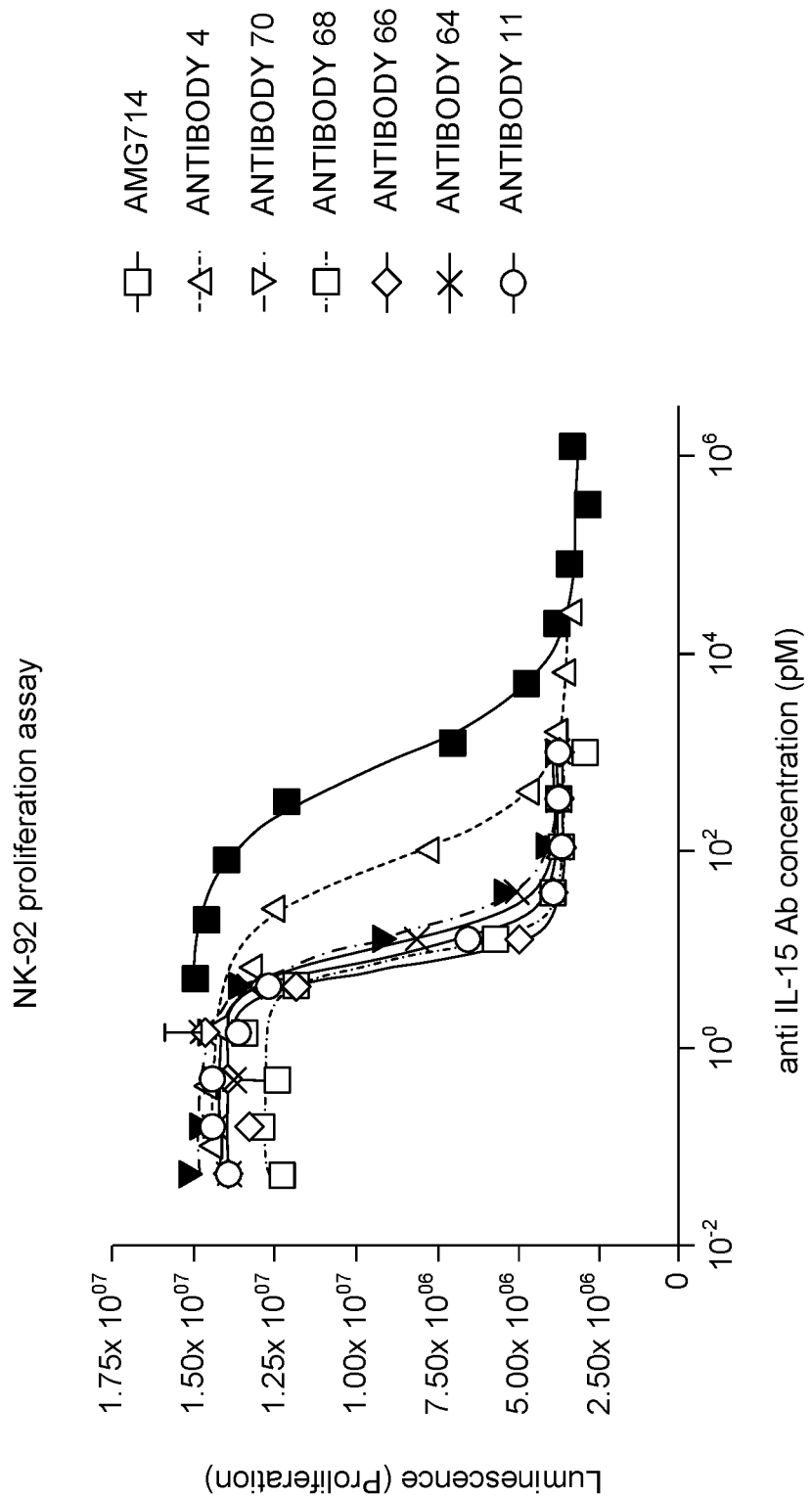
FIG. 35 shows Antibody 4 variants with improved inhibition of IL-15-mediated NK-92 proliferation relative to the parent antibody, Antibody 4, and other anti-IL-15 antibodies. Readout was taken after 72 hours and is expressed as relative luminescence units.

Antibody 11 (comprising 54Y and 56Y) has at least a 10 fold improvement of $IC_{50}$ in the NK-92 cell proliferation assay compared to Antibody 4 (FIG. 35 and Table 3).

4.2 Modification of Antibody 4 to Reduce Potential Immunogenic Epitopes

To remove potentially immunogenic epitopes in antibodies substitutions can be made to the peptide sequence to revert the sequence in this region back to germline antibody sequence. Substituting I82aS in the heavy chain (Antibody 63) resulted in a germline sequence and removed the predicted immunogenic peptide in this region. This substitution had no impact on potency in the NK-92 assay, as shown in Table 3 (Antibody 63 compared to Antibody 11).

Substitution of N30S in the light chain (Antibody 73) resulted in a germline sequence and removed the predicted immunogenic peptide in this region. This substitution had a minor impact on potency in the NK-92 assay, as shown in Table 3 (Antibody 73 compared to Antibody 11).

When both substitutions were combined into one antibody, Antibody 64, a slight reduction in potency compared to Antibody 11 was observed (FIG. 35).

4.3 Modification of Antibody 64 to Improve Manufacturability

Amino acid analysis of the variable heavy and light chain sequence of Antibody 64 and related antibodies identified amino acids that may undergo isomerization. Changes to these amino acids may, over time, alter the stability of the antibody. In the light chain, D92 and S93, were identified as a potential aspartic acid isomerization site. To reduce the potential impact of these predicted issues variants of Antibody 64 were produced containing conservative or semi-conservative amino acid substitutions in these positions. These substitutions and their impact on the potency of the resulting variants are listed in Table 4. FIG. 35 shows a representative selection of variants tested in the NK-92 cell proliferation assay.

Modifications to enhance manufacturability by changing D92 lead to a loss in potency (see Antibody 68 compared to Antibody 11) Altering S93 to L93 surprisingly resulted in an improvement in potency of the antibody, as shown in Table 3 and in FIG. 35.

A summary of the modifications made to Antibody 4 to generate Antibody 70 is given in Table 4.

TABLE 4

Modification Summary

| Amino acid position | Unmodified residue (Antibody 4) | Modified residue (Antibody 70) | Improved property |
|---|---|---|---|
| H54 | S | Y | Improved potency |
| H56 | N | Y | Improved potency |
| H82a | I | S | Removes potential immunogenic epitope by germlining |
| L30 | N | S | Removes potential immunogenic epitope by germlining |
| L93 | S | L | Reduces potential isomerization site |

TABLE 3

List of reduced immunogenicity variants

| Antibody # | Heavy Chain substitutions | Light Chain substitutions | IC 50 (NK-92) in pM | VH SEQ ID NO: | VL SEQ ID NO: | Full L SEQ ID NO: |
|---|---|---|---|---|---|---|
| Antibody 4 | Wild type | WT | 148 | 7 | 8 | 9 |
| Antibody 11 | S54Y + N56Y | WT | 6.3 | 454 | 8 | 9 |
| Antibody 63 | S54Y + N56Y + I82aS | WT | 4.21075 | 4 | 8 | |
| Antibody 64 | S54Y + N56Y + I82aS | N30S | 13.5975 | 4 | 455 | 456 |
| Antibody 65 | S54Y + N56Y + I82aS | D92E | 42.48 | 4 | 503 | |
| Antibody 66 | S54Y + N56Y + I82aS | S93L | 6.0443 | 4 | 457 | 458 |
| Antibody 67 | S54Y + N56Y + I82aS | S93E | 7.688 | 4 | 505 | |
| Antibody 68 | S54Y + N56Y + I82aS | S93F | 5.338 | 4 | 459 | 460 |
| Antibody 69 | S54Y + N56Y + I82aS | N30S + D92E | 162.5 | 4 | 507 | |
| Antibody 70a | S54Y + N56Y + I82aS | N30S + S93L | 18.178 | 4 | 5 | 6 |
| Antibody 71 | S54Y + N56Y + I82aS | N30S + S93E | 26.39 | 4 | 509 | |
| Antibody 72 | S54Y + N56Y + I82aS | N30S + S93F | 20.93 | 4 | 510 | |
| Antibody 73 | S54Y + N56Y | N30S | 11.842 | 454 | 455 | |
| Antibody 74 | S54Y + N56Y | D92E | 33.9 | 454 | 503 | |
| Antibody 75 | S54Y + N56Y | S93L | 3.136 | 454 | 457 | |
| Antibody 76 | S54Y + N56Y | S93E | 7.686 | 454 | 505 | |
| Antibody 77 | S54Y + N56Y | S93F | 5.694 | 454 | 506 | |
| Antibody 78 | S54Y + N56Y | N30S + D92E | 168 | 454 | 507 | |
| Antibody 79 | S54Y + N56Y | N30S + S93L | 12.38 | 454 | 5 | |
| Antibody 80 | S54Y + N56Y | N30S + S93E | 22.75 | 454 | 509 | |
| Antibody 81 | S54Y + N56Y | N30S + S93F | 17.29 | 454 | 510 | |

Example 5

Receptor Affinity and Selectivity of Antibody 70 Variants

Constant region variants of antibody 70 were generated. The heavy chain variable region of antibody 70 was synthesized in-frame with the human IgG isotype constant domains described in Table 5.

TABLE 5

| Antibody 70 variants | |
|---|---|
| Antibody 70 variants | SEQ ID NO |
| Antibody 70a | 33 |
| Antibody 70b | 35 |
| Antibody 70e | 47 |
| Antibody 70f | 49 |

IL-15 binds to and signals through a complex composed of IL-15Rα, IL-2Rβ and IL-2Rγ. Antibodies were assessed for their ability to bind IL-15Rα, as well as cytokines that share the common receptor IL-2Rβ/γ such as IL-2, IL-4, IL-7, IL-9 and IL-21. Antibody 70 variants did not bind to IL-15Rα, IL-2, IL-4, IL-7, IL-9 and IL-21.

Binding of Antibody 70 variants to human IL-15 complexed with the IL-15 Receptor-alpha were assessed using surface plasmon resonance on a BIACORE® T200 (GE Healthcare) system using a Protein A Sensor Chip (GE Healthcare). Antibodies were captured onto the second flow cell to a level of 150-200 RU. Purified cytokines were diluted to 10 μg/mL in HBS-EP+. Binding was measured by injection of 45 μL of each cytokine at a flow rate of 30 μL/min across both flow cells and allowing 180 s of dissociation time. The chip surface was regenerated between cycles with two 10 sec pulses of 50 mM sodium hydroxide. The running buffer used was HBS-EP+(GE Healthcare) and all interactions were measured at 25° C. and data collection rate set to 10 Hz.

A summary of the surface plasmon resonance data is shown on FIG. 36. The affinity can be measured by the KD (the equilibrium dissociation constant between the antibody and its antigen). The Antibody 70 variants had the lowest KD values (from 0.133 to 0.193 nM), as compared to Antibody 4 (average KD=0.629 nM) and AMG714 (average KD=1.84 nM). The large difference in KD between variants of Antibody 70 and AMG714 is driven by the dissociation rate (kd). IL-15 dissociates from AMG714 ten times faster than the rate of dissociation of IL-15 from Antibody 70 variants. Once bound to IL-15, Antibody 70 and variants thereof remain bound for longer and therefore are superior at inhibiting IL-15 activity. This was tested in a cell based potency assay.

Figure 37:
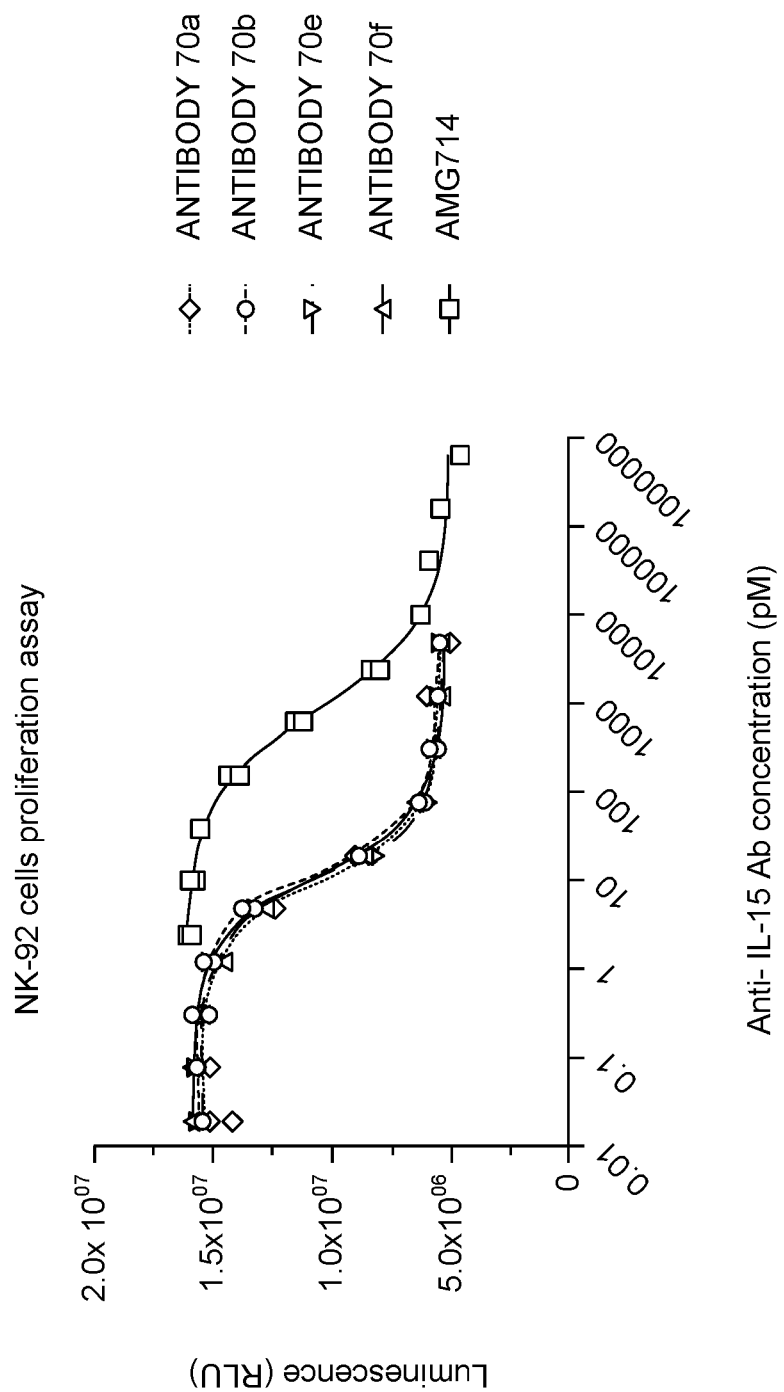
FIG. 37 shows a comparison of anti-IL-15 antibodies in a NK-92 cell based assay. The inhibition of 25 pM of IL-15 complex mediated NK-92 proliferation by anti-IL-15 antibodies for 48 hours is expressed as relative luminescence units. The Antibody 70 variants have similar potency to each other and have a lower IC-50 value than AMG-714.

The potency of Antibody 70 variants and AMG714 was assessed in the NK-92 proliferation assay with IL-15 complexed with the IL-15 Receptor-alpha at 25 pM (EC50) to induce cell proliferation as described in Example 3. FIG. 37 and Table 6 shows that the $IC_{50}$ of the Antibody 70 variants was 83 to 98 times lower than the $IC_{50}$ of AMG714. Therefore, Antibody 70 was superior at inhibiting IL-15 activity in a cell based potency assay.

TABLE 6

| $IC_{50}$ values for anti-IL-15 antibodies in the NK-92 proliferation assay | | | | |
|---|---|---|---|---|
| Antibody | Mean $IC_{50}$ (pM) | Std. Dev. | Min $IC_{50}$ (pM) | Max $IC_{50}$ (pM) |
| AMG714 | 1303.2 | 666.2 | 377.8 | 2653.9 |
| Antibody 70a | 14.7 | 3.8 | 10.2 | 22.0 |
| Antibody 70b | 13.3 | 2.5 | 10.6 | 16.6 |
| Antibody 70e | 15.7 | 4.7 | 11.7 | 20.9 |
| Antibody 70f | 14.6 | 5.0 | 7.3 | 29.8 |

Subsequent studies with antibody 70F resulted in an average affinity for the epitope having a KD of 430 pM. Altogether, these results suggest that Antibody 70 variants have improved binding capacity, affinity and potency to human IL-15 compared to AMG714.

Example 6

Epitope Mapping of Antibody 70

Epitope mapping was performed using alanine scanning experiments. Modelling analysis was carried out to determine probable exposed residues on IL-15 that were not involved in IL-15Rα binding. IL-15 constructs were then designed in which each of these theoretically exposed residues was substituted with an alanine. The list of these variants is listed in Table 7

TABLE 7

| list of IL-15 alanine variants | | |
|---|---|---|
| Residue | Position | Percentage of solvent exposure of side chain |
| N | 1 | 37.7 |
| V | 3 | 52 |
| N | 4 | 55 |
| S | 7 | 55.1 |
| D | 8 | 26.8 |
| K | 10 | 66.1 |
| K | 11 | 53.6 |
| E | 13 | 35.2 |
| D | 14 | 65.5 |
| L | 15 | 35.2 |
| Q | 17 | 70.7 |
| S | 18 | 79.1 |
| H | 20 | 94.5 |
| S | 29 | 34 |
| D | 30 | 78.8 |
| H | 32 | 57.2 |
| P | 33 | 61.1 |
| S | 34 | 69.8 |
| K | 36 | 46 |
| K | 41 | 63.6 |
| Q | 48 | 61.4 |
| D | 56 | 43.7 |
| A | 57 | 66.7 |
| H | 60 | 56.4 |
| D | 61 | 61 |
| E | 64 | 70.4 |
| I | 68 | 64.6 |
| L | 69 | 31.6 |
| N | 72 | 59.6 |
| S | 75 | 70.2 |
| N | 77 | 77.9 |
| N | 79 | 96.5 |
| V | 80 | 96.9 |
| T | 81 | 91.5 |
| E | 82 | 42.9 |
| S | 83 | 93.8 |
| K | 86 | 65.7 |
| E | 92 | 64.1 |

TABLE 7-continued list of IL-15 alanine variants

| Residue | Position | Percentage of solvent exposure of side chain |
|---------|----------|----------------------------------------------|
| K | 94 | 50.5 |
| N | 95 | 59.2 |
| K | 97 | 77.1 |
| E | 98 | 37.6 |
| Q | 101 | 49.5 |
| H | 105 | 55.2 |
| Q | 108 | 60.7 |
| M | 109 | 55.4 |
| I | 111 | 41.3 |
| N | 112 | 93.3 |

These constructs were then co-expressed with IL-15Rα and supernatant from the expression cultures tested for protein expression and binding to Antibody 70a using SPR.

The running buffer used was HBS-EP+(GE Healthcare). All interactions were measured at 25° C. and the data collection rate was set to 10 Hz. Data from FC2-1 was used for analysis. The resultant sensorgrams were analysed by creating two custom report points, each calculated for a 5 s window starting either 10 s after injection of the sample ('early binding') or 10 s before the end of dissociation ('late binding'). These values were subtracted from the values for the untransfected control and a relative dissociation rate was estimated by first, taking a ratio of these two custom report points ('late binding'/'early binding') and then, taking the resultant values as a fraction of the value calculated for wild-type human IL-15 complexed with the IL-15 Receptor-alpha (data not shown).

To confirm the results from the supernatant screen, samples which showed a faster dissociation rate compared to wild-type human IL-15 complexed with the IL-15 Receptor-alpha were purified and retested by SPR. A Protein A Sensor Chip (GE Healthcare) was used to capture Antibody 70a onto the second flow cell to a capture level of 150-200 RU. Purified IL-15 alanine scan constructs were diluted to 10 µg/mL in HBS-EP+ and then a 2-fold dilution series was made. Binding was measured by injection of 45 µL of each dilution at a flow rate of 30 µL/min across both flow cells and allowing 600 s of dissociation time. The chip surface was regenerated between cycles with a 10 sec pulse of 50 mM sodium hydroxide. The running buffer used was HBS-EP+(GE Healthcare) All interactions were measured at 25° C. and the data collection rate was set to 10 Hz. Data from Fc2-1 was used for analysis and generated sensorgrams were fitted using a 1:1 Langmuir equation (using local Rmax fitting) to determine KD. Data are shown in FIG. 38 for all IL-15 alanine variants co-expressed with IL-15Rα that showed a reduction in binding to the tested anti-IL-15 antibodies. Antibody 70a had low binding to mutated IL-15 with a Q108A substitution. AMG714 has no binding or significantly reduced binding to mutated IL-15 with the following amino acid substitutions: E98A, Q101A, H105A and Q108A. These results indicate that mutation of these 4 amino acids disrupts the binding of AMG714 to IL-15 complex with the IL-15 Receptor-alpha, and only the mutation of Q108 disrupts the binding of Antibody 70a to IL-15 complexed with the IL-15 Receptor-alpha. The results in FIG. 38 show that for the residues in IL-15 that were tested, the binding of the AMG714 antibody is reduced upon alteration of the residues, whereas the binding of Antibody 70a was not reduced by alteration given the high affinity of the antibody for IL-15; only alteration of Q108 in IL-15 resulted in binding reduction by Antibody 70a.

Given both antibodies (Antibody 70a and AMG714) had low or no binding to Q108A mutant of IL-15, an additional screen was performed on Antibody 70a with another anti-IL-15 antibody, which bound Q108 and wild-type IL-15 complex with equal affinity demonstrating the Q108A mutant is correctly folded. Alanine scanning identifies residues that, when mutated, can disrupt the binding of the antibody to IL-15. To determine the exact residues that contact IL-15 and thus determine the Antibody 70a binding epitope, the interaction of Antibody 70a with human IL-15 was characterized by X-ray crystallography.

In preparation for crystallization experiments, recombinant human IL-15 was expressed and purified from bacteria. Antibody 70a Fab (where FAb is Fragment antigen binding) was prepared by papain-mediated cleavage of the antibody hinge, which separates the antibody FAb from the Fc. The FAb was purified via standard protein-A chromatography methods and complexed with IL-15. The FAb:IL-15 was purified by size exclusion chromatography and set up for crystallization screening using sparse matrix crystallization screens. Final crystals used for diffraction data collection were formed in 10% polyethyleneglycol (PEG) 20000, 20% PEG 500 monomethyl ether (MME), 30 mM $CaCl_2$, 30 mM $MgCl_2$, 100 mM of unspecified imidazole/sodium cacodylate/MES (acid)/Bis-Tris buffer mix, pH 6.5. Diffraction data were collected to 2.25 Å at beamline i04 at the Diamond Synchrotron facility. The structure was solved by molecular replacement using published structures of human IL-15 and FAb molecules as templates for model building. The structure was iteratively refined against experimental data to R/Rfree values of 23.6/28.9. The structure shows that the variable regions of Antibody 70a bind at the IL-2Rγ and IL-2Rβ binding sites of human IL-15, thus blocking the interaction of those receptor units with IL-15 (FIGS. 39A and 39B). This is further demonstrated by looking at the interactions of the IL-15 side chains with the side chains of the FAb, comparing these to the IL-15 side chains that interact with IL-2Rγ and IL-2Rβ and looking for side chains or residues in common to both interactions.

Table 8 lists the interactions between the IL-15 side chains and the side chains of the FAb fragment of Antibody 70a. The side chains of Antibody 70a FAb that contact IL-15 form the paratope of Antibody 70a and related antibodies. Interpretations presented in the table correspond to: "hydrophobic interactions"—van der Waals interactions between atom pairs; "water-mediated"—water mediated hydrogen bonds between atom pairs; "hydrogen bond"—hydrogen bonds of heteroatoms between 2.5-3.5 Å; "H-pi hydrogen bond"—hydrogen bond corresponding to a donor/acceptor atom within an aromatic

TABLE 8

Side chain interactions of IL-15 with the FAb of Antibody 70a

| IL-15 residue | | Antibody | | | |
|---|---|---|---|---|---|
| residue | Chemical atom name | 70a Fab CDR | Residue | Chemical atom name | Interpretation |
| Ile6 | side chain | CDR_L1 | Tyr31 | Phenyl ring | Hydrophobic interaction |
| Ser7 | Backbone carbonyl | CDR_L1 | Arg29 | Backbone carbonyl | Water-mediated hydrogen bond |
| Lys10 | Amino group | CDR_L1 | Leu28 | Backbone carbonyl | Hydrogen bond |
| Lys10 | Amino group | CDR_L1 | Arg29 | Backbone carbonyl | Hydrogen bond |
| Lys10 | Backbone carbonyl | CDR_L1 | Tyr32 | Hydroxyl group | Hydrogen bond |
| Lys10 | Aliphatic part of side chain | CDR_L1 | Tyr32 | Phenyl ring | Hydrophobic interaction |
| Glu13 | Carboxylate | CDR_H3 | Trp99 | Indole nitrogen | Hydrogen bond |
| Glu13 | Carboxylate | CDR_L2 | Lys51 | Backbone amide | Water-mediated hydrogen bond |
| Glu13 | Carboxylate | CDR_L2 | Asn53 | Amide nitrogen | Water-mediated hydrogen bond |
| Asp14 | Carboxylate group | CDR_L1 | Tyr32 | Hydroxyl group | Hydrogen bond |
| Asp14 | Carboxylate group | CDR_L2 | Lys51 | Amino group | Hydrogen bond |
| Ser29 | Backbone carbonyl | CDR_H1 | Ser32 | Hydroxyl group | Hydrogen bond |
| Val31 | Backbone carbonyl | CDR_H2 | Tyr52 | Hydroxyl group | Hydrogen bond |
| Pro81 | Side chain | CDR_H2 | Tyr54 | Phenyl rings | Hydrophobic interaction |
| Gln101 | Amide nitrogen | CDR_H3 | Ile97 | Backbone carbonyl | Hydrogen bond |
| Val104 | Side chain | CDR_H3 | Trp99 | Indole group | Hydrophobic interaction |
| His105 | Side chain Nitrogen | CDR_H3 | Gly98 | Backbone amide | Hydrogen bond |
| His105 | Side chain Nitrogen | CDR_H1 | Ser32 | Backbone carbonyl | Hydrogen bond |
| Gln108 | Amide nitrogen | CDR_L3 | Gly95 | Backbone carbonyl | Hydrogen bond |
| Gln108 | Amide oxygen | CDR_L1 | Tyr31 | Hydroxyl group | Hydrogen bond |
| Gln108 | Amide oxygen | CDR_H3 | Gly99 | Backbone carbonyl | Water-mediated hydrogen bond |
| Ile111 | Backbone carbonyl | CDR_L3 | Lys95A | Amino group | Hydrogen bond |
| Asn112 | Amide nitrogen | CDR_H1 | Trp34 | Indole group | H-pi hydrogen bond |
| Asn112 | Backbone carbonyl | CDR_H2 | Asn58 | Amide nitrogen | Hydrogen bond |
| Thr113 | Side chain Methyl | CDR_H2 | Tyr56 | Phenyl ring | Hydrophobic interaction |
| Ser114 | C-terminus | CDR_L3 | Lys95A | Amino group | Hydrogen bond |

A similar analysis was performed on the X-ray structure of the quaternary IL-15 receptor complex (pdb code 4GS7). Table 9 shows the IL-15 residues important for binding of the IL-15 complex to IL-2Rγ and IL-2Rβ based on the hydrogen bonding that occurs between the side chains of IL-15 and the side chains of IL-2Rγ and IL-2Rβ.

TABLE 9

Side chain interactions of IL-15 with IL-2Rγ and IL-2Rβ

| IL-15 residue | | IL-2Rγ residue | | |
|---|---|---|---|---|
| Residue | Chemical atom name | Residue | Chemical atom name | Interpretation |
| Asp30 | Amide oxygen | Asn71 | Side chain nitrogen | Hydrogen bond |
| Asp30 | Carboxylate group | Thr105 | Hydroxyl group | Hydrogen bond |
| His32 | Side chain nitrogen | Asp73 | Carobxylate group | Hydrogen bond |
| Gln108 | Amide oxygen | Tyr103 | Hydroxyl group | Hydrogen bond |
| Gln108 | Amino group | Pro207 | Amide oxygen | Hydrogen bond |
| Gln108 | Amino group | Ser211 | Hydroxyl group | Hydrogen bond |
| Asn112 | Carboxylate group | Cys160 | Sulfide | Hydrogen bond |
| Asn112 | Amino group | Tyr103 | Hydroxyl group | Hydrogen bond |

| IL-15 residue | | IL-2Rβ residue | | |
|---|---|---|---|---|
| Residue | Chemical atom name | Residue | Chemical atom name | Interpretation |
| Asn1 | Carboxylate group | Thr74 | Hydroxyl group | Hydrogen bond |
| Asp8 | Carboxylate group | His133 | Side chain nitrogen | Hydrogen bond |

TABLE 9-continued

| Side chain interactions of IL-15 with IL-2Rγ and IL-2Rβ | | | | |
|---|---|---|---|---|
| Asp8 | Carboxylate group | Tyr134 | Hydroxyl group | Hydrogen bond |
| Glu64 | Carboxylate group | Arg42 | Amino group | Hydrogen bond |
| Asn65 | Carboxylate group | Arg42 | Amino group | Hydrogen bond |
| Asn65 | Carboxylate group | Arg42 | Amino group | Hydrogen bond |
| Ser7 | Hydroxyl group | Glu136 | Carboxylate group | Hydrogen bond |
| Asn65 | Side chain nitrogen | Gln70 | Backbone carbonyl | Hydrogen bond |

The solvent accessible surface area, formed on interaction of antibody 70 with human IL-15, is 2270.9 Å2. This value was calculated in PYMOL using the method of Strake and Rupley (1973) J. Mol. Biol. 79: 351-71.

Comparison of the side chain interactions of Antibody 70a FAb with IL-15 and the side chain interactions of the IL2R beta and gamma chains with IL-15 identifies several common residues. S7 (Ser7) forms a hydrogen bond with IL-2Rβ, and Q108 (Gln108) and N112 (Asn112) form hydrogen bonds with IL-2Rγ, (FIGS. 39C-39E). These 3 residues also form the epitope on IL-15 to which Antibody 70a FAb binds and forms hydrogen bonds, thereby preventing the interaction of IL-15 with IL-2Rβ and IL-2Rγ.

The triple tyrosine motif comprising Y52/54/56 in CDRH2, discovered during the affinity and potency maturation of the Antibody 70a, is a key binding determinant of the antibody with human IL-15. Examining the crystal structure (FIGS. 39F-39H) it can be seen that this motif veils and protects hydrophobic residues around helix-4 of IL-15 preventing solvation and stabilizing the structure.

Example 7

Flow Cytometry Detection of Variants Binding to 11-15 on Primary Human Cells

To further characterize antibody, their ability to bind IL-15 on primary human cells was tested. Human Peripheral Mononuclear Cells (PBMCs) were isolated and purified from buffy coats using Lymphoprep (Axis-Shield, Lymphoprep) and the binding of the lead Ab was assessed by flow cytometry analysis.

$1 \times 10^6$ viable PBMCs were initially seeded per well, in a 96-well polypropylene plate (Sigma/Corning) and stained with Zombie Violet dye (Biolegend) for 20 min at 4° C. Cells were further stained with TruStain FcX Fc block (Biolegend) diluted in FACS buffer for 10 min at room temperature. For surface staining, PBMC were stained with 10 μg/mL of test or isotype control antibodies (listed in Table 10), and incubated for 20 min at 4° C. Following immunostaining, samples were then fixed with BD cytofix/cytoperm (BD Biosciences) according to the manufacturer's instructions and stored at 4° C. until analysed. For intracellular staining, PBMC were fixed with BD cytofix/cytoperm (BD Biosciences) prior staining. Samples were analysed using a BD FACSCanto II (BD Biosciences).

Initial doublet discrimination was performed on all cell events to remove cell aggregates from analysis. Live cells were selected after exclusion of dead cells using a viability dye. Initial gating of leukocytes separated cells into the following: CD3$^-$CD8$^-$ cells, CD3$^+$CD8$^+$ T cells, and CD3$^+$CD8$^-$ (putatively CD4+) T cells. Further analysis of the CD3− population separated cells into CD19+ B cells and a CD19− cell population. The latter population was again additionally gated to select for CD56dimCD16+ and CD56briCD16dim/−NK cells. Further, based on levels of CD14 and CD16 expression, monocytes (Hi SSC population) were subsequently subdivided into the three major monocyte subsets: classical (CD14+CD16−), intermediate (CD14intCD16int), and non-classical (CD14dimCD16+).

Data analysis was performed using FLOWJO® analysis software V.10.

TABLE 10

| List of antibodies and conjugates. | | | | |
|---|---|---|---|---|
| Specificity | Conjugate | Clone | Species & Isotype | Supplier |
| Anti-Human Antibodies | | | | |
| CD3 | APC-Vio770 | REA613 | Recombinant Human IgG1 | Miltenyi Biotec |
| CD8 | VioGreen | BW135/80 | Mouse IgG2a | Miltenyi Biotec |
| CD14 | PerCP | TUK4 | Mouse IgG2a κ | Miltenyi Biotec |
| CD16 | FITC | REA423 | Recombinant Human IgG1 | Miltenyi Biotec |
| CD19 | PE | LT19 | Mouse IgG1 κ | Miltenyi Biotec |
| CD56 | PE Vio770 | AF12-7H3 | Mouse IgG1 | Miltenyi Biotec |
| IL-15 | iFluor647 | Antibody 70a | Human IgG1 λ | In-House |
|  | iFluor647 | Antibody 70b | Human IgG1 λ | In-House |
|  | iFluor647 | Antibody 70e | Human IgG4 λ | In-House |
|  | iFluor647 | Antibody 70f | Human IgG4 λ | In-House |
| Isotype Control Antibodies | | | | |
| Anti-KLH C3 IgG1 | iFluor647 |  | Human IgG1 | In-House |
| Anti-KLH C3 IgG4 | iFluor647 |  | Human IgG4 | In-House |

APC: Allophycocyanin;
FITC: Fluorescein isothiocyanate;
PE: Phycoerythrin;
PerCP: Peridinin chlorophyll protein A representative binding of Antibody 70 variants is on monocytes is shown in FIG. 40. Moderate binding of the Antibody 70 variants was detected on the cell surface of all monocyte subsets (classical, intermediate and non-classical). Higher binding levels were reported in intracellular binding in all monocyte subsets. Marginal differences in binding detection levels were found between both Antibody 70 variants. No or low binding was detected at the surface on T CD4+ and CD8+ cells and all subsets of NK cells, data not shown. These results indicate that the Antibody 70 variants were able to bind human IL-15 on primary cells.

Example 8

Efficacy of Anti-IL-15 Antibodies in Animal Models 8.1 In Vivo Neutralization of Human IL-15 and IL-15 Complexed with the IL-15 Receptor-Alpha This study was undertaken to determine the extent to which recombinant human IL-15 or IL-15/IL-15Rα complex could induce NK and NKT cell expansion in C57BL/6 mice, and the extent to which an exemplar antibody of the present invention could neutralize such induction.

Groups of 8 male C57Bl/6 mice were given a single dose of Antibody 70f (at 10, 3, 1, 0.3 or 0.1 mg/kg) or isotype control (10 mg/kg) i.p. on Day 1 (1 hour before first cytokine injection). NK1.1+ cells were induced by i.p. injection of recombinant IL-15 complex (where IL-15Rα is an Fc chimera) (1.5 µg/mouse) daily for 3 days from Day 1 to Day 3. On Day 4, spleens from mice were harvested. Cell suspensions were prepared from the total spleen of each mouse and counted on an automated cell counter. NK1.1+ numbers were assessed from cell suspensions by flow cytometry based on % of total splenocytes. Phycoerythrin-conjugated anti-mouse NK-1.1 (BD553165) was used. 50,000 events/sample were acquired on the cytometer.

As shown in FIG. 41, injection of IL-15/IL-15Rα complex induced NK1.1+ cell accumulation in mouse spleen. This accumulation could be significantly inhibited by treatment with Antibody 70f from 0.3 mg/kg but not with a human isotype control antibody.

8.2 Effect of Anti-IL-15 Antibodies on Circulating NK Cell Numbers in Non-Human Primates Administration of anti-IL-15 antibodies has previously been shown to decreased circulating NK cell numbers in cynomolgus monkeys (Lebrec et al. (2013) J. Immunol. 191:5551-5558). To further characterize Antibody 70, the consequence of antagonising IL-15 activity on circulating NK cells was tested in vivo. Groups of 4 male cynomologus monkeys received a single intravenous injection of Antibody 70f at 1 or 10 mg/kg or Antibody 70b at 10 mg/kg. Circulating numbers of NK cells were quantified by expression of the NK cell marker CD159a (NKG2A), determined by flow cytometry analysis of whole blood samples pre-dose and at study days 2, 5, 8, 15, 30, 45, 60, 75, 90, 102, 120 and 150.

Individual timepoints for each monkey and the median (solid line) peripheral blood NK cell counts are shown in FIG. 42. Administration of Antibody 70f at 1 or 10 mg/kg or Antibody 70b at 10 mg/kg resulted in a significant decrease below pre-dose circulating NK cell numbers from study day 7 which was sustained to study day 120 in the majority of animals.

8.3 Effect of Anti-IL-15 Antibodies in Rhesus Model of Celiac Disease in Non-Human Primates A chronic diarrheal disease named "Gluten-Sensitive Enteropathy" has been described in a subset of captive rhesus monkeys fed gluten-containing chow. When fed with a gluten-containing diet, gluten-sensitive macaques showed signs and symptoms of celiac disease including presence of intestinal tissue transglutaminase autoantibodies, anti-gliadin serum antibodies, decreased resorption of nutrients, decreased xenobiotic metabolism, villous atrophy, lowered diversity of gut microbiome, chronic diarrhea, weight loss, cancer predisposition and immunogenetic (MHC II-linked) association (Bethune M T et al. (2008) PLoS ONE. 3(2): e1614). A gluten-free diet reversed these clinical, histological and serological features, while reintroduction of dietary gluten caused rapid relapse. Interestingly, biopsies from gluten sensitive macaques showed IL-15 overexpression in jejunum tissues (Sestak K et al. (2016) Nutrients. 8(7):401.)

The capacity of an anti-IL-15 antibody of the invention to inhibit the gluten induced symptoms was tested in rhesus macaques with gluten-Sensitive enteropathy. The gluten-free (GFD) and gluten-containing (GD) diets were administered to all 6 gluten sensitive macaques to induce the stages of immunological remission and relapse, respectively, characterized by anti-gliadin (AGA) and anti-transgluataminase 2 (TG2) positive and negative plasma antibody responses as described in Sestak et al., 2015; 2016. After inducing AGA/TG2 antibody relapse, Antibody 70f was intravenously (i.v.) administered weekly in a dose of 10 mg/kg (BW) to three animals for 28 days (Group 1) and three animals for 90 days (Group 2) while macaques were still fed gluten containing diet. Intestinal biopsies were taken at stages of the study to measure the villus height to crypt depth ratio, and intraepithelial lymphocyte (IELs) counts. Presence of auto-antibodies against transglutaminase-2 and anti-gliadin antibodies were measured from serum samples. The study design is shown in FIG. 45A.

The evaluation of AGA and TG2 plasma (IgG) antibodies, GS enteropathy including morphometric evaluation of small intestinal villous heights versus crypt depths, i.e. V/C ratios, was done according to previously established protocols Sestak et al., 2015; 2016. Small intestinal biopsies were collected at times corresponding to immunological relapse (GD) and remission (GFD), as well as the beginning and end of the Anti-IL-15 antibody treatment period. Biopsies were collected and processed for intra-epithelial lymphocyte (IEL) counts as described by Sestak et al., 2016.

Results:

Assessment of jejunum biopsy tissues collected from gluten sensitive rhesus macaques prior, during and after the anti-IL15 antibody treatment revealed amelioration of enteropathy upon morphological evaluation of small intestinal tissue architecture, i.e., villous heights vs. crypt depths (V/C) ratios. On a gluten diet, macaques in both groups had significant loss of villus height, crypt depth tissue architecture (FIG. 45B). The V/C ratios improved significantly with anti-IL15 antibody treatment ($p<0.0001$) benefiting both groups of celiac macaques, as all treated animals exhibited increased heights of their small intestinal villi, i.e., V/C ratios to an extent comparable with healthy, age-matched controls (FIG. 45B).

To evaluate the efficacy of Anti-IL-15 antibody treatment in gluten sensitive rhesus macaques the counts of small intestinal IELs were compared between biopsy samples taken at time points representing the GD diet (6 months), GFD (3 months), and Anti-IL-15 antibody treatment (days 35 and 61) while on GD (FIG. 45C). Compared to the IEL count taken at an earlier timepoint when the animals were on a GD, both Anti-IL15 antibody treatment groups had significantly lower IEL counts (p<0.0001). Despite being fed a gluten containing diet, anti-IL15 antibody treatment measured at post-treatment day 35 (TD35) in Group 1 and at TD61 in Group 2 macaques, resulted in a greater decrease of IELs (p<0.0001) than that associated with 3 months of GFD (FIG. 45C).

Prior to treatment, the levels of anti-gliadin antibodies increased on exposure to gluten and decrease on a gluten free diet in 5/6 animals (animal 1B having no AGA response), indicating the animals were gluten sensitive (FIG. 45D). Anti-IL-15 treatment reduced anti-gliadin (AGA) antibodies in 5/5 animals that had high AGA levels prior to treatment, which was surprising given these animals were still exposed to a GD.

In summary anti-IL15 antibody treatment attenuated gluten-induced small intestinal mucosal injury (improved V/C ratio), attenuated gluten-induced small intestinal mucosal inflammation (reduced IEL counts) and attenuated gluten-induced serum antibodies (reduced anti-gliadin antibodies) as measured in a rhesus macaque model of celiac disease.

The disclosure is not limited to the embodiments described and exemplified above, but is capable of variation and modification within the scope of the appended claims.

---

The invention claimed is:

1. A polynucleotide encoding an antibody, wherein the antibody comprises an HCDR1, an HCDR2 and an HCDR3 comprising the amino acid sequences of SEQ ID NO: 16, 17 and 20, respectively; and an LCDR1, an LCDR2 and an LCDR3 comprising the amino acid sequences of SEQ ID NO:25, 28 and 29, respectively; and wherein the antibody specifically binds to human IL-15 when the IL-15 is complexed with IL-15Ra.

2. The polynucleotide according to claim 1, wherein the antibody comprises a heavy chain variable region comprising the amino acid sequence of SEQ ID NO: 5, a heavy chain constant region comprising the amino acid sequence of SEQ ID NO:49, and an light chain comprising the amino acid sequence of SEQ ID NO:6.

3. A vector comprising the polynucleotide according to claim 1.

4. A cell transfected with the vector according to claim 3.

5. A polynucleotide encoding an antibody heavy chain variable region comprising the amino acid sequence of SEQ ID NO: 1, or an antibody light chain variable region comprising the amino acid sequence of SEQ ID NO:2.

6. The polynucleotide according to claim 5, wherein the antibody heavy chain variable region comprises the amino acid sequence of SEQ ID NO: 4.

7. The polynucleotide of claim 6, comprising the nucleic acid sequence of SEQ ID NO: 517.

8. The polynucleotide according to claim 5, wherein the antibody light chain variable region comprises the amino acid sequence of SEQ ID NO: 5.

9. The polynucleotide of claim 8, comprising the nucleic acid sequence of SEQ ID NO: 518.

10. A polynucleotide encoding an antibody heavy chain variable region comprising the amino acid sequence of SEQ ID NO: 1, and an antibody light chain variable region comprising the amino acid sequence of SEQ ID NO:2.

11. The polynucleotide according to claim 10, wherein the antibody heavy chain variable region comprises the amino acid sequence of SEQ ID NO: 4, and the antibody light chain variable region comprises the amino acid sequence of SEQ ID NO:5.

12. An isolated host cell comprising a first polynucleotide comprising a nucleic acid sequence encoding an antibody heavy chain variable region comprising an HCDR1, an HCDR2 and an HCDR3 comprising the amino acid sequences of SEQ ID NO: 16, 17 and 20, respectively; and a second polynucleotide comprising a nucleic acid sequence encoding an antibody light chain variable region comprising an LCDR1, an LCDR2 and an LCDR3 comprising the amino acid sequences of SEQ ID NO:25, 28 and 29, respectively, wherein the antibody specifically binds to human IL-15 when the IL-15 is complexed with IL-15Ra.

13. The isolated host cell of claim 12, wherein the two polynucleotides are contained in a same vector.

14. The isolated host cell of claim 12, wherein the two polynucleotides are contained in different vectors.

15. The isolated host cell according to claim 12, wherein the first polynucleotide encodes an antibody heavy chain comprising a heavy chain variable region comprising the amino acid sequence of SEQ ID NO:5, and a heavy chain constant region comprising the amino acid sequence of SEQ ID NO:4; and wherein the second polynucleotide encodes an antibody light chain comprising the amino acid sequence of SEQ ID NO:6.

16. A transformed cell that comprises one or more expression vectors comprising one or more polynucleotides encoding an antibody, wherein the antibody comprises an HCDR1, an HCDR2 and an HCDR3 comprising the amino acid sequences of SEQ ID NO: 16, 17 and 20, respectively; and an LCDR1, an LCDR2 and an LCDR3 comprising the amino acid sequences of SEQ ID NO:25, 28 and 29, respectively; and wherein the antibody specifically binds to human IL-15 when the IL-15 is complexed with IL-15 Receptor alpha (IL-15Ra).

17. The transformed cell according to claim 16, wherein the antibody comprises a heavy chain variable region comprising the amino acid sequence of SEQ ID NO:5, a heavy chain constant region comprising the amino acid sequence of SEQ ID NO:49, and a light chain comprising the amino acid sequence of SEQ ID NO:6.

18. The transformed cell according to claim 16, wherein the cell is a mammalian cell.

19. The transformed cell according to claim 18, wherein the mammalian cell is a Chinese Hamster Ovary cell.

20. A method of producing an antibody comprising an HCDR1, an HCDR2 and an HCDR3 comprising the amino acid sequences of SEQ ID NO: 16, 17 and 20, respectively; and an LCDR1, an LCDR2 and an LCDR3 comprising the amino acid sequences of SEQ ID NO:25, 28 and 29, respectively, the method comprising culturing the cell of claim 16 to produce the antibody.

* * * * *

SEQUENCE LISTING

```
<160> NUMBER OF SEQ ID NOS: 520

<210> SEQ ID NO 1
<211> LENGTH: 119
<212> TYPE: PRT
<213> ORGANISM: Homo sapiens
<220> FEATURE:
<221> NAME/KEY: VARIANT
<222> LOCATION: (55)..(55)
<223> OTHER INFORMATION: X is S, Y, W, or F
<220> FEATURE:
<221> NAME/KEY: VARIANT
<222> LOCATION: (57)..(57)
<223> OTHER INFORMATION: X is N, Y, W, or F
<220> FEATURE:
<221> NAME/KEY: VARIANT
<222> LOCATION: (84)..(84)
<223> OTHER INFORMATION: X is I or S

<400> SEQUENCE: 1

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Xaa Gly Xaa Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Xaa Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 2
<211> LENGTH: 108
<212> TYPE: PRT
<213> ORGANISM: Homo sapiens
<220> FEATURE:
<221> NAME/KEY: VARIANT
<222> LOCATION: (29)..(29)
<223> OTHER INFORMATION: X is N or S
<220> FEATURE:
<221> NAME/KEY: VARIANT
<222> LOCATION: (92)..(92)
<223> OTHER INFORMATION: X is S, L, or F

<400> SEQUENCE: 2
```

-continued

```
Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Xaa Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Xaa Ser Gly Lys Asn
                85                  90                  95

Leu Val Phe Gly Gly Gly Thr Lys Leu Thr Val Leu
            100                 105

<210> SEQ ID NO 3
<211> LENGTH: 214
<212> TYPE: PRT
<213> ORGANISM: Homo sapiens
<220> FEATURE:
<221> NAME/KEY: VARIANT
<222> LOCATION: (29)..(29)
<223> OTHER INFORMATION: X is N or S
<220> FEATURE:
<221> NAME/KEY: VARIANT
<222> LOCATION: (92)..(92)
<223> OTHER INFORMATION: X is S, L, or F

<400> SEQUENCE: 3

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Xaa Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Xaa Ser Gly Lys Asn
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 4
<211> LENGTH: 119
<212> TYPE: PRT
<213> ORGANISM: Homo sapiens

<400> SEQUENCE: 4

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Tyr Gly Tyr Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 5
<211> LENGTH: 108
<212> TYPE: PRT
<213> ORGANISM: Homo sapiens

<400> SEQUENCE: 5

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Leu Ser Gly Lys Asn
                85                  90                  95

Leu Val Phe Gly Gly Gly Thr Lys Leu Thr Val Leu
            100                 105

<210> SEQ ID NO 6
<211> LENGTH: 214
<212> TYPE: PRT
<213> ORGANISM: Homo sapiens

<400> SEQUENCE: 6

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
```

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Leu Ser Gly Lys Asn
                85                  90                  95

Leu Val Phe Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 7
<211> LENGTH: 119
<212> TYPE: PRT
<213> ORGANISM: Homo sapiens

<400> SEQUENCE: 7

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 8
<211> LENGTH: 108
<212> TYPE: PRT
<213> ORGANISM: Homo sapiens

<400> SEQUENCE: 8

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr

```
                    35                  40                  45
Gly Lys Asn Asn Arg Pro Ser Gly Ile Pro Asp Arg Phe Ser Gly Ser
             50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Lys Asn
                85                  90                  95
Leu Val Phe Gly Gly Gly Thr Lys Leu Thr Val Leu
            100                 105
```

<210> SEQ ID NO 9
<211> LENGTH: 214
<212> TYPE: PRT
<213> ORGANISM: Homo sapiens

<400> SEQUENCE: 9

```
Ser Ser Glu Leu Thr Gln Asp Pro Ala Ala Ser Val Ala Leu Gly Gln
1               5                   10                  15
Thr Val Arg Ile Thr Cys Gln Gly Asp Thr Leu Arg Asn Tyr Tyr Ala
                20                  25                  30
Ser Trp Tyr Gln Gln Lys Pro Gly Gln Ala Pro Ile Leu Val Ile Tyr
            35                  40                  45
Gly Lys Asn Asn Arg Pro Ser Gly Ile Pro Asp Arg Phe Ser Gly Ser
         50                 55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Lys Asn
                85                  90                  95
Leu Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser
    210
```

<210> SEQ ID NO 10
<211> LENGTH: 30
<212> TYPE: PRT
<213> ORGANISM: Homo sapiens

<400> SEQUENCE: 10

```
Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser
                20                  25                  30
```

```
<210> SEQ ID NO 11
<211> LENGTH: 14
<212> TYPE: PRT
<213> ORGANISM: Homo sapiens

<400> SEQUENCE: 11

Trp Val Arg Gln Pro Pro Gly Lys Gly Leu Glu Trp Ile Gly
1               5                   10

<210> SEQ ID NO 12
<211> LENGTH: 32
<212> TYPE: PRT
<213> ORGANISM: Homo sapiens
<220> FEATURE:
<221> NAME/KEY: VARIANT
<222> LOCATION: (18)..(18)
<223> OTHER INFORMATION: X is I or S

<400> SEQUENCE: 12

Arg Val Thr Ile Ser Val Asp Lys Ser Lys Asn Gln Phe Ser Leu Lys
1               5                   10                  15

Leu Xaa Ser Val Thr Ala Ala Asp Thr Ala Val Tyr Tyr Cys Ala Arg
            20                  25                  30

<210> SEQ ID NO 13
<211> LENGTH: 32
<212> TYPE: PRT
<213> ORGANISM: Homo sapiens

<400> SEQUENCE: 13

Arg Val Thr Ile Ser Val Asp Lys Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 14
<211> LENGTH: 32
<212> TYPE: PRT
<213> ORGANISM: Homo sapiens

<400> SEQUENCE: 14

Arg Val Thr Ile Ser Val Asp Lys Ser Lys Asn Gln Phe Ser Leu Lys
1               5                   10                  15

Leu Ile Ser Val Thr Ala Ala Asp Thr Ala Val Tyr Tyr Cys Ala Arg
            20                  25                  30

<210> SEQ ID NO 15
<211> LENGTH: 11
<212> TYPE: PRT
<213> ORGANISM: Homo sapiens

<400> SEQUENCE: 15

Trp Gly Gln Gly Thr Leu Val Thr Val Ser Ser
1               5                   10

<210> SEQ ID NO 16
<211> LENGTH: 6
<212> TYPE: PRT
<213> ORGANISM: Homo sapiens

<400> SEQUENCE: 16

Ser Ser Asn Trp Trp Ser
1               5
```

```
<210> SEQ ID NO 17
<211> LENGTH: 16
<212> TYPE: PRT
<213> ORGANISM: Homo sapiens
<220> FEATURE:
<221> NAME/KEY: VARIANT
<222> LOCATION: (5)..(5)
<223> OTHER INFORMATION: X is S, Y, W, or F
<220> FEATURE:
<221> NAME/KEY: VARIANT
<222> LOCATION: (7)..(7)
<223> OTHER INFORMATION: X is N, Y, W, or F

<400> SEQUENCE: 17

Glu Ile Tyr His Xaa Gly Xaa Thr Asn Tyr Asn Pro Ser Leu Lys Ser
1               5                   10                  15

<210> SEQ ID NO 18
<211> LENGTH: 16
<212> TYPE: PRT
<213> ORGANISM: Homo sapiens

<400> SEQUENCE: 18

Glu Ile Tyr His Tyr Gly Tyr Thr Asn Tyr Asn Pro Ser Leu Lys Ser
1               5                   10                  15

<210> SEQ ID NO 19
<211> LENGTH: 16
<212> TYPE: PRT
<213> ORGANISM: Homo sapiens

<400> SEQUENCE: 19

Glu Ile Tyr His Ser Gly Asn Thr Asn Tyr Asn Pro Ser Leu Lys Ser
1               5                   10                  15

<210> SEQ ID NO 20
<211> LENGTH: 10
<212> TYPE: PRT
<213> ORGANISM: Homo sapiens

<400> SEQUENCE: 20

Glu Gly Ile Gly Trp Pro Ser Phe Asp Tyr
1               5                   10

<210> SEQ ID NO 21
<211> LENGTH: 22
<212> TYPE: PRT
<213> ORGANISM: Homo sapiens

<400> SEQUENCE: 21

Ser Ser Glu Leu Thr Gln Asp Pro Ala Ala Ser Val Ala Leu Gly Gln
1               5                   10                  15

Thr Val Arg Ile Thr Cys
            20

<210> SEQ ID NO 22
<211> LENGTH: 15
<212> TYPE: PRT
<213> ORGANISM: Homo sapiens

<400> SEQUENCE: 22

Trp Tyr Gln Gln Lys Pro Gly Gln Ala Pro Ile Leu Val Ile Tyr
1               5                   10                  15

<210> SEQ ID NO 23
<211> LENGTH: 32
```

```
<212> TYPE: PRT
<213> ORGANISM: Homo sapiens

<400> SEQUENCE: 23

Gly Ile Pro Asp Arg Phe Ser Gly Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 24
<211> LENGTH: 10
<212> TYPE: PRT
<213> ORGANISM: Homo sapiens

<400> SEQUENCE: 24

Phe Gly Gly Gly Thr Lys Leu Thr Val Leu
1               5                   10

<210> SEQ ID NO 25
<211> LENGTH: 11
<212> TYPE: PRT
<213> ORGANISM: Homo sapiens
<220> FEATURE:
<221> NAME/KEY: VARIANT
<222> LOCATION: (7)..(7)
<223> OTHER INFORMATION: X is N or S

<400> SEQUENCE: 25

Gln Gly Asp Thr Leu Arg Xaa Tyr Tyr Ala Ser
1               5                   10

<210> SEQ ID NO 26
<211> LENGTH: 11
<212> TYPE: PRT
<213> ORGANISM: Homo sapiens

<400> SEQUENCE: 26

Gln Gly Asp Thr Leu Arg Ser Tyr Tyr Ala Ser
1               5                   10

<210> SEQ ID NO 27
<211> LENGTH: 11
<212> TYPE: PRT
<213> ORGANISM: Homo sapiens

<400> SEQUENCE: 27

Gln Gly Asp Thr Leu Arg Asn Tyr Tyr Ala Ser
1               5                   10

<210> SEQ ID NO 28
<211> LENGTH: 7
<212> TYPE: PRT
<213> ORGANISM: Homo sapiens

<400> SEQUENCE: 28

Gly Lys Asn Asn Arg Pro Ser
1               5

<210> SEQ ID NO 29
<211> LENGTH: 11
<212> TYPE: PRT
<213> ORGANISM: Homo sapiens
<220> FEATURE:
<221> NAME/KEY: VARIANT
<222> LOCATION: (5)..(5)
<223> OTHER INFORMATION: X is S, L, or F
```

```
<400> SEQUENCE: 29

Asn Ser Arg Asp Xaa Ser Gly Lys Asn Leu Val
1               5                   10

<210> SEQ ID NO 30
<211> LENGTH: 11
<212> TYPE: PRT
<213> ORGANISM: Homo sapiens

<400> SEQUENCE: 30

Asn Ser Arg Asp Leu Ser Gly Lys Asn Leu Val
1               5                   10

<210> SEQ ID NO 31
<211> LENGTH: 11
<212> TYPE: PRT
<213> ORGANISM: Homo sapiens

<400> SEQUENCE: 31

Asn Ser Arg Asp Ser Ser Gly Lys Asn Leu Val
1               5                   10

<210> SEQ ID NO 32
<211> LENGTH: 330
<212> TYPE: PRT
<213> ORGANISM: Homo sapiens

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 33
<211> LENGTH: 329
<212> TYPE: PRT
<213> ORGANISM: Homo sapiens

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 34
<211> LENGTH: 330
<212> TYPE: PRT
<213> ORGANISM: Homo sapiens

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 35
<211> LENGTH: 329
<212> TYPE: PRT
<213> ORGANISM: Homo sapiens

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 36
<211> LENGTH: 330
<212> TYPE: PRT

<213> ORGANISM: Homo sapiens

<400> SEQUENCE: 36

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Ala Gly Ala Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 37
<211> LENGTH: 329
<212> TYPE: PRT
<213> ORGANISM: Homo sapiens

<400> SEQUENCE: 37

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Ala Gly Ala Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 38
<211> LENGTH: 330
<212> TYPE: PRT
<213> ORGANISM: Homo sapiens

<400> SEQUENCE: 38

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 39
<211> LENGTH: 329
<212> TYPE: PRT
<213> ORGANISM: Homo sapiens

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 40
<211> LENGTH: 326
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
```

```
                145                 150                 155                 160
Val Glu Val His Asn Ala Lys Thr Lys Pro Arg Glu Glu Gln Phe Asn
                    165                 170                 175
Ser Thr Phe Arg Val Val Ser Val Leu Thr Val Val His Gln Asp Trp
                180                 185                 190
Leu Asn Gly Lys Glu Tyr Lys Cys Lys Val Ser Asn Lys Gly Leu Pro
                195                 200                 205
Ala Pro Ile Glu Lys Thr Ile Ser Lys Thr Lys Gly Gln Pro Arg Glu
            210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
                260                 265                 270
Thr Pro Pro Met Leu Asp Ser Asp Gly Ser Phe Phe Leu Tyr Ser Lys
                275                 280                 285
Leu Thr Val Asp Lys Ser Arg Trp Gln Gln Gly Asn Val Phe Ser Cys
        290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 41
<211> LENGTH: 325
<212> TYPE: PRT
<213> ORGANISM: Homo sapiens

<400> SEQUENCE: 41

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
                100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
        130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 42
<211> LENGTH: 326
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 43
<211> LENGTH: 325
<212> TYPE: PRT
<213> ORGANISM: Homo sapiens

<400> SEQUENCE: 43

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

```
                 275                 280                 285
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 44
<211> LENGTH: 327
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

```
Leu Ser Leu Ser Leu Gly Lys
            325
```

```
<210> SEQ ID NO 45
<211> LENGTH: 326
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 46
<211> LENGTH: 327
<212> TYPE: PRT
<213> ORGANISM: Homo sapiens
```

<400> SEQUENCE: 46

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 47
<211> LENGTH: 326
<212> TYPE: PRT
<213> ORGANISM: Homo sapiens

<400> SEQUENCE: 47

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 48
<211> LENGTH: 327
<212> TYPE: PRT
<213> ORGANISM: Homo sapiens

<400> SEQUENCE: 48

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
```

```
                65                  70                  75                  80
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Tyr Ile Thr Arg Glu Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 49
<211> LENGTH: 326
<212> TYPE: PRT
<213> ORGANISM: Homo sapiens

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110
```

```
Glu Phe Leu Gly Gly Pro Ser Val Phe Leu Phe Pro Pro Lys Pro Lys
            115                 120                 125

Asp Thr Leu Tyr Ile Thr Arg Glu Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 50
<211> LENGTH: 327
<212> TYPE: PRT
<213> ORGANISM: Homo sapiens

<400> SEQUENCE: 50

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 51
<211> LENGTH: 326
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly
                325

<210> SEQ ID NO 52
<211> LENGTH: 6
<212> TYPE: PRT
<213> ORGANISM: Homo sapiens

<400> SEQUENCE: 52

Ala Ser Asn Trp Trp Ser
1               5

<210> SEQ ID NO 53
<211> LENGTH: 6
<212> TYPE: PRT
<213> ORGANISM: Homo sapiens

<400> SEQUENCE: 53

Ser Ala Asn Trp Trp Ser
1               5

<210> SEQ ID NO 54
<211> LENGTH: 6
<212> TYPE: PRT
<213> ORGANISM: Homo sapiens

<400> SEQUENCE: 54

Ser Ser Ala Trp Trp Ser
1               5

<210> SEQ ID NO 55
<211> LENGTH: 6
<212> TYPE: PRT
<213> ORGANISM: Homo sapiens

<400> SEQUENCE: 55

Ser Ser Asn Ala Trp Ser
1               5

<210> SEQ ID NO 56
<211> LENGTH: 6
<212> TYPE: PRT
<213> ORGANISM: Homo sapiens

<400> SEQUENCE: 56

Ser Ser Asn Trp Ala Ser
```

```
<210> SEQ ID NO 57
<211> LENGTH: 6
<212> TYPE: PRT
<213> ORGANISM: Homo sapiens

<400> SEQUENCE: 57

Ser Ser Asn Trp Trp Ala
1               5

<210> SEQ ID NO 58
<211> LENGTH: 11
<212> TYPE: PRT
<213> ORGANISM: Homo sapiens

<400> SEQUENCE: 58

Gly Ala Ser Ile Ser Ser Ser Asn Trp Trp Ser
1               5                   10

<210> SEQ ID NO 59
<211> LENGTH: 11
<212> TYPE: PRT
<213> ORGANISM: Homo sapiens

<400> SEQUENCE: 59

Gly Gly Ala Ile Ser Ser Ser Asn Trp Trp Ser
1               5                   10

<210> SEQ ID NO 60
<211> LENGTH: 11
<212> TYPE: PRT
<213> ORGANISM: Homo sapiens

<400> SEQUENCE: 60

Gly Gly Ser Ala Ser Ser Ser Asn Trp Trp Ser
1               5                   10

<210> SEQ ID NO 61
<211> LENGTH: 11
<212> TYPE: PRT
<213> ORGANISM: Homo sapiens

<400> SEQUENCE: 61

Gly Gly Ser Ile Ala Ser Ser Asn Trp Trp Ser
1               5                   10

<210> SEQ ID NO 62
<211> LENGTH: 11
<212> TYPE: PRT
<213> ORGANISM: Homo sapiens

<400> SEQUENCE: 62

Gly Gly Ser Ile Ser Ala Ser Asn Trp Trp Ser
1               5                   10

<210> SEQ ID NO 63
<211> LENGTH: 11
<212> TYPE: PRT
<213> ORGANISM: Homo sapiens

<400> SEQUENCE: 63

Gly Gly Ser Ile Ser Ser Ala Asn Trp Trp Ser
1               5                   10
```

<210> SEQ ID NO 64
<211> LENGTH: 11
<212> TYPE: PRT
<213> ORGANISM: Homo sapiens

<400> SEQUENCE: 64

Gly Gly Ser Ile Ser Ser Ser Ala Trp Trp Ser
1               5                   10

<210> SEQ ID NO 65
<211> LENGTH: 11
<212> TYPE: PRT
<213> ORGANISM: Homo sapiens

<400> SEQUENCE: 65

Gly Gly Ser Ile Ser Ser Ser Asn Trp Trp Ala
1               5                   10

<210> SEQ ID NO 66
<211> LENGTH: 11
<212> TYPE: PRT
<213> ORGANISM: Homo sapiens

<400> SEQUENCE: 66

Asp Gly Ser Ile Ser Ser Ser Asn Trp Trp Ser
1               5                   10

<210> SEQ ID NO 67
<211> LENGTH: 11
<212> TYPE: PRT
<213> ORGANISM: Homo sapiens

<400> SEQUENCE: 67

Gly Asp Ser Ile Ser Ser Ser Asn Trp Trp Ser
1               5                   10

<210> SEQ ID NO 68
<211> LENGTH: 11
<212> TYPE: PRT
<213> ORGANISM: Homo sapiens

<400> SEQUENCE: 68

Gly Gly Asp Ile Ser Ser Ser Asn Trp Trp Ser
1               5                   10

<210> SEQ ID NO 69
<211> LENGTH: 11
<212> TYPE: PRT
<213> ORGANISM: Homo sapiens

<400> SEQUENCE: 69

Gly Gly Ser Asp Ser Ser Ser Asn Trp Trp Ser
1               5                   10

<210> SEQ ID NO 70
<211> LENGTH: 11
<212> TYPE: PRT
<213> ORGANISM: Homo sapiens

<400> SEQUENCE: 70

Gly Gly Ser Ile Asp Ser Ser Asn Trp Trp Ser
1               5                   10

<210> SEQ ID NO 71

```
<211> LENGTH: 11
<212> TYPE: PRT
<213> ORGANISM: Homo sapiens

<400> SEQUENCE: 71

Gly Gly Ser Ile Ser Asp Ser Asn Trp Trp Ser
1               5                   10

<210> SEQ ID NO 72
<211> LENGTH: 11
<212> TYPE: PRT
<213> ORGANISM: Homo sapiens

<400> SEQUENCE: 72

Gly Gly Ser Ile Ser Ser Asp Asn Trp Trp Ser
1               5                   10

<210> SEQ ID NO 73
<211> LENGTH: 11
<212> TYPE: PRT
<213> ORGANISM: Homo sapiens

<400> SEQUENCE: 73

Gly Gly Ser Ile Ser Ser Ser Asp Trp Trp Ser
1               5                   10

<210> SEQ ID NO 74
<211> LENGTH: 11
<212> TYPE: PRT
<213> ORGANISM: Homo sapiens

<400> SEQUENCE: 74

Gly Gly Ser Ile Ser Ser Ser Asn Asp Trp Ser
1               5                   10

<210> SEQ ID NO 75
<211> LENGTH: 11
<212> TYPE: PRT
<213> ORGANISM: Homo sapiens

<400> SEQUENCE: 75

Gly Gly Ser Ile Ser Ser Ser Asn Trp Trp Asp
1               5                   10

<210> SEQ ID NO 76
<211> LENGTH: 11
<212> TYPE: PRT
<213> ORGANISM: Homo sapiens

<400> SEQUENCE: 76

His Gly Ser Ile Ser Ser Ser Asn Trp Trp Ser
1               5                   10

<210> SEQ ID NO 77
<211> LENGTH: 11
<212> TYPE: PRT
<213> ORGANISM: Homo sapiens

<400> SEQUENCE: 77

Gly His Ser Ile Ser Ser Ser Asn Trp Trp Ser
1               5                   10

<210> SEQ ID NO 78
<211> LENGTH: 11
<212> TYPE: PRT
```

<213> ORGANISM: Homo sapiens

<400> SEQUENCE: 78

Gly Gly His Ile Ser Ser Ser Asn Trp Trp Ser
1               5                   10

<210> SEQ ID NO 79
<211> LENGTH: 11
<212> TYPE: PRT
<213> ORGANISM: Homo sapiens

<400> SEQUENCE: 79

Gly Gly Ser His Ser Ser Ser Asn Trp Trp Ser
1               5                   10

<210> SEQ ID NO 80
<211> LENGTH: 11
<212> TYPE: PRT
<213> ORGANISM: Homo sapiens

<400> SEQUENCE: 80

Gly Gly Ser Ile His Ser Ser Asn Trp Trp Ser
1               5                   10

<210> SEQ ID NO 81
<211> LENGTH: 11
<212> TYPE: PRT
<213> ORGANISM: Homo sapiens

<400> SEQUENCE: 81

Gly Gly Ser Ile Ser His Ser Asn Trp Trp Ser
1               5                   10

<210> SEQ ID NO 82
<211> LENGTH: 11
<212> TYPE: PRT
<213> ORGANISM: Homo sapiens

<400> SEQUENCE: 82

Gly Gly Ser Ile Ser Ser His Asn Trp Trp Ser
1               5                   10

<210> SEQ ID NO 83
<211> LENGTH: 11
<212> TYPE: PRT
<213> ORGANISM: Homo sapiens

<400> SEQUENCE: 83

Gly Gly Ser Ile Ser Ser Ser His Trp Trp Ser
1               5                   10

<210> SEQ ID NO 84
<211> LENGTH: 11
<212> TYPE: PRT
<213> ORGANISM: Homo sapiens

<400> SEQUENCE: 84

Gly Gly Ser Ile Ser Ser Ser Asn His Trp Ser
1               5                   10

<210> SEQ ID NO 85
<211> LENGTH: 11
<212> TYPE: PRT
<213> ORGANISM: Homo sapiens

<400> SEQUENCE: 85

Gly Gly Ser Ile Ser Ser Ser Asn Trp His Ser
1               5                   10

<210> SEQ ID NO 86
<211> LENGTH: 11
<212> TYPE: PRT
<213> ORGANISM: Homo sapiens

<400> SEQUENCE: 86

Lys Gly Ser Ile Ser Ser Ser Asn Trp Trp Ser
1               5                   10

<210> SEQ ID NO 87
<211> LENGTH: 11
<212> TYPE: PRT
<213> ORGANISM: Homo sapiens

<400> SEQUENCE: 87

Gly Lys Ser Ile Ser Ser Ser Asn Trp Trp Ser
1               5                   10

<210> SEQ ID NO 88
<211> LENGTH: 11
<212> TYPE: PRT
<213> ORGANISM: Homo sapiens

<400> SEQUENCE: 88

Gly Gly Lys Ile Ser Ser Ser Asn Trp Trp Ser
1               5                   10

<210> SEQ ID NO 89
<211> LENGTH: 11
<212> TYPE: PRT
<213> ORGANISM: Homo sapiens

<400> SEQUENCE: 89

Gly Gly Ser Lys Ser Ser Ser Asn Trp Trp Ser
1               5                   10

<210> SEQ ID NO 90
<211> LENGTH: 11
<212> TYPE: PRT
<213> ORGANISM: Homo sapiens

<400> SEQUENCE: 90

Gly Gly Ser Ile Lys Ser Ser Asn Trp Trp Ser
1               5                   10

<210> SEQ ID NO 91
<211> LENGTH: 11
<212> TYPE: PRT
<213> ORGANISM: Homo sapiens

<400> SEQUENCE: 91

Gly Gly Ser Ile Ser Lys Ser Asn Trp Trp Ser
1               5                   10

<210> SEQ ID NO 92
<211> LENGTH: 11
<212> TYPE: PRT
<213> ORGANISM: Homo sapiens

<400> SEQUENCE: 92

Gly Gly Ser Ile Ser Ser Lys Asn Trp Trp Ser
1               5                   10

<210> SEQ ID NO 93
<211> LENGTH: 11
<212> TYPE: PRT
<213> ORGANISM: Homo sapiens

<400> SEQUENCE: 93

Leu Gly Ser Ile Ser Ser Ser Asn Trp Trp Ser
1               5                   10

<210> SEQ ID NO 94
<211> LENGTH: 11
<212> TYPE: PRT
<213> ORGANISM: Homo sapiens

<400> SEQUENCE: 94

Gly Leu Ser Ile Ser Ser Ser Asn Trp Trp Ser
1               5                   10

<210> SEQ ID NO 95
<211> LENGTH: 11
<212> TYPE: PRT
<213> ORGANISM: Homo sapiens

<400> SEQUENCE: 95

Gly Gly Leu Ile Ser Ser Ser Asn Trp Trp Ser
1               5                   10

<210> SEQ ID NO 96
<211> LENGTH: 11
<212> TYPE: PRT
<213> ORGANISM: Homo sapiens

<400> SEQUENCE: 96

Gly Gly Ser Leu Ser Ser Ser Asn Trp Trp Ser
1               5                   10

<210> SEQ ID NO 97
<211> LENGTH: 11
<212> TYPE: PRT
<213> ORGANISM: Homo sapiens

<400> SEQUENCE: 97

Gly Gly Ser Ile Leu Ser Ser Asn Trp Trp Ser
1               5                   10

<210> SEQ ID NO 98
<211> LENGTH: 11
<212> TYPE: PRT
<213> ORGANISM: Homo sapiens

<400> SEQUENCE: 98

Gly Gly Ser Ile Ser Leu Ser Asn Trp Trp Ser
1               5                   10

<210> SEQ ID NO 99
<211> LENGTH: 11
<212> TYPE: PRT
<213> ORGANISM: Homo sapiens

<400> SEQUENCE: 99

Gly Gly Ser Ile Ser Ser Leu Asn Trp Trp Ser
1               5                   10

<210> SEQ ID NO 100
<211> LENGTH: 11
<212> TYPE: PRT
<213> ORGANISM: Homo sapiens

<400> SEQUENCE: 100

Gly Gly Ser Ile Ser Ser Ser Leu Trp Trp Ser
1               5                   10

<210> SEQ ID NO 101
<211> LENGTH: 11
<212> TYPE: PRT
<213> ORGANISM: Homo sapiens

<400> SEQUENCE: 101

Gly Gly Ser Ile Ser Ser Ser Asn Leu Trp Ser
1               5                   10

<210> SEQ ID NO 102
<211> LENGTH: 11
<212> TYPE: PRT
<213> ORGANISM: Homo sapiens

<400> SEQUENCE: 102

Gly Gly Ser Ile Ser Ser Ser Asn Trp Leu Ser
1               5                   10

<210> SEQ ID NO 103
<211> LENGTH: 11
<212> TYPE: PRT
<213> ORGANISM: Homo sapiens

<400> SEQUENCE: 103

Gly Gly Ser Ile Ser Ser Ser Asn Trp Trp Leu
1               5                   10

<210> SEQ ID NO 104
<211> LENGTH: 11
<212> TYPE: PRT
<213> ORGANISM: Homo sapiens

<400> SEQUENCE: 104

Gln Gly Ser Ile Ser Ser Ser Asn Trp Trp Ser
1               5                   10

<210> SEQ ID NO 105
<211> LENGTH: 11
<212> TYPE: PRT
<213> ORGANISM: Homo sapiens

<400> SEQUENCE: 105

Gly Gln Ser Ile Ser Ser Ser Asn Trp Trp Ser
1               5                   10

<210> SEQ ID NO 106
<211> LENGTH: 11
<212> TYPE: PRT
<213> ORGANISM: Homo sapiens

<400> SEQUENCE: 106

Gly Gly Gln Ile Ser Ser Ser Asn Trp Trp Ser
1               5                   10

```
<210> SEQ ID NO 107
<211> LENGTH: 11
<212> TYPE: PRT
<213> ORGANISM: Homo sapiens

<400> SEQUENCE: 107

Gly Gly Ser Gln Ser Ser Asn Trp Trp Ser
1               5                   10

<210> SEQ ID NO 108
<211> LENGTH: 11
<212> TYPE: PRT
<213> ORGANISM: Homo sapiens

<400> SEQUENCE: 108

Gly Gly Ser Ile Gln Ser Ser Asn Trp Trp Ser
1               5                   10

<210> SEQ ID NO 109
<211> LENGTH: 11
<212> TYPE: PRT
<213> ORGANISM: Homo sapiens

<400> SEQUENCE: 109

Gly Gly Ser Ile Ser Gln Ser Asn Trp Trp Ser
1               5                   10

<210> SEQ ID NO 110
<211> LENGTH: 11
<212> TYPE: PRT
<213> ORGANISM: Homo sapiens

<400> SEQUENCE: 110

Gly Gly Ser Ile Ser Ser Gln Asn Trp Trp Ser
1               5                   10

<210> SEQ ID NO 111
<211> LENGTH: 11
<212> TYPE: PRT
<213> ORGANISM: Homo sapiens

<400> SEQUENCE: 111

Gly Gly Ser Ile Ser Ser Ser Gln Trp Trp Ser
1               5                   10

<210> SEQ ID NO 112
<211> LENGTH: 11
<212> TYPE: PRT
<213> ORGANISM: Homo sapiens

<400> SEQUENCE: 112

Gly Gly Ser Ile Ser Ser Ser Asn Gln Trp Ser
1               5                   10

<210> SEQ ID NO 113
<211> LENGTH: 11
<212> TYPE: PRT
<213> ORGANISM: Homo sapiens

<400> SEQUENCE: 113

Ser Gly Ser Ile Ser Ser Ser Asn Trp Trp Ser
1               5                   10

<210> SEQ ID NO 114
<211> LENGTH: 11
```

```
<212> TYPE: PRT
<213> ORGANISM: Homo sapiens

<400> SEQUENCE: 114

Gly Ser Ser Ile Ser Ser Ser Asn Trp Trp Ser
1               5                   10

<210> SEQ ID NO 115
<211> LENGTH: 11
<212> TYPE: PRT
<213> ORGANISM: Homo sapiens

<400> SEQUENCE: 115

Gly Gly Ser Ser Ser Ser Ser Asn Trp Trp Ser
1               5                   10

<210> SEQ ID NO 116
<211> LENGTH: 11
<212> TYPE: PRT
<213> ORGANISM: Homo sapiens

<400> SEQUENCE: 116

Gly Gly Ser Ile Ser Ser Ser Ser Trp Trp Ser
1               5                   10

<210> SEQ ID NO 117
<211> LENGTH: 11
<212> TYPE: PRT
<213> ORGANISM: Homo sapiens

<400> SEQUENCE: 117

Gly Gly Ser Ile Ser Ser Ser Asn Ser Trp Ser
1               5                   10

<210> SEQ ID NO 118
<211> LENGTH: 11
<212> TYPE: PRT
<213> ORGANISM: Homo sapiens

<400> SEQUENCE: 118

Trp Gly Ser Ile Ser Ser Ser Asn Trp Trp Ser
1               5                   10

<210> SEQ ID NO 119
<211> LENGTH: 11
<212> TYPE: PRT
<213> ORGANISM: Homo sapiens

<400> SEQUENCE: 119

Gly Trp Ser Ile Ser Ser Ser Asn Trp Trp Ser
1               5                   10

<210> SEQ ID NO 120
<211> LENGTH: 11
<212> TYPE: PRT
<213> ORGANISM: Homo sapiens

<400> SEQUENCE: 120

Gly Gly Trp Ile Ser Ser Ser Asn Trp Trp Ser
1               5                   10

<210> SEQ ID NO 121
<211> LENGTH: 11
<212> TYPE: PRT
<213> ORGANISM: Homo sapiens
```

<400> SEQUENCE: 121

Gly Gly Ser Trp Ser Ser Asn Trp Trp Ser
1               5                   10

<210> SEQ ID NO 122
<211> LENGTH: 11
<212> TYPE: PRT
<213> ORGANISM: Homo sapiens

<400> SEQUENCE: 122

Gly Gly Ser Ile Trp Ser Ser Asn Trp Trp Ser
1               5                   10

<210> SEQ ID NO 123
<211> LENGTH: 11
<212> TYPE: PRT
<213> ORGANISM: Homo sapiens

<400> SEQUENCE: 123

Gly Gly Ser Ile Ser Trp Ser Asn Trp Trp Ser
1               5                   10

<210> SEQ ID NO 124
<211> LENGTH: 11
<212> TYPE: PRT
<213> ORGANISM: Homo sapiens

<400> SEQUENCE: 124

Gly Gly Ser Ile Ser Ser Trp Asn Trp Trp Ser
1               5                   10

<210> SEQ ID NO 125
<211> LENGTH: 11
<212> TYPE: PRT
<213> ORGANISM: Homo sapiens

<400> SEQUENCE: 125

Gly Gly Ser Ile Ser Ser Ser Trp Trp Trp Ser
1               5                   10

<210> SEQ ID NO 126
<211> LENGTH: 11
<212> TYPE: PRT
<213> ORGANISM: Homo sapiens

<400> SEQUENCE: 126

Tyr Gly Ser Ile Ser Ser Ser Asn Trp Trp Ser
1               5                   10

<210> SEQ ID NO 127
<211> LENGTH: 11
<212> TYPE: PRT
<213> ORGANISM: Homo sapiens

<400> SEQUENCE: 127

Gly Tyr Ser Ile Ser Ser Ser Asn Trp Trp Ser
1               5                   10

<210> SEQ ID NO 128
<211> LENGTH: 11
<212> TYPE: PRT
<213> ORGANISM: Homo sapiens

<400> SEQUENCE: 128

```
Gly Gly Tyr Ile Ser Ser Ser Asn Trp Trp Ser
1               5                   10
```

<210> SEQ ID NO 129
<211> LENGTH: 11
<212> TYPE: PRT
<213> ORGANISM: Homo sapiens

<400> SEQUENCE: 129

```
Gly Gly Ser Tyr Ser Ser Ser Asn Trp Trp Ser
1               5                   10
```

<210> SEQ ID NO 130
<211> LENGTH: 11
<212> TYPE: PRT
<213> ORGANISM: Homo sapiens

<400> SEQUENCE: 130

```
Gly Gly Ser Ile Tyr Ser Ser Asn Trp Trp Ser
1               5                   10
```

<210> SEQ ID NO 131
<211> LENGTH: 11
<212> TYPE: PRT
<213> ORGANISM: Homo sapiens

<400> SEQUENCE: 131

```
Gly Gly Ser Ile Ser Tyr Ser Asn Trp Trp Ser
1               5                   10
```

<210> SEQ ID NO 132
<211> LENGTH: 11
<212> TYPE: PRT
<213> ORGANISM: Homo sapiens

<400> SEQUENCE: 132

```
Gly Gly Ser Ile Ser Ser Tyr Asn Trp Trp Ser
1               5                   10
```

<210> SEQ ID NO 133
<211> LENGTH: 11
<212> TYPE: PRT
<213> ORGANISM: Homo sapiens

<400> SEQUENCE: 133

```
Gly Gly Ser Ile Ser Ser Ser Tyr Trp Trp Ser
1               5                   10
```

<210> SEQ ID NO 134
<211> LENGTH: 11
<212> TYPE: PRT
<213> ORGANISM: Homo sapiens

<400> SEQUENCE: 134

```
Gly Gly Ser Ile Ser Ser Ser Asn Tyr Trp Ser
1               5                   10
```

<210> SEQ ID NO 135
<211> LENGTH: 11
<212> TYPE: PRT
<213> ORGANISM: Homo sapiens

<400> SEQUENCE: 135

```
Gly Gly Ser Ile Ser Ser Ser Asn Trp Tyr Ser
```

```
1               5                   10

<210> SEQ ID NO 136
<211> LENGTH: 11
<212> TYPE: PRT
<213> ORGANISM: Homo sapiens

<400> SEQUENCE: 136

Ala Ile Tyr His Ser Gly Asn Thr Asn Tyr Asn
1               5                   10

<210> SEQ ID NO 137
<211> LENGTH: 11
<212> TYPE: PRT
<213> ORGANISM: Homo sapiens

<400> SEQUENCE: 137

Glu Ala Tyr His Ser Gly Asn Thr Asn Tyr Asn
1               5                   10

<210> SEQ ID NO 138
<211> LENGTH: 11
<212> TYPE: PRT
<213> ORGANISM: Homo sapiens

<400> SEQUENCE: 138

Glu Ile Ala His Ser Gly Asn Thr Asn Tyr Asn
1               5                   10

<210> SEQ ID NO 139
<211> LENGTH: 11
<212> TYPE: PRT
<213> ORGANISM: Homo sapiens

<400> SEQUENCE: 139

Glu Ile Tyr Ala Ser Gly Asn Thr Asn Tyr Asn
1               5                   10

<210> SEQ ID NO 140
<211> LENGTH: 11
<212> TYPE: PRT
<213> ORGANISM: Homo sapiens

<400> SEQUENCE: 140

Glu Ile Tyr His Ala Gly Asn Thr Asn Tyr Asn
1               5                   10

<210> SEQ ID NO 141
<211> LENGTH: 11
<212> TYPE: PRT
<213> ORGANISM: Homo sapiens

<400> SEQUENCE: 141

Glu Ile Tyr His Ser Ala Asn Thr Asn Tyr Asn
1               5                   10

<210> SEQ ID NO 142
<211> LENGTH: 11
<212> TYPE: PRT
<213> ORGANISM: Homo sapiens

<400> SEQUENCE: 142

Glu Ile Tyr His Ser Gly Ala Thr Asn Tyr Asn
1               5                   10
```

```
<210> SEQ ID NO 143
<211> LENGTH: 11
<212> TYPE: PRT
<213> ORGANISM: Homo sapiens

<400> SEQUENCE: 143

Glu Ile Tyr His Ser Gly Asn Ala Asn Tyr Asn
1               5                   10

<210> SEQ ID NO 144
<211> LENGTH: 11
<212> TYPE: PRT
<213> ORGANISM: Homo sapiens

<400> SEQUENCE: 144

Glu Ile Tyr His Ser Gly Asn Thr Ala Tyr Asn
1               5                   10

<210> SEQ ID NO 145
<211> LENGTH: 11
<212> TYPE: PRT
<213> ORGANISM: Homo sapiens

<400> SEQUENCE: 145

Glu Ile Tyr His Ser Gly Asn Thr Asn Ala Asn
1               5                   10

<210> SEQ ID NO 146
<211> LENGTH: 11
<212> TYPE: PRT
<213> ORGANISM: Homo sapiens

<400> SEQUENCE: 146

Glu Ile Tyr His Ser Gly Asn Thr Asn Tyr Ala
1               5                   10

<210> SEQ ID NO 147
<211> LENGTH: 11
<212> TYPE: PRT
<213> ORGANISM: Homo sapiens

<400> SEQUENCE: 147

Asp Ile Tyr His Ser Gly Asn Thr Asn Tyr Asn
1               5                   10

<210> SEQ ID NO 148
<211> LENGTH: 11
<212> TYPE: PRT
<213> ORGANISM: Homo sapiens

<400> SEQUENCE: 148

Glu Ile Asp His Ser Gly Asn Thr Asn Tyr Asn
1               5                   10

<210> SEQ ID NO 149
<211> LENGTH: 11
<212> TYPE: PRT
<213> ORGANISM: Homo sapiens

<400> SEQUENCE: 149

Glu Ile Tyr Asp Ser Gly Asn Thr Asn Tyr Asn
1               5                   10

<210> SEQ ID NO 150
```

-continued

```
<211> LENGTH: 11
<212> TYPE: PRT
<213> ORGANISM: Homo sapiens

<400> SEQUENCE: 150

Glu Ile Tyr His Asp Gly Asn Thr Asn Tyr Asn
1               5                   10

<210> SEQ ID NO 151
<211> LENGTH: 11
<212> TYPE: PRT
<213> ORGANISM: Homo sapiens

<400> SEQUENCE: 151

Glu Ile Tyr His Ser Gly Asp Thr Asn Tyr Asn
1               5                   10

<210> SEQ ID NO 152
<211> LENGTH: 11
<212> TYPE: PRT
<213> ORGANISM: Homo sapiens

<400> SEQUENCE: 152

Glu Ile Tyr His Ser Gly Asn Asp Asn Tyr Asn
1               5                   10

<210> SEQ ID NO 153
<211> LENGTH: 11
<212> TYPE: PRT
<213> ORGANISM: Homo sapiens

<400> SEQUENCE: 153

Glu Ile Tyr His Ser Gly Asn Thr Asp Tyr Asn
1               5                   10

<210> SEQ ID NO 154
<211> LENGTH: 11
<212> TYPE: PRT
<213> ORGANISM: Homo sapiens

<400> SEQUENCE: 154

Glu Ile Tyr His Ser Gly Asn Thr Asn Asp Asn
1               5                   10

<210> SEQ ID NO 155
<211> LENGTH: 11
<212> TYPE: PRT
<213> ORGANISM: Homo sapiens

<400> SEQUENCE: 155

Glu Ile Tyr His Ser Gly Asn Thr Asn Tyr Asp
1               5                   10

<210> SEQ ID NO 156
<211> LENGTH: 11
<212> TYPE: PRT
<213> ORGANISM: Homo sapiens

<400> SEQUENCE: 156

His Ile Tyr His Ser Gly Asn Thr Asn Tyr Asn
1               5                   10

<210> SEQ ID NO 157
<211> LENGTH: 11
<212> TYPE: PRT
```

<213> ORGANISM: Homo sapiens

<400> SEQUENCE: 157

Glu His Tyr His Ser Gly Asn Thr Asn Tyr Asn
1               5                   10

<210> SEQ ID NO 158
<211> LENGTH: 11
<212> TYPE: PRT
<213> ORGANISM: Homo sapiens

<400> SEQUENCE: 158

Glu Ile His His Ser Gly Asn Thr Asn Tyr Asn
1               5                   10

<210> SEQ ID NO 159
<211> LENGTH: 11
<212> TYPE: PRT
<213> ORGANISM: Homo sapiens

<400> SEQUENCE: 159

Glu Ile Tyr His His Gly Asn Thr Asn Tyr Asn
1               5                   10

<210> SEQ ID NO 160
<211> LENGTH: 11
<212> TYPE: PRT
<213> ORGANISM: Homo sapiens

<400> SEQUENCE: 160

Glu Ile Tyr His Ser His Asn Thr Asn Tyr Asn
1               5                   10

<210> SEQ ID NO 161
<211> LENGTH: 11
<212> TYPE: PRT
<213> ORGANISM: Homo sapiens

<400> SEQUENCE: 161

Glu Ile Tyr His Ser Gly His Thr Asn Tyr Asn
1               5                   10

<210> SEQ ID NO 162
<211> LENGTH: 11
<212> TYPE: PRT
<213> ORGANISM: Homo sapiens

<400> SEQUENCE: 162

Glu Ile Tyr His Ser Gly Asn His Asn Tyr Asn
1               5                   10

<210> SEQ ID NO 163
<211> LENGTH: 11
<212> TYPE: PRT
<213> ORGANISM: Homo sapiens

<400> SEQUENCE: 163

Glu Ile Tyr His Ser Gly Asn Thr His Tyr Asn
1               5                   10

<210> SEQ ID NO 164
<211> LENGTH: 11
<212> TYPE: PRT
<213> ORGANISM: Homo sapiens

```
<400> SEQUENCE: 164

Glu Ile Tyr His Ser Gly Asn Thr Asn His Asn
1               5                   10

<210> SEQ ID NO 165
<211> LENGTH: 11
<212> TYPE: PRT
<213> ORGANISM: Homo sapiens

<400> SEQUENCE: 165

Glu Ile Tyr His Ser Gly Asn Thr Asn Tyr His
1               5                   10

<210> SEQ ID NO 166
<211> LENGTH: 11
<212> TYPE: PRT
<213> ORGANISM: Homo sapiens

<400> SEQUENCE: 166

Glu Lys Tyr His Ser Gly Asn Thr Asn Tyr Asn
1               5                   10

<210> SEQ ID NO 167
<211> LENGTH: 11
<212> TYPE: PRT
<213> ORGANISM: Homo sapiens

<400> SEQUENCE: 167

Glu Ile Lys His Ser Gly Asn Thr Asn Tyr Asn
1               5                   10

<210> SEQ ID NO 168
<211> LENGTH: 11
<212> TYPE: PRT
<213> ORGANISM: Homo sapiens

<400> SEQUENCE: 168

Glu Ile Tyr Lys Ser Gly Asn Thr Asn Tyr Asn
1               5                   10

<210> SEQ ID NO 169
<211> LENGTH: 11
<212> TYPE: PRT
<213> ORGANISM: Homo sapiens

<400> SEQUENCE: 169

Glu Ile Tyr His Lys Gly Asn Thr Asn Tyr Asn
1               5                   10

<210> SEQ ID NO 170
<211> LENGTH: 11
<212> TYPE: PRT
<213> ORGANISM: Homo sapiens

<400> SEQUENCE: 170

Glu Ile Tyr His Ser Lys Asn Thr Asn Tyr Asn
1               5                   10

<210> SEQ ID NO 171
<211> LENGTH: 11
<212> TYPE: PRT
<213> ORGANISM: Homo sapiens

<400> SEQUENCE: 171
```

Glu Ile Tyr His Ser Gly Lys Thr Asn Tyr Asn
1               5                   10

<210> SEQ ID NO 172
<211> LENGTH: 11
<212> TYPE: PRT
<213> ORGANISM: Homo sapiens

<400> SEQUENCE: 172

Glu Ile Tyr His Ser Gly Asn Lys Asn Tyr Asn
1               5                   10

<210> SEQ ID NO 173
<211> LENGTH: 11
<212> TYPE: PRT
<213> ORGANISM: Homo sapiens

<400> SEQUENCE: 173

Glu Ile Tyr His Ser Gly Asn Thr Lys Tyr Asn
1               5                   10

<210> SEQ ID NO 174
<211> LENGTH: 11
<212> TYPE: PRT
<213> ORGANISM: Homo sapiens

<400> SEQUENCE: 174

Glu Ile Tyr His Ser Gly Asn Thr Asn Lys Asn
1               5                   10

<210> SEQ ID NO 175
<211> LENGTH: 11
<212> TYPE: PRT
<213> ORGANISM: Homo sapiens

<400> SEQUENCE: 175

Glu Ile Tyr His Ser Gly Asn Thr Asn Tyr Lys
1               5                   10

<210> SEQ ID NO 176
<211> LENGTH: 11
<212> TYPE: PRT
<213> ORGANISM: Homo sapiens

<400> SEQUENCE: 176

Leu Ile Tyr His Ser Gly Asn Thr Asn Tyr Asn
1               5                   10

<210> SEQ ID NO 177
<211> LENGTH: 11
<212> TYPE: PRT
<213> ORGANISM: Homo sapiens

<400> SEQUENCE: 177

Glu Leu Tyr His Ser Gly Asn Thr Asn Tyr Asn
1               5                   10

<210> SEQ ID NO 178
<211> LENGTH: 11
<212> TYPE: PRT
<213> ORGANISM: Homo sapiens

<400> SEQUENCE: 178

Glu Ile Leu His Ser Gly Asn Thr Asn Tyr Asn
1               5                   10

<210> SEQ ID NO 179
<211> LENGTH: 11
<212> TYPE: PRT
<213> ORGANISM: Homo sapiens

<400> SEQUENCE: 179

Glu Ile Tyr Leu Ser Gly Asn Thr Asn Tyr Asn
1               5                   10

<210> SEQ ID NO 180
<211> LENGTH: 11
<212> TYPE: PRT
<213> ORGANISM: Homo sapiens

<400> SEQUENCE: 180

Glu Ile Tyr His Leu Gly Asn Thr Asn Tyr Asn
1               5                   10

<210> SEQ ID NO 181
<211> LENGTH: 11
<212> TYPE: PRT
<213> ORGANISM: Homo sapiens

<400> SEQUENCE: 181

Glu Ile Tyr His Ser Leu Asn Thr Asn Tyr Asn
1               5                   10

<210> SEQ ID NO 182
<211> LENGTH: 11
<212> TYPE: PRT
<213> ORGANISM: Homo sapiens

<400> SEQUENCE: 182

Glu Ile Tyr His Ser Gly Leu Thr Asn Tyr Asn
1               5                   10

<210> SEQ ID NO 183
<211> LENGTH: 11
<212> TYPE: PRT
<213> ORGANISM: Homo sapiens

<400> SEQUENCE: 183

Glu Ile Tyr His Ser Gly Asn Leu Asn Tyr Asn
1               5                   10

<210> SEQ ID NO 184
<211> LENGTH: 11
<212> TYPE: PRT
<213> ORGANISM: Homo sapiens

<400> SEQUENCE: 184

Glu Ile Tyr His Ser Gly Asn Thr Leu Tyr Asn
1               5                   10

<210> SEQ ID NO 185
<211> LENGTH: 11
<212> TYPE: PRT
<213> ORGANISM: Homo sapiens

<400> SEQUENCE: 185

Glu Ile Tyr His Ser Gly Asn Thr Asn Leu Asn
1               5                   10

```
<210> SEQ ID NO 186
<211> LENGTH: 11
<212> TYPE: PRT
<213> ORGANISM: Homo sapiens

<400> SEQUENCE: 186

Glu Ile Tyr His Ser Gly Asn Thr Asn Tyr Leu
1               5                   10

<210> SEQ ID NO 187
<211> LENGTH: 11
<212> TYPE: PRT
<213> ORGANISM: Homo sapiens

<400> SEQUENCE: 187

Gln Ile Tyr His Ser Gly Asn Thr Asn Tyr Asn
1               5                   10

<210> SEQ ID NO 188
<211> LENGTH: 11
<212> TYPE: PRT
<213> ORGANISM: Homo sapiens

<400> SEQUENCE: 188

Glu Gln Tyr His Ser Gly Asn Thr Asn Tyr Asn
1               5                   10

<210> SEQ ID NO 189
<211> LENGTH: 11
<212> TYPE: PRT
<213> ORGANISM: Homo sapiens

<400> SEQUENCE: 189

Glu Ile Gln His Ser Gly Asn Thr Asn Tyr Asn
1               5                   10

<210> SEQ ID NO 190
<211> LENGTH: 11
<212> TYPE: PRT
<213> ORGANISM: Homo sapiens

<400> SEQUENCE: 190

Glu Ile Tyr Gln Ser Gly Asn Thr Asn Tyr Asn
1               5                   10

<210> SEQ ID NO 191
<211> LENGTH: 11
<212> TYPE: PRT
<213> ORGANISM: Homo sapiens

<400> SEQUENCE: 191

Glu Ile Tyr His Gln Gly Asn Thr Asn Tyr Asn
1               5                   10

<210> SEQ ID NO 192
<211> LENGTH: 11
<212> TYPE: PRT
<213> ORGANISM: Homo sapiens

<400> SEQUENCE: 192

Glu Ile Tyr His Ser Gln Asn Thr Asn Tyr Asn
1               5                   10

<210> SEQ ID NO 193
<211> LENGTH: 11
```

```
<212> TYPE: PRT
<213> ORGANISM: Homo sapiens

<400> SEQUENCE: 193

Glu Ile Tyr His Ser Gly Gln Thr Asn Tyr Asn
1               5                   10

<210> SEQ ID NO 194
<211> LENGTH: 11
<212> TYPE: PRT
<213> ORGANISM: Homo sapiens

<400> SEQUENCE: 194

Glu Ile Tyr His Ser Gly Asn Gln Asn Tyr Asn
1               5                   10

<210> SEQ ID NO 195
<211> LENGTH: 11
<212> TYPE: PRT
<213> ORGANISM: Homo sapiens

<400> SEQUENCE: 195

Glu Ile Tyr His Ser Gly Asn Thr Gln Tyr Asn
1               5                   10

<210> SEQ ID NO 196
<211> LENGTH: 11
<212> TYPE: PRT
<213> ORGANISM: Homo sapiens

<400> SEQUENCE: 196

Glu Ile Tyr His Ser Gly Asn Thr Asn Gln Asn
1               5                   10

<210> SEQ ID NO 197
<211> LENGTH: 11
<212> TYPE: PRT
<213> ORGANISM: Homo sapiens

<400> SEQUENCE: 197

Glu Ile Tyr His Ser Gly Asn Thr Asn Tyr Gln
1               5                   10

<210> SEQ ID NO 198
<211> LENGTH: 11
<212> TYPE: PRT
<213> ORGANISM: Homo sapiens

<400> SEQUENCE: 198

Ser Ile Tyr His Ser Gly Asn Thr Asn Tyr Asn
1               5                   10

<210> SEQ ID NO 199
<211> LENGTH: 11
<212> TYPE: PRT
<213> ORGANISM: Homo sapiens

<400> SEQUENCE: 199

Glu Ser Tyr His Ser Gly Asn Thr Asn Tyr Asn
1               5                   10

<210> SEQ ID NO 200
<211> LENGTH: 11
<212> TYPE: PRT
<213> ORGANISM: Homo sapiens
```

<400> SEQUENCE: 200

Glu Ile Ser His Ser Gly Asn Thr Asn Tyr Asn
1               5                   10

<210> SEQ ID NO 201
<211> LENGTH: 11
<212> TYPE: PRT
<213> ORGANISM: Homo sapiens

<400> SEQUENCE: 201

Glu Ile Tyr Ser Ser Gly Asn Thr Asn Tyr Asn
1               5                   10

<210> SEQ ID NO 202
<211> LENGTH: 11
<212> TYPE: PRT
<213> ORGANISM: Homo sapiens

<400> SEQUENCE: 202

Glu Ile Tyr His Ser Ser Asn Thr Asn Tyr Asn
1               5                   10

<210> SEQ ID NO 203
<211> LENGTH: 11
<212> TYPE: PRT
<213> ORGANISM: Homo sapiens

<400> SEQUENCE: 203

Glu Ile Tyr His Ser Gly Ser Thr Asn Tyr Asn
1               5                   10

<210> SEQ ID NO 204
<211> LENGTH: 11
<212> TYPE: PRT
<213> ORGANISM: Homo sapiens

<400> SEQUENCE: 204

Glu Ile Tyr His Ser Gly Asn Ser Asn Tyr Asn
1               5                   10

<210> SEQ ID NO 205
<211> LENGTH: 11
<212> TYPE: PRT
<213> ORGANISM: Homo sapiens

<400> SEQUENCE: 205

Glu Ile Tyr His Ser Gly Asn Thr Ser Tyr Asn
1               5                   10

<210> SEQ ID NO 206
<211> LENGTH: 11
<212> TYPE: PRT
<213> ORGANISM: Homo sapiens

<400> SEQUENCE: 206

Glu Ile Tyr His Ser Gly Asn Thr Asn Ser Asn
1               5                   10

<210> SEQ ID NO 207
<211> LENGTH: 11
<212> TYPE: PRT
<213> ORGANISM: Homo sapiens

<400> SEQUENCE: 207

```
Glu Ile Tyr His Ser Gly Asn Thr Asn Tyr Ser
1               5                   10

<210> SEQ ID NO 208
<211> LENGTH: 11
<212> TYPE: PRT
<213> ORGANISM: Homo sapiens

<400> SEQUENCE: 208

Trp Ile Tyr His Ser Gly Asn Thr Asn Tyr Asn
1               5                   10

<210> SEQ ID NO 209
<211> LENGTH: 11
<212> TYPE: PRT
<213> ORGANISM: Homo sapiens

<400> SEQUENCE: 209

Glu Ile Trp His Ser Gly Asn Thr Asn Tyr Asn
1               5                   10

<210> SEQ ID NO 210
<211> LENGTH: 11
<212> TYPE: PRT
<213> ORGANISM: Homo sapiens

<400> SEQUENCE: 210

Glu Ile Tyr Trp Ser Gly Asn Thr Asn Tyr Asn
1               5                   10

<210> SEQ ID NO 211
<211> LENGTH: 11
<212> TYPE: PRT
<213> ORGANISM: Homo sapiens

<400> SEQUENCE: 211

Glu Ile Tyr His Trp Gly Asn Thr Asn Tyr Asn
1               5                   10

<210> SEQ ID NO 212
<211> LENGTH: 11
<212> TYPE: PRT
<213> ORGANISM: Homo sapiens

<400> SEQUENCE: 212

Glu Ile Tyr His Ser Trp Asn Thr Asn Tyr Asn
1               5                   10

<210> SEQ ID NO 213
<211> LENGTH: 11
<212> TYPE: PRT
<213> ORGANISM: Homo sapiens

<400> SEQUENCE: 213

Glu Ile Tyr His Ser Gly Trp Thr Asn Tyr Asn
1               5                   10

<210> SEQ ID NO 214
<211> LENGTH: 11
<212> TYPE: PRT
<213> ORGANISM: Homo sapiens

<400> SEQUENCE: 214

Glu Ile Tyr His Ser Gly Asn Trp Asn Tyr Asn
```

```
1               5                   10
```

<210> SEQ ID NO 215
<211> LENGTH: 11
<212> TYPE: PRT
<213> ORGANISM: Homo sapiens

<400> SEQUENCE: 215

```
Glu Ile Tyr His Ser Gly Asn Thr Trp Tyr Asn
1               5                   10
```

<210> SEQ ID NO 216
<211> LENGTH: 11
<212> TYPE: PRT
<213> ORGANISM: Homo sapiens

<400> SEQUENCE: 216

```
Glu Ile Tyr His Ser Gly Asn Thr Asn Trp Asn
1               5                   10
```

<210> SEQ ID NO 217
<211> LENGTH: 11
<212> TYPE: PRT
<213> ORGANISM: Homo sapiens

<400> SEQUENCE: 217

```
Glu Ile Tyr His Ser Gly Asn Thr Asn Tyr Trp
1               5                   10
```

<210> SEQ ID NO 218
<211> LENGTH: 11
<212> TYPE: PRT
<213> ORGANISM: Homo sapiens

<400> SEQUENCE: 218

```
Tyr Ile Tyr His Ser Gly Asn Thr Asn Tyr Asn
1               5                   10
```

<210> SEQ ID NO 219
<211> LENGTH: 11
<212> TYPE: PRT
<213> ORGANISM: Homo sapiens

<400> SEQUENCE: 219

```
Glu Tyr Tyr His Ser Gly Asn Thr Asn Tyr Asn
1               5                   10
```

<210> SEQ ID NO 220
<211> LENGTH: 11
<212> TYPE: PRT
<213> ORGANISM: Homo sapiens

<400> SEQUENCE: 220

```
Glu Ile Tyr Tyr Ser Gly Asn Thr Asn Tyr Asn
1               5                   10
```

<210> SEQ ID NO 221
<211> LENGTH: 11
<212> TYPE: PRT
<213> ORGANISM: Homo sapiens

<400> SEQUENCE: 221

```
Glu Ile Tyr His Tyr Gly Asn Thr Asn Tyr Asn
1               5                   10
```

```
<210> SEQ ID NO 222
<211> LENGTH: 11
<212> TYPE: PRT
<213> ORGANISM: Homo sapiens

<400> SEQUENCE: 222

Glu Ile Tyr His Ser Tyr Asn Thr Asn Tyr Asn
1               5                   10

<210> SEQ ID NO 223
<211> LENGTH: 11
<212> TYPE: PRT
<213> ORGANISM: Homo sapiens

<400> SEQUENCE: 223

Glu Ile Tyr His Ser Gly Tyr Thr Asn Tyr Asn
1               5                   10

<210> SEQ ID NO 224
<211> LENGTH: 11
<212> TYPE: PRT
<213> ORGANISM: Homo sapiens

<400> SEQUENCE: 224

Glu Ile Tyr His Ser Gly Asn Tyr Asn Tyr Asn
1               5                   10

<210> SEQ ID NO 225
<211> LENGTH: 11
<212> TYPE: PRT
<213> ORGANISM: Homo sapiens

<400> SEQUENCE: 225

Glu Ile Tyr His Ser Gly Asn Thr Tyr Tyr Asn
1               5                   10

<210> SEQ ID NO 226
<211> LENGTH: 11
<212> TYPE: PRT
<213> ORGANISM: Homo sapiens

<400> SEQUENCE: 226

Glu Ile Tyr His Ser Gly Asn Thr Asn Tyr Tyr
1               5                   10

<210> SEQ ID NO 227
<211> LENGTH: 10
<212> TYPE: PRT
<213> ORGANISM: Homo sapiens

<400> SEQUENCE: 227

Ala Gly Ile Gly Trp Pro Ser Phe Asp Tyr
1               5                   10

<210> SEQ ID NO 228
<211> LENGTH: 10
<212> TYPE: PRT
<213> ORGANISM: Homo sapiens

<400> SEQUENCE: 228

Glu Ala Ile Gly Trp Pro Ser Phe Asp Tyr
1               5                   10

<210> SEQ ID NO 229
```

```
<211> LENGTH: 10
<212> TYPE: PRT
<213> ORGANISM: Homo sapiens

<400> SEQUENCE: 229

Glu Gly Ala Gly Trp Pro Ser Phe Asp Tyr
1               5                   10

<210> SEQ ID NO 230
<211> LENGTH: 10
<212> TYPE: PRT
<213> ORGANISM: Homo sapiens

<400> SEQUENCE: 230

Glu Gly Ile Ala Trp Pro Ser Phe Asp Tyr
1               5                   10

<210> SEQ ID NO 231
<211> LENGTH: 10
<212> TYPE: PRT
<213> ORGANISM: Homo sapiens

<400> SEQUENCE: 231

Glu Gly Ile Gly Trp Pro Ala Phe Asp Tyr
1               5                   10

<210> SEQ ID NO 232
<211> LENGTH: 10
<212> TYPE: PRT
<213> ORGANISM: Homo sapiens

<400> SEQUENCE: 232

Glu Gly Ile Gly Trp Pro Ser Phe Asp Ala
1               5                   10

<210> SEQ ID NO 233
<211> LENGTH: 10
<212> TYPE: PRT
<213> ORGANISM: Homo sapiens

<400> SEQUENCE: 233

Asp Gly Ile Gly Trp Pro Ser Phe Asp Tyr
1               5                   10

<210> SEQ ID NO 234
<211> LENGTH: 10
<212> TYPE: PRT
<213> ORGANISM: Homo sapiens

<400> SEQUENCE: 234

Glu Asp Ile Gly Trp Pro Ser Phe Asp Tyr
1               5                   10

<210> SEQ ID NO 235
<211> LENGTH: 10
<212> TYPE: PRT
<213> ORGANISM: Homo sapiens

<400> SEQUENCE: 235

Glu Gly Asp Gly Trp Pro Ser Phe Asp Tyr
1               5                   10

<210> SEQ ID NO 236
<211> LENGTH: 10
<212> TYPE: PRT
```

-continued

<213> ORGANISM: Homo sapiens

<400> SEQUENCE: 236

Glu Gly Ile Gly Trp Pro Ser Phe Asp Asp
1               5                   10

<210> SEQ ID NO 237
<211> LENGTH: 10
<212> TYPE: PRT
<213> ORGANISM: Homo sapiens

<400> SEQUENCE: 237

His Gly Ile Gly Trp Pro Ser Phe Asp Tyr
1               5                   10

<210> SEQ ID NO 238
<211> LENGTH: 10
<212> TYPE: PRT
<213> ORGANISM: Homo sapiens

<400> SEQUENCE: 238

Glu His Ile Gly Trp Pro Ser Phe Asp Tyr
1               5                   10

<210> SEQ ID NO 239
<211> LENGTH: 10
<212> TYPE: PRT
<213> ORGANISM: Homo sapiens

<400> SEQUENCE: 239

Glu Gly His Gly Trp Pro Ser Phe Asp Tyr
1               5                   10

<210> SEQ ID NO 240
<211> LENGTH: 10
<212> TYPE: PRT
<213> ORGANISM: Homo sapiens

<400> SEQUENCE: 240

Glu Gly Ile Gly Trp Pro His Phe Asp Tyr
1               5                   10

<210> SEQ ID NO 241
<211> LENGTH: 10
<212> TYPE: PRT
<213> ORGANISM: Homo sapiens

<400> SEQUENCE: 241

Glu Gly Ile Gly Trp Pro Ser His Asp Tyr
1               5                   10

<210> SEQ ID NO 242
<211> LENGTH: 10
<212> TYPE: PRT
<213> ORGANISM: Homo sapiens

<400> SEQUENCE: 242

Glu Gly Ile Gly Trp Pro Ser Phe Asp His
1               5                   10

<210> SEQ ID NO 243
<211> LENGTH: 10
<212> TYPE: PRT
<213> ORGANISM: Homo sapiens

```
<400> SEQUENCE: 243

Glu Lys Ile Gly Trp Pro Ser Phe Asp Tyr
1               5                   10

<210> SEQ ID NO 244
<211> LENGTH: 10
<212> TYPE: PRT
<213> ORGANISM: Homo sapiens

<400> SEQUENCE: 244

Glu Gly Lys Gly Trp Pro Ser Phe Asp Tyr
1               5                   10

<210> SEQ ID NO 245
<211> LENGTH: 10
<212> TYPE: PRT
<213> ORGANISM: Homo sapiens

<400> SEQUENCE: 245

Glu Gly Ile Gly Trp Pro Ser Phe Lys Tyr
1               5                   10

<210> SEQ ID NO 246
<211> LENGTH: 10
<212> TYPE: PRT
<213> ORGANISM: Homo sapiens

<400> SEQUENCE: 246

Glu Gly Ile Gly Trp Pro Ser Phe Asp Lys
1               5                   10

<210> SEQ ID NO 247
<211> LENGTH: 10
<212> TYPE: PRT
<213> ORGANISM: Homo sapiens

<400> SEQUENCE: 247

Leu Gly Ile Gly Trp Pro Ser Phe Asp Tyr
1               5                   10

<210> SEQ ID NO 248
<211> LENGTH: 10
<212> TYPE: PRT
<213> ORGANISM: Homo sapiens

<400> SEQUENCE: 248

Glu Gly Leu Gly Trp Pro Ser Phe Asp Tyr
1               5                   10

<210> SEQ ID NO 249
<211> LENGTH: 10
<212> TYPE: PRT
<213> ORGANISM: Homo sapiens

<400> SEQUENCE: 249

Glu Gly Ile Gly Trp Pro Leu Phe Asp Tyr
1               5                   10

<210> SEQ ID NO 250
<211> LENGTH: 10
<212> TYPE: PRT
<213> ORGANISM: Homo sapiens

<400> SEQUENCE: 250
```

Glu Gly Ile Gly Trp Pro Ser Leu Asp Tyr
1               5                   10

<210> SEQ ID NO 251
<211> LENGTH: 10
<212> TYPE: PRT
<213> ORGANISM: Homo sapiens

<400> SEQUENCE: 251

Glu Gly Ile Gly Trp Pro Ser Phe Asp Leu
1               5                   10

<210> SEQ ID NO 252
<211> LENGTH: 10
<212> TYPE: PRT
<213> ORGANISM: Homo sapiens

<400> SEQUENCE: 252

Gln Gly Ile Gly Trp Pro Ser Phe Asp Tyr
1               5                   10

<210> SEQ ID NO 253
<211> LENGTH: 10
<212> TYPE: PRT
<213> ORGANISM: Homo sapiens

<400> SEQUENCE: 253

Glu Gln Ile Gly Trp Pro Ser Phe Asp Tyr
1               5                   10

<210> SEQ ID NO 254
<211> LENGTH: 10
<212> TYPE: PRT
<213> ORGANISM: Homo sapiens

<400> SEQUENCE: 254

Glu Gly Gln Gly Trp Pro Ser Phe Asp Tyr
1               5                   10

<210> SEQ ID NO 255
<211> LENGTH: 10
<212> TYPE: PRT
<213> ORGANISM: Homo sapiens

<400> SEQUENCE: 255

Glu Gly Ile Gly Trp Pro Gln Phe Asp Tyr
1               5                   10

<210> SEQ ID NO 256
<211> LENGTH: 10
<212> TYPE: PRT
<213> ORGANISM: Homo sapiens

<400> SEQUENCE: 256

Glu Gly Ile Gly Trp Pro Ser Phe Gln Tyr
1               5                   10

<210> SEQ ID NO 257
<211> LENGTH: 10
<212> TYPE: PRT
<213> ORGANISM: Homo sapiens

<400> SEQUENCE: 257

Glu Gly Ile Gly Trp Pro Ser Phe Asp Gln
1               5                   10

```
<210> SEQ ID NO 258
<211> LENGTH: 10
<212> TYPE: PRT
<213> ORGANISM: Homo sapiens

<400> SEQUENCE: 258

Ser Gly Ile Gly Trp Pro Ser Phe Asp Tyr
1               5                   10

<210> SEQ ID NO 259
<211> LENGTH: 10
<212> TYPE: PRT
<213> ORGANISM: Homo sapiens

<400> SEQUENCE: 259

Glu Ser Ile Gly Trp Pro Ser Phe Asp Tyr
1               5                   10

<210> SEQ ID NO 260
<211> LENGTH: 10
<212> TYPE: PRT
<213> ORGANISM: Homo sapiens

<400> SEQUENCE: 260

Glu Gly Ser Gly Trp Pro Ser Phe Asp Tyr
1               5                   10

<210> SEQ ID NO 261
<211> LENGTH: 10
<212> TYPE: PRT
<213> ORGANISM: Homo sapiens

<400> SEQUENCE: 261

Glu Gly Ile Gly Trp Pro Ser Phe Asp Ser
1               5                   10

<210> SEQ ID NO 262
<211> LENGTH: 10
<212> TYPE: PRT
<213> ORGANISM: Homo sapiens

<400> SEQUENCE: 262

Glu Trp Ile Gly Trp Pro Ser Phe Asp Tyr
1               5                   10

<210> SEQ ID NO 263
<211> LENGTH: 10
<212> TYPE: PRT
<213> ORGANISM: Homo sapiens

<400> SEQUENCE: 263

Glu Gly Trp Gly Trp Pro Ser Phe Asp Tyr
1               5                   10

<210> SEQ ID NO 264
<211> LENGTH: 10
<212> TYPE: PRT
<213> ORGANISM: Homo sapiens

<400> SEQUENCE: 264

Glu Gly Ile Gly Trp Pro Trp Phe Asp Tyr
1               5                   10
```

```
<210> SEQ ID NO 265
<211> LENGTH: 10
<212> TYPE: PRT
<213> ORGANISM: Homo sapiens

<400> SEQUENCE: 265

Glu Gly Ile Gly Trp Pro Ser Trp Asp Tyr
1               5                   10

<210> SEQ ID NO 266
<211> LENGTH: 10
<212> TYPE: PRT
<213> ORGANISM: Homo sapiens

<400> SEQUENCE: 266

Glu Gly Ile Gly Trp Pro Ser Phe Asp Trp
1               5                   10

<210> SEQ ID NO 267
<211> LENGTH: 10
<212> TYPE: PRT
<213> ORGANISM: Homo sapiens

<400> SEQUENCE: 267

Glu Tyr Ile Gly Trp Pro Ser Phe Asp Tyr
1               5                   10

<210> SEQ ID NO 268
<211> LENGTH: 10
<212> TYPE: PRT
<213> ORGANISM: Homo sapiens

<400> SEQUENCE: 268

Glu Gly Tyr Gly Trp Pro Ser Phe Asp Tyr
1               5                   10

<210> SEQ ID NO 269
<211> LENGTH: 10
<212> TYPE: PRT
<213> ORGANISM: Homo sapiens

<400> SEQUENCE: 269

Glu Gly Ile Gly Tyr Pro Ser Phe Asp Tyr
1               5                   10

<210> SEQ ID NO 270
<211> LENGTH: 10
<212> TYPE: PRT
<213> ORGANISM: Homo sapiens

<400> SEQUENCE: 270

Glu Gly Ile Gly Trp Pro Tyr Phe Asp Tyr
1               5                   10

<210> SEQ ID NO 271
<211> LENGTH: 10
<212> TYPE: PRT
<213> ORGANISM: Homo sapiens

<400> SEQUENCE: 271

Glu Gly Ile Gly Trp Pro Ser Tyr Asp Tyr
1               5                   10

<210> SEQ ID NO 272
<211> LENGTH: 10
```

-continued

<212> TYPE: PRT
<213> ORGANISM: Homo sapiens

<400> SEQUENCE: 272

Glu Gly Ile Gly Trp Pro Ser Phe Tyr Tyr
1               5                   10

<210> SEQ ID NO 273
<211> LENGTH: 11
<212> TYPE: PRT
<213> ORGANISM: Homo sapiens

<400> SEQUENCE: 273

Ala Gly Asp Thr Leu Arg Asn Tyr Tyr Ala Ser
1               5                   10

<210> SEQ ID NO 274
<211> LENGTH: 11
<212> TYPE: PRT
<213> ORGANISM: Homo sapiens

<400> SEQUENCE: 274

Gln Ala Asp Thr Leu Arg Asn Tyr Tyr Ala Ser
1               5                   10

<210> SEQ ID NO 275
<211> LENGTH: 11
<212> TYPE: PRT
<213> ORGANISM: Homo sapiens

<400> SEQUENCE: 275

Gln Gly Ala Thr Leu Arg Asn Tyr Tyr Ala Ser
1               5                   10

<210> SEQ ID NO 276
<211> LENGTH: 11
<212> TYPE: PRT
<213> ORGANISM: Homo sapiens

<400> SEQUENCE: 276

Gln Gly Asp Ala Leu Arg Asn Tyr Tyr Ala Ser
1               5                   10

<210> SEQ ID NO 277
<211> LENGTH: 11
<212> TYPE: PRT
<213> ORGANISM: Homo sapiens

<400> SEQUENCE: 277

Gln Gly Asp Thr Ala Arg Asn Tyr Tyr Ala Ser
1               5                   10

<210> SEQ ID NO 278
<211> LENGTH: 11
<212> TYPE: PRT
<213> ORGANISM: Homo sapiens

<400> SEQUENCE: 278

Gln Gly Asp Thr Leu Ala Asn Tyr Tyr Ala Ser
1               5                   10

<210> SEQ ID NO 279
<211> LENGTH: 11
<212> TYPE: PRT
<213> ORGANISM: Homo sapiens

<400> SEQUENCE: 279

Gln Gly Asp Thr Leu Arg Ala Tyr Tyr Ala Ser
1               5                   10

<210> SEQ ID NO 280
<211> LENGTH: 11
<212> TYPE: PRT
<213> ORGANISM: Homo sapiens

<400> SEQUENCE: 280

Gln Gly Asp Thr Leu Arg Asn Tyr Ala Ala Ser
1               5                   10

<210> SEQ ID NO 281
<211> LENGTH: 11
<212> TYPE: PRT
<213> ORGANISM: Homo sapiens

<400> SEQUENCE: 281

Gln Gly Asp Thr Leu Arg Asn Tyr Tyr Ala Ala
1               5                   10

<210> SEQ ID NO 282
<211> LENGTH: 11
<212> TYPE: PRT
<213> ORGANISM: Homo sapiens

<400> SEQUENCE: 282

Asp Gly Asp Thr Leu Arg Asn Tyr Tyr Ala Ser
1               5                   10

<210> SEQ ID NO 283
<211> LENGTH: 11
<212> TYPE: PRT
<213> ORGANISM: Homo sapiens

<400> SEQUENCE: 283

Gln Asp Asp Thr Leu Arg Asn Tyr Tyr Ala Ser
1               5                   10

<210> SEQ ID NO 284
<211> LENGTH: 11
<212> TYPE: PRT
<213> ORGANISM: Homo sapiens

<400> SEQUENCE: 284

Gln Gly Asp Asp Leu Arg Asn Tyr Tyr Ala Ser
1               5                   10

<210> SEQ ID NO 285
<211> LENGTH: 11
<212> TYPE: PRT
<213> ORGANISM: Homo sapiens

<400> SEQUENCE: 285

Gln Gly Asp Thr Leu Asp Asn Tyr Tyr Ala Ser
1               5                   10

<210> SEQ ID NO 286
<211> LENGTH: 11
<212> TYPE: PRT
<213> ORGANISM: Homo sapiens

<400> SEQUENCE: 286

Gln Gly Asp Thr Leu Arg Asp Tyr Tyr Ala Ser
1               5                   10

<210> SEQ ID NO 287
<211> LENGTH: 11
<212> TYPE: PRT
<213> ORGANISM: Homo sapiens

<400> SEQUENCE: 287

His Gly Asp Thr Leu Arg Asn Tyr Tyr Ala Ser
1               5                   10

<210> SEQ ID NO 288
<211> LENGTH: 11
<212> TYPE: PRT
<213> ORGANISM: Homo sapiens

<400> SEQUENCE: 288

Gln His Asp Thr Leu Arg Asn Tyr Tyr Ala Ser
1               5                   10

<210> SEQ ID NO 289
<211> LENGTH: 11
<212> TYPE: PRT
<213> ORGANISM: Homo sapiens

<400> SEQUENCE: 289

Gln Gly His Thr Leu Arg Asn Tyr Tyr Ala Ser
1               5                   10

<210> SEQ ID NO 290
<211> LENGTH: 11
<212> TYPE: PRT
<213> ORGANISM: Homo sapiens

<400> SEQUENCE: 290

Gln Gly Asp His Leu Arg Asn Tyr Tyr Ala Ser
1               5                   10

<210> SEQ ID NO 291
<211> LENGTH: 11
<212> TYPE: PRT
<213> ORGANISM: Homo sapiens

<400> SEQUENCE: 291

Gln Gly Asp Thr His Arg Asn Tyr Tyr Ala Ser
1               5                   10

<210> SEQ ID NO 292
<211> LENGTH: 11
<212> TYPE: PRT
<213> ORGANISM: Homo sapiens

<400> SEQUENCE: 292

Gln Gly Asp Thr Leu His Asn Tyr Tyr Ala Ser
1               5                   10

<210> SEQ ID NO 293
<211> LENGTH: 11
<212> TYPE: PRT
<213> ORGANISM: Homo sapiens

<400> SEQUENCE: 293

Gln Gly Asp Thr Leu Arg His Tyr Tyr Ala Ser

```
1               5                   10
```

<210> SEQ ID NO 294
<211> LENGTH: 11
<212> TYPE: PRT
<213> ORGANISM: Homo sapiens

<400> SEQUENCE: 294

```
Gln Gly Asp Thr Leu Arg Asn Tyr His Ala Ser
1               5                   10
```

<210> SEQ ID NO 295
<211> LENGTH: 11
<212> TYPE: PRT
<213> ORGANISM: Homo sapiens

<400> SEQUENCE: 295

```
Lys Gly Asp Thr Leu Arg Asn Tyr Tyr Ala Ser
1               5                   10
```

<210> SEQ ID NO 296
<211> LENGTH: 11
<212> TYPE: PRT
<213> ORGANISM: Homo sapiens

<400> SEQUENCE: 296

```
Gln Lys Asp Thr Leu Arg Asn Tyr Tyr Ala Ser
1               5                   10
```

<210> SEQ ID NO 297
<211> LENGTH: 11
<212> TYPE: PRT
<213> ORGANISM: Homo sapiens

<400> SEQUENCE: 297

```
Gln Gly Lys Thr Leu Arg Asn Tyr Tyr Ala Ser
1               5                   10
```

<210> SEQ ID NO 298
<211> LENGTH: 11
<212> TYPE: PRT
<213> ORGANISM: Homo sapiens

<400> SEQUENCE: 298

```
Gln Gly Asp Thr Leu Lys Asn Tyr Tyr Ala Ser
1               5                   10
```

<210> SEQ ID NO 299
<211> LENGTH: 11
<212> TYPE: PRT
<213> ORGANISM: Homo sapiens

<400> SEQUENCE: 299

```
Gln Gly Asp Thr Leu Arg Lys Tyr Tyr Ala Ser
1               5                   10
```

<210> SEQ ID NO 300
<211> LENGTH: 11
<212> TYPE: PRT
<213> ORGANISM: Homo sapiens

<400> SEQUENCE: 300

```
Leu Gly Asp Thr Leu Arg Asn Tyr Tyr Ala Ser
1               5                   10
```

<210> SEQ ID NO 301
<211> LENGTH: 11
<212> TYPE: PRT
<213> ORGANISM: Homo sapiens

<400> SEQUENCE: 301

Gln Gly Leu Thr Leu Arg Asn Tyr Tyr Ala Ser
1               5                   10

<210> SEQ ID NO 302
<211> LENGTH: 11
<212> TYPE: PRT
<213> ORGANISM: Homo sapiens

<400> SEQUENCE: 302

Gln Gly Asp Leu Leu Arg Asn Tyr Tyr Ala Ser
1               5                   10

<210> SEQ ID NO 303
<211> LENGTH: 11
<212> TYPE: PRT
<213> ORGANISM: Homo sapiens

<400> SEQUENCE: 303

Gln Gly Asp Thr Leu Leu Asn Tyr Tyr Ala Ser
1               5                   10

<210> SEQ ID NO 304
<211> LENGTH: 11
<212> TYPE: PRT
<213> ORGANISM: Homo sapiens

<400> SEQUENCE: 304

Gln Gly Asp Thr Leu Arg Leu Tyr Tyr Ala Ser
1               5                   10

<210> SEQ ID NO 305
<211> LENGTH: 11
<212> TYPE: PRT
<213> ORGANISM: Homo sapiens

<400> SEQUENCE: 305

Gln Gly Asp Thr Leu Arg Asn Tyr Leu Ala Ser
1               5                   10

<210> SEQ ID NO 306
<211> LENGTH: 11
<212> TYPE: PRT
<213> ORGANISM: Homo sapiens

<400> SEQUENCE: 306

Gln Gln Asp Thr Leu Arg Asn Tyr Tyr Ala Ser
1               5                   10

<210> SEQ ID NO 307
<211> LENGTH: 11
<212> TYPE: PRT
<213> ORGANISM: Homo sapiens

<400> SEQUENCE: 307

Gln Gly Gln Thr Leu Arg Asn Tyr Tyr Ala Ser
1               5                   10

<210> SEQ ID NO 308

```
<211> LENGTH: 11
<212> TYPE: PRT
<213> ORGANISM: Homo sapiens

<400> SEQUENCE: 308

Gln Gly Asp Gln Leu Arg Asn Tyr Tyr Ala Ser
1               5                   10

<210> SEQ ID NO 309
<211> LENGTH: 11
<212> TYPE: PRT
<213> ORGANISM: Homo sapiens

<400> SEQUENCE: 309

Gln Gly Asp Thr Leu Gln Asn Tyr Tyr Ala Ser
1               5                   10

<210> SEQ ID NO 310
<211> LENGTH: 11
<212> TYPE: PRT
<213> ORGANISM: Homo sapiens

<400> SEQUENCE: 310

Gln Gly Asp Thr Leu Arg Gln Tyr Tyr Ala Ser
1               5                   10

<210> SEQ ID NO 311
<211> LENGTH: 11
<212> TYPE: PRT
<213> ORGANISM: Homo sapiens

<400> SEQUENCE: 311

Gln Gly Asp Thr Leu Arg Asn Tyr Gln Ala Ser
1               5                   10

<210> SEQ ID NO 312
<211> LENGTH: 11
<212> TYPE: PRT
<213> ORGANISM: Homo sapiens

<400> SEQUENCE: 312

Ser Gly Asp Thr Leu Arg Asn Tyr Tyr Ala Ser
1               5                   10

<210> SEQ ID NO 313
<211> LENGTH: 11
<212> TYPE: PRT
<213> ORGANISM: Homo sapiens

<400> SEQUENCE: 313

Gln Ser Asp Thr Leu Arg Asn Tyr Tyr Ala Ser
1               5                   10

<210> SEQ ID NO 314
<211> LENGTH: 11
<212> TYPE: PRT
<213> ORGANISM: Homo sapiens

<400> SEQUENCE: 314

Gln Gly Ser Thr Leu Arg Asn Tyr Tyr Ala Ser
1               5                   10

<210> SEQ ID NO 315
<211> LENGTH: 11
<212> TYPE: PRT
```

```
<213> ORGANISM: Homo sapiens

<400> SEQUENCE: 315

Gln Gly Asp Ser Leu Arg Asn Tyr Tyr Ala Ser
1               5                   10

<210> SEQ ID NO 316
<211> LENGTH: 11
<212> TYPE: PRT
<213> ORGANISM: Homo sapiens

<400> SEQUENCE: 316

Gln Gly Asp Thr Leu Ser Asn Tyr Tyr Ala Ser
1               5                   10

<210> SEQ ID NO 317
<211> LENGTH: 11
<212> TYPE: PRT
<213> ORGANISM: Homo sapiens

<400> SEQUENCE: 317

Gln Gly Asp Thr Leu Arg Ser Tyr Tyr Ala Ser
1               5                   10

<210> SEQ ID NO 318
<211> LENGTH: 11
<212> TYPE: PRT
<213> ORGANISM: Homo sapiens

<400> SEQUENCE: 318

Trp Gly Asp Thr Leu Arg Asn Tyr Tyr Ala Ser
1               5                   10

<210> SEQ ID NO 319
<211> LENGTH: 11
<212> TYPE: PRT
<213> ORGANISM: Homo sapiens

<400> SEQUENCE: 319

Gln Gly Trp Thr Leu Arg Asn Tyr Tyr Ala Ser
1               5                   10

<210> SEQ ID NO 320
<211> LENGTH: 11
<212> TYPE: PRT
<213> ORGANISM: Homo sapiens

<400> SEQUENCE: 320

Gln Gly Asp Trp Leu Arg Asn Tyr Tyr Ala Ser
1               5                   10

<210> SEQ ID NO 321
<211> LENGTH: 11
<212> TYPE: PRT
<213> ORGANISM: Homo sapiens

<400> SEQUENCE: 321

Gln Gly Asp Thr Leu Trp Asn Tyr Tyr Ala Ser
1               5                   10

<210> SEQ ID NO 322
<211> LENGTH: 11
<212> TYPE: PRT
<213> ORGANISM: Homo sapiens
```

```
<400> SEQUENCE: 322

Gln Gly Asp Thr Leu Arg Trp Tyr Tyr Ala Ser
1               5                   10

<210> SEQ ID NO 323
<211> LENGTH: 11
<212> TYPE: PRT
<213> ORGANISM: Homo sapiens

<400> SEQUENCE: 323

Gln Gly Asp Thr Leu Arg Asn Trp Tyr Ala Ser
1               5                   10

<210> SEQ ID NO 324
<211> LENGTH: 11
<212> TYPE: PRT
<213> ORGANISM: Homo sapiens

<400> SEQUENCE: 324

Gln Gly Asp Thr Leu Arg Asn Tyr Trp Ala Ser
1               5                   10

<210> SEQ ID NO 325
<211> LENGTH: 11
<212> TYPE: PRT
<213> ORGANISM: Homo sapiens

<400> SEQUENCE: 325

Tyr Gly Asp Thr Leu Arg Asn Tyr Tyr Ala Ser
1               5                   10

<210> SEQ ID NO 326
<211> LENGTH: 11
<212> TYPE: PRT
<213> ORGANISM: Homo sapiens

<400> SEQUENCE: 326

Gln Gly Tyr Thr Leu Arg Asn Tyr Tyr Ala Ser
1               5                   10

<210> SEQ ID NO 327
<211> LENGTH: 11
<212> TYPE: PRT
<213> ORGANISM: Homo sapiens

<400> SEQUENCE: 327

Gln Gly Asp Tyr Leu Arg Asn Tyr Tyr Ala Ser
1               5                   10

<210> SEQ ID NO 328
<211> LENGTH: 11
<212> TYPE: PRT
<213> ORGANISM: Homo sapiens

<400> SEQUENCE: 328

Gln Gly Asp Thr Leu Tyr Asn Tyr Tyr Ala Ser
1               5                   10

<210> SEQ ID NO 329
<211> LENGTH: 11
<212> TYPE: PRT
<213> ORGANISM: Homo sapiens

<400> SEQUENCE: 329
```

-continued

```
Gln Gly Asp Thr Leu Arg Tyr Tyr Tyr Ala Ser
1               5                   10
```

<210> SEQ ID NO 330
<211> LENGTH: 7
<212> TYPE: PRT
<213> ORGANISM: Homo sapiens

<400> SEQUENCE: 330

```
Ala Lys Asn Asn Arg Pro Ser
1               5
```

<210> SEQ ID NO 331
<211> LENGTH: 7
<212> TYPE: PRT
<213> ORGANISM: Homo sapiens

<400> SEQUENCE: 331

```
Gly Ala Asn Asn Arg Pro Ser
1               5
```

<210> SEQ ID NO 332
<211> LENGTH: 7
<212> TYPE: PRT
<213> ORGANISM: Homo sapiens

<400> SEQUENCE: 332

```
Gly Lys Ala Asn Arg Pro Ser
1               5
```

<210> SEQ ID NO 333
<211> LENGTH: 7
<212> TYPE: PRT
<213> ORGANISM: Homo sapiens

<400> SEQUENCE: 333

```
Gly Lys Asn Ala Arg Pro Ser
1               5
```

<210> SEQ ID NO 334
<211> LENGTH: 7
<212> TYPE: PRT
<213> ORGANISM: Homo sapiens

<400> SEQUENCE: 334

```
Gly Lys Asn Asn Ala Pro Ser
1               5
```

<210> SEQ ID NO 335
<211> LENGTH: 7
<212> TYPE: PRT
<213> ORGANISM: Homo sapiens

<400> SEQUENCE: 335

```
Gly Lys Asn Asn Arg Ala Ser
1               5
```

<210> SEQ ID NO 336
<211> LENGTH: 7
<212> TYPE: PRT
<213> ORGANISM: Homo sapiens

<400> SEQUENCE: 336

```
Gly Lys Asn Asn Arg Pro Ala
1               5
```

<210> SEQ ID NO 337
<211> LENGTH: 7
<212> TYPE: PRT
<213> ORGANISM: Homo sapiens

<400> SEQUENCE: 337

Asp Lys Asn Asn Arg Pro Ser
1               5

<210> SEQ ID NO 338
<211> LENGTH: 7
<212> TYPE: PRT
<213> ORGANISM: Homo sapiens

<400> SEQUENCE: 338

Gly Asp Asn Asn Arg Pro Ser
1               5

<210> SEQ ID NO 339
<211> LENGTH: 7
<212> TYPE: PRT
<213> ORGANISM: Homo sapiens

<400> SEQUENCE: 339

Gly Lys Asp Asn Arg Pro Ser
1               5

<210> SEQ ID NO 340
<211> LENGTH: 7
<212> TYPE: PRT
<213> ORGANISM: Homo sapiens

<400> SEQUENCE: 340

Gly Lys Asn Asp Arg Pro Ser
1               5

<210> SEQ ID NO 341
<211> LENGTH: 7
<212> TYPE: PRT
<213> ORGANISM: Homo sapiens

<400> SEQUENCE: 341

Gly Lys Asn Asn Asp Pro Ser
1               5

<210> SEQ ID NO 342
<211> LENGTH: 7
<212> TYPE: PRT
<213> ORGANISM: Homo sapiens

<400> SEQUENCE: 342

Gly Lys Asn Asn Arg Asp Ser
1               5

<210> SEQ ID NO 343
<211> LENGTH: 7
<212> TYPE: PRT
<213> ORGANISM: Homo sapiens

<400> SEQUENCE: 343

Gly Lys Asn Asn Arg Pro Asp
1               5

```
<210> SEQ ID NO 344
<211> LENGTH: 7
<212> TYPE: PRT
<213> ORGANISM: Homo sapiens

<400> SEQUENCE: 344

His Lys Asn Asn Arg Pro Ser
1               5

<210> SEQ ID NO 345
<211> LENGTH: 7
<212> TYPE: PRT
<213> ORGANISM: Homo sapiens

<400> SEQUENCE: 345

Gly His Asn Asn Arg Pro Ser
1               5

<210> SEQ ID NO 346
<211> LENGTH: 7
<212> TYPE: PRT
<213> ORGANISM: Homo sapiens

<400> SEQUENCE: 346

Gly Lys His Asn Arg Pro Ser
1               5

<210> SEQ ID NO 347
<211> LENGTH: 7
<212> TYPE: PRT
<213> ORGANISM: Homo sapiens

<400> SEQUENCE: 347

Gly Lys Asn His Arg Pro Ser
1               5

<210> SEQ ID NO 348
<211> LENGTH: 7
<212> TYPE: PRT
<213> ORGANISM: Homo sapiens

<400> SEQUENCE: 348

Gly Lys Asn Asn His Pro Ser
1               5

<210> SEQ ID NO 349
<211> LENGTH: 7
<212> TYPE: PRT
<213> ORGANISM: Homo sapiens

<400> SEQUENCE: 349

Gly Lys Asn Asn Arg His Ser
1               5

<210> SEQ ID NO 350
<211> LENGTH: 7
<212> TYPE: PRT
<213> ORGANISM: Homo sapiens

<400> SEQUENCE: 350

Gly Lys Asn Asn Arg Pro His
1               5

<210> SEQ ID NO 351
<211> LENGTH: 7
```

<212> TYPE: PRT
<213> ORGANISM: Homo sapiens

<400> SEQUENCE: 351

Lys Lys Asn Asn Arg Pro Ser
1               5

<210> SEQ ID NO 352
<211> LENGTH: 7
<212> TYPE: PRT
<213> ORGANISM: Homo sapiens

<400> SEQUENCE: 352

Gly Lys Lys Asn Arg Pro Ser
1               5

<210> SEQ ID NO 353
<211> LENGTH: 7
<212> TYPE: PRT
<213> ORGANISM: Homo sapiens

<400> SEQUENCE: 353

Gly Lys Asn Lys Arg Pro Ser
1               5

<210> SEQ ID NO 354
<211> LENGTH: 7
<212> TYPE: PRT
<213> ORGANISM: Homo sapiens

<400> SEQUENCE: 354

Gly Lys Asn Asn Lys Pro Ser
1               5

<210> SEQ ID NO 355
<211> LENGTH: 7
<212> TYPE: PRT
<213> ORGANISM: Homo sapiens

<400> SEQUENCE: 355

Gly Lys Asn Asn Arg Lys Ser
1               5

<210> SEQ ID NO 356
<211> LENGTH: 7
<212> TYPE: PRT
<213> ORGANISM: Homo sapiens

<400> SEQUENCE: 356

Gly Lys Asn Asn Arg Pro Lys
1               5

<210> SEQ ID NO 357
<211> LENGTH: 7
<212> TYPE: PRT
<213> ORGANISM: Homo sapiens

<400> SEQUENCE: 357

Leu Lys Asn Asn Arg Pro Ser
1               5

<210> SEQ ID NO 358
<211> LENGTH: 7
<212> TYPE: PRT
<213> ORGANISM: Homo sapiens

<400> SEQUENCE: 358

Gly Leu Asn Asn Arg Pro Ser
1               5

<210> SEQ ID NO 359
<211> LENGTH: 7
<212> TYPE: PRT
<213> ORGANISM: Homo sapiens

<400> SEQUENCE: 359

Gly Lys Leu Asn Arg Pro Ser
1               5

<210> SEQ ID NO 360
<211> LENGTH: 7
<212> TYPE: PRT
<213> ORGANISM: Homo sapiens

<400> SEQUENCE: 360

Gly Lys Asn Leu Arg Pro Ser
1               5

<210> SEQ ID NO 361
<211> LENGTH: 7
<212> TYPE: PRT
<213> ORGANISM: Homo sapiens

<400> SEQUENCE: 361

Gly Lys Asn Asn Leu Pro Ser
1               5

<210> SEQ ID NO 362
<211> LENGTH: 7
<212> TYPE: PRT
<213> ORGANISM: Homo sapiens

<400> SEQUENCE: 362

Gly Lys Asn Asn Arg Leu Ser
1               5

<210> SEQ ID NO 363
<211> LENGTH: 7
<212> TYPE: PRT
<213> ORGANISM: Homo sapiens

<400> SEQUENCE: 363

Gly Lys Asn Asn Arg Pro Leu
1               5

<210> SEQ ID NO 364
<211> LENGTH: 7
<212> TYPE: PRT
<213> ORGANISM: Homo sapiens

<400> SEQUENCE: 364

Gln Lys Asn Asn Arg Pro Ser
1               5

<210> SEQ ID NO 365
<211> LENGTH: 7
<212> TYPE: PRT
<213> ORGANISM: Homo sapiens

<400> SEQUENCE: 365

Gly Gln Asn Asn Arg Pro Ser
1               5

<210> SEQ ID NO 366
<211> LENGTH: 7
<212> TYPE: PRT
<213> ORGANISM: Homo sapiens

<400> SEQUENCE: 366

Gly Lys Gln Asn Arg Pro Ser
1               5

<210> SEQ ID NO 367
<211> LENGTH: 7
<212> TYPE: PRT
<213> ORGANISM: Homo sapiens

<400> SEQUENCE: 367

Gly Lys Asn Gln Arg Pro Ser
1               5

<210> SEQ ID NO 368
<211> LENGTH: 7
<212> TYPE: PRT
<213> ORGANISM: Homo sapiens

<400> SEQUENCE: 368

Gly Lys Asn Asn Gln Pro Ser
1               5

<210> SEQ ID NO 369
<211> LENGTH: 7
<212> TYPE: PRT
<213> ORGANISM: Homo sapiens

<400> SEQUENCE: 369

Gly Lys Asn Asn Arg Gln Ser
1               5

<210> SEQ ID NO 370
<211> LENGTH: 7
<212> TYPE: PRT
<213> ORGANISM: Homo sapiens

<400> SEQUENCE: 370

Gly Lys Asn Asn Arg Pro Gln
1               5

<210> SEQ ID NO 371
<211> LENGTH: 7
<212> TYPE: PRT
<213> ORGANISM: Homo sapiens

<400> SEQUENCE: 371

Ser Lys Asn Asn Arg Pro Ser
1               5

<210> SEQ ID NO 372
<211> LENGTH: 7
<212> TYPE: PRT
<213> ORGANISM: Homo sapiens

<400> SEQUENCE: 372

Gly Ser Asn Asn Arg Pro Ser

```
1               5

<210> SEQ ID NO 373
<211> LENGTH: 7
<212> TYPE: PRT
<213> ORGANISM: Homo sapiens

<400> SEQUENCE: 373

Gly Lys Ser Asn Arg Pro Ser
1               5

<210> SEQ ID NO 374
<211> LENGTH: 7
<212> TYPE: PRT
<213> ORGANISM: Homo sapiens

<400> SEQUENCE: 374

Gly Lys Asn Ser Arg Pro Ser
1               5

<210> SEQ ID NO 375
<211> LENGTH: 7
<212> TYPE: PRT
<213> ORGANISM: Homo sapiens

<400> SEQUENCE: 375

Gly Lys Asn Asn Ser Pro Ser
1               5

<210> SEQ ID NO 376
<211> LENGTH: 7
<212> TYPE: PRT
<213> ORGANISM: Homo sapiens

<400> SEQUENCE: 376

Gly Lys Asn Asn Arg Ser Ser
1               5

<210> SEQ ID NO 377
<211> LENGTH: 7
<212> TYPE: PRT
<213> ORGANISM: Homo sapiens

<400> SEQUENCE: 377

Trp Lys Asn Asn Arg Pro Ser
1               5

<210> SEQ ID NO 378
<211> LENGTH: 7
<212> TYPE: PRT
<213> ORGANISM: Homo sapiens

<400> SEQUENCE: 378

Gly Trp Asn Asn Arg Pro Ser
1               5

<210> SEQ ID NO 379
<211> LENGTH: 7
<212> TYPE: PRT
<213> ORGANISM: Homo sapiens

<400> SEQUENCE: 379

Gly Lys Trp Asn Arg Pro Ser
1               5
```

<210> SEQ ID NO 380
<211> LENGTH: 7
<212> TYPE: PRT
<213> ORGANISM: Homo sapiens

<400> SEQUENCE: 380

Gly Lys Asn Trp Arg Pro Ser
1               5

<210> SEQ ID NO 381
<211> LENGTH: 7
<212> TYPE: PRT
<213> ORGANISM: Homo sapiens

<400> SEQUENCE: 381

Gly Lys Asn Asn Trp Pro Ser
1               5

<210> SEQ ID NO 382
<211> LENGTH: 7
<212> TYPE: PRT
<213> ORGANISM: Homo sapiens

<400> SEQUENCE: 382

Gly Lys Asn Asn Arg Trp Ser
1               5

<210> SEQ ID NO 383
<211> LENGTH: 7
<212> TYPE: PRT
<213> ORGANISM: Homo sapiens

<400> SEQUENCE: 383

Gly Lys Asn Asn Arg Pro Trp
1               5

<210> SEQ ID NO 384
<211> LENGTH: 7
<212> TYPE: PRT
<213> ORGANISM: Homo sapiens

<400> SEQUENCE: 384

Tyr Lys Asn Asn Arg Pro Ser
1               5

<210> SEQ ID NO 385
<211> LENGTH: 7
<212> TYPE: PRT
<213> ORGANISM: Homo sapiens

<400> SEQUENCE: 385

Gly Tyr Asn Asn Arg Pro Ser
1               5

<210> SEQ ID NO 386
<211> LENGTH: 7
<212> TYPE: PRT
<213> ORGANISM: Homo sapiens

<400> SEQUENCE: 386

Gly Lys Tyr Asn Arg Pro Ser
1               5

<210> SEQ ID NO 387

```
<211> LENGTH: 7
<212> TYPE: PRT
<213> ORGANISM: Homo sapiens

<400> SEQUENCE: 387

Gly Lys Asn Tyr Arg Pro Ser
1               5

<210> SEQ ID NO 388
<211> LENGTH: 7
<212> TYPE: PRT
<213> ORGANISM: Homo sapiens

<400> SEQUENCE: 388

Gly Lys Asn Asn Tyr Pro Ser
1               5

<210> SEQ ID NO 389
<211> LENGTH: 7
<212> TYPE: PRT
<213> ORGANISM: Homo sapiens

<400> SEQUENCE: 389

Gly Lys Asn Asn Arg Tyr Ser
1               5

<210> SEQ ID NO 390
<211> LENGTH: 7
<212> TYPE: PRT
<213> ORGANISM: Homo sapiens

<400> SEQUENCE: 390

Gly Lys Asn Asn Arg Pro Tyr
1               5

<210> SEQ ID NO 391
<211> LENGTH: 11
<212> TYPE: PRT
<213> ORGANISM: Homo sapiens

<400> SEQUENCE: 391

Asn Ala Arg Asp Ser Ser Gly Lys Asn Leu Val
1               5                   10

<210> SEQ ID NO 392
<211> LENGTH: 11
<212> TYPE: PRT
<213> ORGANISM: Homo sapiens

<400> SEQUENCE: 392

Asn Ser Arg Asp Ala Ser Gly Lys Asn Leu Val
1               5                   10

<210> SEQ ID NO 393
<211> LENGTH: 11
<212> TYPE: PRT
<213> ORGANISM: Homo sapiens

<400> SEQUENCE: 393

Asn Ser Arg Asp Ser Ala Gly Lys Asn Leu Val
1               5                   10

<210> SEQ ID NO 394
<211> LENGTH: 11
<212> TYPE: PRT
```

<213> ORGANISM: Homo sapiens

<400> SEQUENCE: 394

Asn Ser Arg Asp Ser Ser Ala Lys Asn Leu Val
1               5                   10

<210> SEQ ID NO 395
<211> LENGTH: 11
<212> TYPE: PRT
<213> ORGANISM: Homo sapiens

<400> SEQUENCE: 395

Asn Ser Arg Asp Ser Ser Gly Ala Asn Leu Val
1               5                   10

<210> SEQ ID NO 396
<211> LENGTH: 11
<212> TYPE: PRT
<213> ORGANISM: Homo sapiens

<400> SEQUENCE: 396

Asn Ser Arg Asp Ser Ser Gly Lys Ala Leu Val
1               5                   10

<210> SEQ ID NO 397
<211> LENGTH: 11
<212> TYPE: PRT
<213> ORGANISM: Homo sapiens

<400> SEQUENCE: 397

Asn Ser Arg Asp Ser Ser Gly Lys Asn Ala Val
1               5                   10

<210> SEQ ID NO 398
<211> LENGTH: 11
<212> TYPE: PRT
<213> ORGANISM: Homo sapiens

<400> SEQUENCE: 398

Asn Ser Arg Asp Ser Ser Gly Lys Asn Leu Ala
1               5                   10

<210> SEQ ID NO 399
<211> LENGTH: 11
<212> TYPE: PRT
<213> ORGANISM: Homo sapiens

<400> SEQUENCE: 399

Asp Ser Arg Asp Ser Ser Gly Lys Asn Leu Val
1               5                   10

<210> SEQ ID NO 400
<211> LENGTH: 11
<212> TYPE: PRT
<213> ORGANISM: Homo sapiens

<400> SEQUENCE: 400

Asn Asp Arg Asp Ser Ser Gly Lys Asn Leu Val
1               5                   10

<210> SEQ ID NO 401
<211> LENGTH: 11
<212> TYPE: PRT
<213> ORGANISM: Homo sapiens

<400> SEQUENCE: 401

Asn Ser Arg Asp Asp Ser Gly Lys Asn Leu Val
1               5                   10

<210> SEQ ID NO 402
<211> LENGTH: 11
<212> TYPE: PRT
<213> ORGANISM: Homo sapiens

<400> SEQUENCE: 402

Asn Ser Arg Asp Ser Asp Gly Lys Asn Leu Val
1               5                   10

<210> SEQ ID NO 403
<211> LENGTH: 11
<212> TYPE: PRT
<213> ORGANISM: Homo sapiens

<400> SEQUENCE: 403

Asn Ser Arg Asp Ser Ser Gly Asp Asn Leu Val
1               5                   10

<210> SEQ ID NO 404
<211> LENGTH: 11
<212> TYPE: PRT
<213> ORGANISM: Homo sapiens

<400> SEQUENCE: 404

Asn Ser Arg Asp Ser Ser Gly Lys Asp Leu Val
1               5                   10

<210> SEQ ID NO 405
<211> LENGTH: 11
<212> TYPE: PRT
<213> ORGANISM: Homo sapiens

<400> SEQUENCE: 405

Asn Ser Arg Asp Ser Ser Gly Lys Asn Leu Asp
1               5                   10

<210> SEQ ID NO 406
<211> LENGTH: 11
<212> TYPE: PRT
<213> ORGANISM: Homo sapiens

<400> SEQUENCE: 406

His Ser Arg Asp Ser Ser Gly Lys Asn Leu Val
1               5                   10

<210> SEQ ID NO 407
<211> LENGTH: 11
<212> TYPE: PRT
<213> ORGANISM: Homo sapiens

<400> SEQUENCE: 407

Asn Ser Arg Asp His Ser Gly Lys Asn Leu Val
1               5                   10

<210> SEQ ID NO 408
<211> LENGTH: 11
<212> TYPE: PRT
<213> ORGANISM: Homo sapiens

<400> SEQUENCE: 408

Asn Ser Arg Asp Ser His Gly Lys Asn Leu Val
1               5                   10

<210> SEQ ID NO 409
<211> LENGTH: 11
<212> TYPE: PRT
<213> ORGANISM: Homo sapiens

<400> SEQUENCE: 409

Asn Ser Arg Asp Ser Ser Gly His Asn Leu Val
1               5                   10

<210> SEQ ID NO 410
<211> LENGTH: 11
<212> TYPE: PRT
<213> ORGANISM: Homo sapiens

<400> SEQUENCE: 410

Asn Ser Arg Asp Ser Ser Gly Lys His Leu Val
1               5                   10

<210> SEQ ID NO 411
<211> LENGTH: 11
<212> TYPE: PRT
<213> ORGANISM: Homo sapiens

<400> SEQUENCE: 411

Asn Ser Arg Asp Ser Ser Gly Lys Asn His Val
1               5                   10

<210> SEQ ID NO 412
<211> LENGTH: 11
<212> TYPE: PRT
<213> ORGANISM: Homo sapiens

<400> SEQUENCE: 412

Asn Ser Arg Asp Ser Ser Gly Lys Asn Leu His
1               5                   10

<210> SEQ ID NO 413
<211> LENGTH: 11
<212> TYPE: PRT
<213> ORGANISM: Homo sapiens

<400> SEQUENCE: 413

Lys Ser Arg Asp Ser Ser Gly Lys Asn Leu Val
1               5                   10

<210> SEQ ID NO 414
<211> LENGTH: 11
<212> TYPE: PRT
<213> ORGANISM: Homo sapiens

<400> SEQUENCE: 414

Asn Ser Lys Asp Ser Ser Gly Lys Asn Leu Val
1               5                   10

<210> SEQ ID NO 415
<211> LENGTH: 11
<212> TYPE: PRT
<213> ORGANISM: Homo sapiens

<400> SEQUENCE: 415

Asn Ser Arg Asp Lys Ser Gly Lys Asn Leu Val
1               5                   10

```
<210> SEQ ID NO 416
<211> LENGTH: 11
<212> TYPE: PRT
<213> ORGANISM: Homo sapiens

<400> SEQUENCE: 416

Asn Ser Arg Asp Ser Lys Gly Lys Asn Leu Val
1               5                   10

<210> SEQ ID NO 417
<211> LENGTH: 11
<212> TYPE: PRT
<213> ORGANISM: Homo sapiens

<400> SEQUENCE: 417

Asn Ser Arg Asp Ser Ser Gly Lys Lys Leu Val
1               5                   10

<210> SEQ ID NO 418
<211> LENGTH: 11
<212> TYPE: PRT
<213> ORGANISM: Homo sapiens

<400> SEQUENCE: 418

Asn Ser Arg Asp Ser Ser Gly Lys Asn Leu Lys
1               5                   10

<210> SEQ ID NO 419
<211> LENGTH: 11
<212> TYPE: PRT
<213> ORGANISM: Homo sapiens

<400> SEQUENCE: 419

Leu Ser Arg Asp Ser Ser Gly Lys Asn Leu Val
1               5                   10

<210> SEQ ID NO 420
<211> LENGTH: 11
<212> TYPE: PRT
<213> ORGANISM: Homo sapiens

<400> SEQUENCE: 420

Asn Ser Arg Asp Leu Ser Gly Lys Asn Leu Val
1               5                   10

<210> SEQ ID NO 421
<211> LENGTH: 11
<212> TYPE: PRT
<213> ORGANISM: Homo sapiens

<400> SEQUENCE: 421

Asn Ser Arg Asp Ser Leu Gly Lys Asn Leu Val
1               5                   10

<210> SEQ ID NO 422
<211> LENGTH: 11
<212> TYPE: PRT
<213> ORGANISM: Homo sapiens

<400> SEQUENCE: 422

Asn Ser Arg Asp Ser Ser Leu Lys Asn Leu Val
1               5                   10
```

```
<210> SEQ ID NO 423
<211> LENGTH: 11
<212> TYPE: PRT
<213> ORGANISM: Homo sapiens

<400> SEQUENCE: 423

Asn Ser Arg Asp Ser Ser Gly Leu Asn Leu Val
1               5                   10

<210> SEQ ID NO 424
<211> LENGTH: 11
<212> TYPE: PRT
<213> ORGANISM: Homo sapiens

<400> SEQUENCE: 424

Asn Ser Arg Asp Ser Ser Gly Lys Leu Leu Val
1               5                   10

<210> SEQ ID NO 425
<211> LENGTH: 11
<212> TYPE: PRT
<213> ORGANISM: Homo sapiens

<400> SEQUENCE: 425

Asn Ser Arg Asp Ser Ser Gly Lys Asn Leu Leu
1               5                   10

<210> SEQ ID NO 426
<211> LENGTH: 11
<212> TYPE: PRT
<213> ORGANISM: Homo sapiens

<400> SEQUENCE: 426

Gln Ser Arg Asp Ser Ser Gly Lys Asn Leu Val
1               5                   10

<210> SEQ ID NO 427
<211> LENGTH: 11
<212> TYPE: PRT
<213> ORGANISM: Homo sapiens

<400> SEQUENCE: 427

Asn Ser Arg Asp Gln Ser Gly Lys Asn Leu Val
1               5                   10

<210> SEQ ID NO 428
<211> LENGTH: 11
<212> TYPE: PRT
<213> ORGANISM: Homo sapiens

<400> SEQUENCE: 428

Asn Ser Arg Asp Ser Gln Gly Lys Asn Leu Val
1               5                   10

<210> SEQ ID NO 429
<211> LENGTH: 11
<212> TYPE: PRT
<213> ORGANISM: Homo sapiens

<400> SEQUENCE: 429

Asn Ser Arg Asp Ser Ser Gly Gln Asn Leu Val
1               5                   10

<210> SEQ ID NO 430
<211> LENGTH: 11
```

<212> TYPE: PRT
<213> ORGANISM: Homo sapiens

<400> SEQUENCE: 430

Asn Ser Arg Asp Ser Ser Gly Lys Gln Leu Val
1               5                   10

<210> SEQ ID NO 431
<211> LENGTH: 11
<212> TYPE: PRT
<213> ORGANISM: Homo sapiens

<400> SEQUENCE: 431

Asn Ser Arg Asp Ser Ser Gly Lys Asn Gln Val
1               5                   10

<210> SEQ ID NO 432
<211> LENGTH: 11
<212> TYPE: PRT
<213> ORGANISM: Homo sapiens

<400> SEQUENCE: 432

Asn Ser Arg Asp Ser Ser Gly Lys Asn Leu Gln
1               5                   10

<210> SEQ ID NO 433
<211> LENGTH: 11
<212> TYPE: PRT
<213> ORGANISM: Homo sapiens

<400> SEQUENCE: 433

Ser Ser Arg Asp Ser Ser Gly Lys Asn Leu Val
1               5                   10

<210> SEQ ID NO 434
<211> LENGTH: 11
<212> TYPE: PRT
<213> ORGANISM: Homo sapiens

<400> SEQUENCE: 434

Asn Ser Arg Asp Ser Ser Ser Lys Asn Leu Val
1               5                   10

<210> SEQ ID NO 435
<211> LENGTH: 11
<212> TYPE: PRT
<213> ORGANISM: Homo sapiens

<400> SEQUENCE: 435

Asn Ser Arg Asp Ser Ser Gly Ser Asn Leu Val
1               5                   10

<210> SEQ ID NO 436
<211> LENGTH: 11
<212> TYPE: PRT
<213> ORGANISM: Homo sapiens

<400> SEQUENCE: 436

Asn Ser Arg Asp Ser Ser Gly Lys Ser Leu Val
1               5                   10

<210> SEQ ID NO 437
<211> LENGTH: 11
<212> TYPE: PRT
<213> ORGANISM: Homo sapiens

<400> SEQUENCE: 437

Asn Ser Arg Asp Ser Ser Gly Lys Asn Ser Val
1               5                   10

<210> SEQ ID NO 438
<211> LENGTH: 11
<212> TYPE: PRT
<213> ORGANISM: Homo sapiens

<400> SEQUENCE: 438

Asn Ser Arg Asp Ser Ser Gly Lys Asn Leu Ser
1               5                   10

<210> SEQ ID NO 439
<211> LENGTH: 11
<212> TYPE: PRT
<213> ORGANISM: Homo sapiens

<400> SEQUENCE: 439

Asn Ser Arg Asp Trp Ser Gly Lys Asn Leu Val
1               5                   10

<210> SEQ ID NO 440
<211> LENGTH: 11
<212> TYPE: PRT
<213> ORGANISM: Homo sapiens

<400> SEQUENCE: 440

Asn Ser Arg Asp Ser Trp Gly Lys Asn Leu Val
1               5                   10

<210> SEQ ID NO 441
<211> LENGTH: 11
<212> TYPE: PRT
<213> ORGANISM: Homo sapiens

<400> SEQUENCE: 441

Asn Ser Arg Asp Ser Ser Gly Trp Asn Leu Val
1               5                   10

<210> SEQ ID NO 442
<211> LENGTH: 11
<212> TYPE: PRT
<213> ORGANISM: Homo sapiens

<400> SEQUENCE: 442

Asn Ser Arg Asp Ser Ser Gly Lys Trp Leu Val
1               5                   10

<210> SEQ ID NO 443
<211> LENGTH: 11
<212> TYPE: PRT
<213> ORGANISM: Homo sapiens

<400> SEQUENCE: 443

Asn Ser Arg Asp Ser Ser Gly Lys Asn Trp Val
1               5                   10

<210> SEQ ID NO 444
<211> LENGTH: 11
<212> TYPE: PRT
<213> ORGANISM: Homo sapiens

<400> SEQUENCE: 444

Asn Ser Arg Asp Ser Ser Gly Lys Asn Leu Trp
1               5                   10

<210> SEQ ID NO 445
<211> LENGTH: 11
<212> TYPE: PRT
<213> ORGANISM: Homo sapiens

<400> SEQUENCE: 445

Tyr Ser Arg Asp Ser Ser Gly Lys Asn Leu Val
1               5                   10

<210> SEQ ID NO 446
<211> LENGTH: 11
<212> TYPE: PRT
<213> ORGANISM: Homo sapiens

<400> SEQUENCE: 446

Asn Ser Arg Asp Tyr Ser Gly Lys Asn Leu Val
1               5                   10

<210> SEQ ID NO 447
<211> LENGTH: 11
<212> TYPE: PRT
<213> ORGANISM: Homo sapiens

<400> SEQUENCE: 447

Asn Ser Arg Asp Ser Tyr Gly Lys Asn Leu Val
1               5                   10

<210> SEQ ID NO 448
<211> LENGTH: 11
<212> TYPE: PRT
<213> ORGANISM: Homo sapiens

<400> SEQUENCE: 448

Asn Ser Arg Asp Ser Ser Tyr Lys Asn Leu Val
1               5                   10

<210> SEQ ID NO 449
<211> LENGTH: 11
<212> TYPE: PRT
<213> ORGANISM: Homo sapiens

<400> SEQUENCE: 449

Asn Ser Arg Asp Ser Ser Gly Tyr Asn Leu Val
1               5                   10

<210> SEQ ID NO 450
<211> LENGTH: 11
<212> TYPE: PRT
<213> ORGANISM: Homo sapiens

<400> SEQUENCE: 450

Asn Ser Arg Asp Ser Ser Gly Lys Tyr Leu Val
1               5                   10

<210> SEQ ID NO 451
<211> LENGTH: 11
<212> TYPE: PRT
<213> ORGANISM: Homo sapiens

<400> SEQUENCE: 451

Asn Ser Arg Asp Ser Ser Gly Lys Asn Tyr Val

<210> SEQ ID NO 452
<211> LENGTH: 11
<212> TYPE: PRT
<213> ORGANISM: Homo sapiens

<400> SEQUENCE: 452

Asn Ser Arg Asp Ser Ser Gly Lys Asn Leu Tyr
1               5                   10

<210> SEQ ID NO 453
<211> LENGTH: 11
<212> TYPE: PRT
<213> ORGANISM: Homo sapiens

<400> SEQUENCE: 453

Gly Gly Ser Ile Ser Ser Ser Asn Trp Trp Ser
1               5                   10

<210> SEQ ID NO 454
<211> LENGTH: 119
<212> TYPE: PRT
<213> ORGANISM: Homo sapiens

<400> SEQUENCE: 454

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Tyr Gly Tyr Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 455
<211> LENGTH: 108
<212> TYPE: PRT
<213> ORGANISM: Homo sapiens

<400> SEQUENCE: 455

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
                20                  25                  30

Ser Trp Tyr Gln Gln Lys Pro Gly Gln Ala Pro Ile Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

```
Asp Glu Ala Asp Tyr Tyr Cys Asn Ser Arg Asp Ser Ser Gly Lys Asn
            85                  90                  95

Leu Val Phe Gly Gly Gly Thr Lys Leu Thr Val Leu
            100                 105

<210> SEQ ID NO 456
<211> LENGTH: 214
<212> TYPE: PRT
<213> ORGANISM: Homo sapiens

<400> SEQUENCE: 456

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
            20                  25                  30

Ser Trp Tyr Gln Gln Lys Pro Gly Gln Ala Pro Ile Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
            85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
        210

<210> SEQ ID NO 457
<211> LENGTH: 108
<212> TYPE: PRT
<213> ORGANISM: Homo sapiens

<400> SEQUENCE: 457

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80
```

Asp Glu Ala Asp Tyr Tyr Cys Asn Ser Arg Asp Leu Ser Gly Lys Asn
            85                  90                  95

Leu Val Phe Gly Gly Gly Thr Lys Leu Thr Val Leu
            100                 105

<210> SEQ ID NO 458
<211> LENGTH: 214
<212> TYPE: PRT
<213> ORGANISM: Homo sapiens

<400> SEQUENCE: 458

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Leu Ser Gly Lys Asn
            85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
        180                 185                 190

Tyr Ser Cys Gln Val Thr His Glu Gly Ser Thr Val Glu Lys Thr Val
    195                 200                 205

Ala Pro Thr Glu Cys Ser
    210

<210> SEQ ID NO 459
<211> LENGTH: 108
<212> TYPE: PRT
<213> ORGANISM: Homo sapiens

<400> SEQUENCE: 459

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Phe Ser Gly Lys Asn
            85                  90                  95

Leu Val Phe Gly Gly Gly Thr Lys Leu Thr Val Leu
            100                 105

<210> SEQ ID NO 460
<211> LENGTH: 214
<212> TYPE: PRT
<213> ORGANISM: Homo sapiens

<400> SEQUENCE: 460

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Phe Ser Gly Lys Asn
            85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
        180                 185                 190

Tyr Ser Cys Gln Val Thr His Glu Gly Ser Thr Val Glu Lys Thr Val
    195                 200                 205

Ala Pro Thr Glu Cys Ser
    210

<210> SEQ ID NO 461
<211> LENGTH: 119
<212> TYPE: PRT
<213> ORGANISM: Homo sapiens

<400> SEQUENCE: 461

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

```
Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 462
<211> LENGTH: 119
<212> TYPE: PRT
<213> ORGANISM: Homo sapiens

<400> SEQUENCE: 462

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Phe Gly Asn Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 463
<211> LENGTH: 119
<212> TYPE: PRT
<213> ORGANISM: Homo sapiens

<400> SEQUENCE: 463

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Tyr Gly Asn Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 464
<211> LENGTH: 119
<212> TYPE: PRT
<213> ORGANISM: Homo sapiens
```

<400> SEQUENCE: 464

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Trp Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 465
<211> LENGTH: 119
<212> TYPE: PRT
<213> ORGANISM: Homo sapiens

<400> SEQUENCE: 465

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Trp Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 466
<211> LENGTH: 119
<212> TYPE: PRT
<213> ORGANISM: Homo sapiens

<400> SEQUENCE: 466

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Phe Gly Phe Thr Asn Tyr Asn Pro Ser Leu
    50                  55                  60

Lys Ser Arg Val Thr Ile Ser Val Asp Lys Ser Lys Asn Gln Phe Ser

```
              65                  70                  75                  80
Leu Lys Leu Ile Ser Val Thr Ala Ala Asp Thr Ala Val Tyr Tyr Cys
                85                  90                  95
Ala Arg Glu Gly Ile Gly Trp Pro Ser Phe Asp Tyr Trp Gly Gln Gly
            100                 105                 110
Thr Leu Val Thr Val Ser Ser
        115
```

<210> SEQ ID NO 467
<211> LENGTH: 119
<212> TYPE: PRT
<213> ORGANISM: Homo sapiens

<400> SEQUENCE: 467

```
Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Ser
            20                  25                  30
Asn Trp Trp Ser Trp Val Arg Gln Pro Pro Gly Lys Gly Leu Glu Trp
        35                  40                  45
Ile Gly Glu Ile Tyr His Tyr Gly Phe Thr Asn Tyr Asn Pro Ser Leu
    50                  55                  60
Lys Ser Arg Val Thr Ile Ser Val Asp Lys Ser Lys Asn Gln Phe Ser
65                  70                  75                  80
Leu Lys Leu Ile Ser Val Thr Ala Ala Asp Thr Ala Val Tyr Tyr Cys
                85                  90                  95
Ala Arg Glu Gly Ile Gly Trp Pro Ser Phe Asp Tyr Trp Gly Gln Gly
            100                 105                 110
Thr Leu Val Thr Val Ser Ser
        115
```

<210> SEQ ID NO 468
<211> LENGTH: 119
<212> TYPE: PRT
<213> ORGANISM: Homo sapiens

<400> SEQUENCE: 468

```
Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Ser
            20                  25                  30
Asn Trp Trp Ser Trp Val Arg Gln Pro Pro Gly Lys Gly Leu Glu Trp
        35                  40                  45
Ile Gly Glu Ile Tyr His Trp Gly Phe Thr Asn Tyr Asn Pro Ser Leu
    50                  55                  60
Lys Ser Arg Val Thr Ile Ser Val Asp Lys Ser Lys Asn Gln Phe Ser
65                  70                  75                  80
Leu Lys Leu Ile Ser Val Thr Ala Ala Asp Thr Ala Val Tyr Tyr Cys
                85                  90                  95
Ala Arg Glu Gly Ile Gly Trp Pro Ser Phe Asp Tyr Trp Gly Gln Gly
            100                 105                 110
Thr Leu Val Thr Val Ser Ser
        115
```

<210> SEQ ID NO 469
<211> LENGTH: 119
<212> TYPE: PRT

<213> ORGANISM: Homo sapiens

<400> SEQUENCE: 469

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Phe Gly Tyr Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 470
<211> LENGTH: 119
<212> TYPE: PRT
<213> ORGANISM: Homo sapiens

<400> SEQUENCE: 470

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Tyr Gly Tyr Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 471
<211> LENGTH: 119
<212> TYPE: PRT
<213> ORGANISM: Homo sapiens

<400> SEQUENCE: 471

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Trp Gly Tyr Thr Asn Tyr Asn Pro Ser Leu
    50                  55                  60

```
Lys Ser Arg Val Thr Ile Ser Val Asp Lys Ser Lys Asn Gln Phe Ser
 65                  70                  75                  80

Leu Lys Leu Ile Ser Val Thr Ala Ala Asp Thr Ala Val Tyr Tyr Cys
                 85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 472
<211> LENGTH: 119
<212> TYPE: PRT
<213> ORGANISM: Homo sapiens

<400> SEQUENCE: 472

Gln Val Gln Leu Gln Glu Ser Gly Pro Gly Leu Val Lys Pro Ser Gly
  1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Gly Lys Gly Leu Glu Trp
             35                  40                  45

Ile Gly Glu Ile Tyr His Phe Gly Trp Thr Asn Tyr Asn Pro Ser Leu
         50                  55                  60

Lys Ser Arg Val Thr Ile Ser Val Asp Lys Ser Lys Asn Gln Phe Ser
 65                  70                  75                  80

Leu Lys Leu Ile Ser Val Thr Ala Ala Asp Thr Ala Val Tyr Tyr Cys
                 85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 473
<211> LENGTH: 119
<212> TYPE: PRT
<213> ORGANISM: Homo sapiens

<400> SEQUENCE: 473

Gln Val Gln Leu Gln Glu Ser Gly Pro Gly Leu Val Lys Pro Ser Gly
  1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Gly Lys Gly Leu Glu Trp
             35                  40                  45

Ile Gly Glu Ile Tyr His Tyr Gly Trp Thr Asn Tyr Asn Pro Ser Leu
         50                  55                  60

Lys Ser Arg Val Thr Ile Ser Val Asp Lys Ser Lys Asn Gln Phe Ser
 65                  70                  75                  80

Leu Lys Leu Ile Ser Val Thr Ala Ala Asp Thr Ala Val Tyr Tyr Cys
                 85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 474
```

-continued

```
<211> LENGTH: 119
<212> TYPE: PRT
<213> ORGANISM: Homo sapiens

<400> SEQUENCE: 474

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Trp Gly Trp Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 475
<211> LENGTH: 119
<212> TYPE: PRT
<213> ORGANISM: Homo sapiens

<400> SEQUENCE: 475

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ala Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 476
<211> LENGTH: 119
<212> TYPE: PRT
<213> ORGANISM: Homo sapiens

<400> SEQUENCE: 476

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Leu Ser Trp Val Arg Gln Pro Pro Gly Lys Gly Leu Glu Trp
        35                  40                  45
```

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                    85                  90                  95

Ala Arg Glu Gly Ile Gly Trp Pro Ser Phe Asp Tyr Trp Gly Gln Gly
                100                 105                 110

Thr Leu Val Thr Val Ser Ser
            115

<210> SEQ ID NO 477
<211> LENGTH: 119
<212> TYPE: PRT
<213> ORGANISM: Homo sapiens

<400> SEQUENCE: 477

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Trp His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                    85                  90                  95

Ala Arg Glu Gly Ile Gly Trp Pro Ser Phe Asp Tyr Trp Gly Gln Gly
                100                 105                 110

Thr Leu Val Thr Val Ser Ser
            115

<210> SEQ ID NO 478
<211> LENGTH: 119
<212> TYPE: PRT
<213> ORGANISM: Homo sapiens

<400> SEQUENCE: 478

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly His Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                    85                  90                  95

Ala Arg Glu Gly Ile Gly Trp Pro Ser Phe Asp Tyr Trp Gly Gln Gly
                100                 105                 110

Thr Leu Val Thr Val Ser Ser
            115

<210> SEQ ID NO 479
<211> LENGTH: 119
<212> TYPE: PRT
<213> ORGANISM: Homo sapiens

<400> SEQUENCE: 479

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Leu Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 480
<211> LENGTH: 119
<212> TYPE: PRT
<213> ORGANISM: Homo sapiens

<400> SEQUENCE: 480

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Asp Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 481
<211> LENGTH: 119
<212> TYPE: PRT
<213> ORGANISM: Homo sapiens

<400> SEQUENCE: 481

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp

```
            35                  40                  45
Ile Gly Glu Ile Tyr His Ser Gly Asn Thr Gln Tyr Asn Pro Ser Leu
        50                  55                  60
Lys Ser Arg Val Thr Ile Ser Val Asp Lys Ser Lys Asn Gln Phe Ser
65                  70                  75                  80
Leu Lys Leu Ile Ser Val Thr Ala Ala Asp Thr Ala Val Tyr Tyr Cys
                85                  90                  95
Ala Arg Glu Gly Ile Gly Trp Pro Ser Phe Asp Tyr Trp Gly Gln Gly
            100                 105                 110
Thr Leu Val Thr Val Ser Ser
            115
```

<210> SEQ ID NO 482
<211> LENGTH: 119
<212> TYPE: PRT
<213> ORGANISM: Homo sapiens

<400> SEQUENCE: 482

```
Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Ser
            20                  25                  30
Asn Trp Trp Ser Trp Val Arg Gln Pro Pro Gly Lys Gly Leu Glu Trp
        35                  40                  45
Ile Gly Glu Ile Tyr His Ser Gly Asn Thr Asn Tyr Tyr Pro Ser Leu
        50                  55                  60
Lys Ser Arg Val Thr Ile Ser Val Asp Lys Ser Lys Asn Gln Phe Ser
65                  70                  75                  80
Leu Lys Leu Ile Ser Val Thr Ala Ala Asp Thr Ala Val Tyr Tyr Cys
                85                  90                  95
Ala Arg Glu Gly Ile Gly Trp Pro Ser Phe Asp Tyr Trp Gly Gln Gly
            100                 105                 110
Thr Leu Val Thr Val Ser Ser
            115
```

<210> SEQ ID NO 483
<211> LENGTH: 119
<212> TYPE: PRT
<213> ORGANISM: Homo sapiens

<400> SEQUENCE: 483

```
Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Ser
            20                  25                  30
Asn Trp Trp Ser Trp Val Arg Gln Pro Pro Gly Lys Gly Leu Glu Trp
        35                  40                  45
Ile Gly Glu Ile Tyr His Ser Gly Asn Thr Asn Tyr Asn Pro Ser Leu
        50                  55                  60
Lys Ser Arg Val Thr Ile Ser Val Asp Lys Ser Lys Asn Gln Phe Ser
65                  70                  75                  80
Leu Lys Leu Ile Ser Val Thr Ala Ala Asp Thr Ala Val Tyr Tyr Cys
                85                  90                  95
Ala Arg Glu Gly Ile Gly Trp Pro Ser Phe Asp Ser Trp Gly Gln Gly
            100                 105                 110
Thr Leu Val Thr Val Ser Ser
```

<210> SEQ ID NO 484
<211> LENGTH: 119
<212> TYPE: PRT
<213> ORGANISM: Homo sapiens

<400> SEQUENCE: 484

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Leu Trp Gly Gln Gly
            100                 105                 110

Thr Leu Val Thr Val Ser Ser
        115

<210> SEQ ID NO 485
<211> LENGTH: 119
<212> TYPE: PRT
<213> ORGANISM: Homo sapiens

<400> SEQUENCE: 485

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ile Ser Val Thr Ala Ala Asp Thr Ala Val Tyr Tyr Cys
                85                  90                  95

Ala Arg Glu Gly Ile Gly Trp Pro Ser Phe Asp Ala Trp Gly Gln Gly
            100                 105                 110

Thr Leu Val Thr Val Ser Ser
        115

<210> SEQ ID NO 486
<211> LENGTH: 119
<212> TYPE: PRT
<213> ORGANISM: Homo sapiens

<400> SEQUENCE: 486

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

```
Asn Trp Trp Ser Trp Val Arg Gln Pro Pro Gly Lys Gly Leu Glu Trp
            35                  40                  45

Ile Gly Glu Ile Tyr His Ser Gly Asn Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ile Ser Val Thr Ala Ala Asp Thr Ala Val Tyr Tyr Cys
                 85                  90                  95

Ala Arg Glu Gly Ile Gly Trp Pro Ser Phe Asp His Trp Gly Gln Gly
                100                 105                 110

Thr Leu Val Thr Val Ser Ser
            115

<210> SEQ ID NO 487
<211> LENGTH: 119
<212> TYPE: PRT
<213> ORGANISM: Homo sapiens

<400> SEQUENCE: 487

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Trp Gly Trp Thr Asn Tyr Tyr Pro Ser Leu
 50                  55                  60

Lys Ser Arg Val Thr Ile Ser Val Asp Lys Ser Lys Asn Gln Phe Ser
 65                  70                  75                  80

Leu Lys Leu Ile Ser Val Thr Ala Ala Asp Thr Ala Val Tyr Tyr Cys
                 85                  90                  95

Ala Arg Glu Gly Ile Gly Trp Pro Ser Phe Asp Tyr Trp Gly Gln Gly
                100                 105                 110

Thr Leu Val Thr Val Ser Ser
            115

<210> SEQ ID NO 488
<211> LENGTH: 119
<212> TYPE: PRT
<213> ORGANISM: Homo sapiens

<400> SEQUENCE: 488

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Asn Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Gly Ile Gly Trp Pro Ser Phe Asp Tyr Trp Gly Gln Gly
                100                 105                 110
```

Thr Leu Val Thr Val Ser Ser
        115

<210> SEQ ID NO 489
<211> LENGTH: 119
<212> TYPE: PRT
<213> ORGANISM: Homo sapiens

<400> SEQUENCE: 489

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Tyr Gly Trp Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 490
<211> LENGTH: 119
<212> TYPE: PRT
<213> ORGANISM: Homo sapiens

<400> SEQUENCE: 490

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Tyr Gly Tyr Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Ile Gly Trp Pro Ser Phe Asp Tyr Trp Gly Gln Gly
            100                 105                 110

Thr Leu Val Thr Val Ser Ser
        115

<210> SEQ ID NO 491
<211> LENGTH: 108
<212> TYPE: PRT
<213> ORGANISM: Homo sapiens

<400> SEQUENCE: 491

Ser Ser Glu Leu Thr Gln Asp Pro Ala Ala Ser Val Ala Leu Gly Gln
1               5                   10                  15

-continued

```
Thr Val Arg Ile Thr Cys Gln Gly Asp Thr Leu Arg Asn Tyr Tyr Ala
             20                  25                  30

Ser Trp Tyr Gln Gln Lys Pro Gly Gln Ala Pro Ile Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                 85                  90                  95

Leu Val Phe Gly Gly Gly Thr Lys Leu Thr Val Leu
            100                 105
```

<210> SEQ ID NO 492
<211> LENGTH: 108
<212> TYPE: PRT
<213> ORGANISM: Homo sapiens

<400> SEQUENCE: 492

```
Ser Ser Glu Leu Thr Gln Asp Pro Ala Ala Ser Val Ala Leu Gly Gln
1               5                  10                  15

Thr Val Arg Ile Thr Cys Gln Gly Asp Thr Leu Arg Asn Tyr Tyr Ala
             20                  25                  30

Ser Trp Tyr Gln Gln Lys Pro Gly Gln Ala Pro Ile Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Ser Ser Gly Lys Asn
                 85                  90                  95

Leu Val Phe Gly Gly Gly Thr Lys Leu Thr Val Leu
            100                 105
```

<210> SEQ ID NO 493
<211> LENGTH: 108
<212> TYPE: PRT
<213> ORGANISM: Homo sapiens

<400> SEQUENCE: 493

```
Ser Ser Glu Leu Thr Gln Asp Pro Ala Ala Ser Val Ala Leu Gly Gln
1               5                  10                  15

Thr Val Arg Ile Thr Cys Gln Gly Asp Thr Leu Arg Asn Tyr Tyr Ala
             20                  25                  30

Ser Trp Tyr Gln Gln Lys Pro Gly Gln Ala Pro Ile Leu Val Ile Tyr
         35                  40                  45

Ser Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                 85                  90                  95

Leu Val Phe Gly Gly Gly Thr Lys Leu Thr Val Leu
            100                 105
```

<210> SEQ ID NO 494
<211> LENGTH: 108

<212> TYPE: PRT
<213> ORGANISM: Homo sapiens

<400> SEQUENCE: 494

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Ala Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105

<210> SEQ ID NO 495
<211> LENGTH: 108
<212> TYPE: PRT
<213> ORGANISM: Homo sapiens

<400> SEQUENCE: 495

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly His Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105

<210> SEQ ID NO 496
<211> LENGTH: 108
<212> TYPE: PRT
<213> ORGANISM: Homo sapiens

<400> SEQUENCE: 496

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Leu Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn

-continued

```
                85                  90                  95

Leu Val Phe Gly Gly Gly Thr Lys Leu Thr Val Leu
            100                 105

<210> SEQ ID NO 497
<211> LENGTH: 108
<212> TYPE: PRT
<213> ORGANISM: Homo sapiens

<400> SEQUENCE: 497

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Leu Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105

<210> SEQ ID NO 498
<211> LENGTH: 108
<212> TYPE: PRT
<213> ORGANISM: Homo sapiens

<400> SEQUENCE: 498

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Gln Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105

<210> SEQ ID NO 499
<211> LENGTH: 108
<212> TYPE: PRT
<213> ORGANISM: Homo sapiens

<400> SEQUENCE: 499

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45
```

```
Gly Lys Asn Asn Tyr Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105

<210> SEQ ID NO 500
<211> LENGTH: 108
<212> TYPE: PRT
<213> ORGANISM: Homo sapiens

<400> SEQUENCE: 500

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly His Asn Asn Leu Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105

<210> SEQ ID NO 501
<211> LENGTH: 108
<212> TYPE: PRT
<213> ORGANISM: Homo sapiens

<400> SEQUENCE: 501

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly His Asn Tyr Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105

<210> SEQ ID NO 502
<211> LENGTH: 108
<212> TYPE: PRT
<213> ORGANISM: Homo sapiens

<400> SEQUENCE: 502
```

```
Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
                20                  25                  30

Ser Trp Tyr Gln Gln Lys Pro Gly Gln Ala Pro Ile Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys Asn
                85                  90                  95

Leu Val Phe Gly Gly Gly Thr Lys Leu Thr Val Leu
            100                 105
```

<210> SEQ ID NO 503
<211> LENGTH: 108
<212> TYPE: PRT
<213> ORGANISM: Homo sapiens

<400> SEQUENCE: 503

```
Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
                20                  25                  30

Ser Trp Tyr Gln Gln Lys Pro Gly Gln Ala Pro Ile Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Glu Ser Ser Gly Lys Asn
                85                  90                  95

Leu Val Phe Gly Gly Gly Thr Lys Leu Thr Val Leu
            100                 105
```

<210> SEQ ID NO 504
<211> LENGTH: 108
<212> TYPE: PRT
<213> ORGANISM: Homo sapiens

<400> SEQUENCE: 504

```
Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
                20                  25                  30

Ser Trp Tyr Gln Gln Lys Pro Gly Gln Ala Pro Ile Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Leu Ser Gly Lys Asn
                85                  90                  95

Leu Val Phe Gly Gly Gly Thr Lys Leu Thr Val Leu
            100                 105
```

<210> SEQ ID NO 505
<211> LENGTH: 108
<212> TYPE: PRT
<213> ORGANISM: Homo sapiens

<400> SEQUENCE: 505

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Glu Ser Gly Lys Asn
                85                  90                  95

Leu Val Phe Gly Gly Gly Thr Lys Leu Thr Val Leu
            100                 105

<210> SEQ ID NO 506
<211> LENGTH: 108
<212> TYPE: PRT
<213> ORGANISM: Homo sapiens

<400> SEQUENCE: 506

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Phe Ser Gly Lys Asn
                85                  90                  95

Leu Val Phe Gly Gly Gly Thr Lys Leu Thr Val Leu
            100                 105

<210> SEQ ID NO 507
<211> LENGTH: 108
<212> TYPE: PRT
<213> ORGANISM: Homo sapiens

<400> SEQUENCE: 507

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu

```
                65                  70                  75                  80
Asp Glu Ala Asp Tyr Tyr Cys Asn Ser Arg Glu Ser Ser Gly Lys Asn
                85                  90                  95

Leu Val Phe Gly Gly Gly Thr Lys Leu Thr Val Leu
            100                 105

<210> SEQ ID NO 508
<211> LENGTH: 108
<212> TYPE: PRT
<213> ORGANISM: Homo sapiens

<400> SEQUENCE: 508

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Leu Ser Gly Lys Asn
                85                  90                  95

Leu Val Phe Gly Gly Gly Thr Lys Leu Thr Val Leu
            100                 105

<210> SEQ ID NO 509
<211> LENGTH: 108
<212> TYPE: PRT
<213> ORGANISM: Homo sapiens

<400> SEQUENCE: 509

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Glu Ser Gly Lys Asn
                85                  90                  95

Leu Val Phe Gly Gly Gly Thr Lys Leu Thr Val Leu
            100                 105

<210> SEQ ID NO 510
<211> LENGTH: 108
<212> TYPE: PRT
<213> ORGANISM: Homo sapiens

<400> SEQUENCE: 510

Ser Ser Glu Leu Thr Gln Asp Pro Ala Ala Ser Val Ala Leu Gly Gln
1               5                   10                  15

Thr Val Arg Ile Thr Cys Gln Gly Asp Thr Leu Arg Ser Tyr Tyr Ala
            20                  25                  30
```

```
Ser Trp Tyr Gln Gln Lys Pro Gly Gln Ala Pro Ile Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Phe Ser Gly Lys Asn
                85                  90                  95

Leu Val Phe Gly Gly Gly Thr Lys Leu Thr Val Leu
                100                 105

<210> SEQ ID NO 511
<211> LENGTH: 114
<212> TYPE: PRT
<213> ORGANISM: Homo sapiens

<400> SEQUENCE: 511

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 512
<211> LENGTH: 211
<212> TYPE: PRT
<213> ORGANISM: Homo sapiens

<400> SEQUENCE: 512

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125
```

```
Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Lys
                165                 170                 175

Arg Val Gly Ser Ile Glu Gly Arg Gly Ser Gly Leu Asn Asp Ile Phe
            180                 185                 190

Glu Ala Gln Lys Ile Glu Trp His Glu Gly Ser His His His His
            195                 200                 205

His His His
    210
```

```
<210> SEQ ID NO 513
<211> LENGTH: 107
<212> TYPE: PRT
<213> ORGANISM: Homo sapiens

<400> SEQUENCE: 513

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 514
<211> LENGTH: 106
<212> TYPE: PRT
<213> ORGANISM: Homo sapiens

<400> SEQUENCE: 514

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

```
<210> SEQ ID NO 515
<211> LENGTH: 448
```

<212> TYPE: PRT
<213> ORGANISM: Homo sapiens

<400> SEQUENCE: 515

```
Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

Trp Ile Gly Trp Val Arg Gln Met Pro Gly Lys Gly Leu Glu Tyr Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 516
<211> LENGTH: 214
<212> TYPE: PRT
<213> ORGANISM: Homo sapiens

<400> SEQUENCE: 516

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

Thr Phe Gly Gln Gly Thr Lys Leu Glu Ile Ser Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 517
<211> LENGTH: 357
<212> TYPE: DNA
<213> ORGANISM: Homo sapiens

<400> SEQUENCE: 517
caggtgcagc tgcaggaatc tggccccgga ctggtgaaac ctagcggcac cctgagcctg      60
acctgcgccg tgagcggcgg cagcatcagc agcagcaact ggtggagctg ggtccgccag     120
cctcctggca agggcctgga atggatcggc gagatctacc actacggcta caccaactac     180
aaccccagcc tgaagtcccg ggtgaccatc agcgtggaca gagcaagaa ccagttcagc      240 ctgaagctgt ccagcgtgac agccgccgac accgccgtgt actactgcgc cagagaggga     300
atcggctggc ccagcttcga ttactggggc cagggcaccc tggtgacagt gtcctca        357
```

<210> SEQ ID NO 518
<211> LENGTH: 327
<212> TYPE: DNA
<213> ORGANISM: Homo sapiens

<400> SEQUENCE: 518

```
agcagcgagc tgacccagga tcccgctgct tccgtggctc tgggccagac cgtgcggatc      60
acctgtcagg gcgacaccct gcggagctac tacgccagct ggtatcagca gaagcccggc     120
caggccccca tcctggtgat ctacggcaag aacaaccggc ccagcggcat ccccgacaga     180
ttcagcggca gcagcagcgg caacaccgcc agcctgacca tcactggcgc tcaggccgag     240
gacgaggccg actactactg caacagccgg gacctttccg gcaagaacct ggtgttcggc     300
ggaggcacca agctgaccgt cctaggt                                         327
```

<210> SEQ ID NO 519
<211> LENGTH: 11
<212> TYPE: PRT
<213> ORGANISM: Homo sapiens

<400> SEQUENCE: 519

Asn Ser Arg Asp Phe Ser Gly Lys Asn Leu Val
1               5                   10

<210> SEQ ID NO 520
<211> LENGTH: 186
<212> TYPE: PRT
<213> ORGANISM: Homo sapiens

<400> SEQUENCE: 520

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Lys
                165                 170                 175

Arg Val Gly Ser Ile Glu Gly Arg Gly Ser
            180                 185